(12) United States Patent
Ananthan et al.

(10) Patent No.: US 9,873,702 B2
(45) Date of Patent: Jan. 23, 2018

(54) HETEROCYCLIC COMPOUNDS AS BIOGENIC AMINE TRANSPORT MODULATORS

(71) Applicants: Subramaniam Ananthan, Birmingham, AL (US); Richard B. Rothman, Ellicott City, MD (US)

(72) Inventors: Subramaniam Ananthan, Birmingham, AL (US); Richard B. Rothman, Ellicott City, MD (US)

(73) Assignees: Southern Research Institute, Birmingham, AL (US); The United States of America as Represented by the Secretary, Department of Health and Human Services, Washington, DC (US)

(*) Notice: Subject to any disclaimer, the term of this patent is extended or adjusted under 35 U.S.C. 154(b) by 0 days.

(21) Appl. No.: 14/960,012

(22) Filed: Dec. 4, 2015

(65) Prior Publication Data
US 2016/0159809 A1 Jun. 9, 2016

Related U.S. Application Data

(60) Provisional application No. 62/087,983, filed on Dec. 5, 2014.

(51) Int. Cl.
| | | |
|---|---|---|
| *C07D 487/04* | (2006.01) | |
| *C07D 239/95* | (2006.01) | |
| *C07D 401/04* | (2006.01) | |
| *C07D 403/04* | (2006.01) | |
| *C07D 401/14* | (2006.01) | |
| *C07D 409/04* | (2006.01) | |
| *C07D 471/04* | (2006.01) | |
| *C07D 473/00* | (2006.01) | |

(52) U.S. Cl.
CPC ......... *C07D 487/04* (2013.01); *C07D 239/95* (2013.01); *C07D 401/04* (2013.01); *C07D 401/14* (2013.01); *C07D 403/04* (2013.01); *C07D 409/04* (2013.01); *C07D 471/04* (2013.01); *C07D 473/00* (2013.01)

(58) Field of Classification Search
None
See application file for complete search history.

(56) References Cited

U.S. PATENT DOCUMENTS

| | | | | |
|---|---|---|---|---|
| 5,439,895 A * | 8/1995 | Lee | ...................... | C07D 231/12 514/210.21 |
| 7,410,975 B2 | 8/2008 | Lipford et al. | | |
| 2009/0137623 A1 | 5/2009 | Kumar et al. | | |
| 2011/0118289 A1 | 5/2011 | Giordani et al. | | |

FOREIGN PATENT DOCUMENTS

| | | | | |
|---|---|---|---|---|
| AU | 2015357505 | 12/2014 | | |
| CA | 2969856 | 12/2014 | | |
| EP | PCT/US2015/064079 | 12/2014 | | |
| IN | WO 2011028741 A1 * | 3/2011 | .......... | C07D 239/95 |
| JP | 2017-530213 | 12/2014 | | |
| KR | 10-2017-7017638 | 12/2014 | | |
| WO | WO 2004092196 A2 * | 10/2004 | .......... | C07D 239/94 |
| WO | WO-2006/071095 A1 | 7/2006 | | |
| WO | WO 2009001060 A2 * | 12/2008 | .......... | C07D 239/95 |
| WO | WO-2011/072695 A1 | 6/2011 | | |
| WO | PCT/US2015/064079 | 12/2014 | | |
| WO | PCT/US15/64075 | 12/2015 | | |

OTHER PUBLICATIONS

International Search Report and Written Opinion dated Feb. 11, 2016 for international application PCT/US2015/064075, filed on Dec. 4, 2015 (Applicant—Subramaniam Ananthan) (14 pages).
Ananthan et al., "Identification of a Novel Partial Inhibitor of Dopamine Transporter Among 4-Substituted 2-Phenylquinazolines," Bioorg. Med. Chem. Lett. 12, 2225-2228 (2002).
Basile et al., "Characterization of the Antinociceptive Actions of Bicifadine in Models of Acute, Persistent, and Chronic Pain," J. Pharmacol. Exp. Ther. 321, 1208-1225 (2007).
Cao, et al., (2002) "Nitric oxide inhibits uptake of dopamine and N-methyl-4-phenylpyridinium (MPP+) but not release of MPP+ in rat C6 glioma cells expressing human dopamine transporter,". Br J Pharmacol 137:1155-1162.
Charney et al., "Monoamine Dysfunction and the Pathophysiology and Treatment of Depression," J. Clin. Psychiatry, 59, 11-14 (1998).
Delgado et al., "Depression: the case for a monoamine deficiency," J. Clin. Psychiatry, 61 (Suppl 6), 7-11 (2000).
Felten, et al., (2011) "Genetically determined dopamine availability predicts disposition for depression. Brain and behavior, "1:109-118.
Forrest, et al., (2011) "The structural basis of secondary active transport mechanisms," Biochem Biophys Acta 1807:167-188.
Gainetdinov RR and Caron MG (2003) "Monoamine transporters: from genes to behavior," Annu Rev Pharmacol Toxicol 43:261-284.
Gether U, et al., (2006) "Neurotransmitter transporters: molecular function of important drug targets," Trends Pharmacol Sci 27:375-383.
Greengard P (2001) "The neurobiology of slow synaptic transmission," Science 294:1024-1030.

(Continued)

*Primary Examiner* — Kortney L Klinkel
*Assistant Examiner* — Tori M Strong
(74) *Attorney, Agent, or Firm* — Ballard Spahr LLP

(57) ABSTRACT

The present disclosure relates to certain amine derivatives of fused bicyclic heterocycles that inhibit the amine reuptake function of the biogenic amine transporters, dopamine transporter (DAT), serotonin transporter (SERT) and norepinephrine transporter (NET). Compounds of the present disclosure are potent inhibitors of the reuptake of dopamine (DA), serotonin (5-hydroxytryptamine, 5-HT) and norepinephrine (NE) with full or partial maximal efficacy. The compounds with partial maximal efficacy in inhibiting reuptake of all three biogenic amines are herein referred to as partial triple uptake inhibitors (PTRIs). Compounds of the present disclosure are useful for treating depression, pain and substance abuse and relapse to substance abuse and addiction to substances such as cocaine, methamphetamine, nicotine and alcohol. This abstract is intended as a scanning tool for purposes of searching in the particular art and is not intended to be limiting of the present invention.

4 Claims, 11 Drawing Sheets

(56) References Cited

OTHER PUBLICATIONS

Hache et al., "Monoaminergic Antidepressants in the Relief of Pain: Potential Therapeutic Utility of Triple Reuptake Inhibitors (TRIs)," Pharmaceuticals, 4, 285-342 (2011).

Hirschfeld, "History and Evolution of the Monoamine Hypothesis of Depression," J. Clin. Psychiatry, 61 (Suppl 6), 4-6 (2000).

Khoshbouei H, et al., (2003) "Amphetamine-induced dopamine efflux. A voltage-sensitive and intracellular Na+-dependent mechanism," J Biol Chem 278:12070-12077.

Kurian, et al., (2011) "Clinical and molecular characterization of hereditary dopamine transporter deficiency syndrome: an observational cohort and experimental study," The Lancet Neurology 10:54-62.

Montague PR and Berns GS (2002) "Neural economics and the biological substrates of valuation," Neuron 36:265-284.

Nightingale, et al. (2005) "Studies of the Biogenic Amine Transporters. XI. Identification of a 1-[2-[Bis(4-fluorophenyl)methoxy]ethyl]-4-(3-phenylpropyl)piperazine (GBR12909) Analog That Allosterically Modulates the Serotonin Transporter," J Pharmacol Exp Ther 314:906-915.

Pariser et al., "Studies of the Biogenic Amine Transporters. 12. Identification of Novel Partial Inhibitors of Amphetamine-Induced Dopamine Release," J. Pharmacol. Exp. Ther. 326, 286-295 (2008).

Prins et al., "Triple reuptake inhibitors for treating subtypes of major depressive disorder: the monoamine hypothesis revisited," Expert Opin. Investig. Drugs 20, 1107-1130 (2011).

Ren et al., "Descending modulation in persistent pain: an update," Pain 100, 1-6 (2002).

Ressler et al., "Role of Serotonergic and Noradrenergic Systems in the Pathophysiology of Depression and Anxiety Disorders," Depress. Anxiety, 12 (Suppl 1), 2-19 (2000).

Rothman et al., "Studies of the Biogenic Amine Transporters. 13. Identification of "Agonist" and "Antagonist" Allosteric Modulators of Amphetamine-Induced Dopamine Release," J. Pharmacol. Exp. Ther. 329, 718-728 (2009).

Rothman et al., "Studies of the Biogenic Amine Transporters. VIII. Identification of a Novel Partial Inhibitor of Dopamine Uptake and Dopamine Transporter Binding,"Synapse, 43, 268-274 (2002).

Rothman, et al., (2001) "Amphetamine-type central nervous system stimulants release norepinephrine more potently than they release dopamine and serotonin," Synapse 39:32-41.

Rothman, et al., (2002) "Interaction of the anorectic medication, phendimetrazine, and its metabolites with monoamine transporters in rat brain," Eur J Pharmacol 447:51-57.

Rothman, et al., (2003) "In vitro characterization of ephedrine-related stereoisomers at biogenic amine transporters and the receptorome reveals selective actions as norepinephrine transporter substrates," J Pharmacol Exp Ther 307:138-145.

Rothman, et al., (2009) "Studies of the Biogenic Amine Transporters. 13. Identification of "Agonist" and "Antagonist" Allosteric Modulators of Amphetamine-Induced Dopamine Release," J Pharmacol Exp Ther. 392:718-728.

Salamone, et al., (2009) "Dopamine, behavioral economics, and effort," Frontiers in behavioral neuroscience 3:13.

Schmitt KC and Reith ME (2010) "Regulation of the dopamine transporter: aspects relevant to psychostimulant drugs of abuse," Ann NY Acad Sci 1187:316-340.

Schmitt, et al., (2013) "Non-classical pharmacology of the dopamine transporter: atypical inhibitors, allosteric modulators, and partial substrates," The Journal of pharmacology and experimental therapeutics 346:2-10.

Sitte, et al., (1998) "Carrier-mediated release, transport rates, and charge transfer induced by amphetamine, tyramine, and dopamine in mammalian cells transfected with the human dopamine transporter," J Neurochem 71:1289-1297.

Tanda, et al., (2009) "Discovery of drugs to treat cocaine dependence: behavioral and neurochemical effects of atypical dopamine transport inhibitors," Adv Pharmacol 57:253-289.

Zhou et al., "Spinal serotonin receptors mediate descending facilitation of a nociceptive reflex from the nuclei reticularis gigantocellularis and gigantocellularis pars alpha in the rat," Brain Res. 550, 35-48 (1991).

Zhu et al., "Recombinant HIV-1TAT1-86 allosterically modulates dopamine transporter activity," Synapse, 65, 1251-54 (2011).

Requirement for Restriction or Election dated Nov. 28, 2016 for U.S. Appl. No. 14/960,023, filed Dec. 4, 2015 (Applicant/Inventor—Subtamaniam Ananthan) (9 pages).

U.S. Appl. No. 14/960,023, filed Dec. 4, 2015, Ananthan.

U.S. Appl. No. 62/087,998, filed Dec. 5, 2014, Subramaniam Ananthan.

Dass et al., Studies in Anti-malarials: Quinazoline Series—Part 1. J Sci Ind Res. 1952; 11B: 461-3.

Wawer et al., Systematic Extraction of Structure-Activity Relationship Information from Biological Screening Data. ChemMedChem. 2009; 4(9):1431-8.

International Preliminary Report on Patentability dated Jun. 6, 2017 by the International Searching Authority for International Application No. PCT/US15/64075, which was filed on Dec. 4, 2015 and published as WO 2016/090296 on Jun. 9, 2016 (Applicant—Subramaniam Ananthan) (5 pages).

International Preliminary Report on Patentability dated Jun. 6, 2017 by the International Searching Authority for International Application No. PCT/US2015/064079, which was filed on Dec. 4, 2015 and published as WO 2016/090299 on Jun. 9, 2016 (Applicant—Subramaniam Ananthan) (5 pages).

Response to Restriction Requirement/Election dated Feb. 23, 2017 to the USPTO for U.S. Appl. No. 14/960,023, filed May 18, 2017 and published as US 2016/0159751 A1 on Jun. 9, 2016 (Inventor—Subramaniam Ananthan) (14 pages).

Non Final Rejection dated May 18, 2017 by the USPTO for U.S. Appl. No. 14/960,023, filed Dec. 4, 2015 and published as US 2016/0159751 A1 on Jun. 9, 2016 (Inventor—Subramaniam Ananthan) (10 pages).

Amendment and Response to Non-Final Office Action filed on Aug. 16, 2017 with the USPTO for U.S. Appl. No. 14/960,023, filed Dec. 4, 2015 and published as US 2016/0159751 A1 on Jun. 9, 2016 (Inventor—Subramaniam Ananthan) (15 pages).

* cited by examiner

HETEROCYCLIC COMPOUNDS AS BIOGENIC AMINE TRANSPORT MODULATORS

CROSS-REFERENCE TO RELATED APPLICATIONS

This application claims the benefit of U.S. Provisional Application No. 62/087,983, filed on Dec. 5, 2014, which is incorporated herein fully by reference in its entirety.

STATEMENT REGARDING FEDERALLY SPONSORED RESEARCH

This invention was made with government support under grant number DA029962, awarded by the National Institute on Drug Abuse of the National Institutes of Health. The government has certain rights in the invention.

BACKGROUND

Dopamine, serotonin and norepinephrine are three important neurotransmitters in the human brain. The extracellular concentration of these neurotransmitters is regulated by the membrane bound transporters, the dopamine transporter (DAT), the serotonin transporter (SERT), and the norepinephrine transporter (NET) by reuptake of the neurotransmitters from the neuronal cleft.

Dysfunction of the monoamine neurotransmitter function has been implicated in a number of CNS (Central Nervous System) diseases such as depression (see, e.g. Charney et al., *J. Clin. Psychiatry*, 59, 11-14 (1998); Delgado et al., *J. Clin. Psychiatry*, 61 (Suppl 6), 7-11 (2000); Ressler et al., *Depress. Anxiety*, 12 (Suppl 1), 2-19 (2000); Hirschfeld, J. Clin. Psychiatry, 61 (Suppl 6), 4-6 (2000); Prins et al., *Expert Opin. Investig. Drugs* 20, 1107-1130 (2011)). Selective serotonin reuptake inhibitors (SSRIs) and dual serotonin and norepinephrine reuptake inhibitors (SNRIs) have been widely used as antidepressants. The SSRIs and SNRIs, however, have slow onset of action, take several weeks of treatment before improvement in symptoms, and some inhibitors cause side effects such as insomnia and sexual dysfunction. Moreover, a significant number of patients do not respond to currently available antidepressants.

Reduced levels of endogenous DA, 5-HT, and NE have been suggested to play a role in acute and chronic pain at both the spinal and supraspinal levels (Ren et al., Pain 100, 1-6 (2002)). Reuptake inhibitors of these neurotransmitters consequently can attenuate pain by preventing presynaptic uptake of these neurotransmitters leading to sustained activation of the descending pain inhibitory pathways (Zhuo et al., *Brain Res.* 550, 35-48 (1991)). Pharmacological studies suggest that drugs simultaneously inhibiting reuptake of DA, 5-HT, and NE may provide a broader spectrum of pain relief than single or dual acting agents (see Hache et al., *Pharmaceuticals*, 4, 285-342 (2011)). Indeed, studies with the triple reuptake inhibitor bacifacidine have shown that it is efficacious as an antinociceptive agent with antiallodynic and antihyperalgesic activity in acute, persistent, and chronic pain models (Basile et al., *J. Pharmacol. Exp. Ther.* 321, 1208-1225 (2007)). Further, bacifacidine has been evaluated in clinical trials for the treatment of pain.

Despite the identification of weak partial inhibitors of the dopamine transporter in earlier studies (Ananthan et al., *Bioorg. Med. Chem. Lett.* 12, 2225-2228 (2002); Rothman et al., *Synapse*, 43, 268-274 (2002); Pariser et al., *J. Pharmacol. Exp. Ther.* 326, 286-295 (2008); Rothman et al., *J. Pharmacol. Exp. Ther.* 329, 718-728 (2009); Zhu et al., *Synapse*, 65, 1251 (2011)), the compounds that can effectively function as reuptake inhibitors of dopamine, serotonin, and norepinephrine have remained elusive. Thus, there remains a need for reuptake inhibitors selective for all three neurotransmitters. In addition to a favorable balance of inhibition potency among the three transporters, compounds that have submaximal efficacy in inhibiting the reuptake by allosteric or other mechanisms could provide therapeutic advantages over full efficacy inhibitors due to their ability to normalize the neurotransmitter levels depending upon the state of neurotransmitter.

SUMMARY

In accordance with the purpose(s) of the invention, as embodied and broadly described herein, the invention, in one aspect, relates to reuptake inhibitors of dopamine, serotonin, and norepinephrine and methods of making and using same.

The present disclosure relates to the synthesis and pharmacological profiles of the new triple reuptake inhibitors. Disclosed are compounds represented by formula (I):

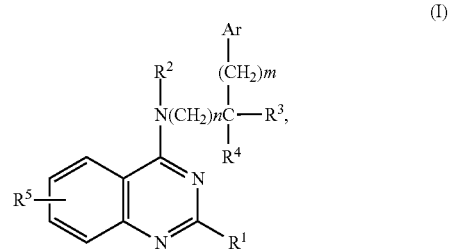

wherein n is 0, 1 or 2; m is 0, 1 or 2; $R^1$ is a heterocycle; $R^2$ is H or lower alkyl group; Ar is a phenyl or heterocyclic group; $R^3$ is H, alkyl, aryl, cycloalkyl, heterocycloalkyl, aralkyl, heteroaryl or heteroarylalkyl; $R^4$ is H, alkyl, hydroxy, alkoxy, aryloxy, heteroaryloxy, amino, alkylamino or dialkylamino; $R^3$ and $R^4$ together form a carbocycle or heterocycle; $R^5$ is H, halogen, alkyl, aryl, hydroxy, alkoxy, aryloxy, amino, alkylamino or dialkylamino, pharmaceutically acceptable salts thereof, deuterated forms thereof, isomers thereof, solvates thereof, and mixtures thereof.

Also disclosed are pharmaceutical compositions comprising a pharmaceutically acceptable carrier and at least one of the above disclosed compounds of Formula I, pharmaceutically acceptable salts thereof, deuterated forms thereof, isomers thereof, solvates thereof, and mixtures thereof.

Also disclosed are methods for treating a patient suffering from depression, pain, or addiction to substances including, but not limited to, cocaine, methamphetamine, nicotine, and alcohol, the methods comprising administering to said patient an effective amount of at least one of the above disclosed compounds of Formula I, pharmaceutically acceptable salts thereof, deuterated forms thereof, isomers thereof, solvates thereof, and mixtures thereof.

Also disclosed are methods of inhibiting binding of a monoamine transporter ligand to a monoamine transporter including, but not limited to, a dopamine transporter, a serotonin transporter, and a norepinephrine transporter.

Also disclosed are methods of inhibiting the activity of at least one monoamine transporter.

Also disclosed are methods of preparing compounds of Formula I. For example, the method can comprise reacting 2,4-dichloroquinazolines with an amine, followed by coupling with a heterocyclic compound.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

Figure 1A:
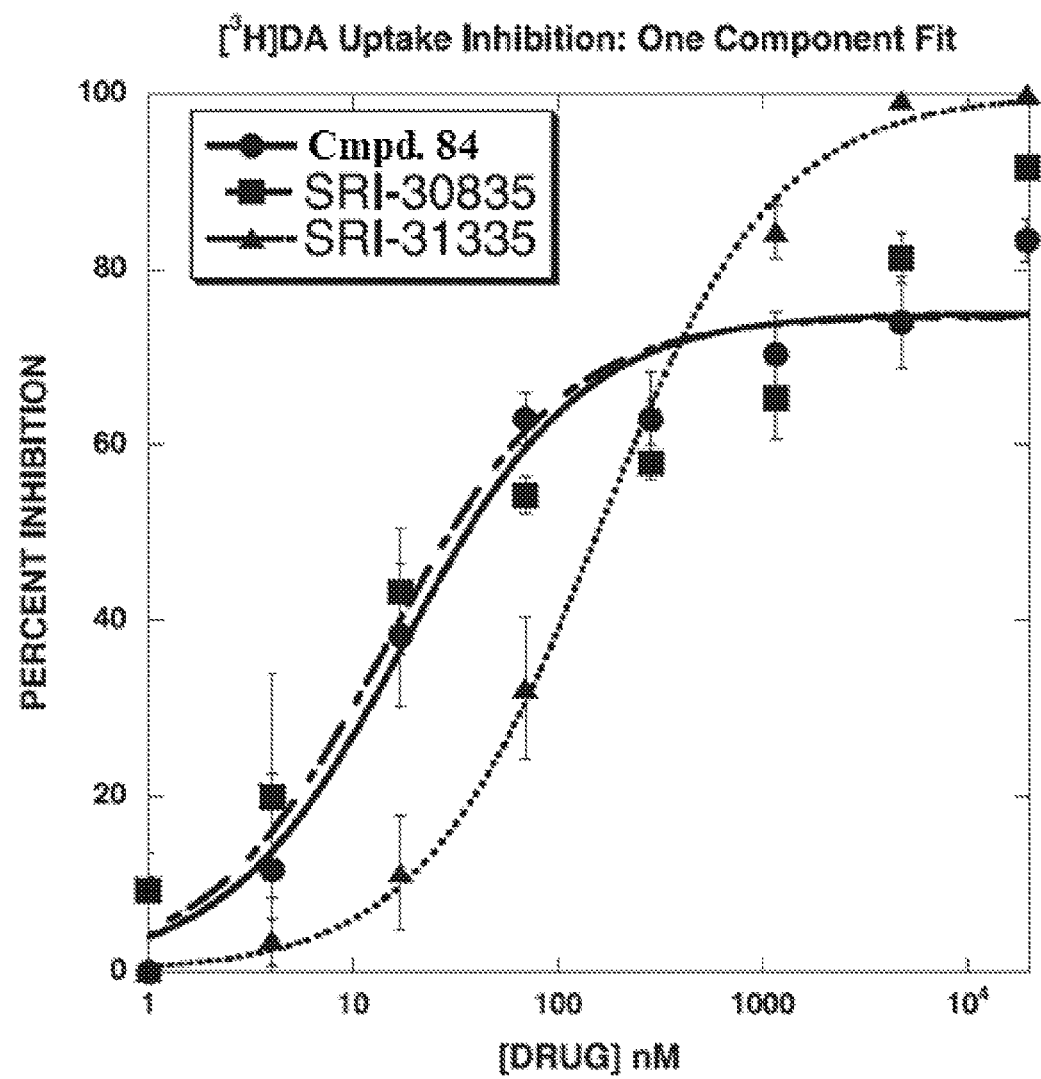
FIG. 1A and FIG. 1B show representative data illustrating that compound 84 and SRI-30835 partially inhibit [$^3$H]DA uptake and SRI-31335 fully inhibits [$^3$H]DA uptake when fit to a one-component (1A) or a two-component (1B) model.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorders prior to the administering step. In various aspects, the one or more disorders are a CNS disorder.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a CNS disorder prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "aryl" refers to monocyclic or bicyclic aromatic hydrocarbon groups having 6 to 12 carbon atoms in the ring portion, such as phenyl, naphthyl, biphenyl, and diphenyl groups, each of which may be substituted. Some typical substitutions for the aryl group include alkyl, alkenyl, alkynyl, cycloalkyl, halogen substituted alkyl, alkoxy, halogen substituted alkoxy, nitro, cyano, halogen, aryl, aryloxy, alkoxycarbonyl, hydroxy, protected hydroxyl, alkanoyl, sulfamoyl, alkylthio, alkylsulfonyl, hydroxysulfonyl, amino which may have groups such as alkyl, alkanoyl, cycloalkyl, aryl and aroyl groups, morpholinylcarbonylalkenyl, morpholinylcarbonylalkyl, pyrrolyl, prazolyl, dihydropyrazolyl, imiazolyl, triazolyl, pyridyl, pyrrolidinyl which may have oxo groups, morpholinyl, thiomorpholinyl, amidino, guanidino or heterocyclic groups.

The term "alkyl" refers to straight or branched chain unsubstituted hydrocarbon groups of 1 to 6 carbon atoms and even more typically 1 to 4 carbon atoms. Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

The term "alkenyl" refers to straight or branched chain unsubstituted hydrocarbon groups typically having 3 to 6 carbon atoms.

The term "aralkyl" or alkylaryl refers to an aryl group bonded directly through an alkyl group, such as benzyl or phenethyl.

The term "cycloalkyl" refers to cyclic hydrocarbon ring systems typically containing 3-9 carbon atoms, with typical examples being cyclopropyl, cyclobutyl, cyclopentyl, cyclohexyl, and cycloheptyl.

The term "cycloalkylalkyl" refers to alkyl substituted cyclic hydrocarbon ring system wherein the cyclic hydrocarbon typically contains 3-6 carbon atoms, a typical example being cyclopropylalkyl.

The term "heteroaryl" refers to 5 membered or 6 membered aromatic ring possessing one or more heteroatoms. Examples of heteroaryl groups are 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl, and each of which can optionally be substituted.

The term "heteroarylalky" refers to a heteroaryl group bonded directly through an alkyl group.

The term "heterocyclo" refers to an optionally substituted, saturated or unsaturated aromatic or nonaromatic cyclic group, for example, which is a 3 to 7 membered monocyclic ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. Examples of N-heterocyclo groups are pyridyl, pyrrolidinyl, piperidinyl, piperazinyl, pyrrolyl, pyrazolyl, pyrazinyl, pyrimidinyl, pyridazinyl, imidazoyl and imidazolidinyl, 1,2,3 triazole and 1,2,4 triazole. Examples of O-heterocyclic groups are furanyl and pyranyl. Examples of S-heterocyclic groups are thiopyran and thiophene. Examples of heterocyclic groups containing both N and O are morpholinyl, oxazole, and isooxazole. Example of heterocyclic groups containing both N and S are thiomorpholine, thiazole and isothiazole.

Examples of halo groups are Cl, F, Br and I. An example of a haloalkyl group is trifluoromethyl.

Compounds described herein may comprise atoms in both their natural isotopic abundance and in non-natural abundance. Thus, it is understood that the compounds of the present disclosure relate to all optical isomers and stereoisomers at the various possible atoms of the molecule, unless specified otherwise. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$ $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent. Thus, in various aspects, the deuterated forms contain heavy hydrogen including deuterium and/or tritium.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g., Almarasson, O., et al. (2004) *The Royal Society of Chemistry*, 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

Compounds of the present disclosure are represented by formula (I):

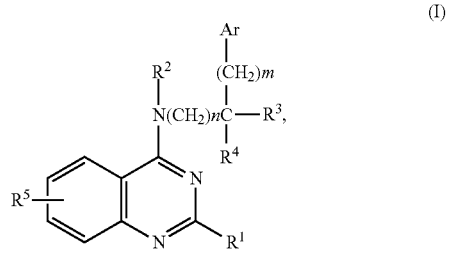

wherein n is 0, 1 or 2; m is 0, 1 or 2; $R^1$ is a heterocycle; $R^2$ is H or lower alkyl group; Ar is a phenyl or heterocyclic group; $R^3$ is H, alkyl, aryl, cycloalkyl, heterocycloalkyl, aralkyl, heteroaryl or heteroarylalkyl; $R^4$ is H, alkyl, hydroxy, alkoxy, aryloxy, heteroaryloxy, amino, alkylamino or dialkylamino; $R^3$ and $R^4$ together form a carbocycle or heterocycle; $R^5$ is H, halogen, alkyl, aryl, hydroxy, alkoxy, aryloxy, alkylamino or dialkylamino.

In one embodiment of the disclosure, n is: 0, 1 or 2; m is: 0, 1 or 2; $R^1$ is a heterocycle such as: (a) bicyclic aromatic heterocycle selected from indolyl, indazolyl, imidazo[1,2-a]pyrindinyl, imidazo[1,2-a]pyrimidinyl, pyrazolo[1,5-a]pyridinyl (g) pyrazolo[1,5-a]pyrimindinyl, triazolo[1,5-a]pyridinyl, tetrazolo[1,5-a]pyridinyl, benzimidazolyl selected from benzimidazol-2-yl, benzimidazol-4-yl, benzimidazol-5-yl, benzofuranyl, benzothiophenyl, benzoxazolyl, benzothiazolyl, benzisoxazolyl, benzisothiazolyl, benzotriazolyl, indolinyl, 1,3-dihydroindol-2-only, quinolinyl, isoquinolinyl, quinoxalinyl, quinazolinyl (x) cinnolinyl and purinyl, each optionally substituted; (b) monocyclic aromatic heterocycle selected from pyridinyl, pyrimidinyl, pyrazinyl, pyridazinyl, triazinyl, thienyl, furanyl, pyrrolyl, oxazolyl, thiazolyl, isoxazolyl, isothiazolyl, imidazolyl, pyrazolyl, triazolyl, and fused aromatic heterocycle, each optionally substituted; (c) 1,2,3,4-tetrahydroquinolinyl, isoindoline-2-yl, 4,5,6,7-tetrahydro-1H-pyrrolo[3,2-c]pyridine-5-yl, 2,3,4,5-tetrahydro-1H-pyrido[4,3-b]indole-2-yl, 2,3,4,9-tetrahydro-1H-pyrido[3,4-b]indole-2-yl, each optionally substituted; or (d) saturated heterocycle selected from piperidinyl, morpholinyl, pyrrolidinyl, piperazinyl and azetidinyl, azepanyl diazepanyl and fused heterocycles such as isoindolinyl, tetrahydoquinolinyl, tetrahydroisoquinolinyl, benzazepanyl, benzodaizepanyl, each optionally substituted; $R^2$ is H or lower alkyl group; Ar is: (a) a phenyl or substituted phenyl; or (b) a heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; $R^3$ is: (a) H, alkyl or cycloalkyl; (b) phenyl or substituted phenyl; or (c) heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; (d) aralkyl selected from benzyl, phenethyl, each optionally substituted; (e) heteroarylalkyl such as 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl, and heteroarylalkyls wherein heteroaryl contains two or more heteroatoms, each optionally substituted; $R^4$ is H, alkyl, hydroxy, alkoxy, aryloxy, heteroaryloxy, amino, alkylamino, or dialkylamino including a dialkylamine that is a nitrogen heterocycle such as aziridine, azetidine, pyrrolidine, piperidine, morpholine, piperazine, azepane, diazepane and azocane. These rings may contain additional substituents or groups such as alkyl, aryl, arylalkyl, heteroaryl, heteroarylalkyl, alkenyl, alkoxy, hydroxyl, protected hydroxyl, alkanoyl, carboxy, alkoxycarbonyl and carbamoyl. They also may have one or more oxo, thioxo, imino, methylene or additional atoms such as O, N, S, P, Se and Te, and be part of a fused bicyclic or polycyclic saturated or unsaturated system; $R^3$ and $R^4$ together form a carbocycle or heterocycle consisting of 3-9 atoms; $R^5$ is: (a) H, lower alkyl or aryl group; (b) halogen such as fluoro, chloro, bromo and iodo; or (c) hydroxyl, alkoxy, dialkylaminoalkoxy, aryloxy, amino, alkylamino and dialkylamino Preferred substituents in the phenyl, aryl and heteroaryl ring include: H, hydroxyl, chlorine, fluorine, bromine, trifluoromethyl, cyano, amino, carboxy, sulfo, sulfamoyl, unsubstituted or hydroxyl substituted C1-C6 alkyl, unsubstituted or hydroxyl substituted C1-C6 alkylthio, unsubstituted or substituted C2-C6 alkenyl, unsubstituted or substituted C2-C6 alkynyl, alkoxy, unsubstituted or substituted aryl or unsubstituted or substituted heteroaryl.

Preferred compounds according to the present disclosure are represented by the following formulae:

A compound having the formula (II):

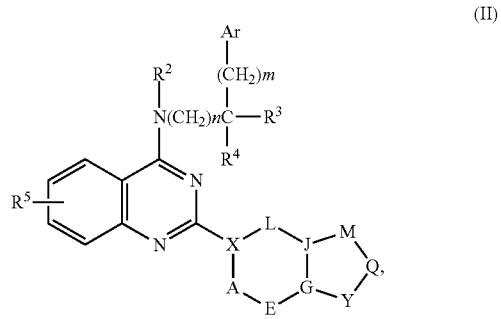

wherein $R^2$ $R^3$, $R^4$, $R^5$, Ar, n and m are as defined hereinabove and

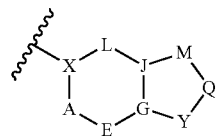

represents a bicyclic heterocycle wherein X is a nitrogen or a carbon atom; wherein each of L and E are independently selected from CR'R", N, O, and S; wherein each of J and G are independently selected from CR' and N; wherein Y is selected from S, O, CR', CR'R", and $NR^{14}$; wherein Q is selected from S, O, NR', C=O, CR'R''', and $CR^{15}$; wherein M is selected from S, O, NR', CR'R''', and $CR^{16}$; wherein A is selected from NR', CR'R", and $CR^{17}$; wherein each occurrence of R' and R" are independently selected from hydrogen and C1-C4 alkyl; and wherein each occurrence of R''' is independently selected from hydrogen and C1-C4 alkyl, or wherein each occurrence of R''', together with the intermediate carbon atoms, comprise a 6-membered ring, with unsaturation allowed for appropriate valence, pharmaceutically acceptable salts thereof, deuterated forms thereof, isomers thereof, solvates thereof, and mixtures thereof. Exemplary bicyclic heterocycles include, but are not limited to:

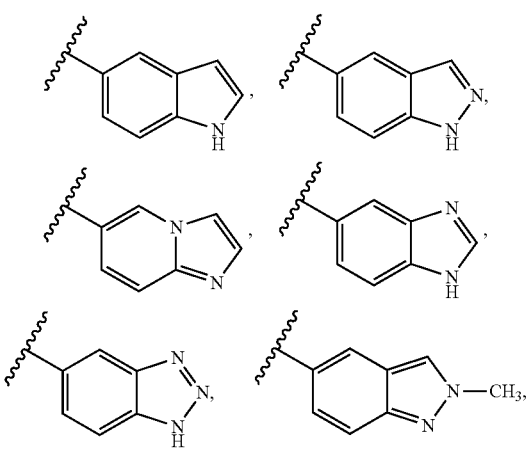

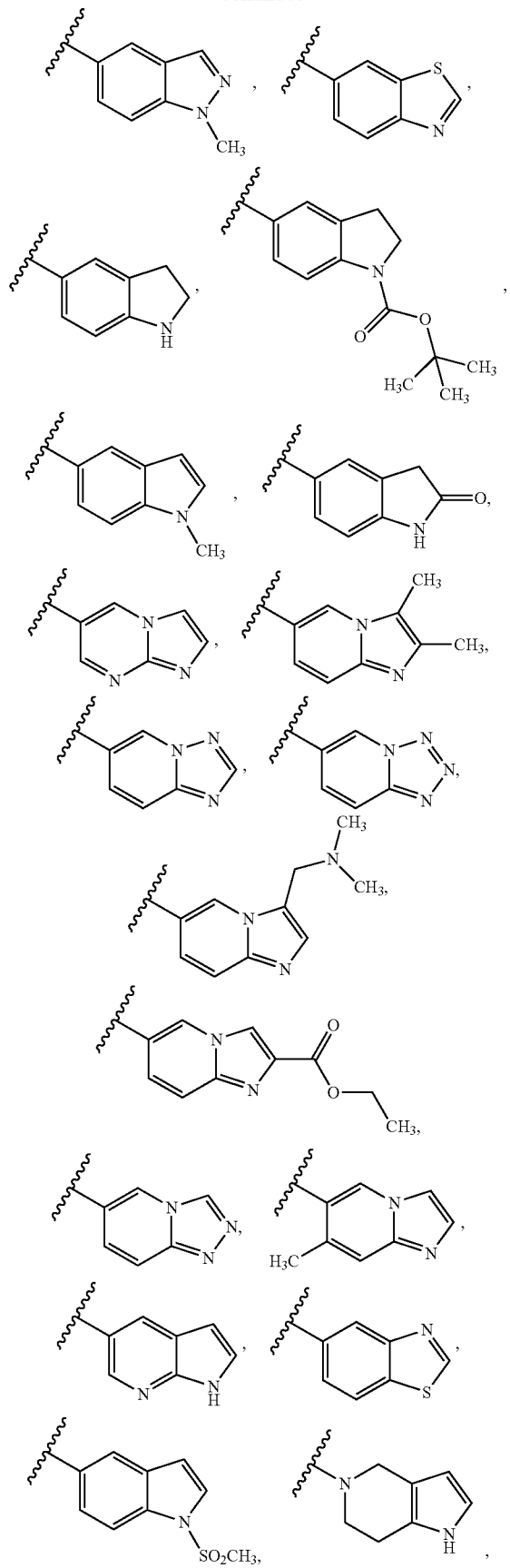

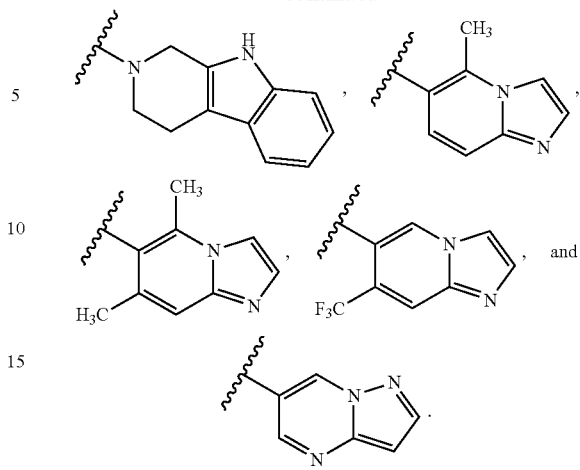

A compound having the formula (III):

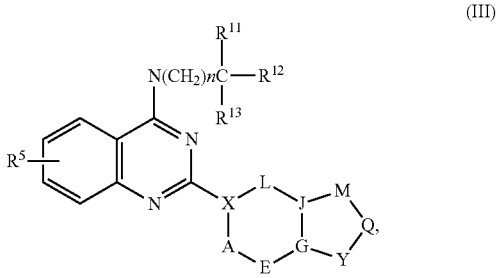

wherein R11 is an aryl or heteroaryl group, R12 is an aryl, heteroaryl or alkyl group, R13 is alkyl, hydroxy, alkoxy, aryloxy, amino, alkylamino or dialkylamino; pharmaceutically acceptable salts thereof, deuterated forms thereof, isomers thereof, solvates thereof, and mixtures thereof.

A compound having the formula (IV):

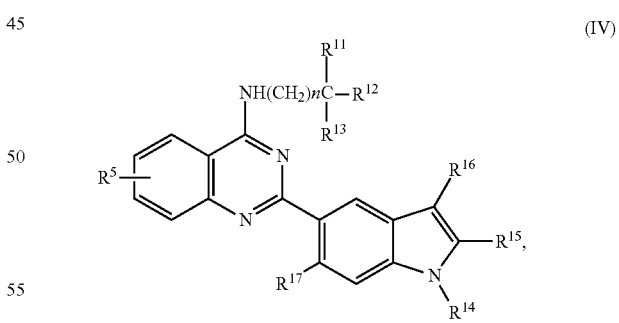

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino and $R^{14}$ is H, lower alkyl, acyl, sulfonyl, aryl or heteroaryl, and $R^{15}$, $R^{16}$ and $R^{17}$ are H, halogen, lower alkyl, hydroxy, alkoxy, aryloxy, acyl, sulfonyl, aryl heteroaryl, amino, alkylamino or dialkylamino; pharmaceutically acceptable salts thereof, deuterated forms thereof, isomers thereof, solvates thereof, and mixtures thereof.

A compound having the formula (V):

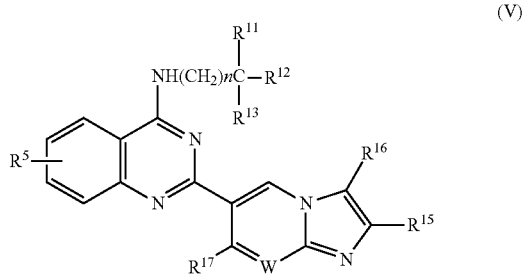

(V)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino and $R^{14}$ is H, lower alkyl, acyl, sulfonyl, aryl or heteroaryl, and $R^{15}$, $R^{16}$ and $R^{17}$ are H, halogen, lower alkyl, hydroxy, alkoxy, aryloxy, acyl, sulfonyl, aryl heteroaryl, amino, alkylamino or dialkylamino and W is CH or N; pharmaceutically acceptable salts thereof, deuterated forms thereof, isomers thereof, solvates thereof, and mixtures thereof.

A compound having the formula (VI):

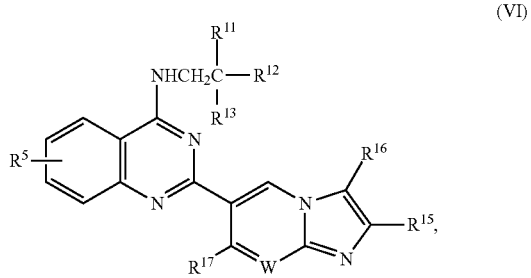

(VI)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino; $R^{15}$ and $R^{16}$ are H, halogen, lower alkyl, hydroxy, alkoxy, aryloxy, acyl, sulfonyl, aryl heteroaryl, amino, alkylamino or dialkylamino and $R^{17}$ is H, chloro, methyl, trifluoromethyl, lower alkyl or alkoxy group; pharmaceutically acceptable salts thereof, deuterated forms thereof, isomers thereof, solvates thereof, and mixtures thereof.

In one aspect, n is selected from 0, 1, and 2. In a still further aspect, n is selected from 0 and 1. In yet a further aspect, n is selected from 1 and 2. In an even further aspect, n is 0. In a still further aspect, n is 1. In yet a further aspect, n is 2.

In one aspect, m is selected from 0, 1, and 2. In a still further aspect, m is selected from 0 and 1. In yet a further aspect, m is selected from 1 and 2. In an even further aspect, m is 0. In a still further aspect, m is 1. In yet a further aspect, m is 2.

1. Structure

Suitable substituents are described herein below.

a. X Groups

In one aspect, X is selected from a nitrogen and a carbon atom. In a further aspect, X is N. In a still further aspect, X is C. In yet a further aspect, X is C substituted with a hydrogen atom.

b. W Groups

In one aspect, W is selected from CH and N. In a further aspect, W is CH. In a still further aspect, W is N.

c. $R^1$ Groups

In one aspect, $R^1$ is an optionally substituted heterocycle. In a further aspect, $R^1$ is selected from a monocyclic heterocycle and a bicyclic heterocycle and optionally substituted. In a still further aspect, $R^1$ is selected from an aromatic heterocycle and a nonaromatic heterocycle and optionally substituted. In yet a further aspect, $R^1$ is selected from a monocyclic aromatic heterocycle, a nonaromatic monocyclic heterocycle, an aromatic bicyclic heterocycle, and a nonaromatic bicyclic heterocycle and optionally substituted.

In a further aspect, $R^1$ is an optionally substituted bicyclic aromatic heterocycle. In a still further aspect, the bicyclic aromatic heterocycle is selected from indolyl, indazolyl, imidazo[1,2-a]pyridinyl, imidazo[1,2-a]pyrimidinyl, pyrazolo[1,5-a]pyridinyl (g) pyrazolo[1,5-a]pyrimidinyl, triazolo[1,5-a]pyridinyl, tetrazolo[1,5-a]pyridinyl, benzimidazolyl selected from benzimidazol-2-yl, benzimidazol-4-yl, benzimidazol-5-yl, benzofuranyl, benzothiophenyl, benzoxazolyl, benzothiazolyl, benzisoxazolyl, benzisothiazolyl, benzotriazolyl, indolinyl, 1,3-dihydroindol-2-only, quinolinyl, isoquinolinyl, quinoxalinyl, quinazolinyl (x) cinnolinyl and purinyl and optionally substituted.

In a further aspect, $R^1$ is an optionally substituted monocyclic aromatic heterocycle. In a still further aspect, the monocyclic aromatic heterocycle is selected from pyridinyl, pyrimidinyl, pyrazinyl, pyridazinyl, triazinyl, thienyl, furanyl, pyrrolyl, oxazolyl, thiazolyl, isoxazolyl, isothiazolyl, imidazolyl, pyrazolyl, and triazolyl and optionally substituted.

In a further aspect, $R^1$ is an optionally substituted bicyclic nonaromatic heterocycle. In a still further aspect, the bicyclic nonaromatic heterocycle is selected from 1,2,3,4-tetrahydroquinolinyl, isoindoline-2-yl, 4,5,6,7-tetrahydro-1H-pyrrolo[3,2-c]pyridine-5-yl, 2,3,4,5-tetrahydro-1H-pyrido[4,3-b]indole-2-yl, and 2,3,4,9-tetrahydro-1H-pyrido[3,4-b]indole-2-yl and optionally substituted.

In a further aspect, $R^1$ is an optionally substituted saturated heterocycle. In a still further aspect, the saturated heterocycle is selected from piperidinyl, morpholinyl, pyrrolidinyl, piperazinyl, azetidinyl, and azepanyl diazepanyl and optionally substituted.

In a further aspect, $R^1$ is an optionally substituted fused heterocycle. In a still further aspect, the fused heterocycle is selected from isoindolinyl, tetrahydoquinolinyl, tetrahydroisoquinolinyl, benzazepanyl, and benzodaizepanyl and optionally substituted.

In a further aspect, $R^1$ is a heterocycle substituted with 0, 1, 2, or 3 groups independently selected from halogen, hydroxy, C1-C4 alkyl, C1-C4 alkoxy, aryloxy, —(C═O)(C1-C4 alkyl), —CO$_2$(C1-C4 alkyl), —SO$_2$H, —SO$_2$(C1-C4 alkyl), —NHSO$_2$(C1-C4 alkyl), —N(CH$_3$)SO$_2$(C1-C4 alkyl), —(C1-C4 alkyl)-C1-C4 alkoxy, —(C1-C4 alkyl)-(C1-C4)(C1-C4)-dialkylamino, aryl, heteroaryl, C1-C4 alkylamino, and (C1-C4)(C1-C4) dialkylamino. In a still further aspect, $R^1$ is a heterocycle substituted with 0, 1, or 2 groups independently selected from halogen, hydroxy, C1-C4 alkyl, C1-C4 alkoxy, aryloxy, —(C═O)(C1-C4 alkyl), —CO$_2$(C1-C4 alkyl), —SO$_2$H, —SO$_2$(C1-C4 alkyl), —NHSO$_2$(C1-C4 alkyl), —N(CH$_3$)SO$_2$(C1-C4 alkyl), —(C1-C4 alkyl)-C1-C4 alkoxy, —(C1-C4 alkyl)-(C1-C4)(C1-C4)-dialkylamino, aryl, heteroaryl, C1-C4 alkylamino, and (C1-C4)(C1-C4) dialkylamino. In yet a further aspect, $R^1$ is a heterocycle substituted with 0 or 1 group selected from halogen, hydroxy, C1-C4 alkyl, C1-C4 alkoxy, aryloxy, —(C═O)(C1-C4 alkyl), —CO$_2$(C1-C4 alkyl), —SO₂H, —SO₂(C1-C4 alkyl), —NHSO₂(C1-C4 alkyl), —N(CH₃)SO₂(C1-C4 alkyl), —(C1-C4 alkyl)-C1-C4 alkoxy, —(C1-C4 alkyl)-(C1-C4)(C1-C4)-dialkylamino, aryl, heteroaryl, C1-C4 alkylamino, and (C1-C4)(C1-C4) dialkylamino. In an even further aspect, $R^1$ is an unsubstituted heterocycle.

In a further aspect, $R^1$ is a heterocycle substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is a heterocycle substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is a heterocycle substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is a heterocycle monosubstituted with a group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is an unsubstituted heterocycle.

In a further aspect, $R^1$ is a C2-C9 heterocycle substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is a C2-C9 heterocycle substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is a C2-C9 heterocycle substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is a C2-C9 heterocycle monosubstituted with a group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is an unsubstituted C2-C9 heterocycle.

In a further aspect, $R^1$ is selected from pyridinyl, pyrimidinyl, indolyl, imidazolyl, indazolyl, quinolinyl, indolinyl, indolin-2-onyl, isoindolinyl, imidazo[1,2-α]pyridinyl, benzo[d]thiazolyl, benzo[d]imidazolyl, imidazo[1,2-α]pyrimidinyl, pyrrolo[2,3-β]pyridinyl, pyrazolo[1,5-α]pyrimidinyl, 3a,4,5,6,7,7a-hexahydro-pyrrolo[3,2-c]pyridinyl, 2,3,4,4a,5,9b-hexahydropyrido[4,3-β]indolyl, and 1,2,3,4-tetrahydroisoquinolinyl and substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is selected from pyridinyl, pyrimidinyl, indolyl, imidazolyl, indazolyl, quinolinyl, indolinyl, indolin-2-onyl, isoindolinyl, imidazo[1,2-α]pyridinyl, benzo[d]thiazolyl, benzo[d]imidazolyl, imidazo[1,2-α]pyrimidinyl, pyrrolo[2,3-β]pyridinyl, pyrazolo[1,5-α]pyrimidinyl, 3a,4,5,6,7,7a-hexahydro-pyrrolo[3,2-c]pyridinyl, 2,3,4,4a,5,9b-hexahydropyrido[4,3-β]indolyl, and 1,2,3,4-tetrahydroisoquinolinyl and substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is selected from pyridinyl, pyrimidinyl, indolyl, imidazolyl, indazolyl, quinolinyl, indolinyl, indolin-2-onyl, isoindolinyl, imidazo[1,2-α]pyridinyl, benzo[d]thiazolyl, benzo[d]imidazolyl, imidazo[1,2-α]pyrimidinyl, pyrrolo[2,3-β]pyridinyl, pyrazolo[1,5-α]pyrimidinyl, 3a,4,5,6,7,7a-hexahydro-pyrrolo[3,2-c]pyridinyl, 2,3,4,4a,5,9b-hexahydropyrido[4,3-β]indolyl, and 1,2,3,4-tetrahydroisoquinolinyl and substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is selected from pyridinyl, pyrimidinyl, indolyl, imidazolyl, indazolyl, quinolinyl, indolinyl, indolin-2-onyl, isoindolinyl, imidazo[1,2-α]pyridinyl, benzo[d]thiazolyl, benzo[d]imidazolyl, imidazo[1,2-α]pyrimidinyl, pyrrolo[2,3-β]pyridinyl, pyrazolo[1,5-c]pyrimidinyl, 3a,4,5,6,7,7a-hexahydro-pyrrolo[3,2-c]pyridinyl, 2,3,4,4a,5,9b-hexahydropyrido[4,3-β]indolyl, and 1,2,3,4-tetrahydroisoquinolinyl and unsubstituted.

In a further aspect, $R^1$ is pyrimidinyl substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is pyrimidinyl substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is pyrimidinyl substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is unsubstituted pyrimidinyl.

In a further aspect, $R^1$ is indolyl substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is indolyl substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is indolyl substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is unsubstituted indolyl.

In a further aspect, $R^1$ is imidazo[1,2-α]pyridinyl substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, $R^1$ is imidazo[1,2-α]pyridinyl substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, $R^1$ is imidazo[1,2-α]pyridinyl substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, $R^1$ is unsubstituted imidazo[1,2-α]pyridinyl.

d. $R^2$ Groups

In one aspect, $R^2$ is selected from hydrogen and a lower alkyl group. In a further aspect, $R^2$ is selected from hydrogen and C1-C4 alkyl. In a still further aspect, $R^2$ is hydrogen.

In a further aspect, $R^2$ is C1-C4 alkyl. In a still further aspect, $R^2$ is selected from n-propyl, i-propyl, ethyl, and methyl. In yet a further aspect, $R^2$ is selected from ethyl and methyl. In an even further aspect, $R^2$ is ethyl. In a still further aspect, $R^2$ is methyl.

In a further aspect, $R^2$ is selected from n-butyl, i-butyl, sec-butyl, t-butyl, n-propyl, i-propyl, ethyl, methyl, and hydrogen. In a still further aspect, $R^2$ is selected from n-propyl, i-propyl, ethyl, methyl, and hydrogen. In yet a further aspect, $R^2$ is selected from ethyl, methyl, and hydrogen. In an even further aspect, $R^2$ is selected from ethyl and hydrogen. In a still further aspect, $R^2$ is selected from methyl and hydrogen.

e. $R^3$ Groups

In one aspect, $R^3$ is selected from hydrogen, alkyl, cycloalkyl, heterocycloalkyl, aryl, aralkyl, heteroaryl, and heteroarylalkyl or $R^3$ and $R^4$ together form a carbocycle or heterocycle.

In a further aspect, $R^3$ is selected from hydrogen, C1-C8 alkyl, C3-C6 cycloalkyl, C2-C5 heterocycloalkyl, C5-C6 aryl, (C1-C4 alkyl)(C5-C6 aryl), C3-C5 heteroaryl, and (C1-C4)(C3-C5 heteroaryl). In a still further aspect, $R^3$ is selected from hydrogen, C1-C4 alkyl, C3-C6 cycloalkyl, C2-C5 heterocycloalkyl, C5-C6 aryl, (C1-C2 alkyl)(C5-C6 aryl), C3-C5 heteroaryl, and (C1-C2)(C3-C5 heteroaryl).

In a further aspect, $R^3$ is selected from hydrogen, alkyl, cycloalkyl, and heterocycloalkyl. In a still further aspect, $R^3$ is selected from hydrogen, C1-C8 alkyl, C3-C6 cycloalkyl, and C2-C5 heterocycloalkyl. In yet a further aspect, $R^3$ is selected from hydrogen, C1-C4 alkyl, C3-C6 cycloalkyl, and C2-C5 heterocycloalkyl. In an even further aspect, $R^3$ is selected from hydrogen, methyl, ethyl, n-propyl, i-propyl, cyclopropyl, cyclobutyl, cyclopentyl, oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from hydrogen, methyl, ethyl, cyclopropyl, cyclobutyl, oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from hydrogen, methyl, cyclopropyl, oxiranyl, thiiranyl, aziridinyl, oxetanyl, thietanyl, azetidinyl, and morpholinyl.

In a further aspect, $R^3$ is selected from hydrogen, alkyl, and cycloalkyl. In a still further aspect, $R^3$ is selected from hydrogen, C1-C8 alkyl, and C3-C6 cycloalkyl. In yet a further aspect, $R^3$ is selected from hydrogen, C1-C4 alkyl, and C3-C6 cycloalkyl. In an even further aspect, $R^3$ is selected from hydrogen, methyl, ethyl, n-propyl, i-propyl, cyclopropyl, cyclobutyl, and cyclopentyl. In a still further aspect, $R^3$ is selected from hydrogen, methyl, ethyl, cyclopropyl, and cyclobutyl. In yet a further aspect, $R^3$ is selected from hydrogen, methyl, and cyclopropyl.

In a further aspect, $R^3$ is selected from hydrogen and alkyl. In a still further aspect, $R^3$ is selected from hydrogen and C1-C8 alkyl. In yet a further aspect, $R^3$ is selected from hydrogen, methyl, ethyl, n-propyl, i-propyl, n-butyl, i-butyl, s-butyl, and t-butyl. In an even further aspect, $R^3$ is selected from hydrogen, methyl, ethyl, n-propyl, and i-propyl. In a still further aspect, $R^3$ is selected from hydrogen, methyl, and ethyl. In yet a further aspect, $R^3$ is selected from hydrogen and ethyl. In an even further aspect, $R^3$ is selected from hydrogen and methyl.

In a further aspect, $R^3$ is selected from cycloalkyl and heterocycloalkyl. In a still further aspect, $R^3$ is selected from C3-C6 cycloalkyl and C2-C5 heterocycloalkyl. In yet a further aspect, $R^3$ is selected from cyclopropyl, cyclobutyl, cyclopentyl, oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from cyclopropyl, cyclobutyl, oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from cyclopropyl, oxiranyl, thiiranyl, aziridinyl, and morpholinyl.

In a further aspect, $R^3$ is cycloalkyl. In a still further aspect, $R^3$ is C3-C6 cycloalkyl. In yet a further aspect, $R^3$ is selected from cyclopropyl, cyclobutyl, cyclopentyl, and cyclohexyl. In an even further aspect, $R^3$ is selected from cyclopropyl, cyclobutyl, and cyclohexyl. In a still further aspect, $R^3$ is selected from cyclopropyl and cyclohexyl. In yet a further aspect, $R^3$ is cyclohexyl.

In a further aspect, $R^3$ is heterocycloalkyl. In a still further aspect, $R^3$ is C2-C5 heterocycloalkyl. In yet a further aspect, $R^3$ is selected from oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, piperidinyl, and morpholinyl. In a still further aspect, $R^3$ is selected from oxiranyl, thiiranyl, aziridinyl, oxetanyl, thietanyl, azetidinyl, tetrahydrofuranyl, tetrahydrothiophenyl, pyrrolidinyl, and morpholinyl. In yet a further aspect, $R^3$ is selected from oxiranyl, thiiranyl, aziridinyl, oxetanyl, thietanyl, azetidinyl, and morpholinyl. In an even further aspect, $R^3$ is selected from oxiranyl, thiiranyl, aziridinyl, and morpholinyl. In a still further aspect, $R^3$ is morpholinyl.

In a further aspect, $R^3$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is monosubstituted with a group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is an unsubstituted.

In a further aspect, $R^3$ is selected from aryl, aralkyl, heteroaryl, and heteroarylalkyl. In a still further aspect, $R^3$ is selected from C5-C6 aryl, (C1-C4 alkyl)(C5-C6 aryl), C3-C5 heteroaryl, and (C1-C4)(C3-C5 heteroaryl). In yet a further aspect, $R^3$ is selected from C5-C6 aryl, (C1-C2 alkyl)(C5-C6 aryl), C3-C5 heteroaryl, and (C1-C2)(C3-C5 heteroaryl).

In a further aspect, $R^3$ is selected from aryl and aralkyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is selected from C5-C6 aryl and (C1-C4 alkyl)(C5-C6 aryl) and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino.

In a further aspect, $R^3$ is aryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is aryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is aryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted aryl.

In a further aspect, $R^3$ is selected from phenyl and unsubstituted phenyl. In a still further aspect, $R^3$ is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is phenyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is phenyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is unsubstituted phenyl.

In a further aspect, $R^3$ is aralkyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is aralkyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is aralkyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted aralkyl.

In a further aspect, $R^3$ is aralkyl selected from benzyl and phenethyl, each optionally substituted.

In a further aspect, $R^3$ is benzyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is benzyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is benzyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted benzyl.

In a further aspect, $R^3$ is phenethyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is phenethyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is phenethyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted phenethyl.

In a further aspect, $R^3$ is selected from heteroaryl and heteroarylalkyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is selected from C3-C5 heteroaryl and (C1-C4)(C3-C5 heteroaryl) and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino.

In a further aspect, $R^3$ is heteroaryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is heteroaryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is heteroaryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted heteroaryl.

In a further aspect, $R^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and optionally substituted. In a still further aspect, $R^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and unsubstituted.

In a further aspect, $R^3$ is pyridinyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is pyridinyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is pyridinyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted pyridinyl.

In a further aspect, $R^3$ is pyrrolyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is pyrrolyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is pyrrolyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted pyrrolyl.

In a further aspect, $R^3$ is heteroarylalkyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is heteroarylalkyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is heteroarylalkyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is unsubstituted heteroarylalkyl.

In a further aspect, $R^3$ is a heteroarylalkyl, wherein the heteroaryl contains two or more heteroatoms and optionally substituted.

In a further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and optionally substituted. In a still further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ is selected from 2-pyridylmethyl, 3-pyridylmethyl, 4-pyridylmethyl, 2-thienylmethyl, 3-thienylmethyl, 2-furanymethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanyethyl, 3-furanylethyl, 2-pyrrolylethyl, 3-pyrrolylethyl and unsubstituted.

In a further aspect, $R^3$ and $R^4$ together form a carbocycle or heterocycle. In a still further aspect, each of $R^3$ and $R^4$ together comprise a C3-C6 carbocycle or a C2-C5 heterocycle.

In a further aspect, each of $R^3$ and $R^4$ together comprise a C3-C6 carbocycle. In a still further aspect, each of $R^3$ and $R^4$ together comprise a C3-C6 carbocycle selected from cyclopropyl, cyclobutyl, and cyclopentyl. In yet a further aspect, each of $R^3$ and $R^4$ together comprise a C3-C6 carbocycle selected from cyclopropyl and cyclobutyl. In an even further aspect, each of $R^3$ and $R^4$ together comprise a cyclopropyl. In a still further aspect, each of $R^3$ and $R^4$ together comprise a cyclobutyl. In yet a further aspect, each of $R^3$ and $R^4$ together comprise a cyclopentyl. In an even further aspect, each of $R^3$ and $R^4$ together comprise a cyclohexyl.

In an even further aspect, each of $R^3$ and $R^4$ together comprise a C2-C5 carbocycle. In a still further aspect, each of $R^3$ and $R^4$ together comprise a C2-C5 carbocycle selected from oxiranyl, thiiranyl, aziridinyl, oxetanyl, thietanyl, azetidinyl, tetrahydrofuranyl, tetrahydrothiophenyl, pyrrolidinyl, tetrahydro-2H-pyranyl, tetrahydro-2H-thiopyranyl, and piperidinyl. In yet a further aspect, each of $R^3$ and $R^4$ together comprise a C2-C5 carbocycle selected from oxiranyl, thiiranyl, aziridinyl, oxetanyl, thietanyl, azetidinyl, tetrahydrofuranyl, tetrahydrothiophenyl, and pyrrolidinyl. In an even further aspect, each of $R^3$ and $R^4$ together comprise a C2-C5 carbocycle selected from oxiranyl, thiiranyl, aziridinyl, oxetanyl, thietanyl, and azetidinyl. In a still further aspect, each of $R^3$ and $R^4$ together comprise a C2-C5 carbocycle selected from oxiranyl, thiiranyl, and aziridinyl.

In a further aspect, $R^3$ and $R^4$ together form a carbocycle or heterocycle and are substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^3$ and $R^4$ together form a carbocycle or heterocycle and are substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^3$ and $R^4$ together form a carbocycle or heterocycle and are substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^3$ and $R^4$ together form a carbocycle or heterocycle and are unsubstituted.

f. $R^4$ Groups

In one aspect, $R^4$ is selected from hydrogen, hydroxy, amino, alkyl, alkoxy, aryloxy, heteroaryloxy, alkylamino, and dialkylamino or $R^3$ and $R^4$ together form a carbocycle or heterocycle.

In a further aspect, $R^4$ is selected from hydrogen, hydroxy, amino, C1-C8 alkyl, C1-C8 alkoxy, C5-C6 aryloxy, C3-C5 heteroaryloxy, C1-C8 alkylamino, and (C1-C8)(C1-C8)dialkylamino. In a still further aspect, $R^4$ is selected from hydrogen, hydroxy, amino, C1-C4 alkyl, C1-C4 alkoxy, C5-C6 aryloxy, C3-C5 heteroaryloxy, C1-C4 alkylamino, and (C1-C4)(C1-C4)dialkylamino.

In a further aspect, $R^4$ is selected from hydrogen, hydroxy, amino, C1-C8 alkyl, C1-C8 alkoxy, C1-C8 alkylamino, and (C1-C8)(C1-C8)dialkylamino. In a still further aspect, $R^4$ is selected from hydrogen, hydroxy, amino, C1-C4 alkyl, C1-C4 alkoxy, C1-C4 alkylamino, and (C1-C4)(C1-C4) dialkylamino. In yet a further aspect, $R^4$ is selected from hydrogen, hydroxy, amino, methyl, ethyl, n-propyl, i-propyl, methoxy, ethoxy, n-propoxy, i-propoxy, —NHCH$_3$, —NHCH$_2$CH$_3$, —NHCH(CH$_3$)$_2$, —NH(CH$_2$)$_2$CH$_3$, —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In an even further aspect, R$^4$ is selected from hydrogen, hydroxy, amino, methyl, ethyl, methoxy, ethoxy, —NHCH$_3$, —NHCH$_2$CH$_3$, —N(CH$_3$)$_2$, —N(CH$_2$CH$_3$)$_2$, and —N(CH$_3$)(CH$_2$CH$_3$). In a still further aspect, R$^4$ is selected from hydrogen, hydroxy, amino, methyl, methoxy, —NHCH$_3$, and —N(CH$_3$)$_2$.

In a further aspect, R$^4$ is dialkylamino, wherein the dialkylamino is a nitrogen-containing heterocycle. In a still further aspect, the nitrogen-containing heterocycle further comprises one or more oxo, thioxo, imino, or methylene groups. In yet a further aspect, the nitrogen-containing heterocycle further comprises at least one atom selected from oxygen, nitrogen, sulphur, phosphorous, selenium, and tellurium. Examples of nitrogen-containing heterocycles include, but are not limited to, aziridine, azetidine, pyrrolidine, piperidine, morpholine, piperazine, azepane, diazepane and azocane. In an even further aspect, the nitrogen-containing heterocycle is optionally substituted with a group selected from alkyl, aryl, arylalkyl, heteroaryl, heteroarylalkyl, alkenyl, alkoxy, hydroxyl, protected hydroxyl, alkanoyl, carboxy, alkoxycarboyl, and carbamoyl.

In a further aspect, R$^4$ is selected from aryloxy and heteroaryloxy. In a still further aspect, R$^4$ is heteroaryloxy. In yet a further aspect, R$^4$ is aryloxy. In an even further aspect, R$^4$ is benzyloxy.

In a further aspect, R$^4$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^4$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^4$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^4$ is unsubstituted.

g. R$^5$ Groups

In one aspect, R$^5$ is selected from hydrogen, halogen, hydroxy, amino, alkyl, aryl, alkoxy, dialkylaminoalkoxy, aryloxy, alkylamino, and dialkylamino. In a further aspect, R$^5$ is selected from hydrogen, halogen, hydroxy, amino, alkyl, aryl, alkoxy, aryloxy, alkylamino, and dialkylamino. In a still further aspect, R$^5$ is hydrogen.

In a further aspect, R$^5$ is selected from hydrogen, lower alkyl, and aryl. In a still further aspect, R$^5$ is selected from hydrogen, C1-C4 alkyl, and aryl. In yet a further aspect, R$^5$ is selected from hydrogen, methyl, ethyl, n-propyl, i-propyl, and phenyl. In an even further aspect, R$^5$ is selected from hydrogen, methyl, ethyl, and phenyl. In a still further aspect, R$^5$ is selected from hydrogen, methyl, and phenyl. In yet a further aspect, R$^5$ is selected from hydrogen and phenyl. In an even further aspect, R$^5$ is selected from hydrogen and methyl.

In a further aspect, R$^5$ is halogen. In a still further aspect, R$^5$ is selected from bromo, chloro, and fluoro. In yet a further aspect, R$^5$ is selected from chloro and fluoro. In an even further aspect, R$^5$ is iodo. In a still further aspect, R$^5$ is bromo. In yet a further aspect, R$^5$ is chloro. In an even further aspect, R$^5$ is fluoro.

In a further aspect, R$^5$ is selected from hydroxyl, amino, alkoxy, dialkylaminoalkoxy, aryloxy, alkylamino, and dialkylamino. In a still further aspect, R$^5$ is selected from hydroxyl, amino, C1-C4 alkoxy, (C1-C4)(C1-C4) dialkylamino-C1-C4 alkoxy, aryloxy, C1-C4 alkylamino, and (C1-C4)(C1-C4) dialkylamino. In yet a further aspect, R$^5$ is selected from hydroxyl, amino, methoxy, ethoxy, n-propoxy, i-propoxy, —OCH$_2$N(CH$_3$)$_2$, —O(CH$_2$)$_2$N(CH$_3$)$_2$, —OCH$_2$N(CH$_2$CH$_3$)$_2$, —O(CH$_2$)$_2$N(CH$_2$CH$_3$)$_2$, —NHCH$_3$, —NHCH$_2$CH$_3$, —NHCH(CH$_3$)$_2$, —NH(CH$_2$)$_2$CH$_3$, —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In an even further aspect, R$^5$ is selected from hydroxyl, amino, methoxy, ethoxy, —OCH$_2$N(CH$_3$)$_2$, —O(CH$_2$)$_2$N(CH$_3$)$_2$, —OCH$_2$N(CH$_2$CH$_3$)$_2$, —O(CH$_2$)$_2$N(CH$_2$CH$_3$)$_2$, —NHCH$_3$, —NHCH$_2$CH$_3$, —N(CH$_3$)$_2$, —N(CH$_2$CH$_3$)$_2$, and —N(CH$_3$)(CH$_2$CH$_3$). In a still further aspect, R$^5$ is selected from hydroxyl, amino, methoxy, —OCH$_2$N(CH$_3$)$_2$, —OCH$_2$N(CH$_2$CH$_3$)$_2$, —NHCH$_3$, —N(CH$_3$)$_2$, and —N(CH$_3$)(CH$_2$CH$_3$).

h. R$^{11}$ Groups

In one aspect, R$^{11}$ is selected from aryl and heteroaryl. In a further aspect, R$^{11}$ is selected from phenyl and heteroaryl.

In a further aspect, R$^{11}$ is phenyl or substituted phenyl. In a still further aspect, R$^{11}$ is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{11}$ is phenyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{11}$ is phenyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{11}$ is unsubstituted phenyl.

In a further aspect, R$^{11}$ is heteroaryl and optionally substituted. In a still further aspect, R$^{11}$ is heteroaryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{11}$ is heteroaryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{11}$ is heteroaryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{11}$ is unsubstituted heteroaryl.

In a further aspect, R$^{11}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and optionally substituted. In a still further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{11}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{11}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and unsubstituted.

i. R$^{12}$ Groups

In one aspect, R$^{12}$ is selected from alkyl, aryl, and heteroaryl. In a further aspect, R$^{12}$ is selected from C1-C8 alkyl, C5-C6 aryl, and C3-C5 heteroaryl. In a still further aspect, R$^{12}$ is selected from C1-C4 alkyl, C5-C6 aryl, and C3-C5 heteroaryl.

In a further aspect, R$^{12}$ is alkyl. In a still further aspect, R$^{12}$ is C1-C8 alkyl. In yet a further aspect, R$^{12}$ is selected from methyl, ethyl, n-propyl, i-propyl, n-butyl, i-butyl, s-butyl, and t-butyl. In an even further aspect, R$^{12}$ is selected from methyl, ethyl, n-propyl, and i-propyl. In a still further aspect, R$^{12}$ is selected from methyl and ethyl. In yet a further aspect, R$^{12}$ is ethyl. In an even further aspect, R$^{12}$ is methyl.

In a further aspect, R$^{12}$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{12}$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{12}$ is monosubstituted with a group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is an unsubstituted.

In a further aspect, R$^{12}$ is selected from aryl and heteroaryl. In a still further aspect, R$^{12}$ is selected from C5-C6 aryl and C3-C5 heteroaryl. In yet a further aspect, R$^{12}$ is selected from C5-C6 aryl and C3-C5 heteroaryl.

In a further aspect, R$^{12}$ is aryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is aryl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{12}$ is aryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{12}$ is unsubstituted aryl.

In a further aspect, R$^{12}$ is selected from phenyl and unsubstituted phenyl. In a still further aspect, R$^{12}$ is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{12}$ is phenyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{12}$ is phenyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is unsubstituted phenyl.

In a further aspect, R$^{12}$ is heteroaryl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is heteroaryl substituted with 0, 1, or 2 groups independently selected from halogen, —OH, —SH, —CN, —NO$_2$, —NH$_2$, C1-C4 alkyl, C1-C4 R$^{12}$ is heteroaryl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{12}$ is unsubstituted heteroaryl.

In a further aspect, R$^{12}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and optionally substituted. In a still further aspect, R$^{12}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, R$^{12}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, R$^{12}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, R$^{12}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl and unsubstituted.

In a further aspect, $R^{12}$ is pyridinyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^{12}$ is pyridinyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^{12}$ is pyridinyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^{12}$ is unsubstituted pyridinyl.

In a further aspect, $R^{12}$ is pyrrolyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^{12}$ is pyrrolyl substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^{12}$ is pyrrolyl substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^{12}$ is unsubstituted pyrrolyl.

j. $R^{13}$ Groups

In one aspect, $R^{13}$ is selected from hydroxy, amino, alkyl, alkoxy, aryloxy, alkylamino, and dialkylamino.

In a further aspect, $R^{13}$ is selected from hydroxy, amino, C1-C8 alkyl, C1-C8 alkoxy, C5-C6 aryloxy, C1-C8 alkylamino, and (C1-C8)(C1-C8)dialkylamino. In a still further aspect, $R^{13}$ is selected from hydroxy, amino, C1-C4 alkyl, C1-C4 alkoxy, C5-C6 aryloxy, C1-C4 alkylamino, and (C1-C4)(C1-C4)dialkylamino.

In a further aspect, $R^{13}$ is selected from hydroxy, amino, C1-C8 alkyl, C1-C8 alkoxy, C1-C8 alkylamino, and (C1-C8)(C1-C8)dialkylamino. In a still further aspect, $R^{13}$ is selected from hydroxy, amino, C1-C4 alkyl, C1-C4 alkoxy, C1-C4 alkylamino, and (C1-C4)(C1-C4)dialkylamino. In yet a further aspect, $R^{13}$ is selected from hydroxy, amino, methyl, ethyl, n-propyl, i-propyl, methoxy, ethoxy, n-propoxy, i-propoxy, —NHCH$_3$, —NHCH$_2$CH$_3$, —NHCH(CH$_3$)$_2$, —NH(CH$_2$)$_2$CH$_3$, —N(CH$_3$)$_2$, —N(CH$_2$CH$_3$)$_2$, —N(CH$_3$)(CH$_2$CH$_3$), —N(CH(CH$_3$)$_2$)$_2$, and —N((CH$_2$)$_2$CH$_3$)$_2$. In an even further aspect, $R^{13}$ is selected from hydroxy, amino, methyl, ethyl, methoxy, ethoxy, —NHCH$_3$, —NHCH$_2$CH$_3$, —N(CH$_3$)$_2$, —N(CH$_2$CH$_3$)$_2$, and —N(CH$_3$)(CH$_2$CH$_3$). In a still further aspect, $R^{13}$ is selected from hydroxy, amino, methyl, methoxy, —NHCH$_3$, and —N(CH$_3$)$_2$.

In a further aspect, $R^{13}$ is dialkylamino, wherein the dialkylamino is a nitrogen-containing heterocycle. In a still further aspect, the nitrogen-containing heterocycle further comprises one or more oxo, thioxo, imino, or methylene groups. In yet a further aspect, the nitrogen-containing heterocycle further comprises at least one atom selected from oxygen, nitrogen, sulphur, phosphorous, selenium, and tellurium. Examples of nitrogen-containing heterocycles include, but are not limited to, aziridine, azetidine, pyrrolidine, piperidine, morpholine, piperazine, azepane, diazepane and azocane. In an even further aspect, the nitrogen-containing heterocycle is optionally substituted with a group selected from alkyl, aryl, arylalkyl, heteroaryl, heteroarylalkyl, alkenyl, alkoxy, hydroxyl, protected hydroxyl, alkanoyl, carboxy, alkoxycarboyl, and carbamoyl.

In a further aspect, $R^{13}$ is aryloxy.

In a further aspect, $R^{13}$ is substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In a still further aspect, $R^{13}$ is substituted with 0, 1, or 2 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, $R^{13}$ is substituted with 0 or 1 group selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In an even further aspect, $R^{13}$ is unsubstituted.

k. $R^{14}$ Groups

In one aspect, $R^{14}$ is selected from hydrogen, lower alkyl, acyl, sulfonyl, aryl and heteroaryl. In a further aspect, $R^{14}$ is selected from hydrogen, C1-C4 alkyl, C1-C4 acyl, sulfonyl, aryl and heteroaryl.

In a further aspect, $R^{14}$ is selected from hydrogen, C1-C4 alkyl, —(C═O)(C1-C4 alkyl), —CO$_2$(C1-C4 alkyl), —SO$_2$H, —SO$_2$(C1-C4 alkyl), —NHSO$_2$(C1-C4 alkyl), —N(CH$_3$)SO$_2$(C1-C4 alkyl), aryl, and heteroaryl. In a still further aspect, $R^{14}$ is selected from hydrogen, methyl, ethyl, n-propyl, i-propyl, —COCH$_3$, —COCH$_2$CH$_3$, —COCH$_2$CH$_2$CH$_3$, —COCH(CH$_3$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —SO$_2$H, —SO$_2$CH$_3$, —SO$_2$CH$_2$CH$_3$, —SO$_2$CH$_2$CH$_2$CH$_3$, —SO$_2$CH(CH$_3$)$_2$, —NHSO$_2$CH$_3$, —NHSO$_2$CH$_2$CH$_3$, —NHSO$_2$CH$_2$CH$_2$CH$_3$, —NHSO$_2$CH(CH$_3$)$_2$, —N(CH$_3$)SO$_2$CH$_3$, —N(CH$_3$)SO$_2$CH$_2$CH$_3$, —N(CH$_3$)SO$_2$CH$_2$CH$_2$CH$_3$, —N(CH$_3$)SO$_2$CH(CH$_3$)$_2$, aryl, and heteroaryl. In yet a further aspect, $R^{14}$ is selected from hydrogen, methyl, ethyl, —COCH$_3$, —COCH$_2$CH$_3$, —CO$_2$CH$_3$, —CO$_2$CH$_2$CH$_3$, —SO$_2$H, —SO$_2$CH$_3$, —SO$_2$CH$_2$CH$_3$, —NHSO$_2$CH$_3$, —NHSO$_2$CH$_2$CH$_3$, —N(CH$_3$)SO$_2$CH$_3$, —N(CH$_3$)SO$_2$CH$_2$CH$_3$, aryl, and heteroaryl. In an even further aspect, $R^{14}$ is selected from hydrogen, methyl, —COCH$_3$, —CO$_2$CH$_3$, —SO$_2$H, —SO$_2$CH$_3$, —NHSO$_2$CH$_3$, —N(CH$_3$)SO$_2$CH$_3$, aryl, and heteroaryl.

In a further aspect, $R^{14}$ is selected from hydrogen, C1-C4 alkyl, —(C═O)(C1-C4 alkyl), —CO$_2$(C1-C4 alkyl), —SO$_2$H, —SO$_2$(C1-C4 alkyl), —NHSO$_2$(C1-C4 alkyl), and —N(CH$_3$)SO$_2$(C1-C4 alkyl). In a still further aspect, $R^{14}$ is selected from hydrogen, methyl, ethyl, n-propyl, i-propyl, —COCH$_3$, —COCH$_2$CH$_3$, —COCH$_2$CH$_2$CH$_3$, —COCH(CH$_3$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —SO$_2$H, —SO$_2$CH$_3$, —SO$_2$CH$_2$CH$_3$, —SO$_2$CH$_2$CH$_2$CH$_3$, —SO$_2$CH(CH$_3$)$_2$, —NHSO$_2$CH$_3$, —NHSO$_2$CH$_2$CH$_3$, —NHSO$_2$CH$_2$CH$_2$CH$_3$, —NHSO$_2$CH(CH$_3$)$_2$, —N(CH$_3$)SO$_2$CH$_3$, —N(CH$_3$)SO$_2$CH$_2$CH$_3$, —N(CH$_3$)SO$_2$CH$_2$CH$_2$CH$_3$, and —N(CH$_3$)SO$_2$CH(CH$_3$)$_2$. In yet a further aspect, $R^{14}$ is selected from hydrogen, methyl, ethyl, —COCH$_3$, —COCH$_2$CH$_3$, —CO$_2$CH$_3$, —CO$_2$CH$_2$CH$_3$, —SO$_2$H, —SO$_2$CH$_3$, —SO$_2$CH$_2$CH$_3$, —NHSO$_2$CH$_3$, —NHSO$_2$CH$_2$CH$_3$, —N(CH$_3$)SO$_2$CH$_3$, —N(CH$_3$)SO$_2$CH$_2$CH$_3$, aryl, and heteroaryl. In an even further aspect, $R^{14}$ is selected from hydrogen, methyl, —COCH$_3$, —CO$_2$CH$_3$, —SO$_2$H, —SO$_2$CH$_3$, —NHSO$_2$CH$_3$, and —N(CH$_3$)SO$_2$CH$_3$.

In a further aspect, $R^{14}$ is selected from aryl and heteroaryl. In a still further aspect, $R^{14}$ is selected from phenyl, 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl.

In a further aspect, $R^{14}$ is aryl. In a still further aspect, $R^{14}$ is phenyl.

In a further aspect, $R^{14}$ is heteroaryl. In a still further aspect, $R^{14}$ is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl.

In a further aspect, $R^{14}$ is selected from hydrogen and C1-C4 alkyl. In a still further aspect, $R^{14}$ is selected from hydrogen, methyl, ethyl, n-propyl, and i-propyl. In yet a further aspect, $R^{14}$ is selected from hydrogen, methyl, and ethyl. In an even further aspect, $R^{14}$ is selected from hydrogen and methyl. In a still further aspect, $R^{14}$ is ethyl. In yet a further aspect, $R^{14}$ is methyl. In an even further aspect, $R^{14}$ is hydrogen.

l. $R^{15}$, $R^{16}$, and $R^{17}$ Groups

In one aspect, each of $R^{15}$, $R^{16}$, and $R^{17}$ is independently selected from hydrogen, halogen, lower alkyl, hydroxy, alkoxy, aryloxy, acyl, sulfonyl, aryl, heteroaryl, amino, alkylamino, and dialkylamino. In a further aspect, each of $R^{15}$, $R^{16}$, and $R^{17}$ is independently selected from hydrogen, halogen, hydroxy, amino, C1-C4 alkyl, C1-C4 haloalkyl, C1-C4 alkoxy, aryloxy, C1-C4 acyl, sulfonyl, aryl, heteroaryl, C1-C4 alkylamino, and (C1-C4)(C1-C4) dialkylamino.

In a further aspect, each of $R^{15}$, $R^{16}$, and $R^{17}$ is independently selected from hydrogen, halogen, hydroxy, amino, C1-C4 alkyl, C1-C4 haloalkyl, (C1-C4 alkyl)(C1-C4 alkoxy), —(C=O)(C1-C4 alkyl), —CO$_2$(C1-C4 alkyl), —SO$_2$H, —SO$_2$(C1-C4 alkyl), —NHSO$_2$(C1-C4 alkyl), —N(CH$_3$)SO$_2$(C1-C4 alkyl), aryl, and heteroaryl. In a still further aspect, each of $R^{15}$, $R^{16}$, and $R^{17}$ is independently selected from hydrogen, —Cl, —F, hydroxy, amino, methyl, ethyl, n-propyl, i-propyl, —CH$_2$F, —CHF$_2$, —CF$_3$, —CH$_2$CH$_2$F, —CH$_2$CHF$_2$, —CH$_2$CF$_3$, —CH$_2$OCH$_3$, —CH$_2$OCH$_2$CH$_3$, —CH$_2$CH$_2$OCH$_3$, —CH$_2$CH$_2$OCH$_2$CH$_3$, —COCH$_3$, —COCH$_2$CH$_3$, —COCH$_2$CH$_2$CH$_3$, —COCH(CH$_3$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —SO$_2$H, —SO$_2$CH$_3$, —SO$_2$CH$_2$CH$_3$, —SO$_2$CH$_2$CH$_2$CH$_3$, —SO$_2$CH(CH$_3$)$_2$, —NHSO$_2$CH$_3$, —NHSO$_2$CH$_2$CH$_3$, —NHSO$_2$CH$_2$CH$_2$CH$_3$, —NHSO$_2$CH(CH$_3$)$_2$, —N(CH$_3$)SO$_2$CH$_3$, —N(CH$_3$)SO$_2$CH$_2$CH$_3$, —N(CH$_3$)SO$_2$CH$_2$CH$_2$CH$_3$, —N(CH$_3$)SO$_2$CH(CH$_3$)$_2$, aryl, and heteroaryl. In yet a further aspect, each of $R^{15}$, $R^{16}$, and $R^{17}$ is independently selected from hydrogen, —Cl, —F, hydroxy, amino, methyl, ethyl, —CH$_2$F, —CHF$_2$, —CF$_3$, —CH$_2$CH$_2$F, —CH$_2$CHF$_2$, —CH$_2$CF$_3$, —CH$_2$OCH$_3$, —CH$_2$OCH$_2$CH$_3$, —CH$_2$CH$_2$OCH$_3$, —CH$_2$CH$_2$OCH$_2$CH$_3$, —COCH$_3$, —COCH$_2$CH$_3$, —CO$_2$CH$_3$, —CO$_2$CH$_2$CH$_3$, —SO$_2$H, —SO$_2$CH$_3$, —SO$_2$CH$_2$CH$_3$, —NHSO$_2$CH$_3$, —NHSO$_2$CH$_2$CH$_3$, —N(CH$_3$)SO$_2$CH$_3$, —N(CH$_3$)SO$_2$CH$_2$CH$_3$, aryl, and heteroaryl. In an even further aspect, each of $R^{15}$, $R^{16}$, and $R^{17}$ is independently selected from hydrogen, —Cl, —F, hydroxy, amino, methyl, —CH$_2$F, —CHF$_2$, —CF$_3$, —CH$_2$OCH$_3$, —COCH$_3$, —CO$_2$CH$_3$, —SO$_2$H, —SO$_2$CH$_3$, —NHSO$_2$CH$_3$, 13 N(CH$_3$)SO$_2$CH$_3$, aryl, and heteroaryl.

In a further aspect, each of $R^{15}$, $R^{16}$, and $R^{17}$ is independently selected from hydrogen, halogen, hydroxy, amino, C1-C4 alkyl, C1-C4 haloalkyl, —(C=O)(C1-C4 alkyl), —CO$_2$(C1-C4 alkyl), —SO$_2$H, —SO$_2$(C1-C4 alkyl), —NHSO$_2$(C1-C4 alkyl), and —N(CH$_3$)SO$_2$(C1-C4 alkyl). In a still further aspect, each of $R^{15}$, $R^{16}$, and $R^{17}$ is independently selected from hydrogen, —Cl, —F, hydroxy, amino, methyl, ethyl, n-propyl, i-propyl, —CH$_2$F, —CHF$_2$, —CF$_3$, —CH$_2$CH$_2$F, —CH$_2$CHF$_2$, —CH$_2$CF$_3$, —COCH$_3$, —COCH$_2$CH$_3$, —COCH$_2$CH$_2$CH$_3$, —COCH(CH$_3$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —SO$_2$H, —SO$_2$CH$_3$, —SO$_2$CH$_2$CH$_3$, —SO$_2$CH$_2$CH$_2$CH$_3$, —SO$_2$CH(CH$_3$)$_2$, —NHSO$_2$CH$_3$, —NHSO$_2$CH$_2$CH$_3$, —NHSO$_2$CH$_2$CH$_2$CH$_3$, —NHSO$_2$CH(CH$_3$)$_2$, —N(CH$_3$)SO$_2$CH$_3$, —N(CH$_3$)SO$_2$CH$_2$CH$_3$, —N(CH$_3$)SO$_2$CH$_2$CH$_2$CH$_3$, and —N(CH$_3$)SO$_2$CH(CH$_3$)$_2$. In yet a further aspect, each of $R^{15}$, $R^{16}$, and $R^{17}$ is independently selected from hydrogen, —Cl, —F, hydroxy, amino, methyl, ethyl, —CH$_2$F, —CHF$_2$, —CF$_3$, —CH$_2$CH$_2$F, —CH$_2$CHF$_2$, —CH$_2$CF$_3$, —COCH$_3$, —COCH$_2$CH$_3$, —CO$_2$CH$_3$, —CO$_2$CH$_2$CH$_3$, —SO$_2$H, —SO$_2$CH$_3$, —SO$_2$CH$_2$CH$_3$, —NHSO$_2$CH$_3$, —NHSO$_2$CH$_2$CH$_3$, —N(CH$_3$)SO$_2$CH$_3$, —N(CH$_3$)SO$_2$CH$_2$CH$_3$, aryl, and heteroaryl. In an even further aspect, each of $R^{15}$, $R^{16}$, and $R^{17}$ is independently selected from hydrogen, —Cl, —F, hydroxy, amino, methyl, —CH$_2$F, —CHF$_2$, —CF$_3$, —COCH$_3$, —CO$_2$CH$_3$, —SO$_2$H, —SO$_2$CH$_3$, —NHSO$_2$CH$_3$, and —N(CH$_3$)SO$_2$CH$_3$.

In a further aspect, each of $R^{15}$, $R^{16}$, and $R^{17}$ is independently selected from hydrogen, aryl, and heteroaryl. In a still further aspect, each of $R^{15}$, $R^{16}$, and $R^{17}$ is independently selected from hydrogen, phenyl, 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl.

In a further aspect, each of $R^{15}$, $R^{16}$, and $R^{17}$ is independently is independently selected from hydrogen and aryl. In a still further aspect, each of $R^{15}$, $R^{16}$, and $R^{17}$ is independently selected from hydrogen and phenyl.

In a further aspect, each of $R^{15}$, $R^{16}$, and $R^{17}$ is independently selected from hydrogen and heteroaryl. In a still further aspect, each of $R^{15}$, $R^{16}$, and $R^{17}$ is independently selected from hydrogen, 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl.

In a further aspect, each of $R^{15}$, $R^{16}$, and $R^{17}$ is independently selected from hydrogen and C1-C4 alkyl. In a still further aspect, each of $R^{15}$, $R^{16}$, and $R^{17}$ is independently selected from hydrogen, methyl, ethyl, n-propyl, and i-propyl. In yet a further aspect, each of $R^{15}$, $R^{16}$, and $R^{17}$ is independently selected from hydrogen, methyl, and ethyl. In an even further aspect, each of $R^{15}$, $R^{16}$, and $R^{17}$ is independently selected from hydrogen and methyl.

In a further aspect, each of $R^{15}$, $R^{16}$, and $R^{17}$ is independently selected from hydrogen and halogen. In a still further aspect, each of $R^{15}$, $R^{16}$, and $R^{17}$ is independently selected from hydrogen, —Cl, and —F. In yet a further aspect, each of $R^{15}$, $R^{16}$, and $R^{17}$ is independently selected from hydrogen and —Cl. In an even further aspect, each of $R^{15}$, $R^{16}$, and $R^{17}$ is independently selected from hydrogen and —F.

m. Ar Groups

In one aspect, Ar is selected from phenyl and a heterocyclic group.

In a further aspect, Ar is phenyl or substituted phenyl. In a still further aspect, Ar is phenyl substituted with 0, 1, 2, or 3 groups independently selected from halogen, —OH, —SH, —CN, —NO$_2$, —NH$_2$, C1-C4 alkyl, C1-C4 alkoxy, C1-C4 alkylamino, and (C1-C4)(C1-C4) dialkylamino. In yet a further aspect, Ar is phenyl substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, Ar is phenyl substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, Ar is unsubstituted phenyl.

In a further aspect, Ar is a heterocyclic group and optionally substituted. In a still further aspect, Ar is a heterocyclic group substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, Ar is a heterocyclic group substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, Ar is a heterocyclic group substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, Ar is unsubstituted a heterocyclic group.

In a further aspect, Ar is heteroaryl and optionally substituted. In a still further aspect, Ar is heteroaryl substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, Ar is heteroaryl substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, Ar is heteroaryl substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, Ar is unsubstituted heteroaryl.

In a further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and optionally substituted. In a still further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, 2, or 3 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In yet a further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0, 1, or 2 groups independently selected from halogen, —OH, —SH, —CN, —NO₂, —NH₂, C1-C4 alkyl, C1-C4 alkoxy, C1-C4 alkylamino, and (C1-C4)(C1-C4) dialkylamino. In an even further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and substituted with 0 or 1 group selected from halogen, —OH, —SH, —CN, —NO₂, —NH₂, C1-C4 alkyl, C1-C4 alkoxy, C1-C4 alkylamino, and (C1-C4)(C1-C4) dialkylamino. In a still further aspect, Ar is selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, and 5-imidazolyl and unsubstituted.

2. Example Compounds

Representative compounds according to the present disclosure are shown in Table 1.

TABLE 1

| No. | Structure | Name | M + H |
|---|---|---|---|
| 1 | 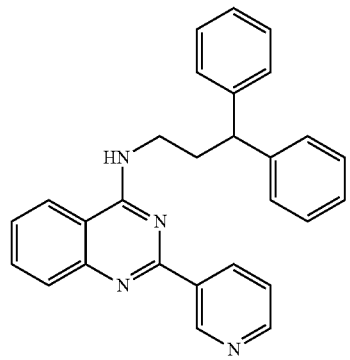 [SMILES: c1ccc(C(CCNc2nc(-c3cccnc3)nc3ccccc23)c2ccccc2)cc1] | N-(3,3-Diphenylpropyl)-2-(pyridin-3-yl)quinazolin-4-amine | 417 |

TABLE 1-continued

| No. | Structure | Name | M + H |
|---|---|---|---|
| 2 | 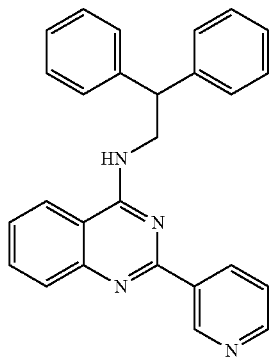 [SMILES: c1ccc(C(CNc2nc(-c3cccnc3)nc3ccccc23)c2ccccc2)cc1] | N-(2,2-Diphenylethyl)-2-(pyridin-3-yl)quinazolin-4-amine | 403 |
| 3 | 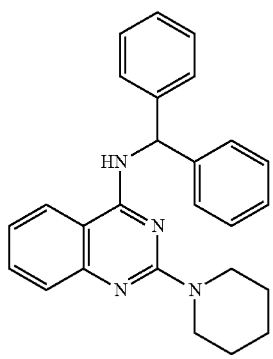 [SMILES: c1ccc(C(Nc2nc(N3CCCCC3)nc3ccccc23)c2ccccc2)cc1] | N-Benzhydryl-2-(piperidin-1-yl)quinazolin-4-amine | 395 |
| 4 | 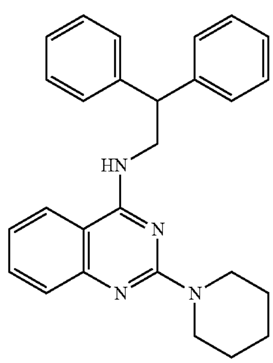 [SMILES: c1ccc(C(CNc2nc(N3CCCCC3)nc3ccccc23)c2ccccc2)cc1] | N-(2,2-Diphenylethyl)-2-(piperidin-1-yl)quinazolin-4-amine | 409 |
| 5 | 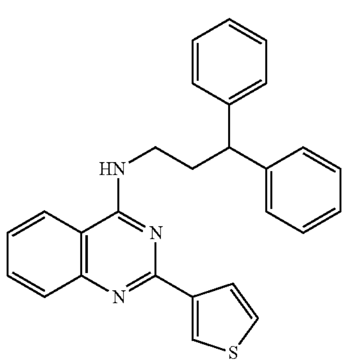 [SMILES: c1ccc(C(CCNc2nc(-c3ccsc3)nc3ccccc23)c2ccccc2)cc1] | N-(3,3-Diphenylpropyl)-2-(thiophen-3-yl)quinazolin-4-amine | 422 |

TABLE 1-continued

| No. | Structure | Name | M + H |
|---|---|---|---|
| 6 | 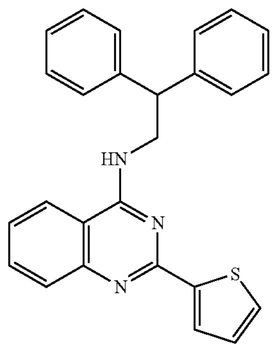 [SMILES: c1ccc(C(CNc2nc(-c3cccs3)nc3ccccc23)c2ccccc2)cc1] | N-(2,2-Diphenylethyl)-2-(thiophen-2-yl)quinazolin-4-amine | 408 |
| 7 | 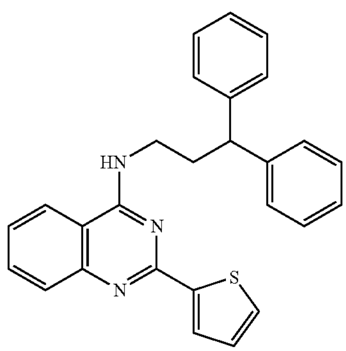 [SMILES: c1ccc(C(CCNc2nc(-c3cccs3)nc3ccccc23)c2ccccc2)cc1] | N-(3,3-Diphenylpropyl)-2-(thiophen-2-yl)quinazolin-4-amine | 422 |
| 8 | 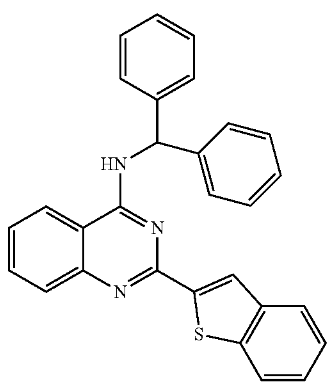 [SMILES: c1ccc(C(Nc2nc(-c3cc4ccccc4s3)nc3ccccc23)c2ccccc2)cc1] | N-Benzhydryl-2-(benzo[b]thiophen-2-yl)quinazolin-4-amine | 444 |
| 9 | 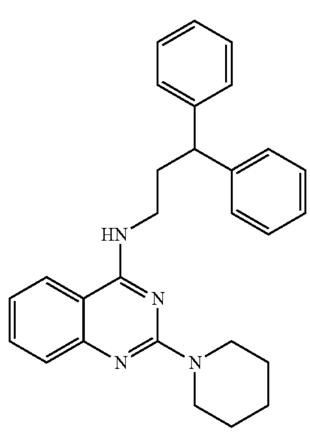 [SMILES: c1ccc(C(CCNc2nc(N3CCCCC3)nc3ccccc23)c2ccccc2)cc1] | N-(3,3-Diphenylpropyl)-2-(piperidin-1-yl)quinazolin-4-amine | 423 |

TABLE 1-continued

| No. | Structure | Name | M + H |
|---|---|---|---|
| 10 | 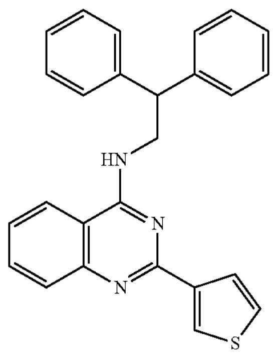 [SMILES: c1ccc(C(CNc2nc(-c3ccsc3)nc3ccccc23)c2ccccc2)cc1] | N-(2,2-Diphenylethyl)-2-(thiophen-3-yl)quinazolin-4-amine | 408 |
| 11 | 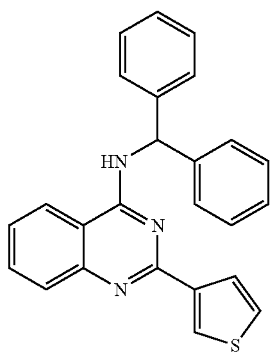 [SMILES: c1ccc(C(Nc2nc(-c3ccsc3)nc3ccccc23)c2ccccc2)cc1] | N-Benzhydryl-2-(thiophen-3-yl)quinazolin-4-amine | 394 |
| 12 | 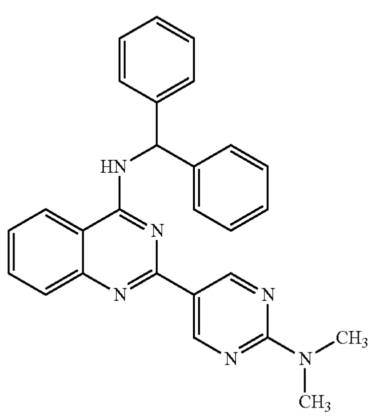 | N-Benzhydryl-2-(2-(dimethylamino)pyrimidin-5-yl)quinazolin-4-amine | 433 |
| 13 | 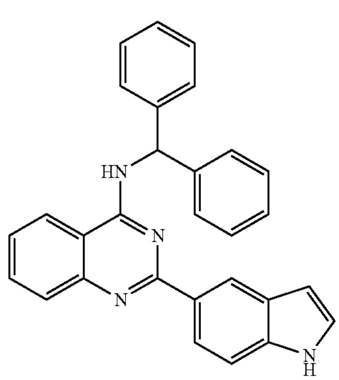 [SMILES: c1ccc(C(Nc2nc(-c3ccc4[nH]ccc4c3)nc3ccccc23)c2ccccc2)cc1] | N-Benzhydryl-2-(1H-indol-5-yl)quinazolin-4-amine | 427 |

TABLE 1-continued

| No. | Structure | Name | M + H |
|---|---|---|---|
| 14 | 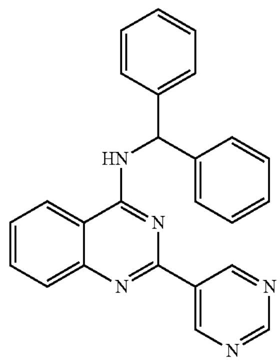 [SMILES: c1ccc(C(Nc2nc(-c3cncnc3)nc3ccccc23)c2ccccc2)cc1] | N-Benzhydryl-2-(pyrimidin-5-yl)quinazolin-4-amine | 390 |
| 15 | 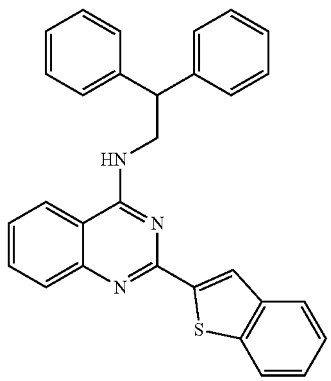 [SMILES: c1ccc(C(CNc2nc(-c3cc4ccccc4s3)nc3ccccc23)c2ccccc2)cc1] | 2-(Benzo[b]thiophen-2-yl)-N-(2,2-diphenylethyl)quinazolin-4-amine | 458 |
| 16 | 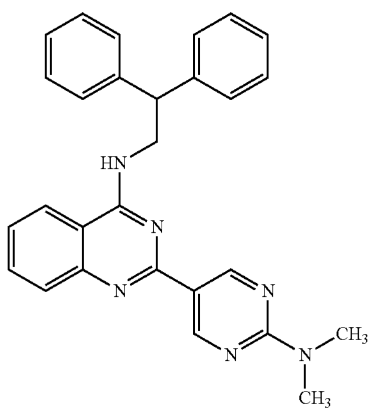 [SMILES: CN(C)c1ncc(-c2nc(NCC(c3ccccc3)c3ccccc3)c3ccccc3n2)cn1] | 2-(2-(Dimethylamino)pyrimidin-5-yl)-N-(2,2-diphenylethyl)quinazolin-4-amine | 447 |
| 17 | 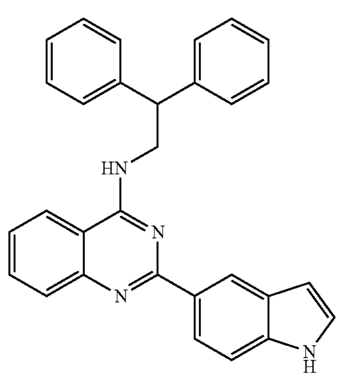 [SMILES: c1ccc(C(CNc2nc(-c3ccc4[nH]ccc4c3)nc3ccccc23)c2ccccc2)cc1] | N-(2,2-Diphenylethyl)-2-(1H-indol-5-yl)quinazolin-4-amine | 441 |

TABLE 1-continued

| No. | Structure | Name | M + H |
|---|---|---|---|
| 18 | 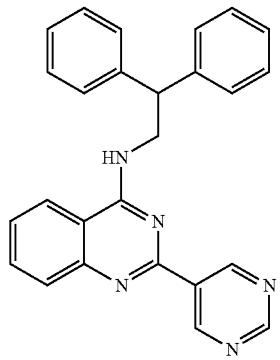 [SMILES: c1ccc(C(CNc2nc(-c3cncnc3)nc3ccccc23)c2ccccc2)cc1] | N-(2,2-Diphenylethyl)-2-(pyrimidin-5-yl)quinazolin-4-amine | 404 |
| 19 | 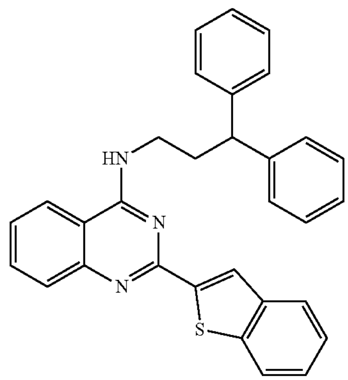 [SMILES: c1ccc(C(CCNc2nc(-c3cc4ccccc4s3)nc3ccccc23)c2ccccc2)cc1] | 2-(Benzo[b]thiophen-2-yl)-N-(3,3-diphenylpropyl)quinazolin-4-amine | 472 |
| 20 | 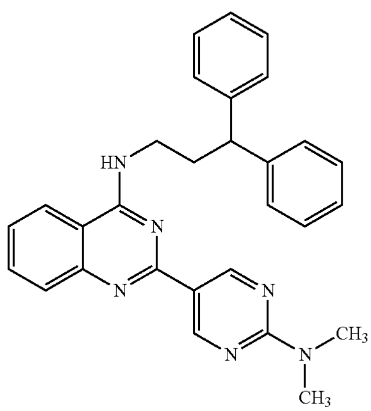 | 2-(2-(Dimethylamino)pyrimidin-5-yl)-N-(3,3-diphenylpropyl)quinazolin-4-amine | 461 |
| 21 | 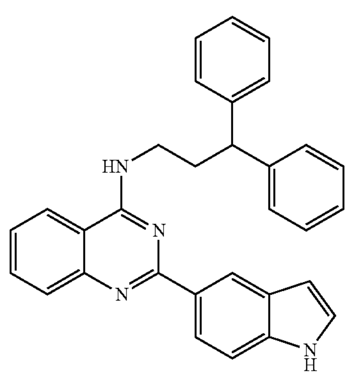 [SMILES: c1ccc(C(CCNc2nc(-c3ccc4[nH]ccc4c3)nc3ccccc23)c2ccccc2)cc1] | N-(3,3-Diphenylpropyl)-2-(1H-indol-5-yl)quinazolin-4-amine | 455 |

TABLE 1-continued

| No. | Structure | Name | M + H |
|---|---|---|---|
| 22 | 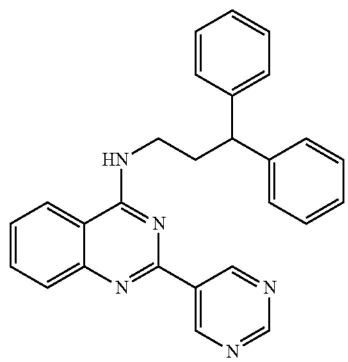 [SMILES: c1ccc(C(CCNc2nc(-c3cncnc3)nc3ccccc23)c2ccccc2)cc1] | N-(3,3-Diphenylpropyl)-2-(pyrimidin-5-yl)quinazolin-4-amine | 418 |
| 23 | 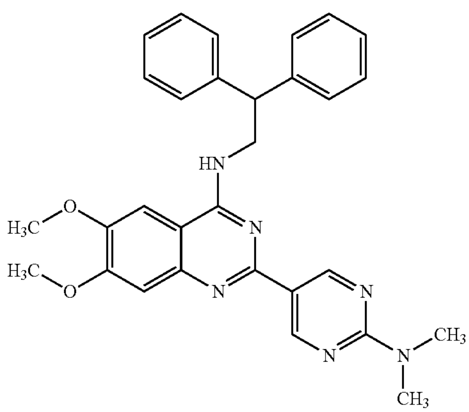 | 2-(2-(Dimethylamino)pyrimidin-5-yl)-N-(2,2-diphenylethyl)-6,7-dimethoxyquinazolin-4-amine | 507 |
| 24 | 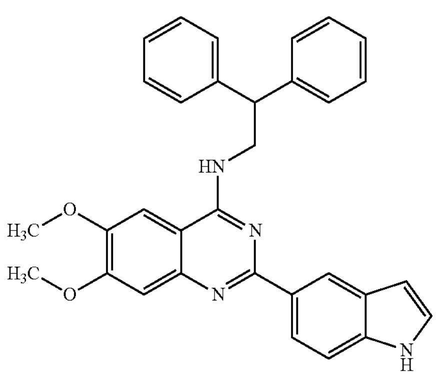 [SMILES: COc1cc2nc(-c3ccc4[nH]ccc4c3)nc(NCC(c3ccccc3)c3ccccc3)c2cc1OC] | N-(2,2-Diphenylethyl)-2-(1H-indol-5-yl)-6,7-dimethoxyquinazolin-4-amine | 501 |
| 25 | 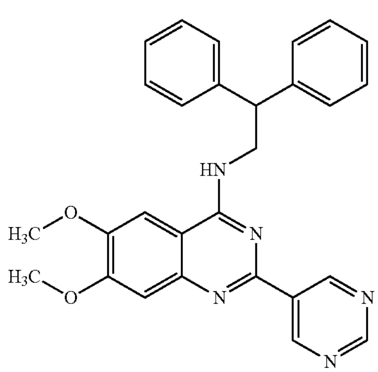 [SMILES: COc1cc2nc(-c3cncnc3)nc(NCC(c3ccccc3)c3ccccc3)c2cc1OC] | N-(2,2-Diphenylethyl)-6,7-dimethoxy-2-(pyrimidin-5-yl)quinazolin-4-amine | 464 |

TABLE 1-continued

| No. | Structure | Name | M + H |
|---|---|---|---|
| 26 | 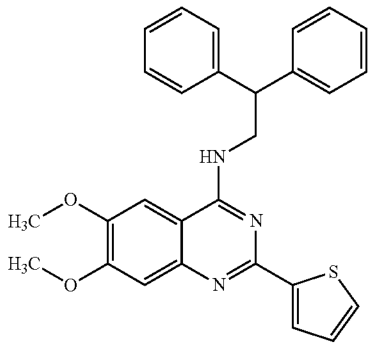 [SMILES: COc1cc2nc(-c3cccs3)nc(NCC(c3ccccc3)c3ccccc3)c2cc1OC] | N-(2,2-Diphenylethyl)-6,7-dimethoxy-2-(thiophen-2-yl)quinazolin-4-amine | 468 |
| 27 | 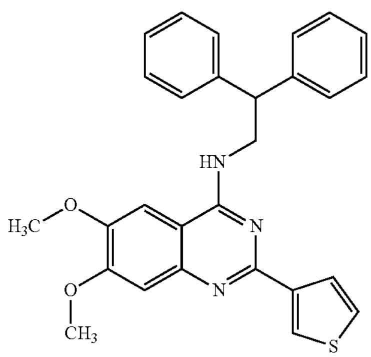 [SMILES: COc1cc2nc(-c3ccsc3)nc(NCC(c3ccccc3)c3ccccc3)c2cc1OC] | N-(2,2-Diphenylethyl)-6,7-dimethoxy-2-(thiophen-3-yl)quinazolin-4-amine | 468 |
| 28 | 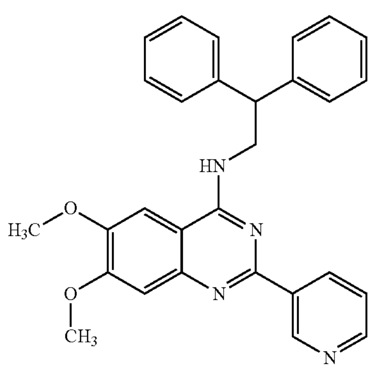 [SMILES: COc1cc2nc(-c3cccnc3)nc(NCC(c3ccccc3)c3ccccc3)c2cc1OC] | N-(2,2-Diphenylethyl)-6,7-dimethoxy-2-(pyridin-3-yl)quinazolin-4-amine | 463 |
| 29 | 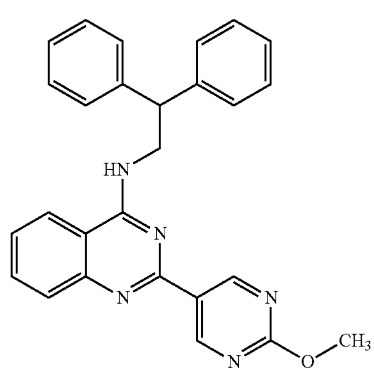 [SMILES: COc1ncc(-c2nc(NCC(c3ccccc3)c3ccccc3)c3ccccc3n2)cn1] | N-(2,2-Diphenylethyl)-2-(2-methoxypyrimidin-5-yl)quinazolin-4-amine | 434 |

TABLE 1-continued

| No. | Structure | Name | M + H |
|---|---|---|---|
| 30 | 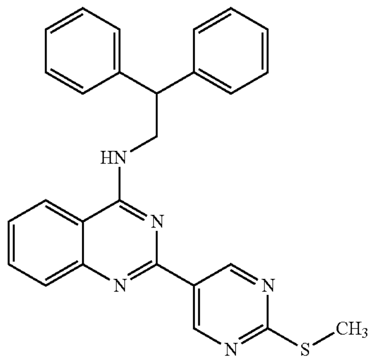 [SMILES: CSc1ncc(-c2nc(NCC(c3ccccc3)c3ccccc3)c3ccccc3n2)cn1] | N-(2,2-Diphenylethyl)-2-(2-(methylthio)pyrimidin-5-yl)quinazolin-4-amine | 450 |
| 31 | 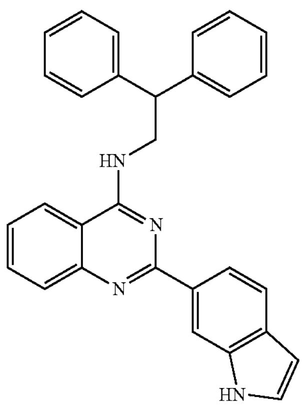 [SMILES: c1ccc(C(CNc2nc(-c3ccc4cc[nH]c4c3)nc3ccccc23)c2ccccc2)cc1] | N-(2,2-Diphenylethyl)-2-(1H-indol-6-yl)quinazolin-4-amine | 441 |
| 32 | 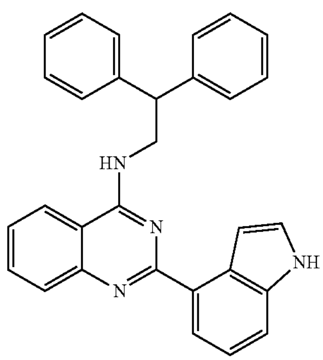 [SMILES: c1ccc(C(CNc2nc(-c3cccc4[nH]ccc34)nc3ccccc23)c2ccccc2)cc1] | N-(2,2-Diphenylethyl)-2-(1H-indol-4-yl)quinazolin-4-amine | 441 |
| 33 | 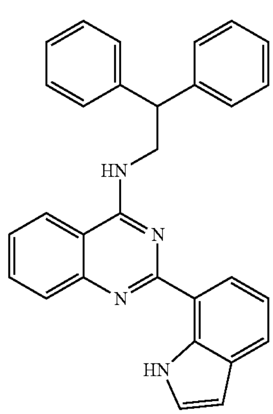 [SMILES: c1ccc(C(CNc2nc(-c3cccc4cc[nH]c34)nc3ccccc23)c2ccccc2)cc1] | N-(2,2-Diphenylethyl)-2-(1H-indol-7-yl)quinazolin-4-amine | 441 |

TABLE 1-continued
| No. | Structure | Name | M + H |
|---|---|---|---|
| 34 | 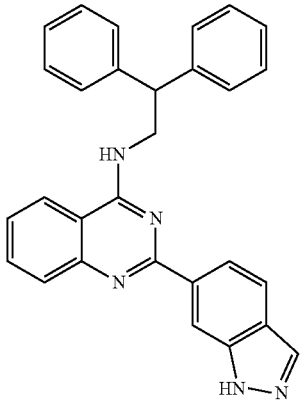 [SMILES: c1ccc(C(CNc2nc(-c3ccc4cn[nH]c4c3)nc3ccccc23)c2ccccc2)cc1] | N-(2,2-Diphenylethyl)-2-(1H-indazol-6-yl)quinazolin-4-amine | 442 |
| 35 | 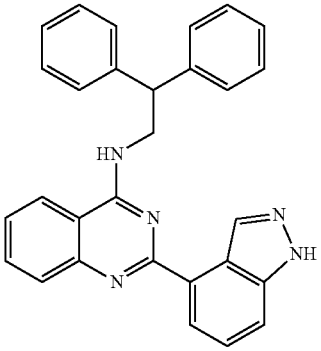 [SMILES: c1ccc(C(CNc2nc(-c3cccc4[nH]ncc34)nc3ccccc23)c2ccccc2)cc1] | N-(2,2-Diphenylethyl)-2-(1H-indazol-4-yl)quinazolin-4-amine | 442 |
| 36 | 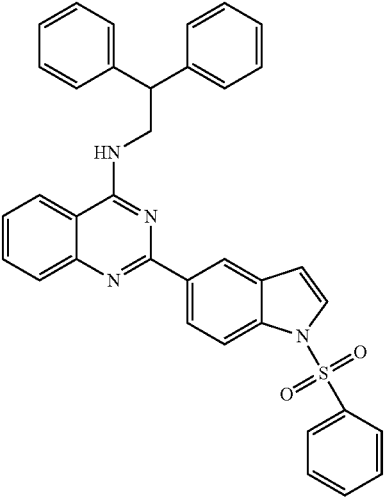 [SMILES: O=S(=O)(c1ccccc1)n1ccc2cc(-c3nc(NCC(c4ccccc4)c4ccccc4)c4ccccc4n3)ccc21] | N-(2,2-Diphenylethyl)-2-(1-(phenylsulfonyl)-1H-indol-5-yl)quinazolin-4-amine | 581 |

TABLE 1-continued

| No. | Structure | Name | M + H |
|---|---|---|---|
| 37 | 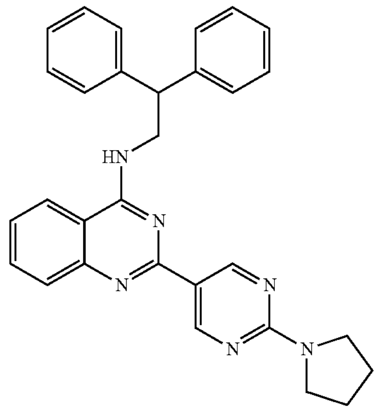 [SMILES: c1ccc(C(CNc2nc(-c3cnc(N4CCCC4)nc3)nc3ccccc23)c2ccccc2)cc1] | N-(2,2-Diphenylethyl)-2-(2-(pyrrolidin-1-yl)pyrimidin-5-yl)quinazolin-4-amine | 473 |
| 38 | 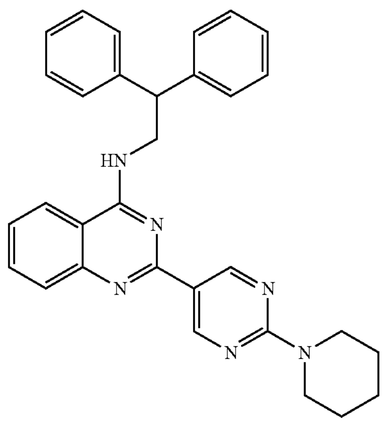 [SMILES: c1ccc(C(CNc2nc(-c3cnc(N4CCCCC4)nc3)nc3ccccc23)c2ccccc2)cc1] | N-(2,2-Diphenylethyl)-2-(2-(piperidin-1-yl)pyrimidin-5-yl)quinazolin-4-amine | 487 |
| 39 | 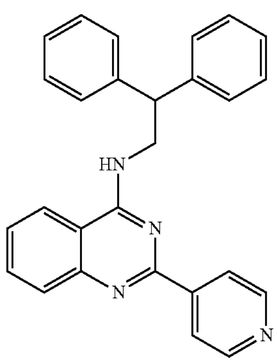 [SMILES: c1ccc(C(CNc2nc(-c3ccncc3)nc3ccccc23)c2ccccc2)cc1] | N-(2,2-Diphenylethyl)-2-(pyridin-4-yl)quinazolin-4-amine | 403 |
| 40 | 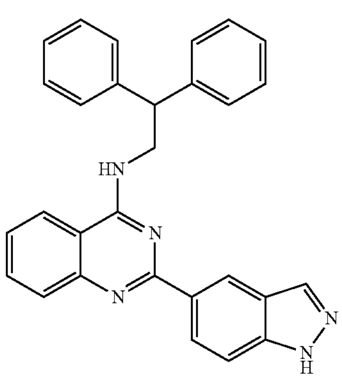 [SMILES: c1ccc(C(CNc2nc(-c3ccc4[nH]ncc4c3)nc3ccccc23)c2ccccc2)cc1] | N-(2,2-Diphenylethyl)-2-(1H-indazol-5-yl)quinazolin-4-amine | 442 |

TABLE 1-continued

| No. | Structure | Name | M + H |
|---|---|---|---|
| 41 | 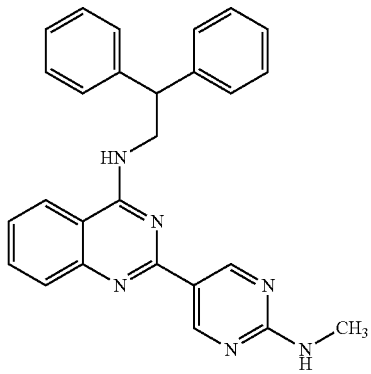 [SMILES: CNc1ncc(-c2nc(NCC(c3ccccc3)c3ccccc3)c3ccccc3n2)cn1] | N-(2,2-Diphenylethyl)-2-(2-(methylamino)pyrimidin-5-yl)quinazolin-4-amine | 433 |
| 42 | 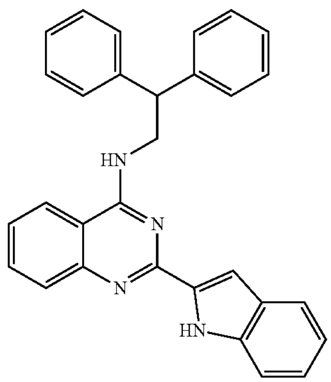 [SMILES: c1ccc(C(CNc2nc(-c3cc4ccccc4[nH]3)nc3ccccc23)c2ccccc2)cc1] | N-(2,2-Diphenylethyl)-2-(1H-indol-2-yl)quinazolin-4-amine | 441 |
| 43 | 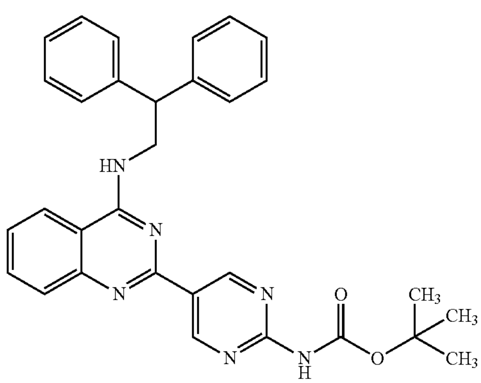 [SMILES: CC(C)(C)OC(=O)Nc1ncc(-c2nc(NCC(c3ccccc3)c3ccccc3)c3ccccc3n2)cn1] | tert-Butyl (5-(4-((2,2-diphenylethyl)amino)quinazolin-2-yl)pyrimidin-2-yl)carbamate | 519 |
| 44 | 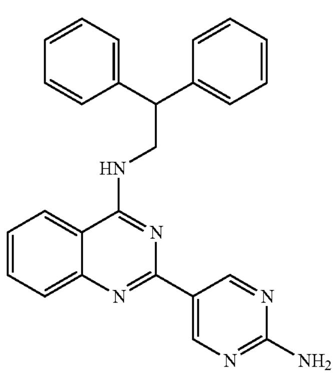 | 2-(2-Aminopyrimidin-5-yl)-N-(2,2-diphenylethyl)quinazolin-4-amine | 419 |

TABLE 1-continued

| No. | Structure | Name | M + H |
|---|---|---|---|
| 45 | 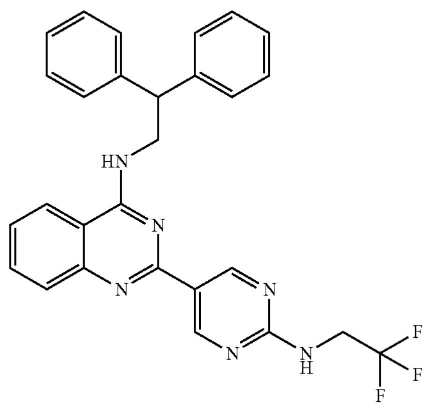 [SMILES: FC(F)(F)CNc1ncc(-c2nc(NCC(c3ccccc3)c3ccccc3)c3ccccc3n2)cn1] | N-(2,2-Diphenylethyl)-2-(2-((2,2,2-trifluoroethyl)amino)pyrimidin-5-yl)quinazolin-4-amine | 501 |
| 46 | 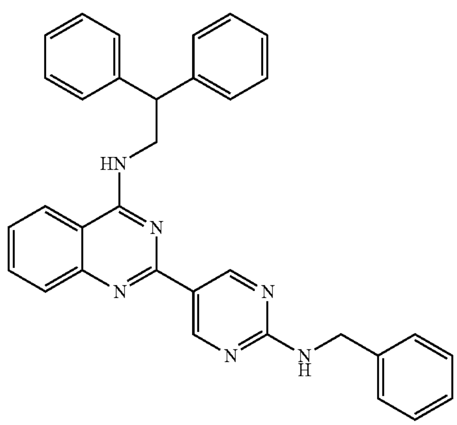 [SMILES: c1ccc(CNc2ncc(-c3nc(NCC(c4ccccc4)c4ccccc4)c4ccccc4n3)cn2)cc1] | 2-(2-(Benzylamino)pyrimidin-5-yl)-N-(2,2-diphenylethyl)quinazolin-4-amine | 509 |
| 47 | 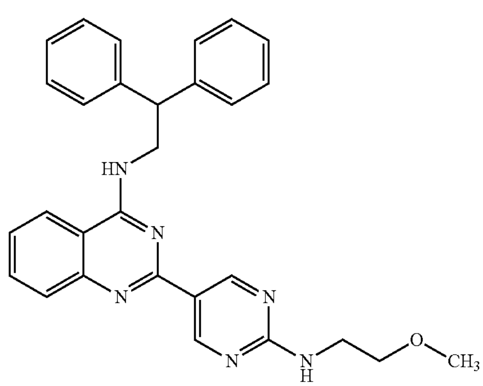 [SMILES: COCCNc1ncc(-c2nc(NCC(c3ccccc3)c3ccccc3)c3ccccc3n2)cn1] | N-(2,2-Diphenylethyl)-2-(2-((2-methoxyethyl)amino)pyrimidin-5-yl)quinazolin-4-amine | 477 |
| 48 | 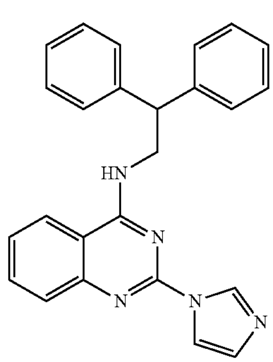 [SMILES: c1ccc(C(CNc2nc(-n3ccnc3)nc3ccccc23)c2ccccc2)cc1] | N-(2,2-Diphenylethyl)-2-(1H-imidazol-1-yl)quinazolin-4-amine | 392 |

TABLE 1-continued

| No. | Structure | Name | M + H |
|---|---|---|---|
| 49 | 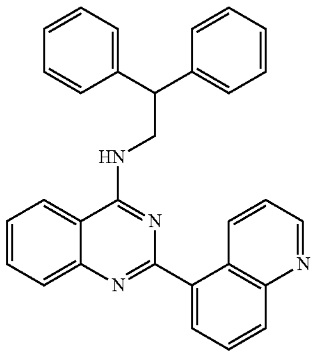 [SMILES: c1ccc(C(CNc2nc(-c3cccc4ncccc34)nc3ccccc23)c2ccccc2)cc1] | N-(2,2-Diphenylethyl)-2-(quinolin-5-yl)quinazolin-4-amine | 453 |
| 50 | 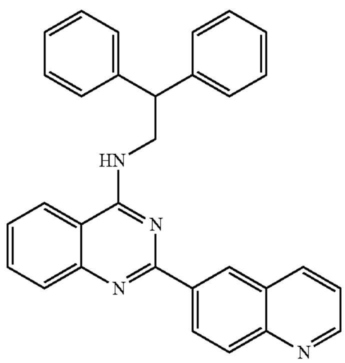 [SMILES: c1ccc(C(CNc2nc(-c3ccc4ncccc4c3)nc3ccccc23)c2ccccc2)cc1] | N-(2,2-Diphenylethyl)-2-(quinolin-6-yl)quinazolin-4-amine | 463 |
| 51 | 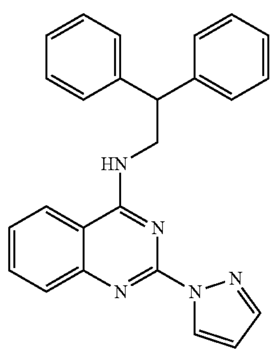 [SMILES: c1ccc(C(CNc2nc(-n3cccn3)nc3ccccc23)c2ccccc2)cc1] | N-(2,2-Diphenylethyl)-2-(1H-pyrazol-1-yl)quinazolin-4-amine | 392 |
| 52 | 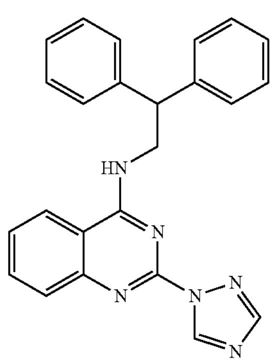 [SMILES: c1ccc(C(CNc2nc(-n3cncn3)nc3ccccc23)c2ccccc2)cc1] | N-(2,2-Diphenylethyl)-2-(1H-1,2,4-triazol-1-yl)quinazolin-4-amine | 393 |

TABLE 1-continued

| No. | Structure | Name | M + H |
|---|---|---|---|
| 53 | 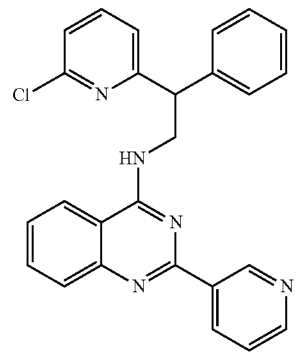 [SMILES: Clc1cccc(C(CNc2nc(-c3cccnc3)nc3ccccc23)c2ccccc2)n1] | N-(2-(6-Chloropyridin-2-yl)-2-phenylethyl)-2-(pyridin-3-yl)quinazolin-4-amine | 438 |
| 54 | 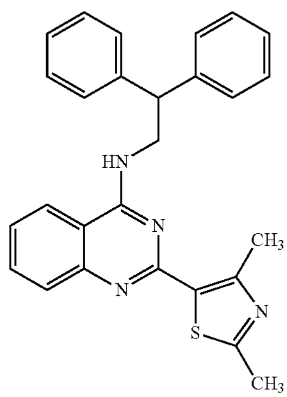 [SMILES: Cc1nc(C)c(-c2nc(NCC(c3ccccc3)c3ccccc3)c3ccccc3n2)s1] | 2-(2,4-Dimethylthiazol-5-yl)-N-(2,2-diphenylethyl)quinazolin-4-amine | 437 |
| 55 | 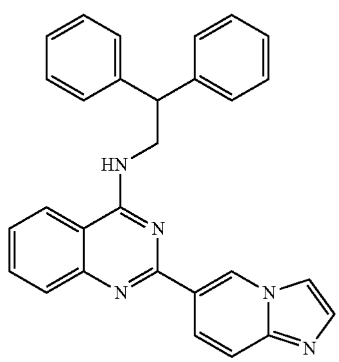 [SMILES: c1ccc(C(CNc2nc(-c3ccc4nccn4c3)nc3ccccc23)c2ccccc2)cc1] | N-(2,2-Diphenylethyl)-2-(imidazo[1,2-a]pyridin-6-yl)quinazolin-4-amine | 442 |
| 56 | 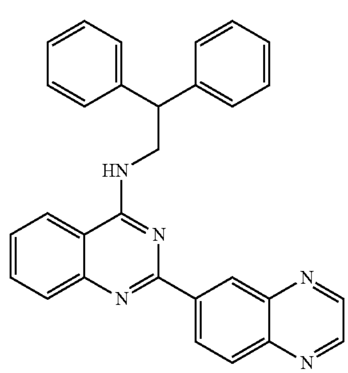 [SMILES: c1ccc(C(CNc2nc(-c3ccc4nccnc4c3)nc3ccccc23)c2ccccc2)cc1] | N-(2,2-Diphenylethyl)-2-(quinoxalin-6-yl)quinazolin-4-amine | 454 |

TABLE 1-continued

| No. | Structure | Name | M + H |
|---|---|---|---|
| 57 | 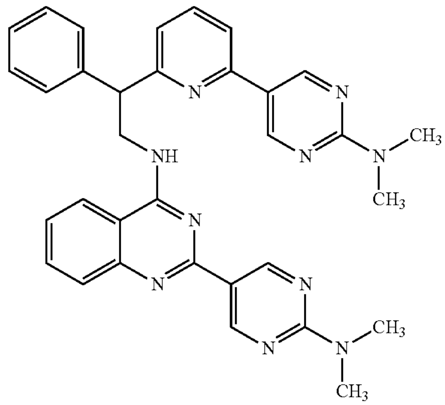 [SMILES: CN(C)c1ncc(-c2cccc(C(CNc3nc(-c4cnc(N(C)C)nc4)nc4ccccc34)c3ccccc3)n2)cn1] | 2-(2-(Dimethylamino)pyrimidin-5-yl)-N-(2-(6-(2-(dimethylamino)pyrimidin-5-yl)pyridin-2-yl)-2-phenylethyl)quinazolin-4-amine | 569 |
| 58 | 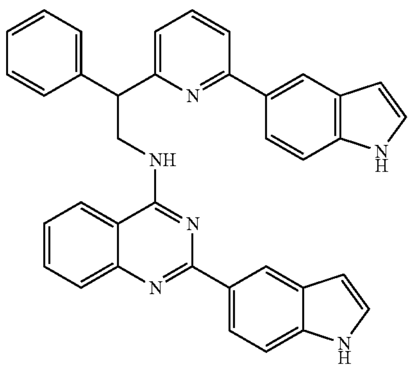 [SMILES: c1ccc(C(CNc2nc(-c3ccc4[nH]ccc4c3)nc3ccccc23)c2cccc(-c3ccc4[nH]ccc4c3)n2)cc1] | N-(2-(6-(1H-Indol-5-yl)pyridin-2-yl)-2-phenylethyl)-2-(1H-indol-5-yl)quinazolin-4-amine | 557 |
| 59 | 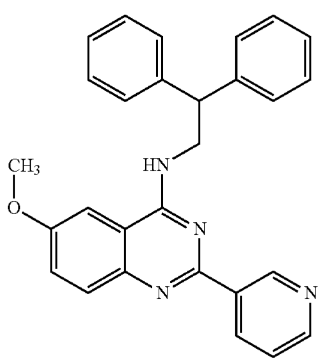 [SMILES: COc1ccc2nc(-c3cccnc3)nc(NCC(c3ccccc3)c3ccccc3)c2c1] | N-(2,2-Diphenylethyl)-6-methoxy-2-(pyridin-3-yl)quinazolin-4-amine | 433 |
| 60 | 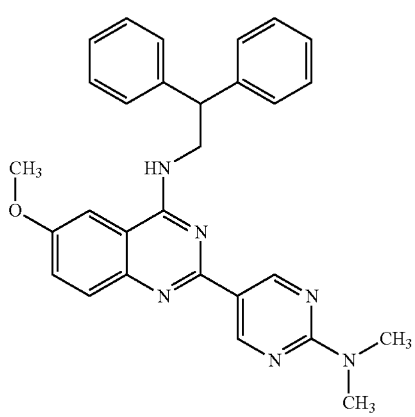 [SMILES: COc1ccc2nc(-c3cnc(N(C)C)nc3)nc(NCC(c3ccccc3)c3ccccc3)c2c1] | 2-(2-(Dimethylamino)pyrimidin-5-yl)-N-(2,2-diphenylethyl)-6-methoxyquinazolin-4-amine | 477 |

TABLE 1-continued

| No. | Structure | Name | M + H |
|---|---|---|---|
| 61 | 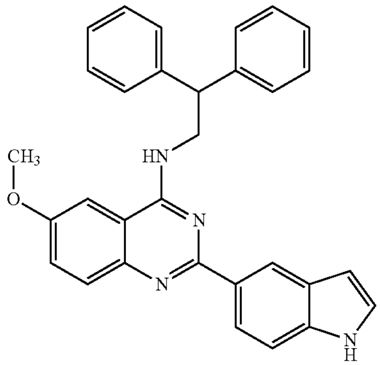 [SMILES: COc1ccc2nc(-c3ccc4[nH]ccc4c3)nc(NCC(c3ccccc3)c3ccccc3)c2c1] | N-(2,2-Diphenylethyl)-2-(1H-indol-5-yl)-6-methoxyquinazolin-4-amine | 471 |
| 62 | 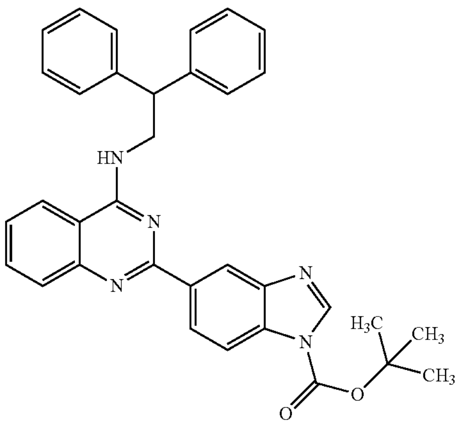 [SMILES: CC(C)(C)OC(=O)n1cnc2cc(-c3nc(NCC(c4ccccc4)c4ccccc4)c4ccccc4n3)ccc21] | tert-Butyl 5-(4-((2,2-diphenylethyl)amino)quinazolin-2-yl)-1H-benzo[d]imidazole-1-carboxylate | 542 |
| 63 | 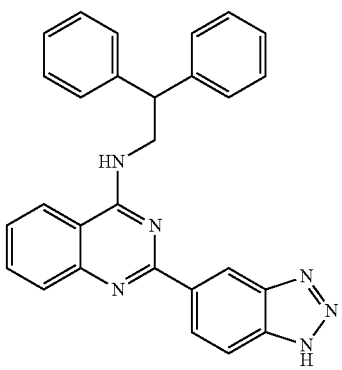 [SMILES: c1ccc(C(CNc2nc(-c3ccc4[nH]nnc4c3)nc3ccccc23)c2ccccc2)cc1] | 2-(1H-Benzo[d][1,2,3]triazol-5-yl)-N-(2,2-diphenylethyl)quinazolin-4-amine | 443 |
| 64 | 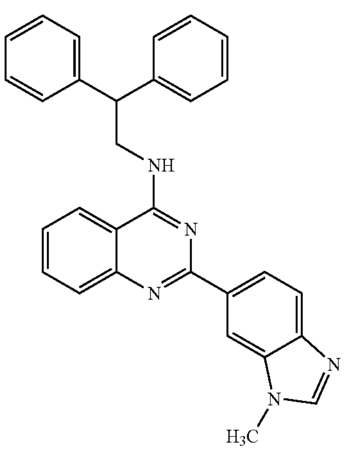 [SMILES: Cn1cnc2ccc(-c3nc(NCC(c4ccccc4)c4ccccc4)c4ccccc4n3)cc21] | N-(2,2-Diphenylethyl)-2-(1-methyl-1H-benzo[d]imidazol-6-yl)quinazolin-4-amine | 456 |

TABLE 1-continued

| No. | Structure | Name | M + H |
|---|---|---|---|
| 65 | 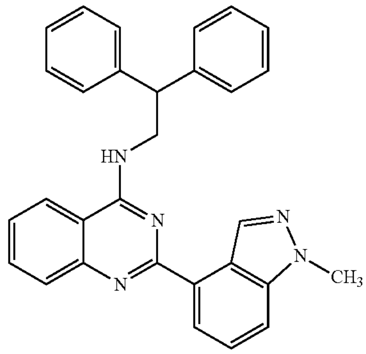 [SMILES: Cn1ncc2c(-c3nc(NCC(c4ccccc4)c4ccccc4)c4ccccc4n3)cccc21] | N-(2,2-Diphenylethyl)-2-(1-methyl-1H-indazol-4-yl)quinazolin-4-amine | 456 |
| 66 | 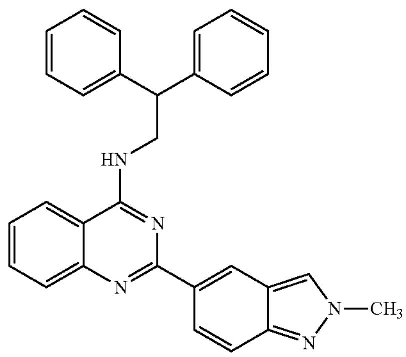 [SMILES: Cn1cc2cc(-c3nc(NCC(c4ccccc4)c4ccccc4)c4ccccc4n3)ccc2n1] | N-(2,2-Diphenylethyl)-2-(2-methyl-2H-indazol-5-yl)quinazolin-4-amine | 456 |
| 67 | 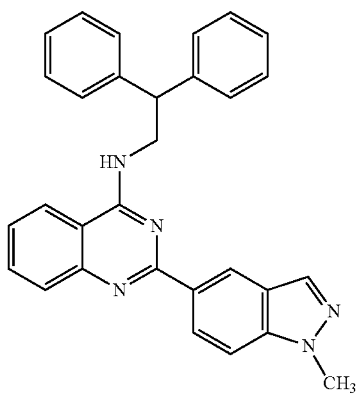 [SMILES: Cn1ncc2cc(-c3nc(NCC(c4ccccc4)c4ccccc4)c4ccccc4n3)ccc21] | N-(2,2-Diphenylethyl)-2-(1-methyl-1H-indazol-5-yl)quinazolin-4-amine | 456 |
| 68 | 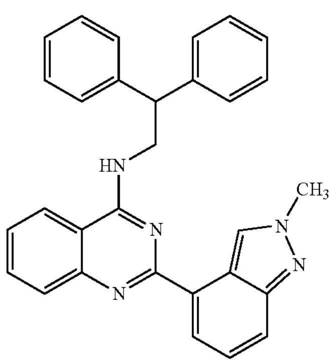 [SMILES: Cn1cc2c(-c3nc(NCC(c4ccccc4)c4ccccc4)c4ccccc4n3)cccc2n1] | N-(2,2-Diphenylethyl)-2-(2-methyl-2H-indazol-4-yl)quinazolin-4-amine | 456 |

TABLE 1-continued

| No. | Structure | Name | M + H |
|---|---|---|---|
| 69 | 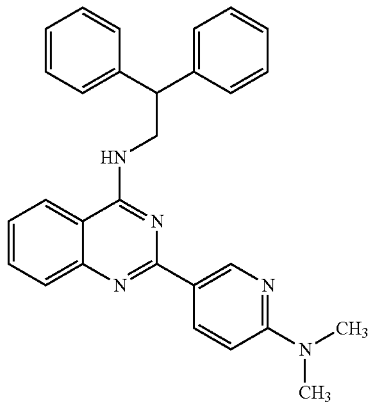 [SMILES: CN(C)c1ccc(-c2nc(NCC(c3ccccc3)c3ccccc3)c3ccccc3n2)cn1] | 2-(6-(Dimethylamino)pyridin-3-yl)-N-(2,2-diphenylethyl)quinazolin-4-amine | 446 |
| 70 | 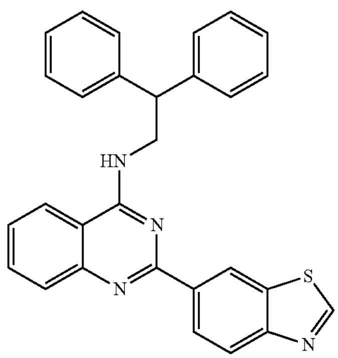 [SMILES: c1ccc(C(CNc2nc(-c3ccc4ncsc4c3)nc3ccccc23)c2ccccc2)cc1] | 2-(Benzo[d]thiazol-6-yl)-N-(2,2-diphenylethyl)quinazolin-4-amine | 459 |
| 71 | 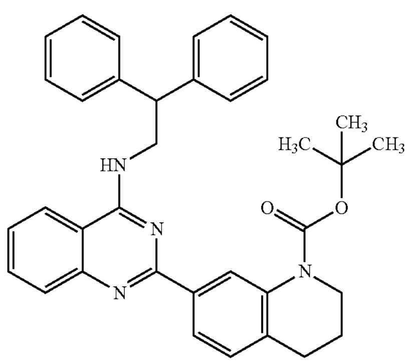 [SMILES: CC(C)(C)OC(=O)N1CCCc2ccc(-c3nc(NCC(c4ccccc4)c4ccccc4)c4ccccc4n3)cc21] | tert-Butyl 7-(4-((2,2-diphenylethyl)amino)quinazolin-2-yl)-3,4-dihydroquinoline-1(2H)-carboxylate | 557 |
| 72 | 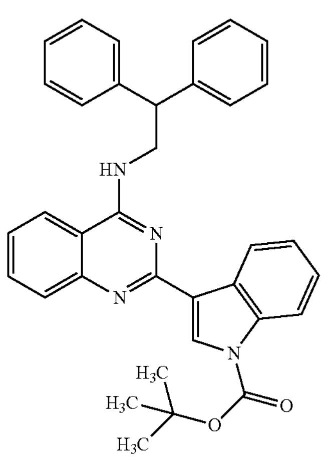 [SMILES: CC(C)(C)OC(=O)n1cc(-c2nc(NCC(c3ccccc3)c3ccccc3)c3ccccc3n2)c2ccccc21] | tert-Butyl 3-(4-((2,2-diphenylethyl)amino)quinazolin-2-yl)-1H-indole-1-carboxylate | 541 |

TABLE 1-continued

| No. | Structure | Name | M + H |
|---|---|---|---|
| 73 | 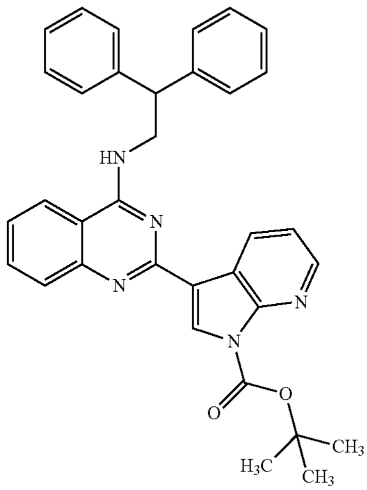 [SMILES: CC(C)(C)OC(=O)n1cc(-c2nc(NCC(c3ccccc3)c3ccccc3)c3ccccc3n2)c2cccnc21] | tert-Butyl 3-(4-((2,2-diphenylethyl)amino)quinazolin-2-yl)-1H-pyrrolo[2,3-b]pyridine-1-carboxylate | 542 |
| 74 | 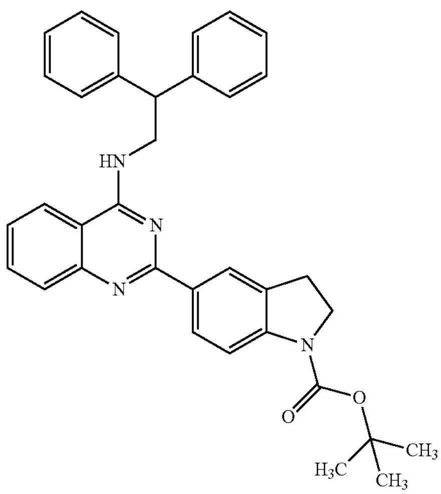 [SMILES: CC(C)(C)OC(=O)N1CCc2cc(-c3nc(NCC(c4ccccc4)c4ccccc4)c4ccccc4n3)ccc21] | tert-Butyl 5-(4-((2,2-diphenylethyl)amino)quinazolin-2-yl)indoline-1-carboxylate | 543 |
| 75 | 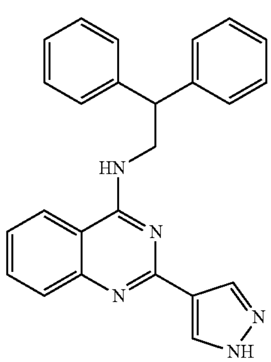 [SMILES: c1ccc(C(CNc2nc(-c3cn[nH]c3)nc3ccccc23)c2ccccc2)cc1] | N-(2,2-Diphenylethyl)-2-(1H-pyrazol-4-yl)quinazolin-4-amine | 392 |

TABLE 1-continued

| No. | Structure | Name | M + H |
|---|---|---|---|
| 76 | 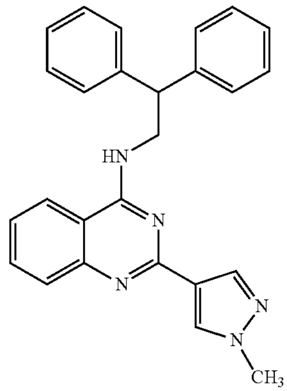 [SMILES: Cn1cc(-c2nc(NCC(c3ccccc3)c3ccccc3)c3ccccc3n2)cn1] | N-(2,2-Diphenylethyl)-2-(1-methyl-1H-pyrazol-4-yl)quinazolin-4-amine | 406 |
| 77 | 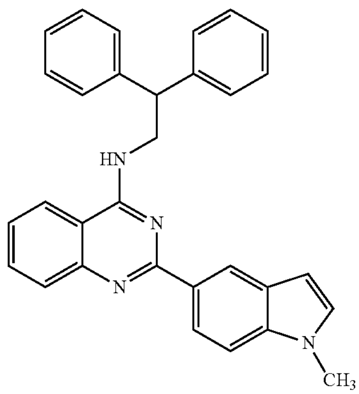 [SMILES: Cn1ccc2cc(-c3nc(NCC(c4ccccc4)c4ccccc4)c4ccccc4n3)ccc21] | N-(2,2-Diphenylethyl)-2-(1-methyl-1H-indol-5-yl)quinazolin-4-amine | 455 |
| 78 | 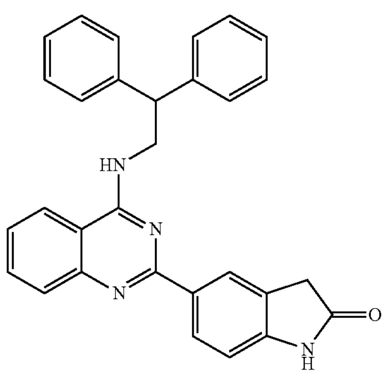 [SMILES: O=C1Cc2cc(-c3nc(NCC(c4ccccc4)c4ccccc4)c4ccccc4n3)ccc2N1] | 5-(4-((2,2-Diphenylethyl)amino)quinazolin-2-yl)indolin-2-one | 457 |
| 79 | 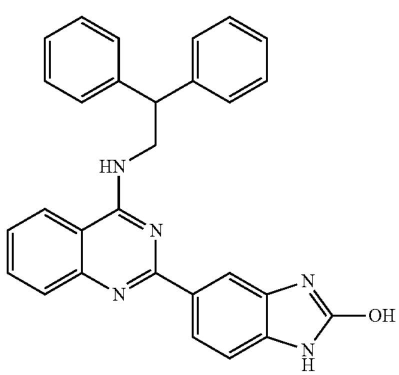 [SMILES: Oc1nc2cc(-c3nc(NCC(c4ccccc4)c4ccccc4)c4ccccc4n3)ccc2[nH]1] | 5-(4-((2,2-Diphenylethyl)amino)quinazolin-2-yl)-1H-benzo[d]imidazol-2-ol | 458 |

TABLE 1-continued

| No. | Structure | Name | M + H |
|---|---|---|---|
| 80 | 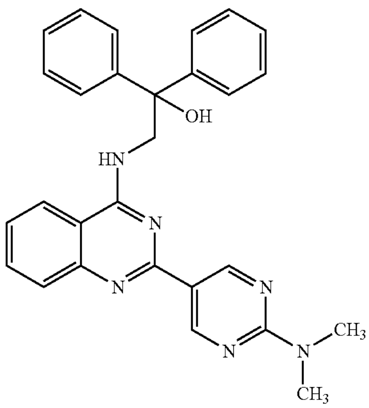 [SMILES: CN(C)c1ncc(-c2nc(NCC(O)(c3ccccc3)c3ccccc3)c3ccccc3n2)cn1] | 2-((2-(2-(Dimethylamino)pyrimidin-5-yl)quinazolin-4-yl)amino)-1,1-diphenylethanol | 463 |
| 81 | 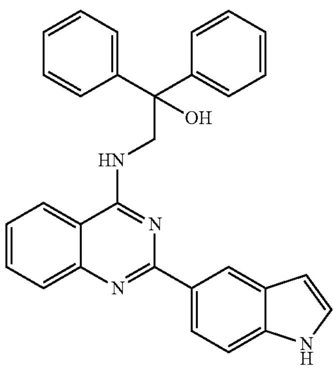 [SMILES: OC(CNc1nc(-c2ccc3[nH]ccc3c2)nc2ccccc12)(c1ccccc1)c1ccccc1] | 2-((2-(1H-Indol-5-yl)quinazolin-4-yl)amino)-1,1-diphenylethanol | 457 |
| 82 | 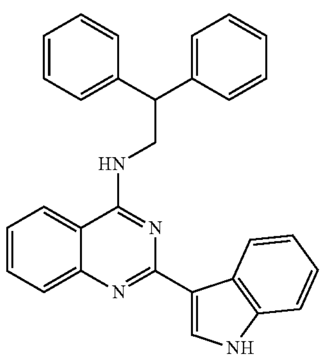 [SMILES: c1ccc(C(CNc2nc(-c3c[nH]c4ccccc34)nc3ccccc23)c2ccccc2)cc1] | N-(2,2-Diphenylethyl)-2-(1H-indol-3-yl)quinazolin-4-amine | 441 |
| 83 | 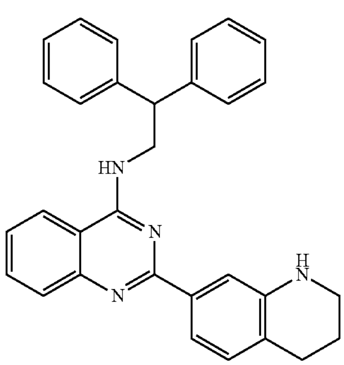 [SMILES: c1ccc(C(CNc2nc(-c3ccc4c(c3)NCCC4)nc3ccccc23)c2ccccc2)cc1] | N-(2,2-Diphenylethyl)-2-(1,2,3,4-tetrahydroquinolin-7-yl)quinazolin-4-amine | 457 |

TABLE 1-continued

| No. | Structure | Name | M + H |
|---|---|---|---|
| 84 | 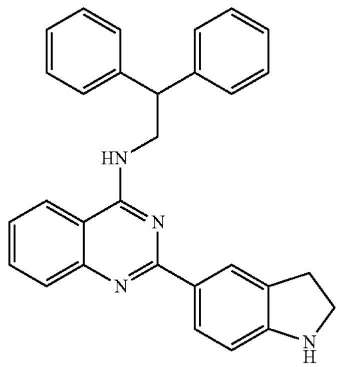 [SMILES: c1ccc(C(CNc2nc(-c3ccc4c(c3)CCN4)nc3ccccc23)c2ccccc2)cc1] | N-(2,2-Diphenylethyl)-2-(indolin-5-yl)quinazolin-4-amine | 443 |
| 85 | 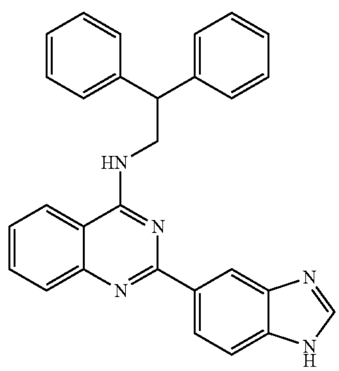 [SMILES: c1ccc(C(CNc2nc(-c3ccc4[nH]cnc4c3)nc3ccccc23)c2ccccc2)cc1] | 2-(1H-Benzo[d]imidazol-5-yl)-N-(2,2-diphenylethyl)quinazolin-4-amine | 442 |
| 86 | 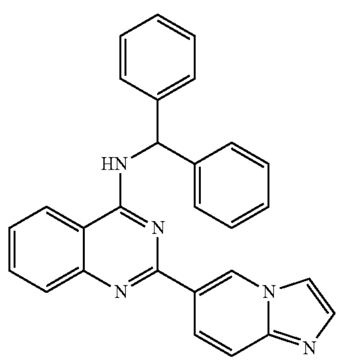 [SMILES: c1ccc(C(Nc2nc(-c3ccc4nccn4c3)nc3ccccc23)c2ccccc2)cc1] | N-Benzhydryl-2-(imidazo[1,2-a]pyridin-6-yl)quinazolin-4-amine | 428 |
| 87 | 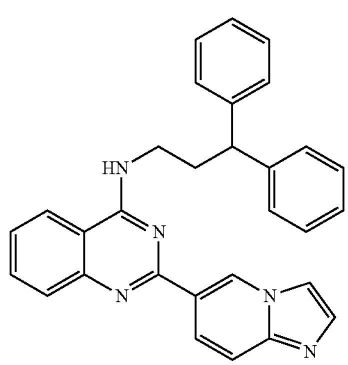 [SMILES: c1ccc(C(CCNc2nc(-c3ccc4nccn4c3)nc3ccccc23)c2ccccc2)cc1] | N-(3,3-Diphenylpropyl)-2-(imidazo[1,2-a]pyridin-6-yl)quinazolin-4-amine | 456 |

TABLE 1-continued

| No. | Structure | Name | M + H |
|---|---|---|---|
| 88 | 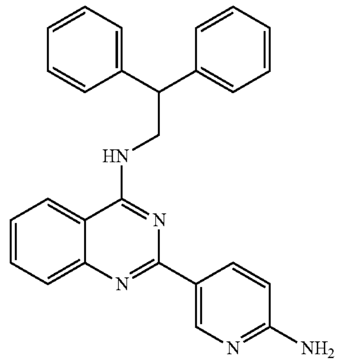 | 2-(6-Aminopyridin-3-yl)-N-(2,2-diphenylethyl)quinazolin-4-amine | 418 |
| 89 | 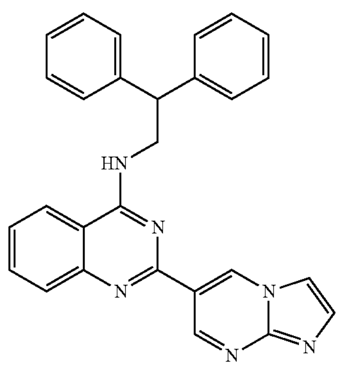 [SMILES: c1ccc(C(CNc2nc(-c3cnc4nccn4c3)nc3ccccc23)c2ccccc2)cc1] | N-(2,2-Diphenylethyl)-2-(imidazo[1,2-a]pyrimidin-6-yl)quinazolin-4-amine | 443 |
| 90 | 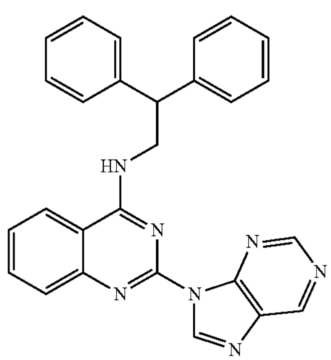 [SMILES: c1ccc(C(CNc2nc(-n3cnc4cncnc43)nc3ccccc23)c2ccccc2)cc1] | N-(2,2-Diphenylethyl)-2-(9H-purin-9-yl)quinazolin-4-amine | 444 |
| 91 | 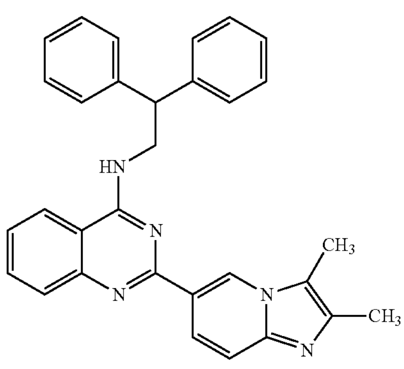 [SMILES: Cc1nc2ccc(-c3nc(NCC(c4ccccc4)c4ccccc4)c4ccccc4n3)cn2c1C] | 2-(2,3-Dimethylimidazo[1,2-a]pyridin-6-yl)-N-(2,2-diphenylethyl)quinazolin-4-amine | 470 |

TABLE 1-continued

| No. | Name | M + H |
|---|---|---|
| 92 | N-Benzhydryl-2-(6-(dimethylamino)pyridin-3-yl)quinazolin-4-amine | 432 |
| 93 | 2-(6-(Dimethylamino)pyridin-3-yl)-N-(3,3-diphenylpropyl)quinazolin-4-amine | 460 |
| 94 | 2-(Imidazo[1,2-a]pyridin-6-yl)-N-(2-phenyl-2-(pyridin-2-yl)ethyl)quinazolin-4-amine | 443 |
| 95 | 2-(2-Aminopyrimidin-5-yl)-N-(2-phenyl-2-(pyridin-2-yl)ethyl)quinazolin-4-amine | 420 |

TABLE 1-continued

| No. | Structure | Name | M + H |
|---|---|---|---|
| 96 | 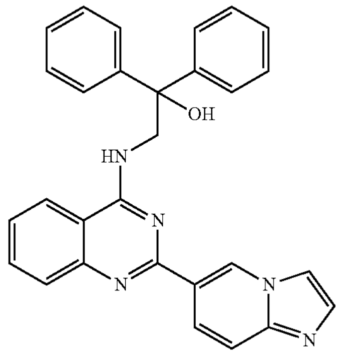 [SMILES: OC(CNc1nc(-c2ccc3nccn3c2)nc2ccccc12)(c1ccccc1)c1ccccc1] | 2-((2-(Imidazo[1,2-a]pyridin-6-yl)quinazolin-4-yl)amino)-1,1-diphenylethanol | 458 |
| 97 | 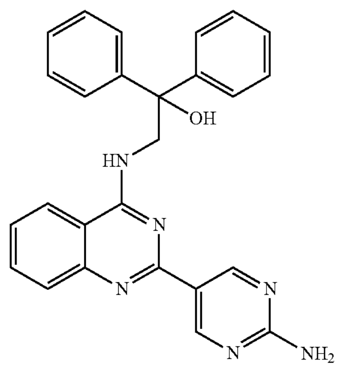 [SMILES: Nc1ncc(-c2nc(NCC(O)(c3ccccc3)c3ccccc3)c3ccccc3n2)cn1] | 2-((2-(2-Aminopyrimidin-5-yl)quinazolin-4-yl)amino)-1,1-diphenylethanol | 435 |
| 98 | 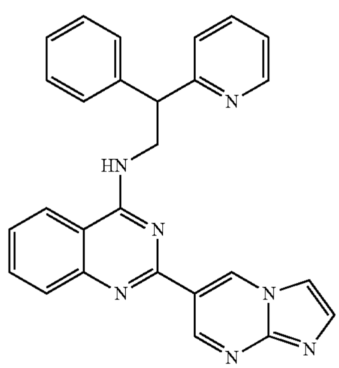 [SMILES: c1ccc(C(CNc2nc(-c3cnc4nccn4c3)nc3ccccc23)c2ccccn2)cc1] | 2-(Imidazo[1,2-a]pyrimidin-6-yl)-N-(2-phenyl-2-(pyridin-2-yl)ethyl)quinazolin-4-amine | 444 |
| 99 | 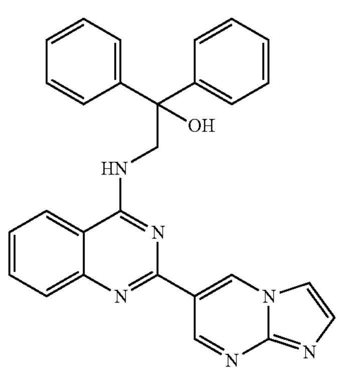 [SMILES: OC(CNc1nc(-c2cnc3nccn3c2)nc2ccccc12)(c1ccccc1)c1ccccc1] | 2-((2-(Imidazo[1,2-a]pyrimidin-6-yl)quinazolin-4-yl)amino)-1,1-diphenylethanol | 459 |

TABLE 1-continued

| No. | Structure | Name | M + H |
|-----|-----------|------|-------|
| 100 | 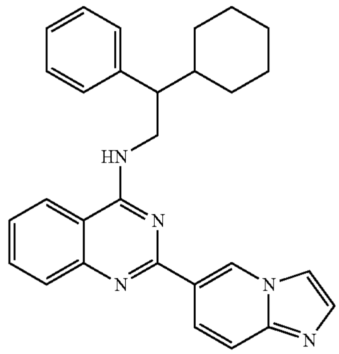 | N-(2-Cyclohexyl-2-phenylethyl)-2-(imidazo[1,2-a]pyridin-6-yl)quinazolin-4-amine | 448 |
| 101 | 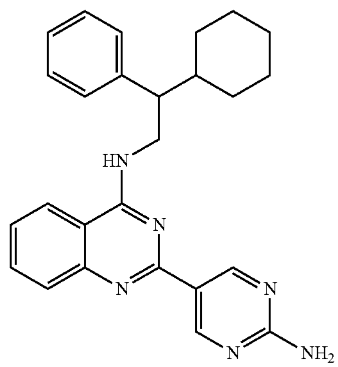 [SMILES: Nc1ncc(-c2nc(NCC(c3ccccc3)C3CCCCC3)c3ccccc3n2)cn1] | 2-(2-Aminopyrimidin-5-yl)-N-(2-cyclohexyl-2-phenylethyl)quinazolin-4-amine | 425 |
| 102 | 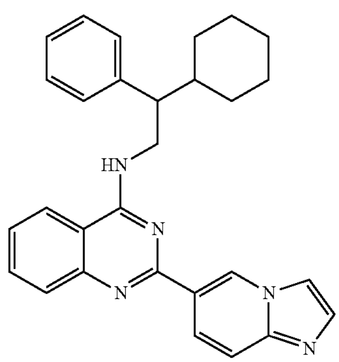 [SMILES: c1ccc(C(CNc2nc(-c3ccc4nccn4c3)nc3ccccc23)C2CCCCC2)cc1] | N-(2-Cyclohexyl-2-phenylethyl)-2-(imidazo[1,2-a]pyrimidin-6-yl)quinazolin-4-amine | 449 |
| 103 | 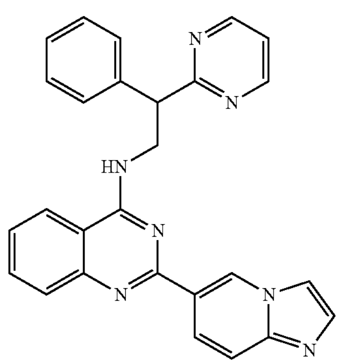 [SMILES: c1ccc(C(CNc2nc(-c3ccc4nccn4c3)nc3ccccc23)c2ncccn2)cc1] | 2-(Imidazo[1,2-a]pyridin-6-yl)-N-(2-phenyl-2-(pyrimidin-2-yl)ethyl)quinazolin-4-amine | 444 |

TABLE 1-continued

| No. | Structure | Name | M + H |
|---|---|---|---|
| 104 | 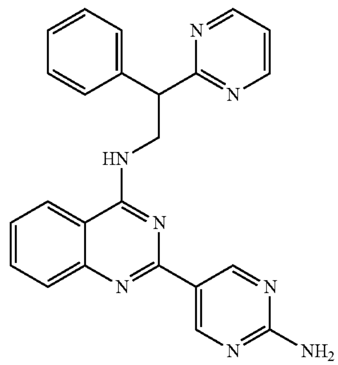 [SMILES: Nc1ncc(-c2nc(NCC(c3ccccc3)c3ncccn3)c3ccccc3n2)cn1] | 2-(2-Aminopyrimidin-5-yl)-N-(2-phenyl-2-(pyrimidin-2-yl)ethyl)quinazolin-4-amine | 421 |
| 105 | 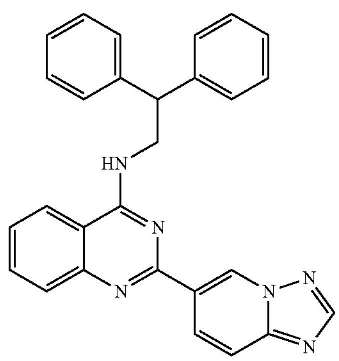 [SMILES: c1ccc(C(CNc2nc(-c3ccc4ncnn4c3)nc3ccccc23)c2ccccc2)cc1] | 2-([1,2,4]Triazolo[1,5-a]pyridin-6-yl)-N-(2,2-diphenylethyl)quinazolin-4-amine | 443 |
| 106 | 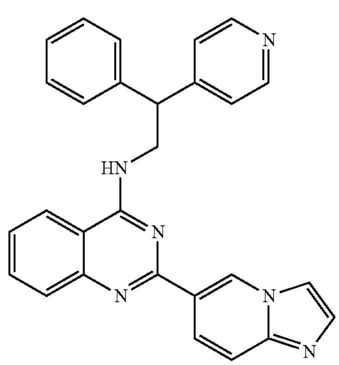 [SMILES: c1ccc(C(CNc2nc(-c3ccc4nccn4c3)nc3ccccc23)c2ccncc2)cc1] | 2-(Imidazo[1,2-a]pyridin-6-yl)-N-(2-phenyl-2-(pyridin-4-yl)ethyl)quinazolin-4-amine | 443 |
| 107 | 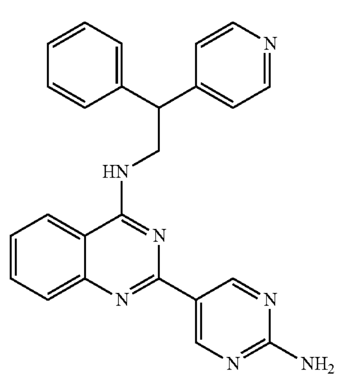 [SMILES: Nc1ncc(-c2nc(NCC(c3ccccc3)c3ccncc3)c3ccccc3n2)cn1] | 2-(2-Aminopyrimidin-5-yl)-N-(2-phenyl-2-(pyridin-4-yl)ethyl)quinazolin-4-amine | 420 |

TABLE 1-continued

| No. | Structure | Name | M + H |
|---|---|---|---|
| 108 | 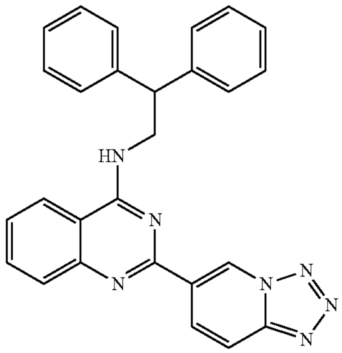 [SMILES: c1ccc(C(CNc2nc(-c3ccc4nnnn4c3)nc3ccccc23)c2ccccc2)cc1] | N-(2,2-Diphenylethyl)-2-(tetrazolo[1,5-a]pyridin-6-yl)quinazolin-4-amine | 444 |
| 109 | 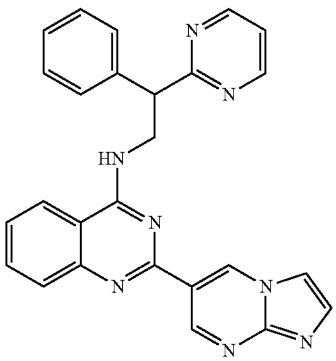 [SMILES: c1ccc(C(CNc2nc(-c3cnc4nccn4c3)nc3ccccc23)c2ncccn2)cc1] | 2-(Imidazo[1,2-a]pyrimidin-6-yl)-N-(2-phenyl-2-(pyrimidin-2-yl)ethyl)quinazolin-4-amine | 445 |
| 110 | 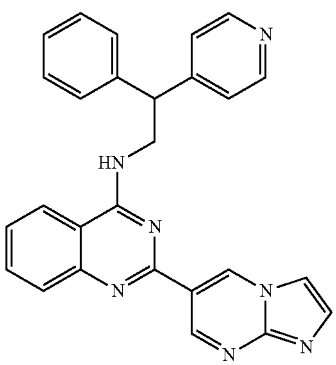 [SMILES: c1ccc(C(CNc2nc(-c3cnc4nccn4c3)nc3ccccc23)c2ccncc2)cc1] | 2-(Imidazo[1,2-a]pyrimidin-6-yl)-N-(2-phenyl-2-(pyridin-4-yl)ethyl)quinazolin-4-amine | 444 |
| 111 | 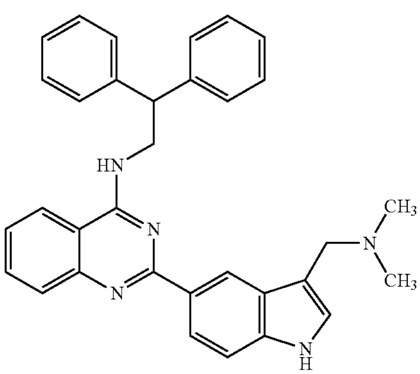 [SMILES: CN(C)Cc1c[nH]c2ccc(-c3nc(NCC(c4ccccc4)c4ccccc4)c4ccccc4n3)cc12] | 2-(3-((Dimethylamino)methyl)-1H-indol-5-yl)-N-(2,2-diphenylethyl)quinazolin-4-amine | 498 |

TABLE 1-continued

| No. | Structure | Name | M + H |
|---|---|---|---|
| 112 | 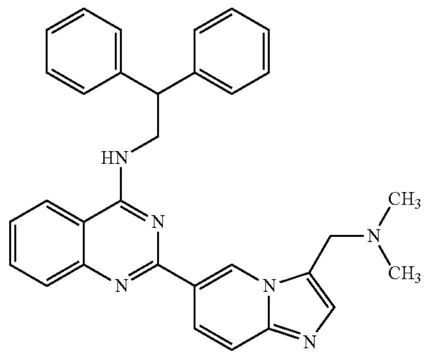 [SMILES: CN(C)Cc1cnc2ccc(-c3nc(NCC(c4ccccc4)c4ccccc4)c4ccccc4n3)cn12] | 2-(3-((Dimethylamino)methyl)imidazo[1,2-a]pyridin-6-yl)-N-(2,2-diphenylethyl)quinazolin-4-amine | 499 |
| 113 | 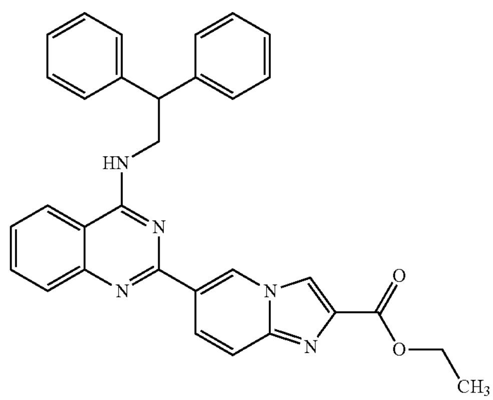 [SMILES: CCOC(=O)c1cn2cc(-c3nc(NCC(c4ccccc4)c4ccccc4)c4ccccc4n3)ccc2n1] | Ethyl 6-(4-((2,2-Diphenylethyl)amino)quinazolin-2-yl)imidazo[1,2-a]pyridine-3-carboxylate | 514 |
| 114 | 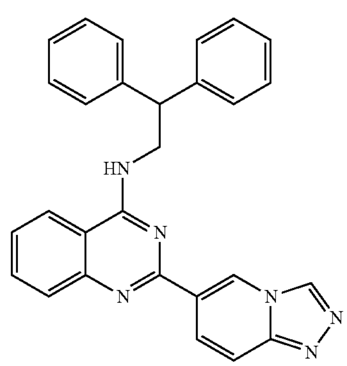 [SMILES: c1ccc(C(CNc2nc(-c3ccc4nncn4c3)nc3ccccc23)c2ccccc2)cc1] | 2-([1,2,4]Triazolo[4,3-a]pyridin-6-yl)-N-(2,2-diphenylethyl)quinazolin-4-amine | 443 |
| 115 | 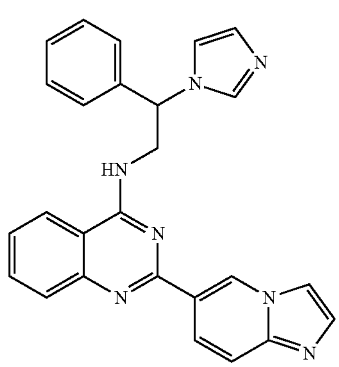 [SMILES: c1ccc(C(CNc2nc(-c3ccc4nccn4c3)nc3ccccc23)n2ccnc2)cc1] | N-(2-(1H-Imidazol-1-yl)-2-phenylethyl)-2-(imidazo[1,2-a]pyridin-6-yl)quinazolin-4-amine | 432 |

TABLE 1-continued

| No. | Structure | Name | M + H |
|---|---|---|---|
| 116 | 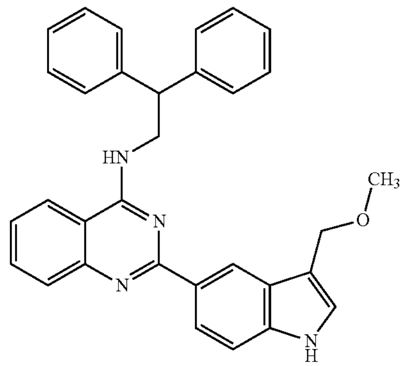 [SMILES: COCc1c[nH]c2ccc(-c3nc(NCC(c4ccccc4)c4ccccc4)c4ccccc4n3)cc12] | N-(2,2-Diphenylethyl)-2-(3-(methoxymethyl)-1H-indol-5-yl)quinazolin-4-amine | 485 |
| 117 | 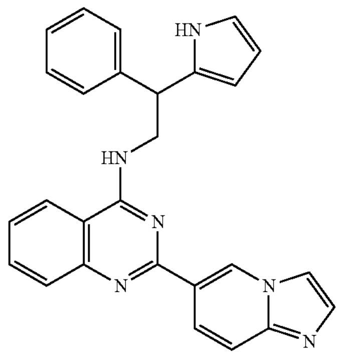 [SMILES: c1ccc(C(CNc2nc(-c3ccc4nccn4c3)nc3ccccc23)c2ccc[nH]2)cc1] | 2-(Imidazo[1,2-a]pyridin-6-yl)-N-(2-phenyl-2-(1H-pyrrol-2-yl)ethyl)quinazolin-4-amine | 431 |
| 118 | 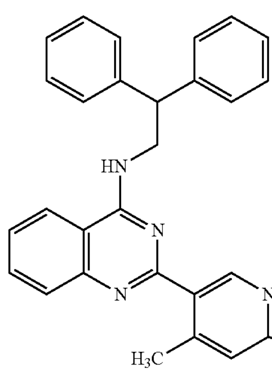 | N-(2,2-Diphenylethyl)-2-(7-methylimidazo[1,2-a]pyridin-6-yl)quinazolin-4-amine | 456 |
| 119 | 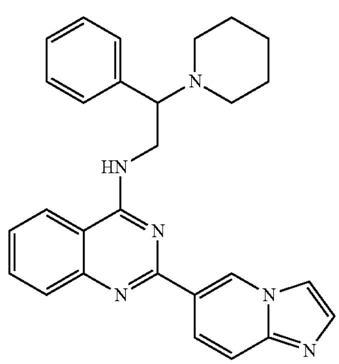 [SMILES: c1ccc(C(CNc2nc(-c3ccc4nccn4c3)nc3ccccc23)N2CCCCC2)cc1] | 2-(Imidazo[1,2-a]pyridin-6-yl)-N-(2-phenyl-2-(piperidin-1-yl)ethyl)quinazolin-4-amine | 449 |

TABLE 1-continued
| No. | Structure | Name | M + H |
|---|---|---|---|
| 120 | 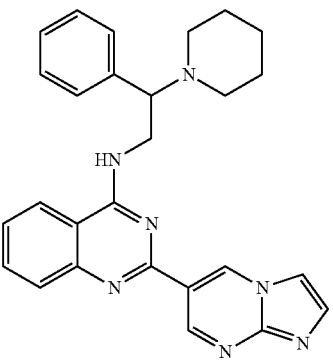 [SMILES: c1ccc(C(CNc2nc(-c3cnc4nccn4c3)nc3ccccc23)N2CCCCC2)cc1] | 2-(Imidazo[1,2-a]pyrimidin-6-yl)-N-(2-phenyl-2-(piperidin-1-yl)ethyl)quinazolin-4-amine | 450 |
| 121 | 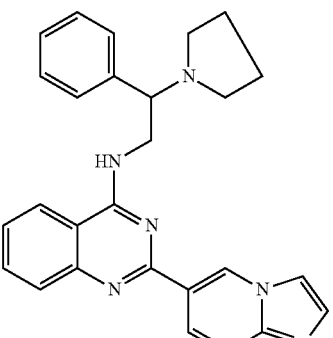 | 2-(Imidazo[1,2-a]pyridin-6-yl)-N-(2-phenyl-2-(pyrrolidin-1-yl)ethyl)quinazolin-4-amine | 435 |
| 122 | 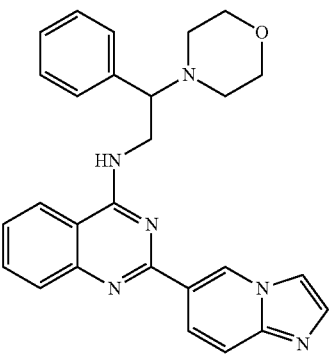 [SMILES: c1ccc(C(CNc2nc(-c3ccc4nccn4c3)nc3ccccc23)N2CCOCC2)cc1] | 2-(Imidazo[1,2-a]pyridin-6-yl)-N-(2-morpholino-2-phenylethyl)quinazolin-4-amine | 451 |
| 123 | 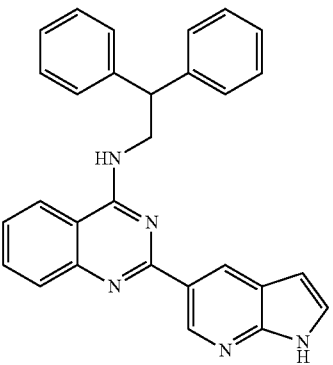 [SMILES: c1ccc(C(CNc2nc(-c3cnc4[nH]ccc4c3)nc3ccccc23)c2ccccc2)cc1] | N-(2,2-Diphenylethyl)-2-(1H-pyrrolo[2,3-b]pyridin-5-yl)quinazolin-4-amine | 442 |

TABLE 1-continued
| No. | Structure | Name | M + H |
|---|---|---|---|
| 124 | 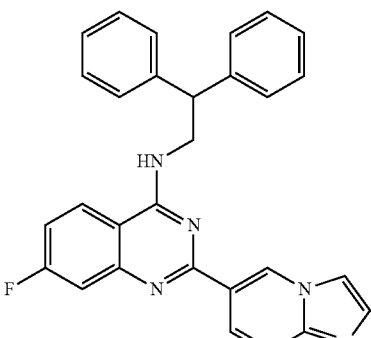 | N-(2,2-Diphenylethyl)-7-fluoro-2-(imidazo[1,2-a]pyridin-6-yl)quinazolin-4-amine hydrochloride | 460 |
| 125 | 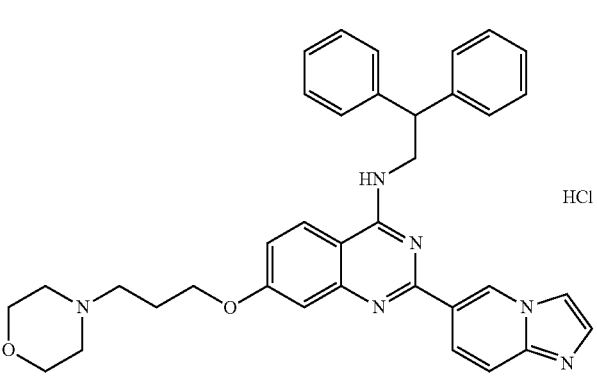 [SMILES: c1ccc(C(CNc2nc(-c3ccc4nccn4c3)nc3cc(OCCCN4CCOCC4)ccc23)c2ccccc2)cc1 ; Cl] | N-(2,2-Diphenylethyl)-2-(imidazo[1,2-a]pyridin-6-yl)-7-(3-morpholinopropoxy)quinazolin-4-amine hydrochloride | 585 |
| 126 | 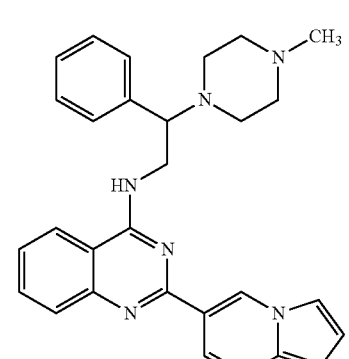 | 2-(Imidazo[1,2-a]pyridin-6-yl)-N-(2-(4-methylpiperazin-1-yl)-2-phenylethyl)quinazolin-4-amine | 464 |
| 127 | 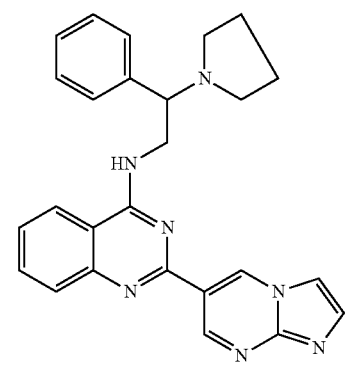 [SMILES: c1ccc(C(CNc2nc(-c3cnc4nccn4c3)nc3ccccc23)N2CCCC2)cc1] | 2-(Imidazo[1,2-a]pyrimidin-6-yl)-N-(2-phenyl-2-(pyrrolidin-1-yl)ethyl)quinazolin-4-amine | 436 |

TABLE 1-continued

| No. | Structure | Name | M + H |
|---|---|---|---|
| 128 | 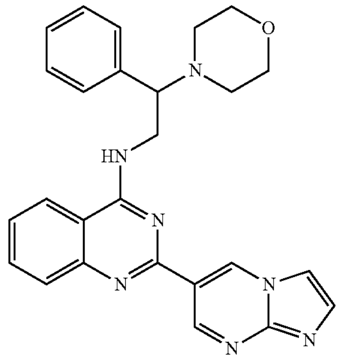 [SMILES: c1ccc(C(CNc2nc(-c3cnc4nccn4c3)nc3ccccc23)N2CCOCC2)cc1] | 2-(Imidazo[1,2-a]pyrimidin-6-yl)-N-(2-morpholino-2-phenylethyl)quinazolin-4-amine | 452 |
| 129 | 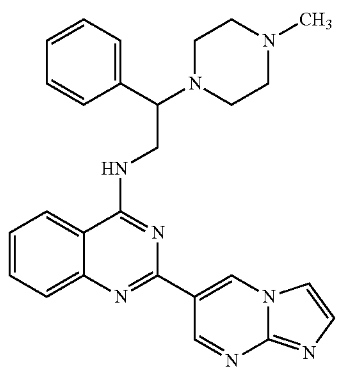 [SMILES: CN1CCN(C(CNc2nc(-c3cnc4nccn4c3)nc3ccccc23)c2ccccc2)CC1] | 2-(Imidazo[1,2-a]pyrimidin-6-yl)-N-(2-(4-methylpiperazin-1-yl)-2-phenylethyl)quinazolin-4-amine | 465 |
| 130 | 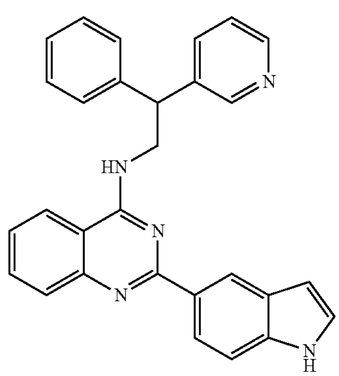 [SMILES: c1ccc(C(CNc2nc(-c3ccc4[nH]ccc4c3)nc3ccccc23)c2cccnc2)cc1] | 2-(1H-Indol-5-yl)-N-(2-phenyl-2-(pyridin-3-yl)ethyl)quinazolin-4-amine | 442 |
| 131 | 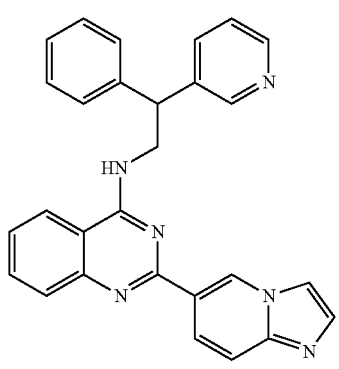 [SMILES: c1ccc(C(CNc2nc(-c3ccc4nccn4c3)nc3ccccc23)c2cccnc2)cc1] | 2-(Imidazo[1,2-a]pyridin-6-yl)-N-(2-phenyl-2-(pyridin-3-yl)ethyl)quinazolin-4-amine | 443 |

TABLE 1-continued

| No. | Structure | Name | M + H |
|---|---|---|---|
| 132 | 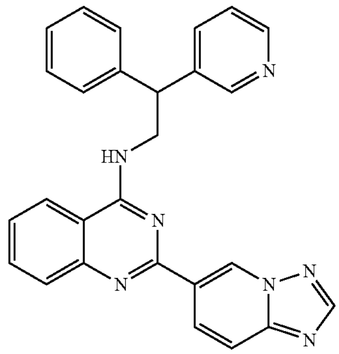 [SMILES: c1ccc(C(CNc2nc(-c3ccc4ncnn4c3)nc3ccccc23)c2cccnc2)cc1] | 2-([1,2,4]Triazolo[1,5-a]pyridin-6-yl)-N-(2-phenyl-2-(pyridin-3-yl)ethyl)quinazolin-4-amine | 444 |
| 133 | 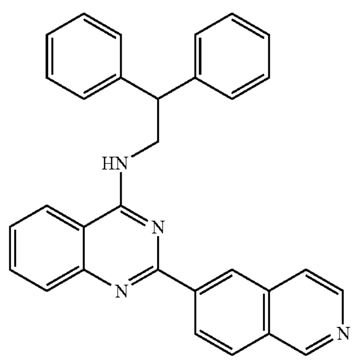 [SMILES: c1ccc(C(CNc2nc(-c3ccc4cnccc4c3)nc3ccccc23)c2ccccc2)cc1] | N-(2,2-Diphenylethyl)-2-(isoquinolin-6-yl)quinazolin-4-amine | 453 |
| 134 | 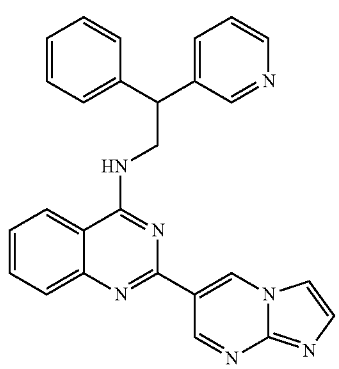 [SMILES: c1ccc(C(CNc2nc(-c3cnc4nccn4c3)nc3ccccc23)c2cccnc2)cc1] | 2-(Imidazo[1,2-a]pyrimidin-6-yl)-N-(2-phenyl-2-(pyridin-3-yl)ethyl)quinazolin-4-amine | 444 |
| 135 | 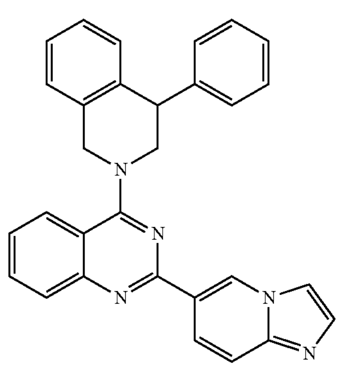 [SMILES: c1ccc(C2CN(c3nc(-c4ccc5nccn5c4)nc4ccccc34)Cc3ccccc32)cc1] | 2-(Imidazo[1,2-a]pyridin-6-yl)-4-(4-phenyl-3,4-dihydroisoquinolin-2(1H)-yl)quinazoline | 454 |

TABLE 1-continued

| No. | Structure | Name | M + H |
|---|---|---|---|
| 136 | 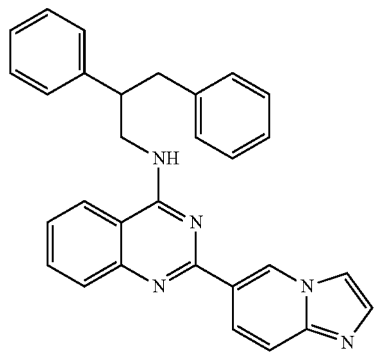 [SMILES: c1ccc(CC(CNc2nc(-c3ccc4nccn4c3)nc3ccccc23)c2ccccc2)cc1] | N-(2,3-Diphenylpropyl)-2-(imidazo[1,2-a]pyridin-6-yl)quinazolin-4-amine | 456 |
| 137 | 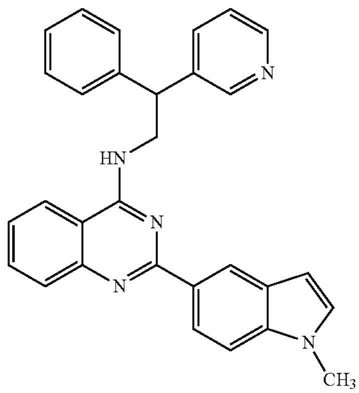 [SMILES: Cn1ccc2cc(-c3nc(NCC(c4ccccc4)c4cccnc4)c4ccccc4n3)ccc21] | 2-(1-Methyl-1H-indol-5-yl)-N-(2-phenyl-2-(pyridin-3-yl)ethyl)quinazolin-4-amine | 456 |
| 138 | 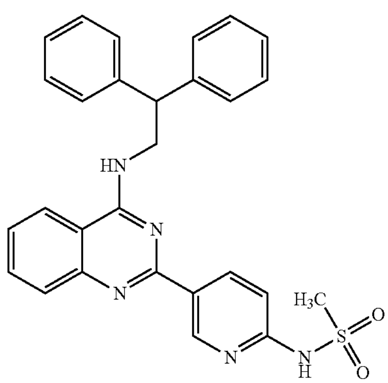 [SMILES: CS(=O)(=O)Nc1ccc(-c2nc(NCC(c3ccccc3)c3ccccc3)c3ccccc3n2)cn1] | N-(5-(4-((2,2-Diphenylethyl)amino)quinazolin-2-yl)pyridin-2-yl)methanesulfonamide | 496 |
| 139 | 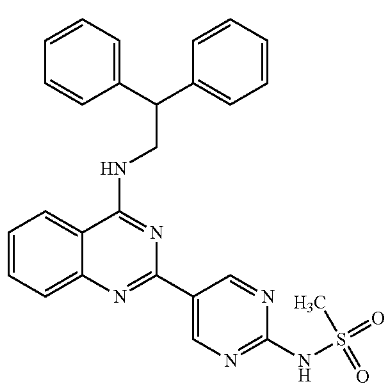 [SMILES: CS(=O)(=O)Nc1ncc(-c2nc(NCC(c3ccccc3)c3ccccc3)c3ccccc3n2)cn1] | N-(5-(4-((2,2-Diphenylethyl)amino)quinazolin-2-yl)pyrimidin-2-yl)methanesulfonamide | 497 |

TABLE 1-continued
| No. | Structure | Name | M + H |
|---|---|---|---|
| 140 | 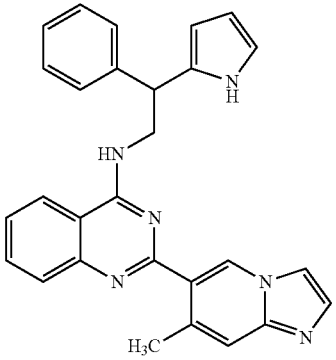 | 2-(7-Methylimidazo[1,2-a]pyridin-6-yl)-N-(2-phenyl-2-(1H-pyrrol-2-yl)ethyl)quinazolin-4-amine | 445 |
| 141 | 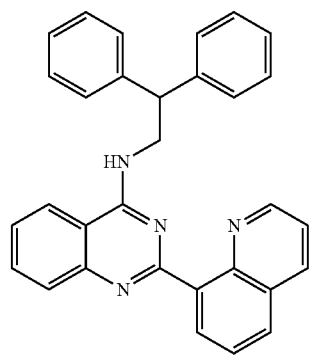 [SMILES: c1ccc(C(CNc2nc(-c3cccc4cccnc34)nc3ccccc23)c2ccccc2)cc1] | N-(2,2-Diphenylethyl)-2-(quinolin-8-yl)quinazolin-4-amine | 453 |
| 142 | 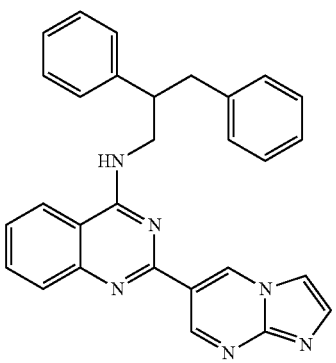 [SMILES: c1ccc(CC(CNc2nc(-c3cnc4nccn4c3)nc3ccccc23)c2ccccc2)cc1] | N-(2,3-Diphenylpropyl)-2-(imidazo[1,2-a]pyrimidin-6-yl)quinazolin-4-amine | 457 |
| 143 | 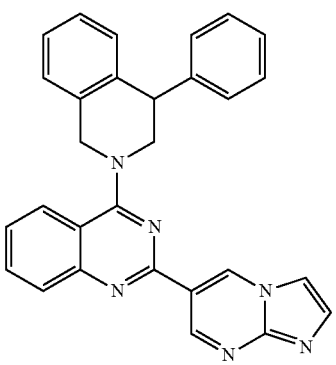 [SMILES: c1ccc(C2CN(c3nc(-c4cnc5nccn5c4)nc4ccccc34)Cc3ccccc32)cc1] | 2-(Imidazo[1,2-a]pyrimidin-6-yl)-4-(4-phenyl-3,4-dihydroisoquinolin-2(1H)-yl)quinazoline | 455 |

TABLE 1-continued

| No. | Structure | Name | M + H |
|---|---|---|---|
| 144 | 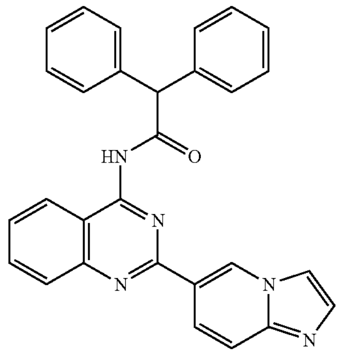 [SMILES: O=C(Nc1nc(-c2ccc3nccn3c2)nc2ccccc12)C(c1ccccc1)c1ccccc1] | N-(2-(Imidazo[1,2-a]pyridin-6-yl)quinazolin-4-yl)-2,2-diphenylacetamide | 456 |
| 145 | 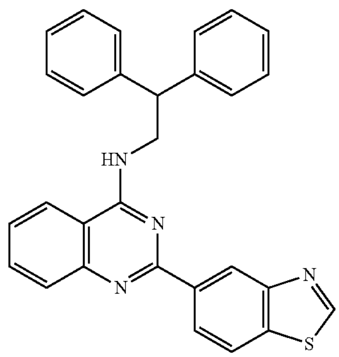 [SMILES: c1ccc(C(CNc2nc(-c3ccc4scnc4c3)nc3ccccc23)c2ccccc2)cc1] | 2-(Benzo[d]thiazol-5-yl)-N-(2,2-diphenylethyl)quinazolin-4-amine | 459 |
| 146 | 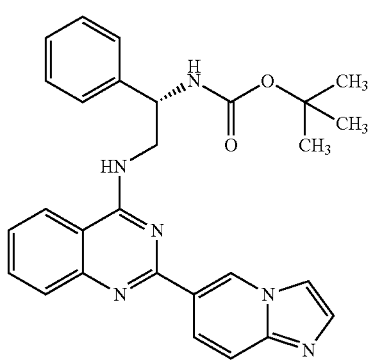 [SMILES: CC(C)(C)OC(=O)N[C@H](CNc1nc(-c2ccc3nccn3c2)nc2ccccc12)c1ccccc1] | (S)-tert-Butyl (2-((2-(imidazo[1,2-a]pyridin-6-yl)quinazolin-4-yl)amino)-1-phenylethyl)carbamate | 481 |
| 147 | 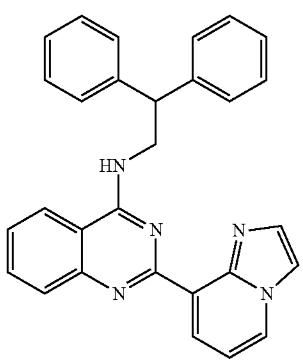 [SMILES: c1ccc(C(CNc2nc(-c3cccn4ccnc34)nc3ccccc23)c2ccccc2)cc1] | N-(2,2-Diphenylethyl)-2-(imidazo[1,2-a]pyridin-8-yl)quinazolin-4-amine | 442 |

| No. | Structure | Name | M + H |
|---|---|---|---|
| 148 | 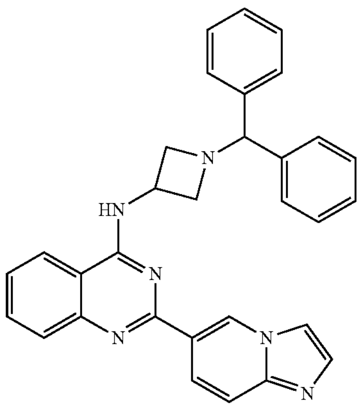 [SMILES: c1ccc(C(c2ccccc2)N2CC(Nc3nc(-c4ccc5nccn5c4)nc4ccccc34)C2)cc1] | N-(1-Benzhydrylazetidin-3-yl)-2-(imidazo[1,2-a]pyridin-6-yl)quinazolin-4-amine | 483 |
| 149 | 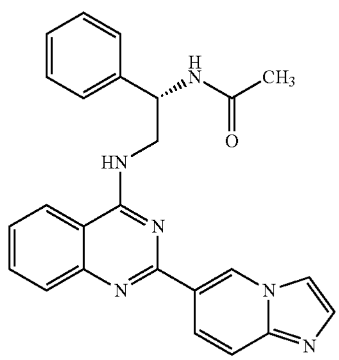 [SMILES: CC(=O)N[C@H](CNc1nc(-c2ccc3nccn3c2)nc2ccccc12)c1ccccc1] | (S)-N-(2-((2-(Imidazo[1,2-a]pyridin-6-yl)quinazolin-4-yl)amino)-1-phenylethyl)acetamide | 423 |
| 150 | 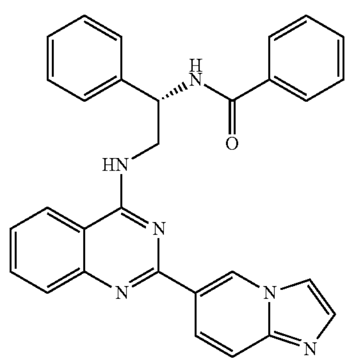 [SMILES: O=C(N[C@H](CNc1nc(-c2ccc3nccn3c2)nc2ccccc12)c1ccccc1)c1ccccc1] | (S)-N-(2-((2-(Imidazo[1,2-a]pyridin-6-yl)quinazolin-4-yl)amino)-1-phenylethyl)benzamide | 484 |
| 151 | 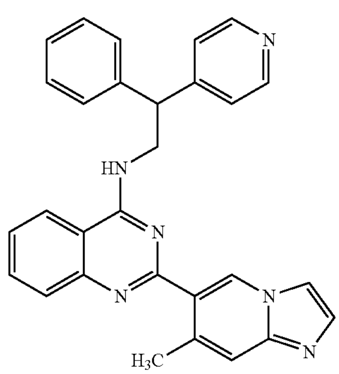 [SMILES: Cc1cc2nccn2cc1-c1nc(NCC(c2ccccc2)c2ccncc2)c2ccccc2n1] | 2-(7-Methylimidazo[1,2-a]pyridin-6-yl)-N-(2-phenyl-2-(pyridin-4-yl)ethyl)quinazolin-4-amine | 457 |

TABLE 1-continued

| No. | Structure | Name | M + H |
|---|---|---|---|
| 152 | 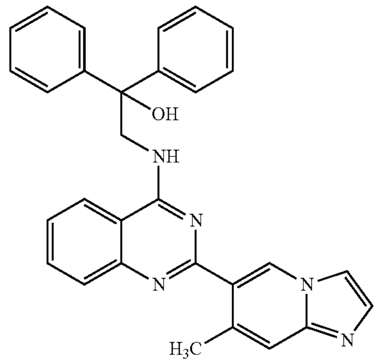 [SMILES: Cc1cc2nccn2cc1-c1nc(NCC(O)(c2ccccc2)c2ccccc2)c2ccccc2n1] | 2-((2-(7-Methylimidazo[1,2-a]pyridin-6-yl)quinazolin-4-yl)amino)-1,1-diphenylethanol | 472 |
| 153 | 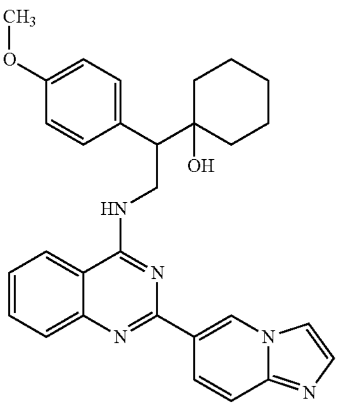 [SMILES: COc1ccc(C(CNc2nc(-c3ccc4nccn4c3)nc3ccccc23)C2(O)CCCCC2)cc1] | 1-(2-((2-(Imidazo[1,2-a]pyridin-6-yl)quinazolin-4-yl)amino)-1-(4-methoxyphenyl)ethyl)cyclohexanol | 494 |
| 154 | 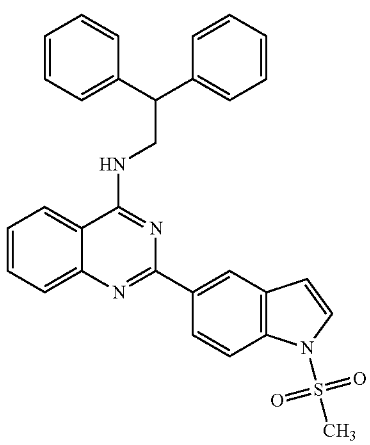 [SMILES: CS(=O)(=O)n1ccc2cc(-c3nc(NCC(c4ccccc4)c4ccccc4)c4ccccc4n3)ccc21] | N-(2,2-Diphenylethyl)-2-(1-(methylsulfonyl)-1H-indol-5-yl)quinazolin-4-amine | 519 |
| 155 | 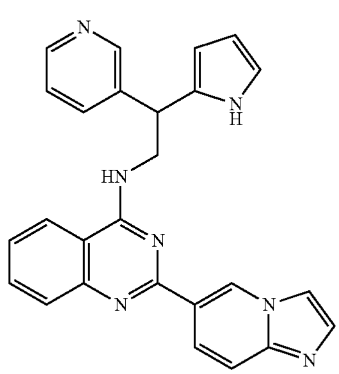 [SMILES: c1cncc(C(CNc2nc(-c3ccc4nccn4c3)nc3ccccc23)c2ccc[nH]2)c1] | 2-(Imidazo[1,2-a]pyridin-6-yl)-N-(2-(pyridin-3-yl)-2-(1H-pyrrol-2-yl)ethyl)quinazolin-4-amine | 432 |

TABLE 1-continued
| No. | Structure | Name | M + H |
|---|---|---|---|
| 156 | 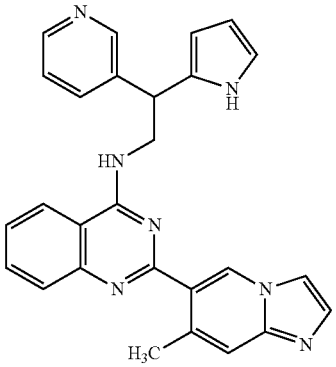 [SMILES: Cc1cc2nccn2cc1-c1nc(NCC(c2cccnc2)c2ccc[nH]2)c2ccccc2n1] | 2-(7-Methylimidazo[1,2-a]pyridin-6-yl)-N-(2-(pyridin-3-yl)-2-(1H-pyrrol-2-yl)ethyl)quinazolin-4-amine | 446 |
| 157 | 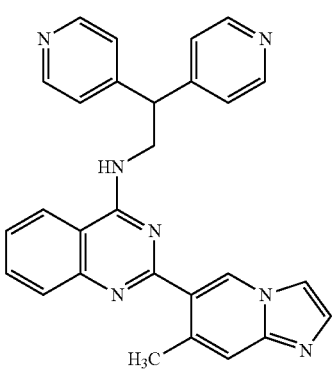 [SMILES: Cc1cc2nccn2cc1-c1nc(NCC(c2ccncc2)c2ccncc2)c2ccccc2n1] | N-(2,2-Di(pyridin-4-yl)ethyl)-2-(7-methylimidazo[1,2-a]pyridin-6-yl)quinazolin-4-amine | 458 |
| 158 | 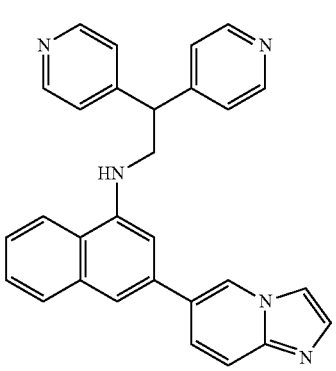 [SMILES: c1ccc2c(NCC(c3ccncc3)c3ccncc3)cc(-c3ccc4nccn4c3)cc2c1] | N-(2,2-Di(pyridin-4-yl)ethyl)-2-(imidazo[1,2-a]pyridin-6-yl)quinazolin-4-amine | 444 |
| 159 | 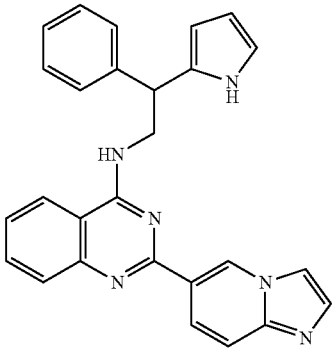 [SMILES: c1ccc(C(CNc2nc(-c3ccc4nccn4c3)nc3ccccc23)c2ccc[nH]2)cc1] | 2-(Imidazo[1,2-a]pyridin-6-yl)-N-(2-(pyridin-2-yl)-2-(1H-pyrrol-2-yl)ethyl)quinazolin-4-amine | 432 |

TABLE 1-continued

| No. | Structure | Name | M + H |
|---|---|---|---|
| 160 | 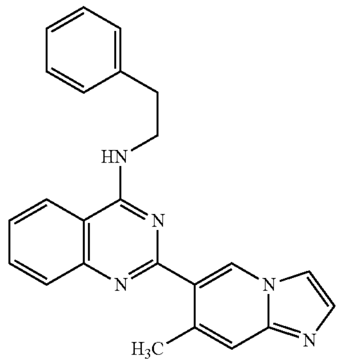 [SMILES: Cc1cc2nccn2cc1-c1nc(NCCc2ccccc2)c2ccccc2n1] | 2-(7-Methylimidazo[1,2-a]pyridin-6-yl)-N-phenethylquinazolin-4-amine | 380 |
| 161 | 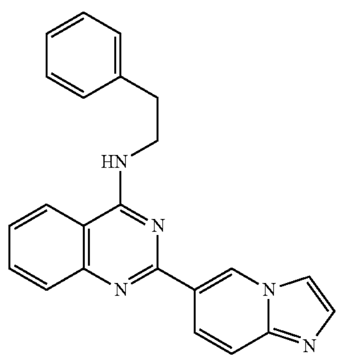 [SMILES: c1ccc(CCNc2nc(-c3ccc4nccn4c3)nc3ccccc23)cc1] | 2-(Imidazo[1,2-a]pyridin-6-yl)-N-phenethylquinazolin-4-amine | 366 |
| 162 | 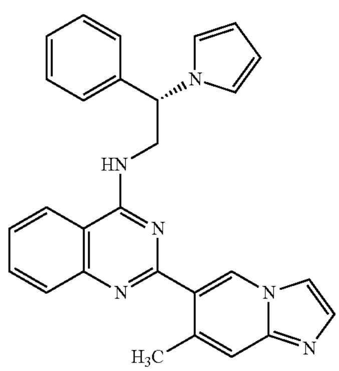 [SMILES: Cc1cc2nccn2cc1-c1nc(NC[C@H](c2ccccc2)n2cccc2)c2ccccc2n1] | (S)-2-(7-Methylimidazo[1,2-a]pyridin-6-yl)-N-(2-phenyl-2-(1H-pyrrol-1-yl)ethyl)quinazolin-4-amine | 445 |
| 163 | 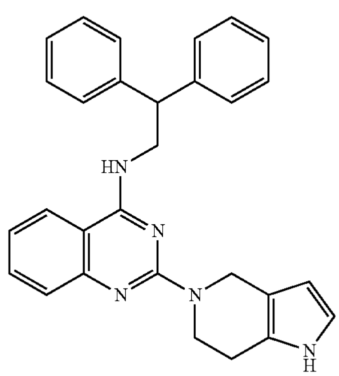 [SMILES: c1ccc(C(CNc2nc(N3CCc4[nH]ccc4C3)nc3ccccc23)c2ccccc2)cc1] | 2-(6,7-Dihydro-1H-pyrrolo[3,2-c]pyridin-5(4H)-yl)-N-(2,2-diphenylethyl)quinazolin-4-amine | 446 |

TABLE 1-continued

| No. | Structure | Name | M + H |
|---|---|---|---|
| 164 | 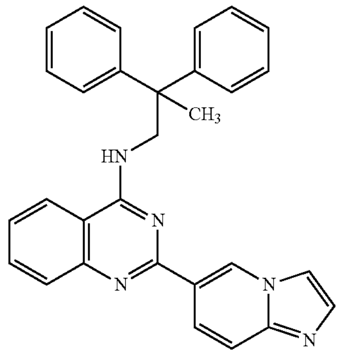 [SMILES: CC(CNc1nc(-c2ccc3nccn3c2)nc2ccccc12)(c1ccccc1)c1ccccc1] | N-(2,2-Diphenylpropyl)-2-(imidazo[1,2-a]pyridin-6-yl)quinazolin-4-amine | 456 |
| 165 | 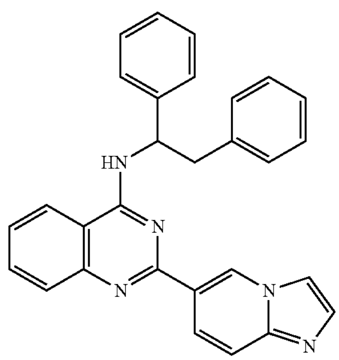 [SMILES: c1ccc(CC(Nc2nc(-c3ccc4nccn4c3)nc3ccccc23)c2ccccc2)cc1] | N-(1,2-Diphenylethyl)-2-(imidazo[1,2-a]pyridin-6-yl)quinazolin-4-amine | 442 |
| 166 | 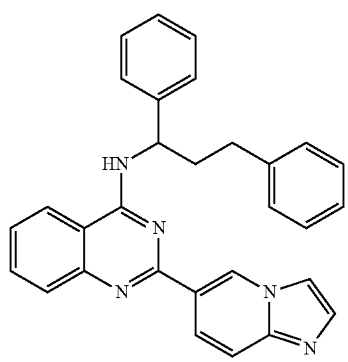 [SMILES: c1ccc(CCC(Nc2nc(-c3ccc4nccn4c3)nc3ccccc23)c2ccccc2)cc1] | N-(1,3-Diphenylpropyl)-2-(imidazo[1,2-a]pyridin-6-yl)quinazolin-4-amine | 456 |
| 167 | 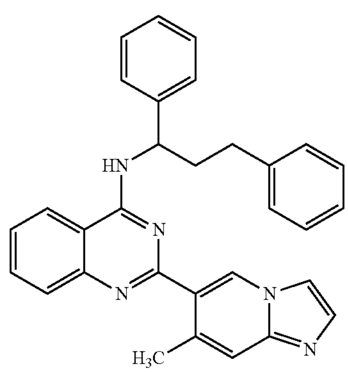 [SMILES: Cc1cc2nccn2cc1-c1nc(NC(CCc2ccccc2)c2ccccc2)c2ccccc2n1] | N-(1,3-Diphenylpropyl)-2-(7-methylimidazo[1,2-a]pyridin-6-yl)quinazolin-4-amine | 470 |

TABLE 1-continued

| No. | Structure | Name | M + H |
|---|---|---|---|
| 168 | 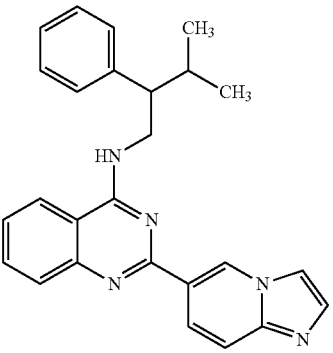 [SMILES: CC(C)C(CNc1nc(-c2ccc3nccn3c2)nc2ccccc12)c1ccccc1] | 2-(Imidazo[1,2-a]pyridin-6-yl)-N-(3-methyl-2-phenylbutyl)quinazolin-4-amine | 408 |
| 169 | 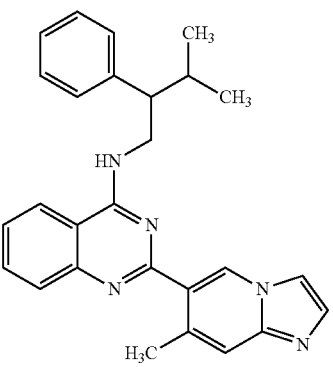 [SMILES: Cc1cc2nccn2cc1-c1nc(NCC(c2ccccc2)C(C)C)c2ccccc2n1] | N-(3-Methyl-2-phenylbutyl)-2-(7-methylimidazo[1,2-a]pyridin-6-yl)quinazolin-4-amine | 422 |
| 170 | 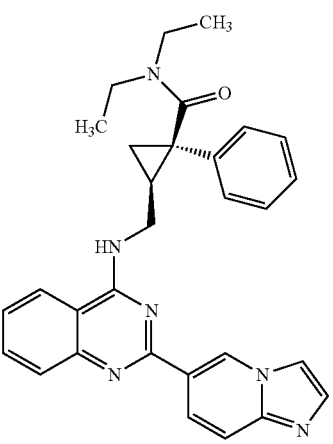 [SMILES: CCN(CC)C(=O)[C@]1(c2ccccc2)C[C@@H]1CNc1nc(-c2ccc3nccn3c2)nc2ccccc12] | (1R,2S)-N,N-Diethyl-2-(((2-(imidazo[1,2-a]pyridin-6-yl)quinazolin-4-yl)amino)methyl)-1-phenylcyclopropanecarboxamide | 491 |
| 171 | 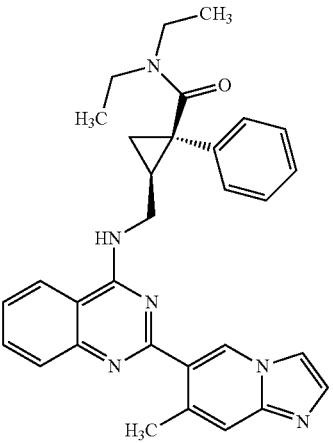 [SMILES: CCN(CC)C(=O)[C@]1(c2ccccc2)C[C@@H]1CNc1nc(-c2cn3ccnc3cc2C)nc2ccccc12] | (1R,2S)-N,N-Diethyl-2-(((2-(7-methylimidazo[1,2-a]pyridin-6-yl)quinazolin-4-yl)amino)methyl)-1-phenylcyclopropanecarboxamide | 505 |

| No. | Structure | Name | M + H |
|-----|-----------|------|-------|
| 172 | 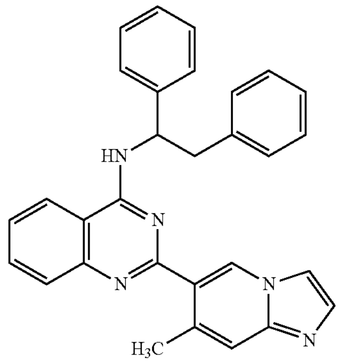 [SMILES: Cc1cc2nccn2cc1-c1nc(NC(Cc2ccccc2)c2ccccc2)c2ccccc2n1] | N-(1,2-Diphenylethyl)-2-(7-methylimidazo[1,2-a]pyridin-6-yl)quinazolin-4-amine | 456 |
| 173 | 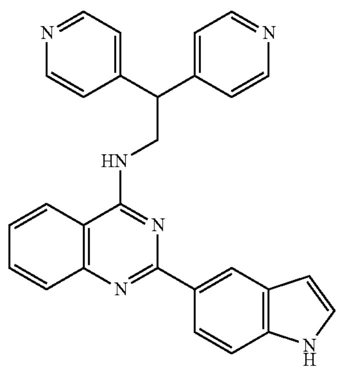 [SMILES: c1ccc2c(NCC(c3ccncc3)c3ccncc3)nc(-c3ccc4[nH]ccc4c3)nc2c1] | N-(2,2-Di(pyridin-4-yl)ethyl)-2-(1H-indol-5-yl)quinazolin-4-amine | 443 |
| 174 | 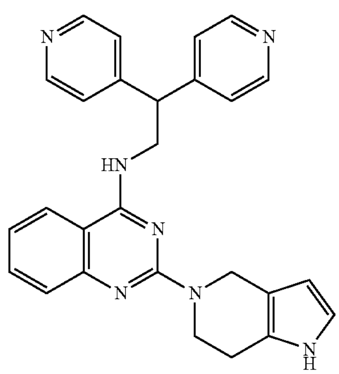 [SMILES: c1ccc2c(NCC(c3ccncc3)c3ccncc3)nc(N3CCc4[nH]ccc4C3)nc2c1] | N-(2,2-Di(pyridin-4-yl)ethyl)-2-(6,7-dihydro-1H-pyrrolo[3,2-c]pyridin-5(4H)-yl)quinazolin-4-amine | 448 |
| 175 | 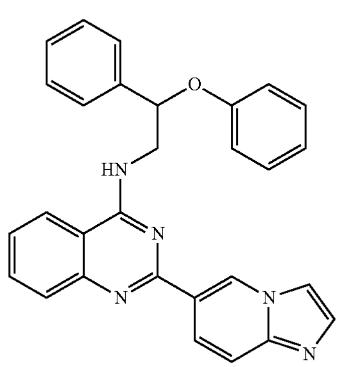 [SMILES: c1ccc(OC(CNc2nc(-c3ccc4nccn4c3)nc3ccccc23)c2ccccc2)cc1] | 2-(Imidazo[1,2-a]pyridin-6-yl)-N-(2-phenoxy-2-phenylethyl)quinazolin-4-amine | 458 |

TABLE 1-continued

| No. | Structure | Name | M + H |
|---|---|---|---|
| 176 | 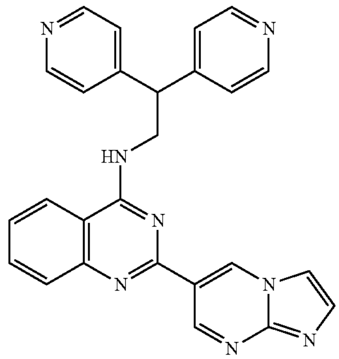 [SMILES: c1ccc2c(NCC(c3ccncc3)c3ccncc3)nc(-c3cnc4nccn4c3)nc2c1] | N-(2,2-Di(pyridin-4-yl)ethyl)-2-(imidazo[1,2-a]pyrimidin-6-yl)quinazolin-4-amine | 445 |
| 177 | 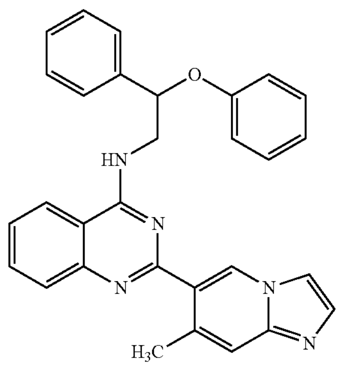 [SMILES: Cc1cc2nccn2cc1-c1nc(NCC(Oc2ccccc2)c2ccccc2)c2ccccc2n1] | 2-(7-Methylimidazo[1,2-a]pyridin-6-yl)-N-(2-phenoxy-2-phenylethyl)quinazolin-4-amine | 472 |
| 178 | 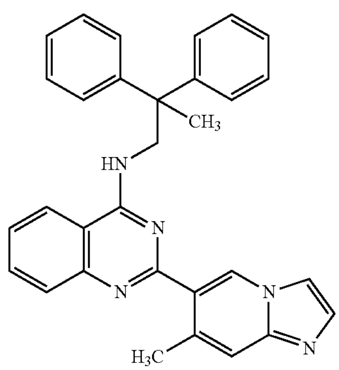 [SMILES: Cc1cc2nccn2cc1-c1nc(NCC(C)(c2ccccc2)c2ccccc2)c2ccccc2n1] | N-(2,2-Diphenylpropyl)-2-(7-methylimidazo[1,2-a]pyridin-6-yl)quinazolin-4-amine | 470 |
| 179 | 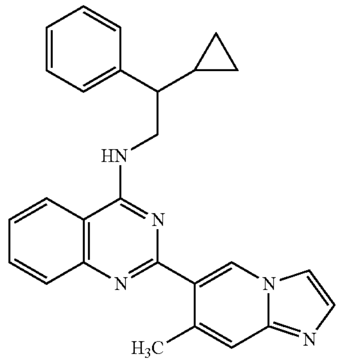 [SMILES: Cc1cc2nccn2cc1-c1nc(NCC(c2ccccc2)C2CC2)c2ccccc2n1] | N-(2-Cyclopropyl-2-phenylethyl)-2-(7-methylimidazo[1,2-a]pyridin-6-yl)quinazolin-4-amine | 420 |

TABLE 1-continued
| No. | Structure | Name | M + H |
|---|---|---|---|
| 180 | 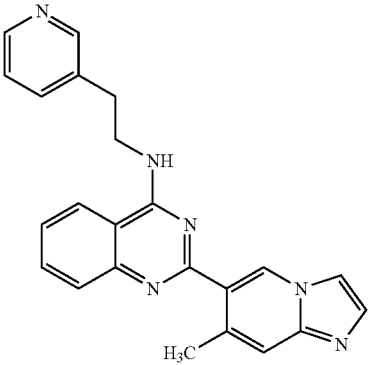 [SMILES: Cc1cc2nccn2cc1-c1nc(NCCc2cccnc2)c2ccccc2n1] | 2-(7-Methylimidazo[1,2-a]pyridin-6-yl)-N-(2-(pyridin-3-yl)ethyl)quinazolin-4-amine | 381 |
| 181 | 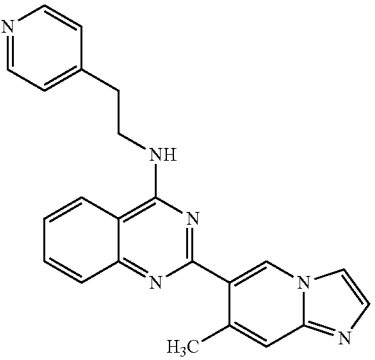 [SMILES: Cc1cc2nccn2cc1-c1nc(NCCc2ccncc2)c2ccccc2n1] | 2-(7-Methylimidazo[1,2-a]pyridin-6-yl)-N-(2-(pyridin-4-yl)ethyl)quinazolin-4-amine | 381 |
| 182 | 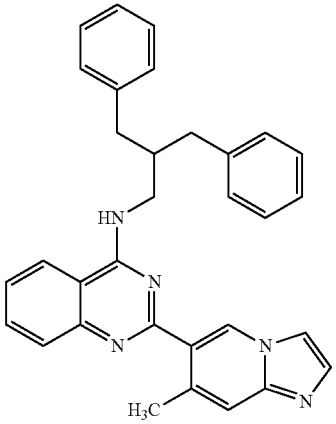 [SMILES: Cc1cc2nccn2cc1-c1nc(NCC(Cc2ccccc2)Cc2ccccc2)c2ccccc2n1] | N-(2-Benzyl-3-phenylpropyl)-2-(7-methylimidazo[1,2-a]pyridin-6-yl)quinazolin-4-amine | 484 |
| 183 | 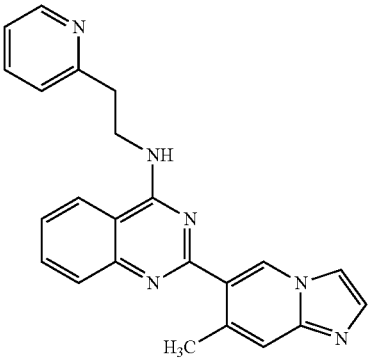 [SMILES: Cc1cc2nccn2cc1-c1nc(NCCc2ccccn2)c2ccccc2n1] | 2-(7-Methylimidazo[1,2-a]pyridin-6-yl)-N-(2-(pyridin-2-yl)ethyl)quinazolin-4-amine | 381 |

TABLE 1-continued
| No. | Structure | Name | M + H |
|---|---|---|---|
| 184 | 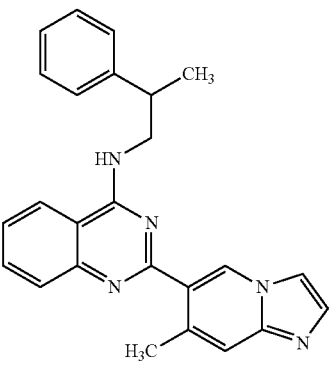 [SMILES: Cc1cc2nccn2cc1-c1nc(NCC(C)c2ccccc2)c2ccccc2n1] | 2-(7-Methylimidazo[1,2-a]pyridin-6-yl)-N-(2-phenylpropyl)quinazolin-4-amine | 394 |
| 185 | 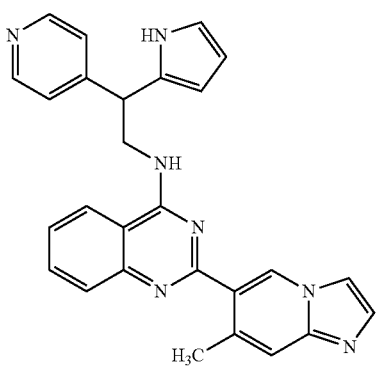 [SMILES: Cc1cc2nccn2cc1-c1nc(NCC(c2ccncc2)c2ccc[nH]2)c2ccccc2n1] | 2-(7-Methylimidazo[1,2-a]pyridin-6-yl)-N-(2-(pyridin-4-yl)-2-(1H-pyrrol-2-yl)ethyl)quinazolin-4-amine | 446 |
| 186 | 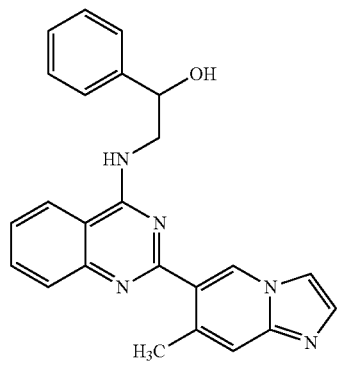 | 2-((2-(7-Methylimidazo[1,2-a]pyridin-6-yl)quinazolin-4-yl)amino)-1-phenylethanol | 396 |
| 187 | 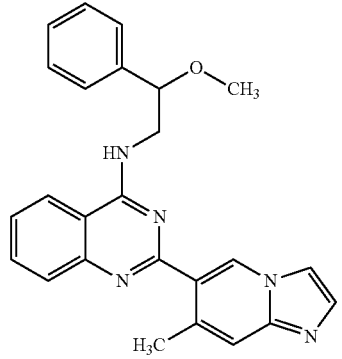 [SMILES: COC(CNc1nc(-c2cn3ccnc3cc2C)nc2ccccc12)c1ccccc1] | N-(2-Methoxy-2-phenylethyl)-2-(7-methylimidazo[1,2-a]pyridin-6-yl)quinazolin-4-amine | 410 |

TABLE 1-continued

| No. | Structure | Name | M + H |
|---|---|---|---|
| 188 | 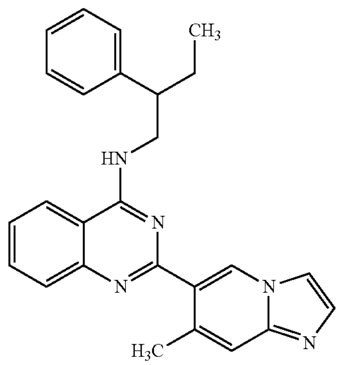 [SMILES: CCC(CNc1nc(-c2cn3ccnc3cc2C)nc2ccccc12)c1ccccc1] | 2-(7-Methylimidazo[1,2-a]pyridin-6-yl)-N-(2-phenylbutyl)quinazolin-4-amine | 408 |
| 189 | 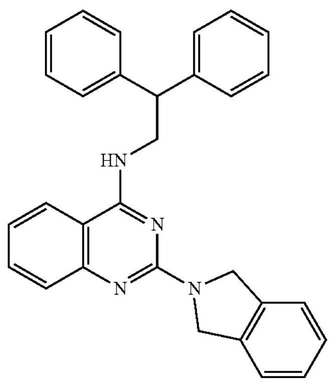 [SMILES: c1ccc(C(CNc2nc(N3Cc4ccccc4C3)nc3ccccc23)c2ccccc2)cc1] | N-(2,2-Diphenylethyl)-2-(isoindolin-2-yl)quinazolin-4-amine | 443 |
| 190 | 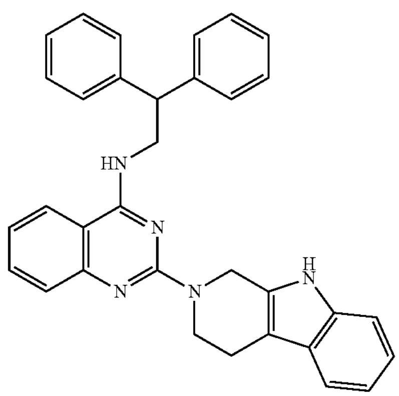 [SMILES: c1ccc(C(CNc2nc(N3CCc4c([nH]c5ccccc45)C3)nc3ccccc23)c2ccccc2)cc1] | 2-(3,4-Dihydro-1H-pyrido[3,4-b]indol-2(9H)-yl)-N-(2,2-diphenylethyl)quinazolin-4-amine | 496 |
| 191 | 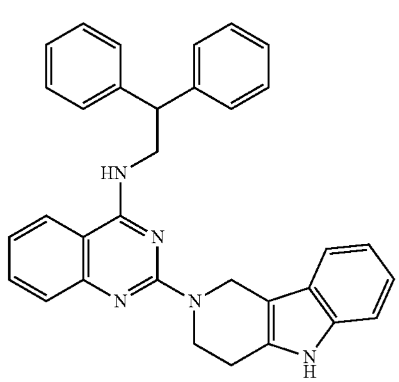 [SMILES: c1ccc(C(CNc2nc(N3CCc4[nH]c5ccccc5c4C3)nc3ccccc23)c2ccccc2)cc1] | 2-(3,4-Dihydro-1H-pyrido[4,3-b]indol-2(5H)-yl)-N-(2,2-diphenylethyl)quinazolin-4-amine | 496 |

TABLE 1-continued

| No. | Structure | Name | M + H |
|---|---|---|---|
| 192 | 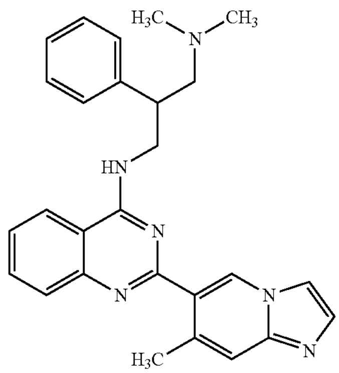 [SMILES: Cc1cc2nccn2cc1-c1nc(NCC(CN(C)C)c2ccccc2)c2ccccc2n1] | N1,N1-Dimethyl-N3-(2-(7-methylimidazo[1,2-a]pyridin-6-yl)quinazolin-4-yl)-2-phenylpropane-1,3 diamine | 437 |
| 193 | 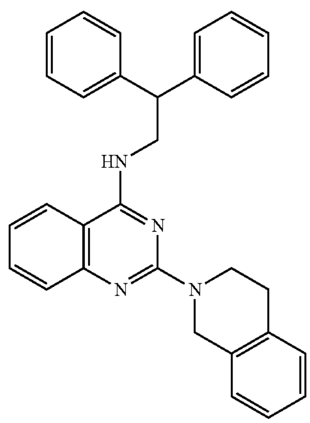 [SMILES: c1ccc(C(CNc2nc(N3CCc4ccccc4C3)nc3ccccc23)c2ccccc2)cc1] | 2-(3,4-Dihydroisoquinolin-2(1H)-yl)-N-(2,2-diphenylethyl)quinazolin-4-amine | 457 |
| 194 | 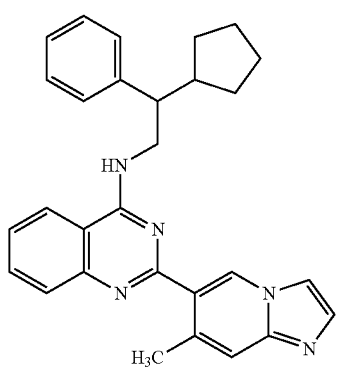 [SMILES: Cc1cc2nccn2cc1-c1nc(NCC(c2ccccc2)C2CCCC2)c2ccccc2n1] | N-(2-Cyclopentyl-2-phenylethyl)-2-(7-methylimidazo[1,2-a]pyridin-6-yl)quinazolin-4-amine | 448 |
| 195 | 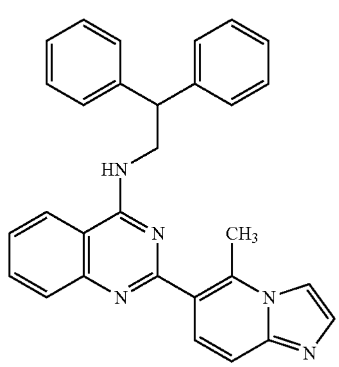 [SMILES: Cc1c(-c2nc(NCC(c3ccccc3)c3ccccc3)c3ccccc3n2)ccc2nccn12] | N-(2,2-Diphenylethyl)-2-(5-methylimidazo[1,2-a]pyridin-6-yl)quinazolin-4-amine | 456 |

TABLE 1-continued

| No. | Structure | Name | M + H |
|-----|-----------|------|-------|
| 196 | 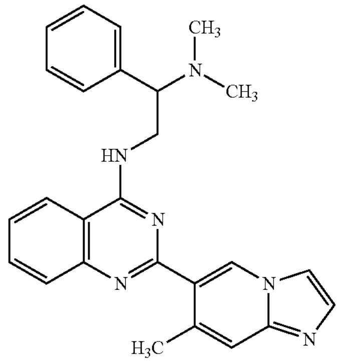 [SMILES: Cc1cc2nccn2cc1-c1nc(NCC(c2ccccc2)N(C)C)c2ccccc2n1] | N1,N1-Dimethyl-N2-(2-(7-methylimidazo[1,2-a]pyridin-6-yl)quinazolin-4-yl)-1-phenylethane-1,2-diamine | 423 |
| 197 | 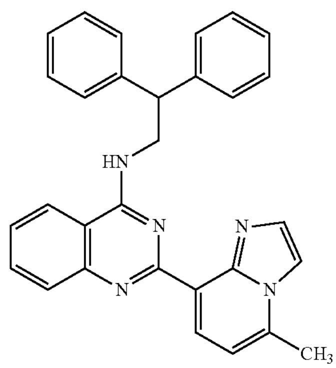 [SMILES: Cc1ccc(-c2nc(NCC(c3ccccc3)c3ccccc3)c3ccccc3n2)c2nccn12] | N-(2,2-Diphenylethyl)-2-(5-methylimidazo[1,2-a]pyridin-8-yl)quinazolin-4-amine | 456 |
| 198 | 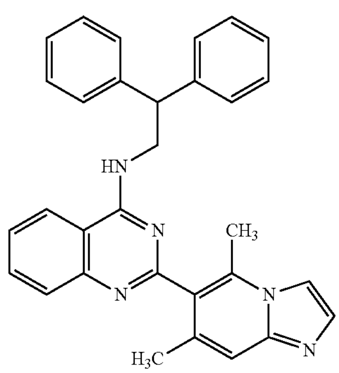 [SMILES: Cc1cc2nccn2c(C)c1-c1nc(NCC(c2ccccc2)c2ccccc2)c2ccccc2n1] | 2-(5,7-Dimethylimidazo[1,2-a]pyridin-6-yl)-N-(2,2-diphenylethyl)quinazolin-4-amine | 470 |
| 199 | 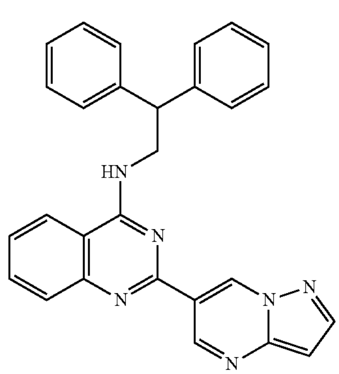 [SMILES: c1ccc(C(CNc2nc(-c3cnc4ccnn4c3)nc3ccccc23)c2ccccc2)cc1] | N-(2,2-Diphenylethyl)-2-(pyrazolo[1,5-a]pyrimidin-6-yl)quinazolin-4-amine | 443 |

TABLE 1-continued

| No. | Structure | Name | M + H |
|---|---|---|---|
| 200 | 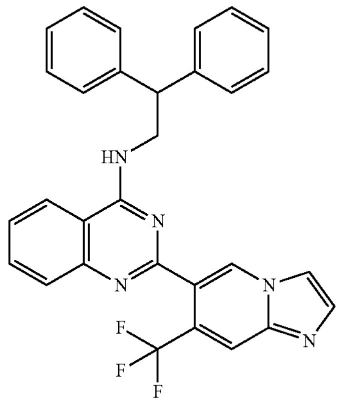 [SMILES: FC(F)(F)c1cc2nccn2cc1-c1nc(NCC(c2ccccc2)c2ccccc2)c2ccccc2n1] | N-(2,2-Diphenylethyl)-2-(7-(trifluoromethyl)imidazo[1,2-a]pyridin-6-yl)quinazolin-4-amine | 510 |
| 201 | 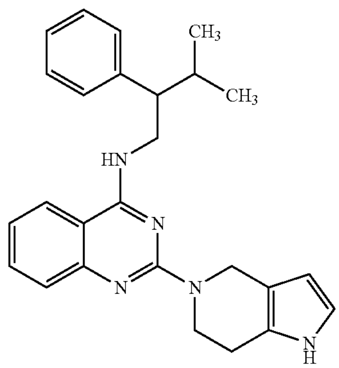 [SMILES: CC(C)C(CNc1nc(N2CCc3[nH]ccc3C2)nc2ccccc12)c1ccccc1] | 2-(6,7-Dihydro-1H-pyrrolo[3,2-c]pyridin-5(4H)-yl)-N-(3-methyl-2-phenylbutyl)quinazolin-4-amine | 412 |
| 202 | 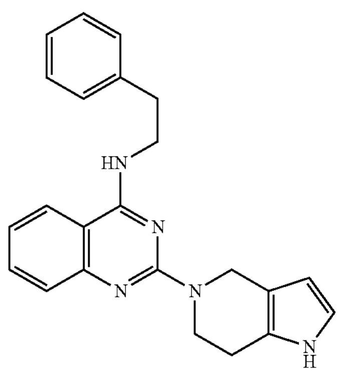 [SMILES: c1ccc(CCNc2nc(N3CCc4[nH]ccc4C3)nc3ccccc23)cc1] | 2-(6,7-Dihydro-1H-pyrrolo[3,2-c]pyridin-5(4H)-yl)-N-phenethylquinazolin-4-amine | 370 |
| 203 | 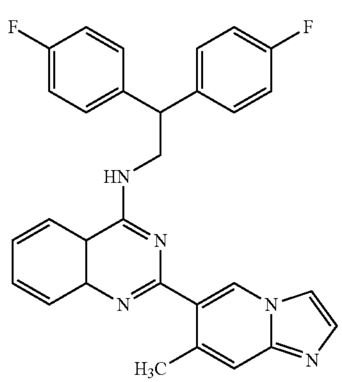 [SMILES: Cc1cc2nccn2cc1C1=NC2C=CC=CC2C(NCC(c2ccc(F)cc2)c2ccc(F)cc2)=N1] | N-(2,2-Bis(4-fluorophenyl)ethyl)-2-(7-methylimidazo[1,2-a]pyridin-6-yl)quinazolin-4-amine | 492 |

TABLE 1-continued

| No. | Structure | Name | M + H |
|-----|-----------|------|-------|
| 204 | 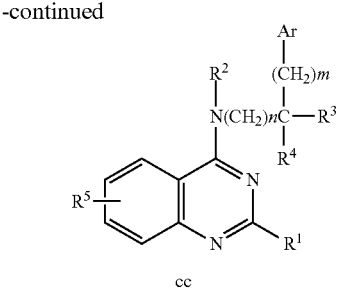 | N-(2,2-Diphenylethyl)-N-methyl-2-(7-methylimidazo[1,2-a]pyridin-6-yl)quinazolin-4-amine | 470 |

C. Methods of Making the Compounds

Compounds of the present disclosure can be prepared by a variety of methods using readily available starting materials or known intermediates. The synthetic schemes shown below provide exemplary synthetic pathways for the preparation of compounds of the invention. The synthetic schemes are merely illustrative of some of the methods by which compounds of the present disclosure can be synthesized, and various modifications to these synthetic reaction schemes would be apparent to one skilled in the art within the scope of the present disclosure. Schemes 1 and 2 illustrate two general synthetic approaches for compounds as described herein. In Schemes 1 and 2, X and Y are leaving groups, such as Cl, Br, I, mercapto, sulfoxo, sulfonyl, alkoxy, aryloxy, sulfonyloxy group; and $R^1Q$ is an organoborane, organozinc or organometallic compound, wherein Q can be $B(OH)_2$, $B(OR')_2$, ZnX or other suitable agents. Other substituents are as defined in Formula (I).

In Scheme 1, the quinazolines (aa) used as starting material are either commercially available or can be readily prepared using literature methods. These starting materials are reacted with appropriate amines under mild reaction conditions to selectively displace the leaving group at the 4-position to obtain the 4-aminoquinazoline intermediates (bb). These intermediates (bb) are further reacted with an organoborane, organozinc or organometallic reagent typically in the presences of suitable palladium complex catalyst to yield compounds (cc).

As shown in Scheme 2, the intermediates (bb) can be reacted with saturated heterocycles or aromatic heterocycles possessing an NH group to displace the leaving group at the 2-position of the quinazoline to yield compounds (dd).

Scheme 1

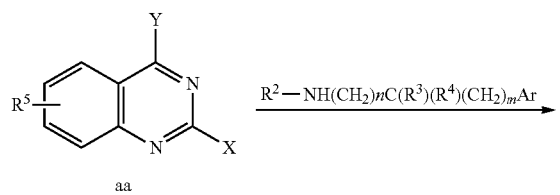

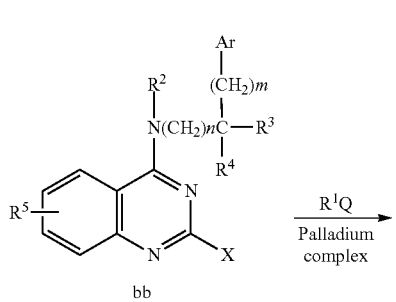

Scheme 2

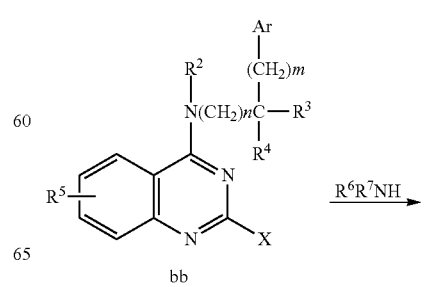

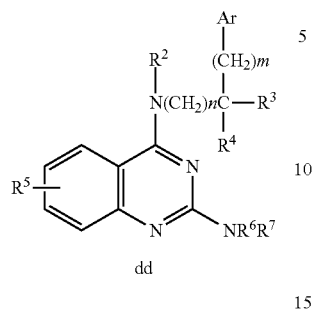

Scheme 3 shown below illustrates another synthetic procedure that may be used in the preparation of compounds of the present invention wherein W is N or $CR^{11}$ and other substituents are as defined herein. As illustrated, the quinazoline intermediates (bb) are coupled with suitable aminoazine intermediates (cc), typically in the presence of a palladium complex catalyst, to obtain the intermediates (dd). These intermediates are further reacted with aldehyde or ketone reagents possessing appropriate leaving group at the alpha carbon to the carbonyl group to yield the desired compounds (III). Depending upon the reactants and reaction conditions this condensation reaction may yield a hydroxy-dihydroimidazoazine intermediate which can be dehydrated to provide the desired compounds (ee).

The synthetic method outlined in Scheme 3 is illustrated with specific examples in Scheme 4.

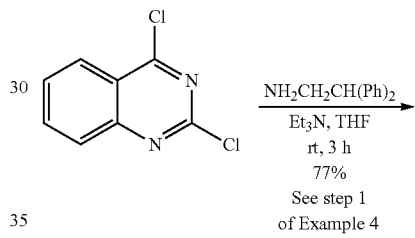

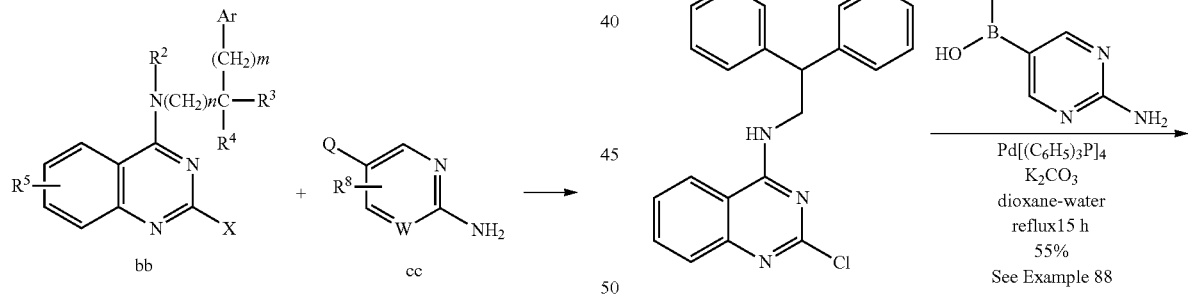

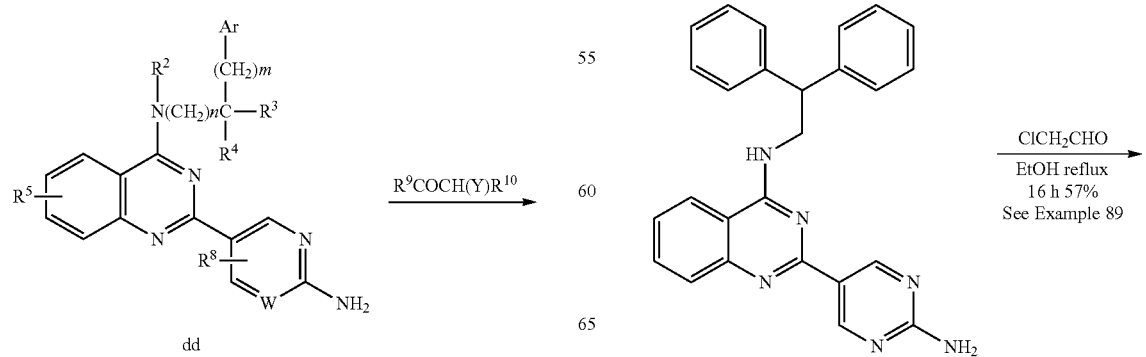

-continued

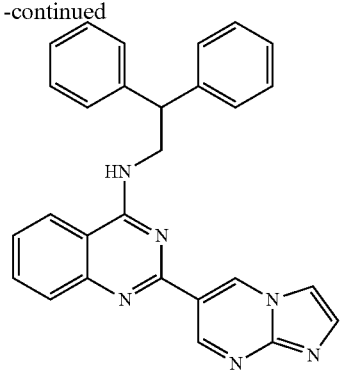

Specific details for producing compounds of the invention are described in the Examples section.

D. Methods of Treating Diseases Associated with Dysfunction of Dopamine Neurotransmission, Serotonin Neurotransmission, and/or Norepinephrine Neurotransmission The compounds of the present disclosure are useful for the treatment of diseases or conditions associated with dysfunction of dopamine neurotransmission, serotonin neurotransmission and/or norepinephrine neurotransmission such as depression.

The compounds of the present disclosure are also useful for the treatment of pain conditions from a wide variety of causes, including, but not limited to, neuropathic pain, inflammatory pain, pain due to burns, migraine or cluster headaches, nerve injury, neuritis, neuralgia, ischemic injury, intestinal cystitis, cancer pain, viral, parasitic or bacterial infections, post-traumatic injuries including fracture and sports injuries, and pain associated with bowel disorders such as irritable bowel syndrome.

The compounds of the present disclosure are also useful for the treatment of addiction to substances such as cocaine, methamphetamine, nicotine and alcohol.

Exemplary embodiments according to the present disclosure are as follows:

Embodiment 1. A compound represented by the formula (I):

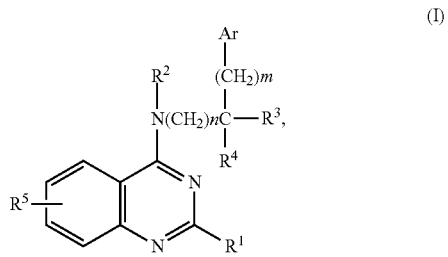

wherein n is 0, 1 or 2; m is 0, 1 or 2; $R^1$ is a heterocycle; $R^2$ is H or lower alkyl group; Ar is a phenyl or heterocyclic group; $R^3$ is H, alkyl, aryl aralkyl, heteroaryl, or heteroarylalkyl; $R^4$ is H, alkyl, hydroxy, alkoxy, aryloxy, heteroaryloxy, amino, alkylamino or dialkylamino; $R^3$ and $R^4$ together form a carbocycle or heterocycle; $R^5$ is H, halogen, alkyl, aryl, hydroxy, alkoxy, aryloxy, amino, alkylamino or dialkylamino; pharmaceutically acceptable salts thereof, deuterated forms thereof, isomers thereof, solvates thereof, and mixtures thereof.

Embodiment 2. The compound according to Embodiment 1 being of the formula (I):

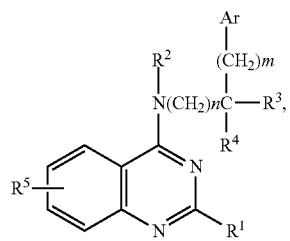

wherein n is: 0, 1 or 2; m is: 0, 1 or 2; $R^1$ is a heterocycle; $R^2$ is H or lower alkyl group; Ar is: (a) a phenyl or substituted phenyl; or (b) a heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; $R^3$ is: (a) H, alkyl or cycloalkyl; (b) phenyl or substituted phenyl; or (c) heteroaryl selected from 2-pyridyl, 3-pyridyl, 4-pyridyl, 2-pyrimidinyl, 4-pyrimidinyl, 5-pyrimidinyl, 6-pyrimidinyl, 2-furanyl, 3-furanyl, 2-thiophenyl, 3-thiophenyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, each optionally substituted; (d) aralkyl selected from benzyl, phenethyl, each optionally substituted; (e) heteroarylalkyl such as 2-pyridylmethyl, 3-pyridylmethyl, 4-pyridylmethyl, 2-thienylmethyl, 3-thienylmethyl, 2-furanylmethyl, 3-furanylmethyl, 2-pyrrolylmethyl, 3-pyrrolylmethyl, 2-pyridylethyl, 3-pyridylethyl, 4-pyridylethyl, 2-thienylethyl, 3-thienylethyl, 2-furanylethyl, 3-furanylethyl, 2-pyrrolylethyl, 3-pyrrolylethyl, and heteroarylalkyls wherein heteroaryl contains two or more heteroatoms, each optionally substituted; $R^4$ is H, alkyl, hydroxy, alkoxy, aryloxy, heteroaryloxy, amino, alkylamino, or dialkylamino including a dialkylamine that is a nitrogen heterocycle such as aziridine, azetidine, pyrrolidine, piperidine, morpholine, piperazine, azepane, diazepane and azocane. These rings may contain additional substituents or groups such as alkyl, aryl, arylalkyl, heteroaryl, heteroarylalkyl, alkenyl, alkoxy, hydroxyl, protected hydroxyl, alkanoyl, carboxy, alkoxycarbonyl and carbamoyl. They also may have one or more oxo, thioxo, imino, methylene or additional atoms such as O, N, S, P, Se and Te, and be part of a fused bicyclic or polycyclic saturated or unsaturated system. $R^3$ and $R^4$ together form a carbocycle or heterocycle consisting of 3-9 atoms; $R^5$ is: (a) H, lower alkyl or aryl group; (b) halogen such as fluoro, chloro, bromo and iodo; or (c) hydroxyl, alkoxy, dialkylaminoalkoxy, aryloxy, amino, alkylamino and dialkylamino; pharmaceutically acceptable salts thereof, deuterated forms thereof, isomers thereof, solvates thereof, and mixtures thereof.

Embodiment 3. The compound according to Embodiment 2, wherein $R^1$ is a heterocycle selected from the group consisting of (a) bicyclic aromatic heterocycle selected from indolyl, indazolyl, imidazo[1,2-a]pyridinyl, imidazo[1,2-a]pyrimidinyl, pyrazolo[1,5-a]pyridinyl (g) pyrazolo[1,5-a]pyrimidinyl, triazolo[1,5-a]pyridinyl, tetrazolo[1,5-a]pyridinyl, benzimidazolyl selected from benzimidazol-2-yl, benzimidazol-4-yl, benzimidazol-5-yl, benzofuranyl, benzothiophenyl, benzoxazolyl, benzothiazolyl, benzisoxazolyl, benzisothiazolyl, benzotriazolyl, indolinyl, 1,3-dihydroindol-2-only, quinolinyl, isoquinolinyl, quinoxalinyl, quinazolinyl (x) cinnolinyl and purinyl, each optionally substituted; (b) monocyclic aromatic heterocycle selected from pyridinyl, pyrimidinyl, pyrazinyl, pyridazinyl, triazinyl, thienyl, furanyl, pyrrolyl, oxazolyl, thiazolyl, isoxazolyl, isothiazolyl, imidazolyl, pyrazolyl, triazolyl, and fused aromatic heterocycle, each optionally substituted; and (c) 1,2,3,4-tetrahydroquinolinyl, isoindoline-2-yl, 4,5,6,7-tetrahydro-1H-pyrrolo[3,2-c]pyridine-5-yl, 2,3,4,5-tetrahydro-1H-pyrido[4,3-b]indole-2-yl, 2,3,4,9-tetrahydro-1H-pyrido[3,4-b]indole-2-yl, each optionally substituted; or (d) saturated heterocycle selected from piperidinyl, morpholinyl, pyrrolidinyl, piperazinyl and azetidinyl, azepanyl diazepanyl and fused heterocycles such as isoindolinyl, tetrahydoquinolinyl, tetrahydroisoquinolinyl, benzazepanyl, benzodaizepanyl, each optionally substituted.

Embodiment 4. The compound according to Embodiment 1 having the formula (II):

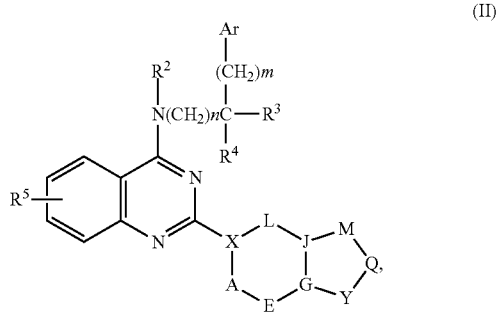

(II)

wherein $R^2$ $R^3$, $R^4$, $R^5$, Ar, n and m are as defined in claim 1 and

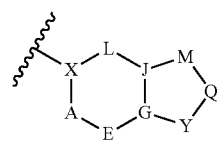

represents a bicyclic heterocycle wherein X is a nitrogen or a carbon atom; pharmaceutically acceptable salts thereof, deuterated forms thereof, isomers thereof, solvates thereof, and mixtures thereof.

Embodiment 5. The compound according to Embodiment 1 having the formula (III):

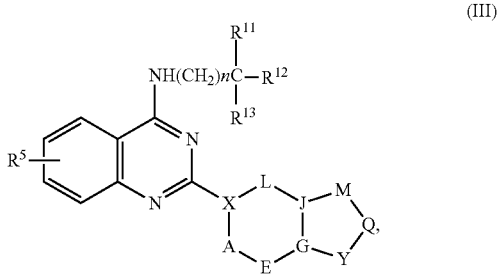

(III)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino; pharmaceutically acceptable salts thereof, deuterated forms thereof, isomers thereof, solvates thereof, and mixtures thereof.

Embodiment 6. The compound according to Embodiment 1 having the formula (IV):

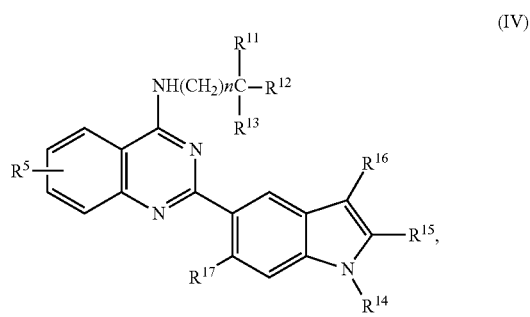

(IV)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino and $R^{14}$ is H, lower alkyl, acyl, sulfonyl, aryl or heteroaryl, and $R^{15}$, $R^{16}$ and $R^{17}$ are H, halogen, lower alkyl, hydroxy, alkoxy, aryloxy, acyl, sulfonyl, aryl heteroaryl, amino, alkylamino or dialkylamino; pharmaceutically acceptable salts thereof, deuterated forms thereof, isomers thereof, solvates thereof, and mixtures thereof.

Embodiment 7. The compound according to Embodiment 1 having the formula (V):

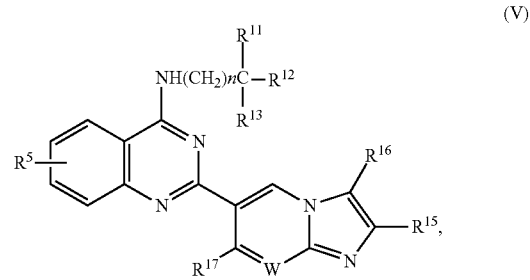

(V)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino and $R^{14}$ is H, lower alkyl, acyl, sulfonyl, aryl or heteroaryl, and $R^{15}$, $R^{16}$ and $R^{17}$ are H, halogen, lower alkyl, hydroxy, alkoxy, aryloxy, acyl, sulfonyl, aryl heteroaryl, amino, alkylamino or dialkylamino and W is CH or N; pharmaceutically acceptable salts thereof, deuterated forms thereof, isomers thereof, solvates thereof, and mixtures thereof.

Embodiment 8. The compound according to Embodiment 1 having the formula (VI):

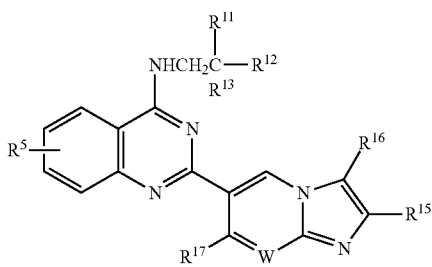

(VI)

wherein $R^{11}$ is an aryl or heteroaryl group, $R^{12}$ is an aryl, heteroaryl or alkyl group, $R^{13}$ is alkyl, hydroxy, alkoxy, aryloxy, amino, alkylamino or dialkylamino; $R^{15}$ and $R^{16}$ are H, halogen, lower alkyl, hydroxy, alkoxy, aryloxy, acyl, sulfonyl, aryl heteroaryl, amino, alkylamino or dialkylamino and $R^{17}$ is H, chloro, methyl, trifluoromethyl, lower alkyl or alkoxy group; pharmaceutically acceptable salts thereof, deuterated forms thereof, isomers thereof, solvates thereof, and mixtures thereof.

Embodiment 9. The compound according to Embodiment 1 being selected from the group consisting of: 2-(2-(Dimethylamino)pyrimidin-5-yl)-N-(2,2-diphenylethyl)quinazolin-4-amine (16); N-(2,2-Diphenylethyl)-2-(1H-indol-5-yl)quinazolin-4-amine (17); N-(3,3-Diphenylpropyl)-2-(1H-indol-5-yl)quinazolin-4-amine (21); N-(2,2-Diphenylethyl)-2-(1H-indol-5-yl)-6,7-dimethoxyquinazolin-4-amine (24); N-(2,2-Diphenylethyl)-2-(2-methoxypyrimidin-5-yl)quinazolin-4-amine (29); N-(2,2-Diphenylethyl)-2-(2-(methylthio)pyrimidin-5-yl)quinazolin-4-amine (30); N-(2,2-Diphenylethyl)-2-(pyridin-4-yl)quinazolin-4-amine (39); N-(2,2-Diphenylethyl)-2-(2-(methylamino)pyrimidin-5-yl)quinazolin-4-amine (41); N-(2,2-Diphenylethyl)-2-(1H-imidazol-1-yl)quinazolin-4-amine (48); N-(2,2-Diphenylethyl)-2-(quinolin-6-yl)quinazolin-4-amine (50); N-(2,2-Diphenylethyl)-2-(imidazo[1,2-a]pyridin-6-yl)quinazolin-4-amine (55); N-(2,2-Diphenylethyl)-2-(1-methyl-1H-benzo[d]imidazol-6-yl)quinazolin-4-amine (64); N-(2,2-Diphenylethyl)-2-(2-methyl-2H-indazol-5-yl)quinazolin-4-amine (66); N-(2,2-Diphenylethyl)-2-(1-methyl-1H-indazol-5-yl)quinazolin-4-amine (67); 2-(6-(Dimethylamino)pyridin-3-yl)-N-(2,2-diphenylethyl)quinazolin-4-amine (69); 2-(Benzo[d]thiazol-6-yl)-N-(2,2-diphenylethyl)quinazolin-4-amine (70); N-(2,2-Diphenylethyl)-2-(1-methyl-1H-indol-5-yl)quinazolin-4-amine (77); 5-(4-((2,2-Diphenylethyl)amino)quinazolin-2-yl)indolin-2-one (78); 2-((2-(2-(Dimethylamino)pyrimidin-5-yl)quinazolin-4-yl)amino)-1,1-diphenylethanol (80); 2-((2-(1H-Indol-5-yl)quinazolin-4-yl)amino)-1,1-diphenylethanol (81); N-(2,2-Diphenylethyl)-2-(indolin-5-yl)quinazolin-4-amine (84); 2-(6-Aminopyridin-3-yl)-N-(2,2-diphenylethyl)quinazolin-4-amine (88); N-(2,2-Diphenylethyl)-2-(imidazo[1,2-a]pyrimidin-6-yl)quinazolin-4-amine (89); 2-(2,3-Dimethylimidazo[1,2-a]pyridin-6-yl)-N-(2,2-diphenylethyl)quinazolin-4-amine (91); N-Benzhydryl-2-(6-(dimethylamino)pyridin-3-yl)quinazolin-4-amine (92); 2-(6-(Dimethylamino)pyridin-3-yl)-N-(3,3-diphenylpropyl)quinazolin-4-amine (93); 2-(Imidazo[1,2-a]pyridin-6-yl)-N-(2-phenyl-2-(pyridin-2-yl)ethyl)quinazolin-4-amine (94); 2-((2-(Imidazo[1,2-a]pyridin-6-yl)quinazolin-4-yl)amino)-1,1-diphenylethanol (96); 2-(Imidazo[1,2-a]pyrimidin-6-yl)-N-(2-phenyl-2-(pyridin-2-yl)ethyl)quinazolin-4-amine (98); 2-((2-(Imidazo[1,2-a]pyrimidin-6-yl)quinazolin-4-yl)amino)-1,1-diphenylethanol (99); N-(2-Cyclohexyl-2-phenylethyl)-2-(imidazo[1,2-a]pyridin-6-yl)quinazolin-4-amine (100); N-(2-Cyclohexyl-2-phenylethyl)-2-(imidazo[1,2-a]pyrimidin-6-yl)quinazolin-4-amine (102); 2-([1,2,4]Triazolo[1,5-a]pyridin-6-yl)-N-(2,2-diphenylethyl)quinazolin-4-amine (105); 2-(Imidazo[1,2-a]pyridin-6-yl)-N-(2-phenyl-2-(pyridin-4-yl)ethyl)quinazolin-4-amine (106); 2-(Imidazo[1,2-a]pyrimidin-6-yl)-N-(2-phenyl-2-(pyridin-4-yl)ethyl)quinazolin-4-amine (110); 2-(Imidazo[1,2-a]pyridin-6-yl)-N-(2-phenyl-2-(1H-pyrrol-2-yl)ethyl)quinazolin-4-amine (117); N-(2,2-Diphenylethyl)-2-(7-methylimidazo[1,2-a]pyridin-6-yl)quinazolin-4-amine (118); N-(2,2-Diphenylethyl)-2-(1H-pyrrolo[2,3-b]pyridin-5-yl)quinazolin-4-amine (123); N-(2,2-Diphenylethyl)-7-fluoro-2-(imidazo[1,2-a]pyridin-6-yl)quinazolin-4-amine hydrochloride (124); 2-(Imidazo[1,2-a]pyrimidin-6-yl)-N-(2-(4-methylpiperazin-1-yl)-2-phenylethyl)quinazolin-4-amine (129); 2-(1H-Indol-5-yl)-N-(2-phenyl-2-(pyridin-3-yl)ethyl)quinazolin-4-amine (130); 2-(Imidazo[1,2-a]pyridin-6-yl)-N-(2-phenyl-2-(pyridin-3-yl)ethyl)quinazolin-4-amine (131); 2-(Imidazo[1,2-a]pyrimidin-6-yl)-N-(2-phenyl-2-(pyridin-3-yl)ethyl)quinazolin-4-amine (134); N-(2,3-Diphenylpropyl)-2-(imidazo[1,2-a]pyridin-6-yl)quinazolin-4-amine (136); 2-(1-Methyl-1H-indol-5-yl)-N-(2-phenyl-2-(pyridin-3-yl)ethyl)quinazolin-4-amine (137); N-(5-(4-((2,2-Diphenylethyl)amino)quinazolin-2-yl)pyridin-2-yl)methanesulfonamide (138); 2-(7-Methylimidazo[1,2-a]pyridin-6-yl)-N-(2-phenyl-2-(1H-pyrrol-2-yl)ethyl)quinazolin-4-amine (140); N-(2,2-Diphenylethyl)-2-(quinolin-8-yl)quinazolin-4-amine (141); N-(2,3-Diphenylpropyl)-2-(imidazo[1,2-a]pyridin-6-yl)quinazolin-4-amine (142); 2-(7-Methylimidazo[1,2-a]pyridin-6-yl)-N-(2-phenyl-2-(pyridin-4-yl)ethyl)quinazolin-4-amine (151); 2-((2-(7-Methylimidazo[1,2-a]pyridin-6-yl)quinazolin-4-yl)amino)-1,1-diphenylethanol (152); 1-(2-((2-(Imidazo[1,2-a]pyridin-6-yl)quinazolin-4-yl)amino)-1-(4-methoxyphenyl)ethyl)cyclohexanol (153); 2-(7-Methylimidazo[1,2-a]pyridin-6-yl)-N-(2-(pyridin-3-yl)-2-(1H-pyrrol-2-yl)ethyl)quinazolin-4-amine (156); N-(2,2-Di(pyridin-4-yl)ethyl)-2-(7-methylimidazo[1,2-a]pyridin-6-yl)quinazolin-4-amine (157); 2-(7-Methylimidazo[1,2-a]pyridin-6-yl)-N-phenethylquinazolin-4-amine (160); (S)-2-(7-Methylimidazo[1,2-a]pyridin-6-yl)-N-(2-phenyl-2-(1H-pyrrol-1-yl)ethyl)quinazolin-4-amine (162); 2-(6,7-Dihydro-1H-pyrrolo[3,2-c]pyridin-5(4H)-yl)-N-(2,2-diphenylethyl)quinazolin-4-amine (163); N-(2,2-Diphenylpropyl)-2-(imidazo[1,2-a]pyridin-6-yl)quinazolin-4-amine (164); N-(1,2-Diphenylethyl)-2-(imidazo[1,2-a]pyridin-6-yl)quinazolin-4-amine (165); N-(1,3-Diphenylpropyl)-2-(imidazo[1,2-a]pyridin-6-yl)quinazolin-4-amine (166); N-(1,3-Diphenylpropyl)-2-(7-methylimidazo[1,2-a]pyridin-6-yl)quinazolin-4-amine (167); 2-(Imidazo[1,2-a]pyridin-6-yl)-N-(3-methyl-2-phenylbutyl)quinazolin-4-amine (168); N-(3-Methyl-2-phenylbutyl)-2-(7-methylimidazo[1,2-a]pyridin-6-yl)quinazolin-4-amine (169); (1R,2S)—N,N-Diethyl-2-(((2-(7-methylimidazo[1,2-a]pyridin-6-yl)quinazolin-4-yl)amino)methyl)-1-phenylcyclopropanecarboxamide (171); N-(1,2-Diphenylethyl)-2-(7-methylimidazo[1,2-a]pyridin-6-yl)quinazolin-4-amine (172); N-(2,2-Di(pyridin-4-yl)ethyl)-2-(6,7-dihydro-1H-pyrrolo[3,2-c]pyridin-5(4H)-yl)quinazolin-4-amine (174); 2-(7-Methylimidazo[1,2-a]pyridin-6-yl)-N-(2-phenoxy-2-phenylethyl)quinazolin-4-amine (177); N-(2,2-Diphenylpropyl)-2-(7-methylimidazo[1,2-a]pyridin-6-yl)quinazolin-4-amine (178); N-(2-Cyclopropyl-2-phenylethyl)-2-(7-methylimidazo[1,2-a]pyridin-6-yl)quinazolin-4-amine (179); N-(2-Benzyl-3-phenylpropyl)-2-(7-methylimidazo[1,2-a]pyridin-6-yl)quinazolin-4-amine (182); 2-(7-Methylimidazo[1,2-a]

pyridin-6-yl)-N-(2-phenylpropyl)quinazolin-4-amine (184); 2-(7-Methylimidazo[1,2-a]pyridin-6-yl)-N-(2-(pyridin-4-yl)-2-(1H-pyrrol-2-yl)ethyl)quinazolin-4-amine (185); 2-((2-(7-Methylimidazo[1,2-a]pyridin-6-yl)quinazolin-4-yl)amino)-1-phenylethanol (186); N-(2-Methoxy-2-phenylethyl)-2-(7-methylimidazo[1,2-a]pyridin-6-yl)quinazolin-4-amine (187); 2-(7-Methylimidazo[1,2-a]pyridin-6-yl)-N-(2-phenylbutyl)quinazolin-4-amine (188); N-(2,2-Diphenylethyl)-2-(isoindolin-2-yl)quinazolin-4-amine (189); 2-(3,4-Dihydro-1H-pyrido[3,4-b]indol-2(9H)-yl)-N-(2,2-diphenylethyl)quinazolin-4-amine (190); 2-(3,4-Dihydro-1H-pyrido[4,3-b]indol-2(5H)-yl)-N-(2,2-diphenylethyl)quinazolin-4-amine (191); N1,N1-Dimethyl-N3-(2-(7-methylimidazo[1,2-a]pyridin-6-yl)quinazolin-4-yl)-2-phenylpropane-1,3-diamine (192); 2-(3,4-Dihydroisoquinolin-2(1H)-yl)-N-(2,2-diphenylethyl)quinazolin-4-amine (193); N-(2-Cyclopentyl-2-phenylethyl)-2-(7-methylimidazo[1,2-a]pyridin-6-yl)quinazolin-4-amine (194); N-(2,2-Diphenylethyl)-2-(5-methylimidazo[1,2-a]pyridin-6-yl)quinazolin-4-amine (195); N1,N1-Dimethyl-N2-(2-(7-methylimidazo[1,2-a]pyridin-6-yl)quinazolin-4-yl)-1-phenylethane-1,2-diamine (196); N-(2,2-Diphenylethyl)-2-(pyrazolo[1,5-a]pyrimidin-6-yl)quinazolin-4-amine (199); N-(2,2-Diphenylethyl)-2-(7-(trifluoromethyl)imidazo[1,2-a]pyridin-6-yl)quinazolin-4-amine (200); 2-(6,7-Dihydro-1H-pyrrolo[3,2-c]pyridin-5(4H)-yl)-N-(3-methyl-2-phenylbutyl)quinazolin-4-amine (201); N-(2,2-Bis(4-fluorophenyl)ethyl)-2-(7-methylimidazo[1,2-a]pyridin-6-yl)quinazolin-4-amine (203); pharmaceutically acceptable salts thereof, deuterated forms thereof, isomers thereof, solvates thereof, and mixtures thereof.

Embodiment 10. A pharmaceutical composition comprising a compound according to any one of Embodiments 1-9, pharmaceutically acceptable salts thereof, deuterated forms thereof, isomers thereof, solvates thereof and mixtures thereof and a pharmaceutically acceptable carrier.

Embodiment 11. A method for treating a patient suffering from depression, pain, or addiction to substances which comprises administering to the patient an effective amount of at least one compound or composition according to any one of Embodiments 1-9, pharmaceutically acceptable salts thereof, deuterium forms thereof, isomers thereof, solvates thereof and mixtures thereof and/or a pharmaceutical composition according to Embodiment 10.

Embodiment 12. The method according to Embodiment 11, wherein said substance is selected from the group consisting of cocaine, methamphetamine, nicotine and alcohol.

Embodiment 13. A process for the preparation of a compound according to any one of Embodiments 1-9.

E. Administration and Pharmaceutical Compositions

In keeping with the present disclosure, the compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The compounds alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-doses or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the treatment of a condition that is capable of treatment with an inhibitor of biogenic amine reuptake. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity.

The total amount of the compound of the present disclosure administered in a typical treatment is preferably between about 10 mg/kg and about 1000 mg/kg of body weight for mice, and between about 10 mg/kg and about 500 mg/kg of body weight, and more preferably between 20 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

F. EXAMPLES

The following preparations and examples are given to enable those skilled in the art to more clearly understand and to practice the present invention. They should not be considered as limiting the scope of the invention, but merely as being illustrative and representative.

1. General Experimental Methods

In the examples for the preparation, purification and characterization of compounds described below, melting points were determined in open capillary tubes with a Mel-Temp melting point apparatus or with an MPA100 OptiMelt automatic melting point apparatus. $^1$H NMR spectra were recorded at 300 MHz or 400 MHz on a Nicolet 300 NB spectrometer. Chemical shifts are expressed in parts per million downfield from tetramethylsilane. Mass spectra were recorded in electrospray ionization (ESI) mode using the Agilent Time of Flight 6210 spectrometer. Thin layer chromatography (TLC) was performed on Analtech silica gel GF 0.25 mm plates. Column chromatographic purifications were performed using Isco-Teledyne purification system. Purified samples were dried overnight in vacuum over $P_2O_5$ at 78° C. HPLC was done using Agilent 1100 LC equipped with a diode array UV detector and monitored at multiple wavelengths on Bondclone 10μ. C18 column using Solvent A: $H_2O$, solvent B: MeOH, 1.0 mL/minute; 30 min linear gradient from 10-90% solvent B. LC-MS was done using the Agilent Time of Flight 6210 spectrometer equipped with the Agilent 1100 HPLC series.

2. Chemistry Experimentals a. Synthesis of N-(3,3-Diphenylpropyl)-2-(Pyridin-3-yl)Quinazolin-4-Amine (1)

4-Chloro-2-(pyridin-3-yl)quinazoline (0.241 g, 1.0 mmol) and 3,3-diphenylpropan-1-amine (0.264 g, 1.25 mmol) were dissolved in 1-methyl-2-pyrrolidone (5 mL). N,N-Diisopropylethylamine (0.162 g, 1.25 mmol) was added and the mixture was stirred under argon overnight. The reaction mixture was diluted with water and extracted with $CHCl_3$. The $CHCl_3$ extract was washed with water and the organic layer was dried over anhydrous $Na_2SO_4$, filtered and the filtrate was concentrated under reduced pressure. The residue thus obtained was purified over a column of silica gel using EtOAc-hexane (20:80) as the eluent to obtain 0.202 g (29%) of the desired product. Mp 180-181° C. $^1$H NMR (400 MHz, DMSO-$d_6$) δ 9.51 (dd, J=2.2, 0.8 Hz, 1H), 8.67 (dd, J=4.8, 1.7 Hz, 1H), 8.59-8.44 (m, 2H), 8.24 (dt, J=8.4, 1.0 Hz, 1H), 7.84-7.74 (m, 2H), 7.60-7.45 (m, 2H), 7.41-7.26 (m, 8H), 7.23-7.14 (m, 2H), 4.16 (t, J=7.7 Hz, 1H), 3.64 (ddd, J=9.2, 7.4, 5.5 Hz, 2H), 2.51-2.44 (m, 1H). MS m/z 417 (M+H)$^+$. Elemental analysis calculated (%) for $C_{28}H_{24}N_4.0.5CHCl_3$: C 79.74, H 5.74, N 13.26. Found: C 79.60, H 5.38, N 13.16.

b. Synthesis of N-(2,2-Diphenylethyl)-2-(Pyridin-3-yl)Quinazolin-4-Amine (2)

To a mixture of 4-chloro-2-(pyridin-3-yl)quinazoline (0.265 g, 1.097 mmol) and 2,2-diphenylethanamine (0.326 g, 1.65 mmol) in 1-methyl-2-pyrrolidone (5 mL) was added N,N-diisopropylethylamine (0.258 g, 2.0 mmol) and the mixture was stirred under argon overnight. Water (1.0 mL) was added and the pH of the mixture was adjusted to 10 with aq $NH_4OH$. The mixture was stirred at room temperature for 15 minutes. The solid that precipitated out was filtered, washed with water and dried. The crude product thus obtained was purified by column chromatography over silica gel to obtain 0.242 g (35%) of the desired product. Mp 175-177° C. $^1$H NMR (400 MHz, $CDCl_3$) δ 9.78 (dd, J=2.2, 0.8 Hz, 1H), 8.82 (dt, J=8.0, 2.0 Hz, 1H), 8.69 (dd, J=4.8, 1.7 Hz, 1H), 7.91 (dt, J=8.3, 0.9 Hz, 1H), 7.72 (ddd, J=8.4, 5.9, 2.4 Hz, 1H), 7.45-7.23 (m, 13H), 5.70 (t, J=5.7 Hz, 1H), 4.57-4.40 (m, 3H). MS m/z 403 (M+H)$^+$. Elemental analysis calculated (%) for $C_{27}H_{22}N_4.0.25H_2O$: C 79.68, H 5.57, N 13.77. Found: C 79.87, H 5.18, N 13.74.

c. Synthesis of N-Benzhydryl-2-(Piperidin-1-yl)Quinazolin-4-Amine (3)

i. Step 1

To a mixture of 2,4-dichloroquinazoline (1.0 g, 5.02 mmol) and diphenylmethanamine (1.16 g, 5.5 mmol) in THF (20 mL) was added triethylamine (0.84 mL, 6.02 mmol) and the mixture was stirred at room temperature for 3 hours. The reaction mixture was filtered and the filtrate was concentrated under reduced pressure. The residue obtained was purified by recrystallization from ethanol to yield 1.42 g (76%) of N-benzhydryl-2-chloroquinazolin-4-amine. Mp 158-160° C. TLC $R_f$ 0.55 (EtOAc-hexane, 75:25). $^1$H NMR (400 MHz, DMSO-$d_6$) δ 9.34 (d, J=8.4 Hz, 2H), 8.81 (s, 1H), 8.61 (ddd, J=8.4, 1.3, 0.6 Hz, 2H), 7.83 (ddd, J=8.3, 6.9, 1.3 Hz, 2H), 7.65 (ddd, J=8.4, 1.2, 0.6 Hz, 2H), 7.61-7.26 (m, 5H), 6.79 (d, J=8.3 Hz, 2H). MS m/z 346 (M+H)$^+$. Elemental analysis calculated (%) for $C_{21}H_{16}N_3Cl$: C 72.94, H 4.66, N 12.15. Found: C 72.84, H 4.47, N 11.87.

ii. Step 2

A solution of the above intermediate (0.5 g, 1.45 mmol) and piperidine (0.37 g, 4.35 mmol) in ethanol (10 mL) was refluxed for 4 hours. The reaction mixture was concentrated under reduced pressure. The residue obtained was dissolved in EtOAc (20 mL) and washed with saturated aqueous $Na_2CO_3$ solution and brine. The organic layer was separated, dried over anhydrous $Na_2SO_4$, and the solvent was removed under reduced pressure. The residue thus obtained was purified over a column of silica using the EtOAc-hexane (1:1). Yield 0.35 g (61%). Mp 190-192° C. TLC $R_f$ 0.49 (EtOAc-Hexane, 75:25). $^1$H NMR (400 MHz, DMSO-$d_6$) δ 8.49 (d, J=7.8 Hz, 1H), 8.33-8.22 (m, 1H), 7.49 (ddd, J=8.4, 6.9, 1.4 Hz, 1H), 7.44-7.38 (m, 4H), 7.38-7.29 (m, 4H), 7.30-7.19 (m, 3H), 7.03 (ddd, J=8.2, 6.9, 1.2 Hz, 1H), 6.66 (d, J=7.7 Hz, 1H), 3.87-3.56 (m, 4H), 1.70-1.49 (m, 2H), 1.39 (dq, J=8.3, 5.1, 4.2 Hz, 4H). MS m/z 395 (M+H)$^+$. Elemental analysis calculated (%) for $C_{26}H_{26}N_4.0.25H_2O$: C 78.26, H 6.69; N 14.04. Found: C 78.51, H 6.45, N 14.00.

d. Synthesis of N-(2,2-Diphenylethyl)-2-(Piperidin-1-yl)Quinazolin-4-Amine (4)

i. Step 1

To a mixture of 2,4-dichloroquinazoline (1.0 g, 5.02 mmol) and 2,2-diphenylethanamine (1.05 g, 5.5 mmol) in THF (20 mL) was added triethylamine (0.84 mL, 6.02 mmol) and the mixture was stirred at room temperature for 3 hours. The reaction mixture was filtered and the filtrate was concentrated under reduced pressure. The residue obtained was purified by recrystallization from ether to yield 1.38 g (77%) of 2-chloro-N-(2,2-diphenylethyl)quinazolin-4-amine. Mp 184-186° C. TLC $R_f$ 0.39 (EtOAc-Hexane, 75:25). $^1$H NMR (400 MHz, DMSO-$d_6$) δ 8.78 (t, J=5.5 Hz, 1H), 8.13 (ddd, J=8.6, 1.3, 0.6 Hz, 1H), 7.76 (ddd, J=8.3, 7.0, 1.2 Hz, 1H), 7.60 (ddd, J=8.3, 1.3, 0.6 Hz, 1H), 7.47 (ddd, J=8.2, 7.0, 1.2 Hz, 1H), 7.36-7.24 (m, 8H), 7.22-7.15 (m, 3H), 4.60 (t, J=7.8 Hz, 1H), 4.15 (dd, J=7.8, 5.4 Hz, 2H). MS m/z 360 (M+H)$^+$. Elemental analysis calculated (%) for $C_{22}H_{18}N_3Cl.H_2O$: C 69.93, H 5.34, N 11.12. Found: C 72.01, H 4.82, N 11.24.

ii. Step 2

A mixture of the above intermediate (0.5 g, 1.445 mmol) and piperidine (0.370 g, 4.35 mmol) in ethanol (10 mL) was refluxed for 4 hours. The reaction mixture was cooled and concentrated under reduced pressure. The residue obtained was dissolved in EtOAc (20 mL) and washed with saturated aq $Na_2CO_3$ solution and brine. The organic layer was separated, dried over anhydrous $Na_2SO_4$, filtered and concentrated under reduced pressure. The residue thus obtained was purified over a column of silica gel using the EtOAc-hexane (1:1) to yield 0.28 g (39%) of the desired product. Mp 160-164° C. TLC $R_f$ 0.29 (EtOAc-hexane, 75:25). $^1$H NMR (400 MHz, DMSO-$d_6$) δ 8.00 (t, J=5.5 Hz, 1H), 7.82 (ddd, J=8.4, 1.4, 0.6 Hz, 1H), 7.47-7.39 (m, 1H), 7.37-7.24 (m, 8H), 7.24-7.12 (m, 3H), 6.95 (ddd, J=8.1, 6.9, 1.2 Hz, 1H), 4.68 (t, J=7.6 Hz, 1H), 4.08 (dd, J=7.6, 5.4 Hz, 2H), 3.87-3.75 (m, 4H), 1.65 (q, J=6.2 Hz, 2H), 1.55 (tt, J=8.1, 4.1 Hz, 4H). MS 409 (M+H)⁺. Elemental analysis calculated (%) for $C_{27}H_{28}N_4$: C 78.51, H 6.96, N 13.56. Found: C 78.13; H 6.69; N 13.26.

e. Synthesis of N-(3,3-Diphenylpropyl)-2-(Thiophen-3-yl)Quinazolin-4-Amine (5)

ii. Step 1

A mixture of 2,4-dichloroquinozoline (1.0 g, 5.02 mmol) and 3,3-diphenylpropan-1-amine (1.167 g, 5.5 mmol) and triethylamine (0.84 mL, 6.02 mmol) in THF (20 mL) was stirred at room temperature for 3 hours. The reaction mixture was filtered and concentrated. The residue was purified by recrystallization from ether to obtain 1.42 g (76%) of 2-chloro-N-(3,3-diphenylpropyl)quinazolin-4-amine. Mp 142-144° C. TLC $R_f$ 0.37 (EtOAc-hexane, 75:25). ¹H NMR (400 MHz, DMSO-d₆) δ 8.73 (t, J=5.4 Hz, 1H), 8.23 (ddd, J=8.5, 1.3, 0.7 Hz, 1H), 7.78 (dddd, J=8.3, 7.0, 1.4, 0.5 Hz, 1H), 7.60 (ddd, J=8.4, 1.2, 0.6 Hz, 1H), 7.52 (dddd, J=8.2, 6.9, 1.3, 0.5 Hz, 1H), 7.41-7.33 (m, 4H), 7.33-7.24 (m, 4H), 7.17 (tdt, J=6.8, 1.7, 0.8 Hz, 2H), 4.10 (t, J=7.7 Hz, 1H), 3.43 (ddd, J=9.0, 7.4, 5.5 Hz, 2H), 2.44 (ddd, J=9.1, 7.5, 5.7 Hz, 2H). MS m/z 374 (M+H)⁺. Elemental analysis calculated (%) for $C_{23}H_{20}N_3Cl.0.5H_2O$: C 72.15, H 5.33, N 10.97. Found: C 72.21, H 4.85, N 10.68.

ii. Step 2

A mixture of the above intermediate (0.2 g, 0.536 mmol) and thiophene-3-boronic acid (0.08 g, 0.643 mmol) tetrakis(triphenylphosphine)palladium (0.038 g, 0.0032 mmol) and $K_2CO_3$ (0.148 g, 1.07 mmol) in dioxane-water (8 mL:2 mL) was refluxed for 4 hours. The reaction mixture was cooled to room temperature and concentrated under reduced pressure. The residue obtained was dissolved in EtOAc (20 mL) and washed with saturated aq $Na_2CO_3$ solution and brine. The organic layer was separated, dried over anhydrous $Na_2SO_4$, and concentrated. The residue was purified over a column of silica gel using the EtOAc-hexane (1:9) to yield 0.16 g (72%) of the desired product. Mp 144-147° C. TLC $R_f$ 0.56 (EtOAc-hexane, 75:25). ¹H NMR (400 MHz, DMSO-d₆) δ 8.33 (t, J=5.7 Hz, 1H), 8.19 (ddd, J=8.5, 1.4, 0.7 Hz, 1H), 8.05 (dt, J=3.1, 0.9 Hz, 1H), 7.76-7.66 (m, 3H), 7.58 (ddd, J=5.0, 3.1, 0.6 Hz, 1H), 7.44 (ddd, J=8.2, 6.6, 1.6 Hz, 1H), 7.39-7.33 (m, 3H), 7.34-7.25 (m, 3H), 7.23-7.13 (m, 2H), 4.14 (t, J=7.6 Hz, 1H), 3.66-3.54 (m, 2H), 2.50 (dq, J=4.1, 2.1 Hz, 3H), 2.47-2.37 (m, 2H). MS m/z 422 (M+H)⁺. Elemental analysis calculated (%) for $C_{27}H_{23}N_3S.0.25H_2O$: C 76.12, H 5.56, N 9.86. Found: C 76.01, H 5.45, N 9.78.

f. Synthesis of N-(2,2-Diphenylethyl)-2-(Thiophen-2-yl)Quinazolin-4-Amine (6)

This compound was prepared from 2-chloro-N-(2,2-diphenylethyl)quinazolin-4-amine (0.2 g, 0.55 mmol) and thiophene-2-boronic acid (0.082 g, 0.643 mmol) in the presence of tetrakis(triphenylphosphine)palladium (0.0038 g, 0.0032 mmol) and $K_2CO_3$ (0.148 g, 1.07 mmol) in dioxane-water (8 mL:2 mL) as described in step 2 for the preparation of compound 5. The product was purified by chromatography over a column of silica using EtOAc-hexane (1:9). Yield 0.09 g (40%). Mp 148-152° C. TLC $R_f$ 0.42 (EtOAc-hexane, 75:25). ¹H NMR (400 MHz, DMSO-d₆) δ 8.44 (t, J=5.5 Hz, 1H), 8.08 (ddd, J=8.4, 1.3, 0.6 Hz, 1H), 8.00-7.94 (m, 1H), 7.75-7.62 (m, 3H), 7.44-7.14 (m, 12H), 4.79 (t, J=7.8 Hz, 1H), 4.25 (dd, J=7.9, 5.4 Hz, 2H). MS m/z 408 (M+H)⁺. Elemental analysis calculated (%) for $C_{26}H_{21}N_3S.0.25H_2O$: C 75.79, H 5.26, N 10.20. Found: C 75.92, H 4.88, N 10.23.

g. Synthesis of N-(3,3-Diphenylpropyl)-2-(Thiophen-2-yl)Quinazolin-4-Amine (7)

2-Chloro-N-(2,2-diphenylethyl)quinazolin-4-amine was (0.2 g, 0.536 mmol) was reacted with thiophene-2-boronic acid (0.103 g, 0.8 mmol) in the presence of tetrakis(triphenylphosphine)palladium (0.0038 g, 0.0032 mmol), $K_2CO_3$ (0.146 g, 1.07 mmol) in dioxane-water (8 mL:2 mL) as described in step 2 for the preparation of compound 5. The crude product was purified by chromatography over a column of silica using the EtOAc-hexane (1:9). Yield 0.086 g (38%). Mp 152-155° C. TLC $R_f$ 0.41 (EtOAc-hexane, 75:25). ¹H NMR (400 MHz, DMSO-d₆) δ 8.38 (t, J=5.6 Hz, 1H), 8.21-8.13 (m, 1H), 7.75 (ddd, J=3.6, 1.3, 0.4 Hz, 1H), 7.68-7.63 (m, 5H), 7.43 (ddd, J=8.2, 6.8, 1.4 Hz, 1H), 7.39-7.33 (m, 4H), 7.33-7.26 (m, 4H), 7.22-7.13 (m, 3H), 4.14 (t, J=7.7 Hz, 1H), 3.56 (ddd, J=9.1, 7.5, 5.5 Hz, 2H). MS m/z 422 (M+H)⁺. Elemental analysis calculated (%) for $C_{27}H_{23}N_3S$: C 76.17, H 5.26, N 10.20. Found: C 76.21, H 5.10, N 9.84.

h. Synthesis of N-Benzhydryl-2-(Benzo[b]Thiophen-2-yl)Quinazolin-4-Amine (8)

To a stirred solution of N-benzhydryl-2-chloroquinazolin-4-amine (0.150 g, 0.43 mmol) in dioxane-water (8 mL:0.8 mL) was added benzo(b)thiophene-2-boronic acid (0.153 g, 0.86 mmol) and $K_2CO_3$ (0.119 g, 0.86 mmol). The reaction mixture was purged with argon and stirred for 15 minutes at room temperature. Tetrakis(triphenylphosphine)palladium (0.050 g, 0.043 mmol) was added and the reaction mixture was heated under reflux for 15 hours. The reaction mixture was then cooled to room temperature, diluted with water and extracted with EtOAc (2×10 mL). The organic layer was separated, dried over anhydrous $Na_2SO_4$ and concentrated under reduced pressure. The residue obtained was purified by column chromatography using hexanes:EtOAc (0-70%) as eluent to obtain 0.100 g (52%) of the desired product. Mp 180-182° C. TLC $R_f$ 0.40 (cyclohexane-EtOAc, 2:1). ¹H NMR (400 MHz, DMSO-d₆) δ 9.08 (d, J=8.3 Hz, 1H), 8.59 (dd, J=8.2, 1.2 Hz, 1H), 8.30 (d, J=0.7 Hz, 1H), 8.04-7.88 (m, 2H), 7.86-7.72 (m, 2H), 7.57-7.49 (m, 5H), 7.46-7.35 (m, 6H), 7.34-7.25 (m, 2H), 7.08 (d, J=8.2 Hz, 1H). HRMS m/z calcd for $C_{29}H_{21}N_3S+H^+$ [M+H⁺]: 444.1529. found: 444.1533. HPLC: 96% ($t_R$=20.9 min).

i. Synthesis of N-(3,3-Diphenylpropyl)-2-(Piperidin-1-yl)Quinazolin-4-Amine (9)

A mixture of 2-chloro-N-(3,3-diphenylpropyl)quinazolin-4-amine (0.5 g, 1.445 mmol) and piperidine (0.370 g, 4.35 mmol) in ethanol was refluxed for 4 hours. The reaction mixture was concentrated under reduced pressure, the residue was dissolved in EtOAc (20 mL), washed with saturated aqueous $Na_2CO_3$ solution and brine. The organic layer was separated, dried over anhydrous $Na_2SO_4$, and the solvent was removed under reduce pressure. The residue thus obtained was purified by chromatography over a column of silica gel using EtOAc-hexane (1:1) as the eluent. Yield 0.142 g (25%). Mp 160-164° C. TLC $R_f$ 0.19 (EtOAc-hexane, 75:25). ¹H NMR (400 MHz, DMSO-d₆) δ 11.86 (s, 1H), 9.02 (s, 1H), 8.13 (d, J=8.1 Hz, 1H), 7.71-7.57 (m, 2H), 7.36-7.23 (m, 8H), 7.17 (ddt, J=7.6, 6.4, 1.5 Hz, 2H), 4.08 (t, J=7.7 Hz, 1H), 3.75-3.67 (m, 4H), 3.53-3.39 (m, 2H), 2.47-2.36 (m, 2H), 1.64 (q, J=6.5, 6.1 Hz, 2H), 1.53 (dd, J=6.9, 3.8 Hz, 4H). MS m/z 422 (M+H)⁺. Elemental analysis calculated (%) for $C_{28}H_{30}N_4 \cdot 0.25H_2O$: C 78.75, H 7.20; N 13.12. Found: C 78.96, H 6.85, N 13.42.

j. Synthesis of N-(2,2-Diphenylethyl)-2-(Thiophen-3-yl)Quinazolin-4-Amine (10)

This compound was prepared by reacting 2-chloro-N-(2,2-diphenylethyl)quinazolin-4-amine (0.2 g, 0.536 mmol) with thiophene-3-boronic acid (0.103 g, 0.8 mmol), in the presence of tetrakis(triphenylphosphine)palladium (0.0038 g, 0.0032 mmol) and $K_2CO_3$ (0.146 g, 1.07 mmol) in dioxane-water (8 mL:2 mL) as described in step 2 for the preparation of compound 5. The crude product was purified by chromatography over a column of silica gel using the EtOAc-hexane (1:9) as the eluent. Yield 0.132 g (58%). Mp 152-155° C. TLC $R_f$ 0.42 (EtOAc-hexane, 75:25). $^1$H NMR (400 MHz, DMSO-$d_6$) δ 8.38-8.30 (m, 2H), 8.09 (d, J=8.2 Hz, 1H), 7.89 (dd, J=5.0, 1.1 Hz, 1H), 7.73-7.65 (m, 2H), 7.65-7.60 (m, 1H), 7.44-7.36 (m, 5H), 7.29 (t, J=7.6 Hz, 4H), 7.22-7.15 (m, 2H), 4.73 (t, J=7.7 Hz, 1H), 4.38-4.03 (m, 2H). MS m/z 408 (M+H)$^+$. Elemental analysis calculated (%) for $C_{26}H_{21}N_3S \cdot 0.25H_2O$: C 75.79, H 5.26, N 10.29. Found: C 75.74, H 4.95, N 10.14.

k. Synthesis oF N-Benzhydryl-2-(Thiophen-3-yL)Quinazolin-4-Amine (11)

2-Chloro-N-(2,2-diphenylmethyl)quinazolin-4-amine (0.2 g, 0.536 mmol) was reacted with thiophene-3-boronic acid (0.088 g, 0.8 mmol) in the presence of tetrakis(triphenylphosphine)palladium (12 mg, 0.01 mmol) and $K_2CO_3$ (157 mg, 1.14 mmol) in dioxane-water (8 mL:2 mL) according to the procedure described in step 2 for the preparation of compound 5. The product obtained was purified over a column of silica gel using the EtOAc-hexane (1:9) to yield 0.076 g (34%) of the title compound. Mp 152-155° C. TLC $R_f$ 0.41 (EtOAc-Hexane, 75:25). $^1$H NMR (400 MHz, DMSO-$d_6$) δ 8.90 (d, J=8.2 Hz, 1H), 8.60-8.49 (m, 1H), 8.34 (dd, J=3.1, 1.1 Hz, 1H), 7.84 (dd, J=5.0, 1.1 Hz, 1H), 7.80-7.67 (m, 2H), 7.58 (dd, J=5.0, 3.1 Hz, 1H), 7.53-7.43 (m, 5H), 7.37 (dd, J=8.3, 6.8 Hz, 4H), 7.32-7.20 (m, 2H), 7.03 (d, J=8.0 Hz, 1H). MS m/z 394 (M+H)$^+$. Elemental analysis calculated (%) for $C_{25}H_{19}N_3S$: C 75.79, H 5.26, N 10.29. Found: C 74.92, H 4.67, N 10.37.

l. Synthesis of N-Benzhydryl-2-(2-(Dimethylamino)Pyrimidin-5-yl)Quinazolin-4-Amine (12)

This compound was prepared from N-benzhydryl-2-chloroquinazolin-4-amine and (2-(dimethylamino)pyrimidin-5-yl)boronic acid according to the procedure described for the preparation of compound 8. Yield 86%. Mp 85-87° C. TLC $R_f$ 0.50 (cyclohexane-EtOAc, 2:1). $^1$H NMR (400 MHz, DMSO-$d_6$) δ 9.23 (d, J=0.3 Hz, 2H), 8.90 (d, J=8.1 Hz, 1H), 8.56 (dd, J=8.3, 1.2 Hz, 1H), 7.81-7.67 (m, 2H), 7.52-7.43 (m, 5H), 7.40-7.33 (m, 4H), 7.32-7.22 (m, 2H), 6.99 (d, J=7.9 Hz, 1H), 3.21 (s, 6H). HRMS m/z calcd for $C_{27}H_{24}N_6 + H^+$ [M+H]$^+$: 433.2135, found: 433.2140. HPLC: 100% ($t_R$=16.3 min).

m. Synthesis of N-Benzhydryl-2-(1H-indol-5-yl)Quinazolin-4-Amine (13)

This compound was prepared from N-benzhydryl-2-chloroquinazolin-4-amine and indole-5-boronic acid according to the procedure described for the preparation of compound 8. Yield 70%. Mp 175-177° C.; TLC $R_f$ 0.35 (cyclohexane-EtOAc, 2:1). $^1$H NMR (400 MHz, DMSO-$d_6$) δ 11.19 (s, 1H), 8.81 (d, J=8.0 Hz, 1H), 8.68 (d, J=1.5 Hz, 1H), 8.58-8.51 (m, 1H), 8.27 (dd, J=8.6, 1.6 Hz, 1H), 7.81-7.71 (m, 2H), 7.53 (ddt, J=6.9, 1.2, 0.7 Hz, 4H), 7.47-7.34 (m, 7H), 7.33-7.23 (m, 2H), 7.09 (d, J=7.9 Hz, 1H), 6.56 (td, J=2.0, 1.0 Hz, 1H). HRMS m/z calcd for $C_{29}H_{22}N_4 + H^+$ [M+H]$^+$: 427.1917, found: 427.1921. HPLC: 99% ($t_R$=14.1 min).

n. Synthesis of N-Benzhydryl-2-(Pyrimidin-5-yl)Quinazolin-4-Amine (14)

This compound was prepared from N-benzhydryl-2-chloroquinazolin-4-amine and pyrimidine-5-boronic acid according to the procedure described for the preparation of compound 8. Yield 59%. Mp 210° C. TLC $R_f$ 0.35 (cyclohexane-EtOAc, 2:1). $^1$H NMR (400 MHz, DMSO-$d_6$) δ 9.62 (s, 2H), 9.27 (s, 1H), 9.13 (d, J=7.9 Hz, 1H), 8.65 (dt, J=8.5, 1.0 Hz, 1H), 7.90-7.80 (m, 2H), 7.58 (ddd, J=8.3, 5.7, 2.5 Hz, 1H), 7.54-7.49 (m, 4H), 7.42-7.33 (m, 4H), 7.33-7.23 (m, 2H), 7.02 (d, J=7.8 Hz, 1H). HRMS m/z calcd for $C_{25}H_{19}N_5 + H^+$ [M+H]$^+$: 390.1713, found: 390.1714. HPLC: 99% ($t_R$=14.2 min).

o. Synthesis of N-(2,2-Diphenylethyl)-2-(Benzo[B]Thiophen-2-yl)Quinazolin-4-Amine (15)

This compound was prepared from 2-chloro-N-(2,2-diphenylethyl)quinazolin-4-amine and benzo(b)thiophene-2-boronic acid according to the procedure described for the preparation of compound 8. Yield 39%. Mp 178-179° C. TLC $R_f$ 0.45 (cyclohexane-EtOAc, 2:1). $^1$H NMR (400 MHz, DMSO-$d_6$) δ 8.52 (t, J=5.5 Hz, 1H), 8.30 (d, J=0.7 Hz, 1H), 8.16-8.09 (m, 1H), 8.06-8.00 (m, 1H), 7.99-7.94 (m, 1H), 7.80-7.67 (m, 2H), 7.49-7.38 (m, 7H), 7.37-7.27 (m, 4H), 7.25-7.15 (m, 2H), 4.79 (t, J=7.7 Hz, 1H), 4.31 (dd, J=7.8, 5.4 Hz, 2H). HRMS m/z calcd for $C_{30}H_{23}N_3S + H^+$ [M+H]$^+$: 458.1685, found: 458.1688, found: 416.2120. HPLC: 100% ($t_R$=19.9 min).

p. Synthesis of N-(2,2-Diphenylethyl)-2-(2-(Dimethylamino)Pyrimidin-5-yl)Quinazolin-4-Amine (16)

This compound was prepared from 2-chloro-N-(2,2-diphenylethyl)quinazolin-4-amine and (2-(dimethylamino)pyrimidin-5-yl)boronic acid according to the procedure described for the preparation of compound 8. Yield 51%. Mp 194-196° C. TLC $R_f$ 0.35 (cyclohexane-EtOAc, 2:1). $^1$H NMR (400 MHz, DMSO-$d_6$) δ 9.30 (s, 1H), 8.36 (t, J=5.5 Hz, 1H), 8.08 (dd, J=8.1, 1.1 Hz, 2H), 7.75-7.62 (m, 2H), 7.43-7.33 (m, 5H), 7.28 (dd, J=8.3, 6.9 Hz, 4H), 7.22-7.13 (m, 2H), 4.69 (t, J=7.7 Hz, 1H), 4.30 (dd, J=7.8, 5.4 Hz, 2H), 3.23 (s, 6H). HRMS m/z calcd for $C_{28}H_{26}N_6 + H^+$ [M+H]$^+$: 447.2292, found: 447.2292. HPLC: 96% ($t_R$=16.3 min).

q. Synthesis of N-(2,2-Diphenylethyl)-2-(1H-indol-5-yl)Quinazolin-4-Amine (17)

This compound was prepared from 2-chloro-N-(2,2-diphenylethyl)quinazolin-4-amine and indole-5-boronic acid according to the procedure described for the preparation of compound 8. Yield 79%. Mp 237° C. TLC $R_f$ 0.30 (cyclohexane-EtOAc, 2:1). $^1$H NMR (400 MHz, DMSO-$d_6$) δ 11.23 (s, 1H), 8.81 (dd, J=1.5, 0.8 Hz, 1H), 8.36 (dd, J=8.6, 1.6 Hz, 1H), 8.33 (t, J=5.4 Hz, 1H), 8.13-8.06 (m, 1H), 7.75-7.65 (m, 2H), 7.51-7.28 (m, 10H), 7.26-7.17 (m, 2H), 6.53 (ddd, J=3.0, 1.9, 0.9 Hz, 1H), 4.85 (t, J=7.5 Hz, 1H), 4.31 (dd, J=7.5, 5.3 Hz, 2H), 3.35-3.21 (m, 1H). HRMS m/z calcd for $C_{30}H_{24}N_4+H^+$ [M+H$^+$]: 441.2074, found: 441.2076. HPLC: 100% ($t_R$=13.0 min).

r. Synthesis of N-(2,2-Diphenylethyl)-2-(Pyrimidin-5-yl)Quinazolin-4-Amine (18)

This compound was prepared from 2-chloro-N-(2,2-diphenylethyl)quinazolin-4-amine and pyrimidin-5-boronic acid according to the procedure described for the preparation of compound 8. Yield 65%. Mp 213-215° C. TLC $R_f$ 0.35 (cyclohexane-EtOAc, 2:1). $^1$H NMR (400 MHz, DMSO-d$_6$) δ 9.69 (s, 2H), 9.31 (s, 1H), 8.66-8.58 (m, 1H), 8.18 (dt, J=8.4, 1.0 Hz, 1H), 7.84-7.74 (m, 2H), 7.50 (dt, J=8.2, 4.1 Hz, 1H), 7.46-7.38 (m, 4H), 7.29 (ddd, J=7.7, 7.0, 1.1 Hz, 4H), 7.21-7.14 (m, 2H), 4.72 (t, J=7.7 Hz, 1H), 4.34 (dd, J=7.7, 5.4 Hz, 2H). HRMS m/z calcd for $C_{26}H_{21}N_5+H^+$ [M+H$^+$]: 404.1871, found: 404.1872. HPLC: 99% ($t_R$=14.2 min).

s. Synthesis of N-(3,3-Diphenylpropyl)-2-(Benzo[B]Thiophen-2-yl)Quinazolin-4-Amine (19)

This compound was prepared from 2-chloro-N-(3,3-diphenylpropyl)quinazolin-4-amine and benzo(b)thiophene-2-boronic acid according to the procedure described for the preparation of compound 8. Yield 40%. Mp 201-203° C. TLC $R_f$ 0.50 (cyclohexane-EtOAc, 2:1). $^1$H NMR (400 MHz, DMSO-d$_6$) δ 8.46 (t, J=5.6 Hz, 1H), 8.26-8.19 (m, 1H), 8.08-8.03 (m, 1H), 8.03-7.97 (m, 1H), 7.97-7.90 (m, 1H), 7.82-7.68 (m, 2H), 7.49 (ddd, J=8.2, 6.7, 1.4 Hz, 1H), 7.46-7.36 (m, 6H), 7.34-7.27 (m, 4H), 7.25-7.16 (m, 2H), 4.18 (t, J=7.6 Hz, 1H), 3.64 (dt, J=8.3, 5.8 Hz, 4H). HRMS m/z calcd for $C_{31}H_{25}N_3S+H^+$ [M+H$^+$]: 472.1842, found: 472.1840. HPLC: 100% ($t_R$=20.9 min).

t. Synthesis of N-(3,3-Diphenylpropyl)-2-(2-(Dimethylamino)Pyrimidin-5-yl)Quinazolin-4-Amine (20)

This compound was prepared from 2-chloro-N-(3,3-diphenylpropyl)quinazolin-4-amine and (2-(dimethylamino)pyrimidin-5-yl)boronic acid according to the procedure described for the preparation of compound 8. Yield 81%. Mp 213° C. TLC $R_f$ 0.35 (cyclohexane-EtOAc, 2:1). $^1$H NMR (400 MHz, DMSO-d$_6$) δ 9.16 (s, 2H), 8.35 (t, J=5.5 Hz, 1H), 8.18 (dd, J=8.3, 1.0 Hz, 1H), 7.77-7.63 (m, 2H), 7.42 (ddd, J=8.3, 6.7, 1.5 Hz, 1H), 7.39-7.34 (m, 4H), 7.33-7.27 (m, 4H), 7.22-7.13 (m, 2H), 4.14 (t, J=7.7 Hz, 1H), 3.63-3.53 (m, 2H), 3.23 (s, 6H), 2.46 (t, J=7.3 Hz, 2H). HRMS m/z calcd for $C_{29}H_{28}N_6+H^+$ [M+H$^+$]: 461.2448, found: 461.2446. HPLC: 96% ($t_R$=14.5 min).

u. Synthesis of N-(3,3-Diphenylpropyl)-2-(1H-Indol-5-yl)Quinazolin-4-Amine (21)

This compound was prepared from 2-chloro-N-(3,3-diphenylpropyl)quinazolin-4-amine and indole-5-boronic acid according to the procedure described for the preparation of compound 8. Yield 63%. Mp 206° C. TLC $R_f$ 0.30 (cyclohexane-EtOAc, 2:1). $^1$H NMR (400 MHz, DMSO-d$_6$) δ 11.19 (s, 1H), 8.63 (dt, J=1.4, 0.6 Hz, 1H), 8.26-8.15 (m, 3H), 7.77-7.67 (m, 2H), 7.46-7.36 (m, 7H), 7.34-7.28 (m, 4H), 7.20 (ddt, J=8.0, 6.6, 1.3 Hz, 2H), 6.54 (ddd, J=3.0, 1.9, 0.9 Hz, 1H), 4.20 (t, J=7.7 Hz, 1H), 3.66 (dt, J=9.3, 6.0 Hz, 2H), 3.37-3.19 (m, 1H), 2.58-2.51 (m, 1H). HRMS m/z calcd for $C_{31}H_{26}N_4+H^+$ [M+H$^+$]: 455.2230, found: 455.2230. HPLC: 100% ($t_R$=10.8 min).

v. Synthesis of N-(3,3-Diphenylpropyl)-2-(Pyrimidin-5-yl)Quinazolin-4-Amine (22)

This compound was prepared from 2-chloro-N-(3,3-diphenylpropyl)quinazolin-4-amine and pyrimidine-5-boronic acid according to the procedure described for the preparation of compound 8. Yield 68%. Mp 154° C.; TLC $R_f$ 0.35 (cyclohexane-EtOAc, 2:1). $^1$H NMR (400 MHz, DMSO-d$_6$) δ 9.53 (s, 2H), 9.30 (s, 1H), 8.58 (t, J=5.7 Hz, 1H), 8.26 (dt, J=8.4, 1.0 Hz, 1H), 7.86-7.76 (m, 2H), 7.54 (ddd, J=8.2, 5.4, 2.8 Hz, 1H), 7.40-7.34 (m, 4H), 7.32-7.26 (m, 4H), 7.22-7.13 (m, 2H), 4.15 (t, J=7.7 Hz, 1H), 3.69-3.59 (m, 2H), 2.51-2.43 (m, 2H). HRMS m/z calcd for $C_{27}H_{23}N_5+H^+$ [M+H$^+$]: 418.2026, found: 418.2023. HPLC: 100% ($t_R$=16.8 min).

w. Synthesis of 2-(2-(Dimethylamino)Pyrimidin-5-yl)-N-(2,2-Diphenylethyl)-6,7-Dimethoxyquinazolin-4-Amine (23)

This compound was prepared from 2-chloro-N-(2,2-diphenylethyl)-6,7-dimethoxyquinazolin-4-amine and (2-(dimethylamino)pyrimidin-5-yl)boronic acid according to the procedure described for the preparation of compound 8. Yield 66%. Mp 92° C.; TLC $R_f$ 0.50 (cyclohexane-EtOAc, 1:1). $^1$H NMR (400 MHz, DMSO-d$_6$) δ 9.26 (s, 2H), 8.04 (t, J=5.5 Hz, 1H), 7.67-7.58 (m, 2H), 7.58-7.51 (m, 2H), 7.48 (s, 1H), 7.43-7.36 (m, 2H), 7.29 (dd, J=8.3, 6.9 Hz, 2H), 7.23-7.13 (m, 2H), 7.09 (s, 1H), 4.68 (t, J=7.6 Hz, 1H), 4.28 (dd, J=7.6, 5.4 Hz, 2H), 3.89 (s, 3H), 3.83 (s, 3H), 3.22 (s, 6H). HRMS m/z calcd for $C_{30}H_{30}N_6O_2+H^+$ [M+H$^+$]: 507.2503, found: 507.2513. HPLC: 99% ($t_R$=16.6 min).

x. Synthesis of N-(2,2-Diphenylethyl)-2-(1H-indol-5-yl)-6,7-Dimethoxyquinazolin-4-Amine (24)

This compound was prepared from 2-chloro-N-(2,2-diphenylethyl)-6,7-dimethoxyquinazolin-4-amine and indole-5-boronic acid according to the procedure described for the preparation of compound 8. Yield 47%. Mp 117° C. TLC $R_f$ 0.30 (cyclohexane-EtOAc, 1:1). $^1$H NMR (400 MHz, DMSO-d$_6$) δ 11.19 (s, 1H), 8.79-8.74 (m, 1H), 8.33 (dd, J=8.6, 1.6 Hz, 1H), 8.02 (t, J=5.5 Hz, 1H), 7.66-7.52 (m, 1H), 7.50 (s, 1H), 7.47-7.41 (m, 4H), 7.40-7.37 (m, 1H), 7.34 (dd, J=8.4, 6.9 Hz, 4H), 7.27-7.17 (m, 2H), 7.14 (s, 1H), 6.50 (ddd, J=2.9, 2.0, 0.9 Hz, 1H), 4.85 (t, J=7.3 Hz, 1H), 4.34-4.25 (m, 2H), 3.91 (s, 3H), 3.83 (s, 3H). HRMS m/z calcd for $C_{32}H_{28}N_4O_2+H^+$ [M+H$^+$]: 501.2285, found: 501.2288. HPLC: 98% ($t_R$=14.4 min).

y. Synthesis of N-(2,2-Diphenylethyl)-6,7-Dimethoxy-2-(Pyrimidin-5-yl)Quinazolin-4-Amine (25)

This compound was prepared from 2-chloro-N-(2,2-diphenylethyl)-6,7-dimethoxyquinazolin-4-amine and pyrimidine-5-boronic acid according to the procedure described for the preparation of compound 8. Yield 81%. Mp 93° C.; TLC $R_f$ 0.30 (cyclohexane-EtOAc, 1:1). $^1$H NMR (400 MHz, DMSO-d$_6$) δ 9.65 (s, 2H), 9.27 (s, 1H), 8.29 (q, J=6.3, 5.6 Hz, 1H), 7.67-7.50 (m, 2H), 7.46-7.38 (m, 4H), 7.34-7.24 (m, 4H), 7.23-7.13 (m, 2H), 4.70 (t, J=7.5 Hz, 1H), 4.32 (dd, J=7.5, 5.5 Hz, 2H), 3.92 (s, 3H), 3.86 (s, 3H). HRMS m/z calcd for $C_{28}H_{25}N_5O_2+H^+$ [M+H$^+$]: 464.2081, found: 464.2082. HPLC: 99% ($t_R$=15.9 min).

z. Synthesis of N-(2,2-Diphenylethyl)-6,7-Dimethoxy-2-(Thiophen-2-yl)Quinazolin-4-Amine (26)

This compound was prepared from 2-chloro-N-(2,2-diphenylethyl)-6,7-dimethoxyquinazolin-4-amine and thiophene-2-boronic acid according to the procedure described for the preparation of compound 8. Yield 78%. Mp 94° C. TLC $R_f$ 0.50 (cyclohexane-EtOAc, 1:1). $^1$H NMR (400 MHz, DMSO-d$_6$) δ 8.10 (t, J=5.5 Hz, 1H), 7.89 (dd, J=3.6, 1.3 Hz, 1H), 7.65 (dd, J=5.0, 1.3 Hz, 1H), 7.48 (s, 1H), 7.44-7.36 (m, 4H), 7.35-7.25 (m, 4H), 7.23-7.14 (m, 3H), 7.08 (s, 1H), 4.78 (t, J=7.7 Hz, 1H), 4.27-4.19 (m, 2H), 3.90 (s, 3H), 3.82 (s, 3H). HRMS m/z calcd for $C_{28}H_{25}N_3O_2S+H^+$ [M+H$^+$]: 468.1740, found: 468.1747. HPLC: 99% ($t_R$=14.6 min).

aa. Synthesis of N-(2,2-Diphenylethyl)-6,7-Dimethoxy-2-(Thiophen-3-yl)Quinazolin-4-Amine (27)

This compound was prepared from 2-chloro-N-(2,2-diphenylethyl)-6,7-dimethoxyquinazolin-4-amine and thiophene-3-boronic acid according to the procedure described for the preparation of compound 8. Yield 87%. Mp 92° C. TLC $R_f$ 0.50 (cyclohexane-EtOAc, 1:1). $^1$H NMR (400 MHz, DMSO-d$_6$) δ 8.25 (dd, J=3.1, 1.2 Hz, 1H), 8.02 (t, J=5.5 Hz, 1H), 7.86 (dd, J=5.0, 1.2 Hz, 1H), 7.60 (dd, J=5.0, 3.1 Hz, 1H), 7.49 (s, 1H), 7.45-7.37 (m, 4H), 7.30 (dd, J=8.4, 6.9 Hz, 4H), 7.23-7.14 (m, 2H), 7.10 (s, 1H), 4.72 (t, J=7.5 Hz, 1H), 4.27 (dd, J=7.6, 5.4 Hz, 2H), 3.90 (s, 3H), 3.83 (s, 3H). HRMS m/z calcd for $C_{28}H_{25}N_3O_2S+H^+$[M+H$^+$]: 468.1740, found: 468.1745. HPLC: 99% ($t_R$=16.9 min).

bb. Synthesis of N-(2,2-Diphenylethyl)-6,7-Dimethoxy-2-(Pyridin-3-yl)Quinazolin-4-Amine (28)

This compound was prepared from 2-chloro-N-(2,2-diphenylethyl)-6,7-dimethoxyquinazolin-4-amine and pyridine-3-boronic acid according to the procedure described for the preparation of compound 8. Yield 82%. mp 89° C. TLC $R_f$ 0.30 (cyclohexane-EtOAc, 1:1). $^1$H NMR (400 MHz, DMSO-d$_6$) δ 9.60 (dd, J=2.2, 0.9 Hz, 1H), 8.72 (dt, J=7.9, 2.0 Hz, 1H), 8.65 (dd, J=4.8, 1.7 Hz, 2H), 8.18 (t, J=5.5 Hz, 2H), 7.67-7.58 (m, 2H), 7.58-7.49 (m, 2H), 7.45-7.37 (m, 2H), 7.35-7.25 (m, 2H), 7.24-7.14 (m, 3H), 4.74 (t, J=7.5 Hz, 1H), 4.31 (dd, J=7.6, 5.4 Hz, 2H), 3.92 (s, 3H), 3.85 (s, 3H). HRMS m/z calcd for $C_{29}H_{26}N_4O_2+H^+$ [M+H$^+$]: 463.2129, found: 463.2133. HPLC: 98% ($t_R$=16.0 min).

cc. Synthesis of N-(2,2-Diphenylethyl)-2-(2-Methoxypyrimidin-5-yl)Quinazolin-4-Amine (29)

This compound was prepared from 2-chloro-N-(2,2-diphenylethyl)quinazolin-4-amine and 2-methoxypyrimidine-5-boronic acid according to the procedure described for the preparation of compound 8. Yield 94%. Mp 67° C. TLC $R_f$ 0.30 (cyclohexane-EtOAc, 2:1). $^1$H NMR (400 MHz, DMSO-d$_6$) δ 9.50 (s, 2H), 8.53 (t, J=5.6 Hz, 1H), 8.18-8.11 (m, 1H), 7.80-7.69 (m, 2H), 7.50-7.37 (m, 5H), 7.28 (dd, J=8.3, 6.9 Hz, 4H), 7.22-7.13 (m, 2H), 4.70 (t, J=7.7 Hz, 1H), 4.32 (dd, J=7.7, 5.4 Hz, 2H), 4.03 (s, 3H). HRMS m/z calcd for $C_{27}H_{23}N_5O+M^+$ [M+H$^+$]: 434.1975, found: 434.1981. HPLC: 100% ($t_R$=16.3 min).

dd. Synthesis of N-(2,2-Diphenylethyl)-2-(2-(Methylthio)Pyrimidin-5-yl)Quinazolin-4-Amine (30)

This compound was prepared from 2-chloro-N-(2,2-diphenylethyl)quinazolin-4-amine and (2-(methylthio)pyrimidin-5-yl)boronic acid according to the procedure described for the preparation of compound 8. Yield 67%. Mp 177° C.; TLC $R_f$ 0.30 (cyclohexane-EtOAc, 2:1), $^1$H NMR (400 MHz, DMSO-d$_6$) δ 9.52 (s, 2H), 8.56 (t, J=5.5 Hz, 1H), 8.19-8.11 (m, 1H), 7.81-7.71 (m, 2H), 7.47 (ddd, J=8.2, 5.8, 2.4 Hz, 1H), 7.44-7.38 (m, 4H), 7.33-7.23 (m, 4H), 7.22-7.13 (m, 2H), 4.69 (t, J=7.6 Hz, 1H), 4.33 (dd, J=7.7, 5.5 Hz, 2H), 2.62 (s, 3H). HRMS m/z calcd for $C_{27}H_{23}N_5S+H^+$ [M+H$^+$]: 450.1747, found: 450.1751. HPLC: 96% ($t_R$=18.5 min).

ee. Synthesis of N-(2,2-Diphenylethyl)-2-(1H-indol-6-yl)Quinazolin-4-Amine (31)

This compound was prepared from 2-chloro-N-(2,2-diphenylethyl)quinazolin-4-amine and indole-6-boronic acid according to the procedure described for the preparation of compound 31. Yield 84%. Mp 102° C. TLC $R_f$ 0.35 (cyclohexane-EtOAc, 2:1). $^1$H NMR (400 MHz, DMSO-d$_6$) δ 11.29 (s, 1H), 8.64 (dt, J=1.6, 0.8 Hz, 1H), 8.32-8.24 (m, 2H), 8.09 (dt, J=8.3, 1.0 Hz, 1H), 7.75-7.67 (m, 2H), 7.64-7.60 (m, 1H), 7.48 (dd, J=3.0, 2.4 Hz, 1H), 7.44-7.40 (m, 4H), 7.37 (ddd, J=8.2, 5.1, 3.1 Hz, 1H), 7.31 (dd, J=8.4, 6.9 Hz, 4H), 7.24-7.15 (m, 2H), 6.49 (ddd, J=2.9, 1.9, 0.9 Hz, 1H), 4.82 (t, J=7.8 Hz, 1H), 4.33 (dd, J=7.8, 5.3 Hz, 2H). HRMS m/z calcd for $C_{30}H_{24}N_4+H^+$ [M+H$^+$]: 441.2074, found: 441.2075. HPLC: 99% ($t_R$=14.8 min).

ff. Synthesis of N-(2,2-Diphenylethyl)-2-(1H-Indol-4-yl)Quinazolin-4-Amine (32)

This compound was prepared from 2-chloro-N-(2,2-diphenylethyl)quinazolin-4-amine and indole-4-boronic acid according to the procedure described for the preparation of compound 8. Yield 69%. Mp 100° C. TLC $R_f$ 0.35 (cyclohexane-EtOAc, 2:1). $^1$H NMR (400 MHz, DMSO-d$_6$) δ 11.20 (s, 1H), 8.32 (dd, J=7.5, 1.0 Hz, 1H), 8.28 (t, J=5.5 Hz, 1H), 8.15-8.08 (m, 1H), 7.82-7.69 (m, 2H), 7.65 (ddd, J=3.0, 2.0, 0.9 Hz, 1H), 7.54 (dt, J=8.0, 0.9 Hz, 1H), 7.44-7.34 (m, 6H), 7.34-7.26 (m, 4H), 7.25-7.16 (m, 3H), 4.86-4.77 (m, 1H), 4.33 (dd, J=7.7, 5.4 Hz, 2H). HRMS m/z calcd for $C_{30}H_{24}N_4+H^+$ [M+H$^+$]: 441.2074, found: 441.2078. HPLC: 100% ($t_R$=14.2 min).

gg. Synthesis Of N-(2,2-Diphenylethyl)-2-(1H-Indol-7-yl)Quinazolin-4-Amine (33)

This compound was prepared from 2-chloro-N-(2,2-diphenylethyl)quinazolin-4-amine and indole-7-boronic acid according to the procedure described for the preparation of compound 8. Yield 81%. Mp 67° C. TLC $R_f$ 0.35 (cyclohexane-EtOAc, 2:1). $^1$H NMR (400 MHz, DMSO-d$_6$) δ 11.75 (s, 1H), 8.49-8.40 (m, 2H), 8.11 (ddd, J=17.3, 8.3, 1.4 Hz, 2H), 7.83-7.71 (m, 2H), 7.48-7.38 (m, 6H), 7.31 (dd, J=8.3, 7.0 Hz, 4H), 7.25-7.14 (m, 3H), 6.56 (dd, J=3.1, 2.1 Hz, 1H), 4.81 (t, J=7.6 Hz, 1H), 4.39-4.31 (m, 2H). HRMS m/z calcd for $C_{30}H_{24}N_4+H^+$ [M+H$^+$]: 441.2074, found: 441.2080. HPLC: 99% ($t_R$=19.0 min).

hh. Synthesis of N-(2,2-Diphenylethyl)-2-(1H-Indazol-6-yl)Quinazolin-4-Amine (34)

This compound was prepared from 2-chloro-N-(2,2-diphenylethyl)quinazolin-4-amine and indazole-6-boronic acid according to the procedure described for the preparation of compound 8. Yield 20%. Mp 223° C. TLC $R_f$ 0.30 (cyclohexane-EtOAc, 2:1). $^1$H NMR (400 MHz, DMSO-$d_6$) δ 13.26 (s, 1H), 8.72 (q, J=1.1 Hz, 1H), 8.40 (t, J=5.5 Hz, 1H), 8.35 (dd, J=8.5, 1.3 Hz, 1H), 8.17-8.09 (m, 2H), 7.85 (dd, J=8.6, 0.8 Hz, 1H), 7.81-7.70 (m, 2H), 7.43 (td, J=8.2, 1.7 Hz, 5H), 7.31 (dd, J=8.4, 6.9 Hz, 4H), 7.24-7.15 (m, 2H), 4.80 (t, J=7.8 Hz, 1H), 4.34 (dd, J=7.8, 5.3 Hz, 2H). HRMS m/z calcd for $C_{29}H_{23}N_5$+H$^+$ [M+H$^+$]: 442.2026, found: 442.2032. HPLC: 99% ($t_R$=15.2 min).

ii. Synthesis of N-(2,2-Diphenylethyl)-2-(1H-Indazol-4-yl)Quinazolin-4-Amine (35)

This compound was prepared from 2-chloro-N-(2,2-diphenylethyl)quinazolin-4-amine and indazole-4-boronic acid according to the procedure described for the preparation of compound 8. Yield 30%. Mp 229° C. TLC $R_f$ 0.30 (cyclohexane-EtOAc, 2:1), $^1$H NMR (400 MHz, DMSO-$d_6$) δ 13.16 (s, 1H), 9.07 (d, J=0.9 Hz, 1H), 8.43-8.35 (m, 2H), 8.14 (dd, J=8.0, 1.1 Hz, 1H), 7.90-7.83 (m, 1H), 7.77 (ddd, J=8.3, 6.9, 1.3 Hz, 1H), 7.69 (dt, J=8.3, 0.9 Hz, 1H), 7.52-7.43 (m, 2H), 7.42-7.37 (m, 4H), 7.30 (dd, J=8.4, 6.9 Hz, 4H), 7.24-7.14 (m, 2H), 4.80 (t, J=7.7 Hz, 1H), 4.35 (dd, J=7.8, 5.4 Hz, 2H). HRMS m/z calcd for $C_{29}H_{23}N_5$+H$^+$ [M+H$^+$]: 442.2026, found: 442.2031. HPLC: 100% ($t_R$=15.0 min).

jj. Synthesis of N-(2,2-Diphenylethyl)-2-(1-(Phenylsulfonyl)-1H-Indol-5-yl)Quinazolin-4-Amine (36)

This compound was prepared from 2-chloro-N-(2,2-diphenylethyl)quinazolin-4-amine and 1-phenylsulfonylindole-5-boronic acid according to the procedure described for the preparation of compound 8. Yield 78%. mp 203° C.; TLC $R_f$ 0.35 (cyclohexane-EtOAc, 2:1). $^1$H NMR (400 MHz, DMSO-$d_6$) δ 8.74 (dd, J=1.6, 0.6 Hz, 1H), 8.55 (dd, J=8.8, 1.7 Hz, 1H), 8.43 (t, J=5.5 Hz, 1H), 8.15-8.10 (m, 1H), 8.08-8.01 (m, 3H), 7.88 (d, J=3.7 Hz, 1H), 7.76-7.68 (m, 3H), 7.66-7.59 (m, 2H), 7.46-7.37 (m, 5H), 7.31 (dd, J=8.4, 6.9 Hz, 4H), 7.24-7.17 (m, 2H), 6.94 (dd, J=3.7, 0.8 Hz, 1H), 4.77 (t, J=7.5 Hz, 1H), 4.35-4.26 (m, 2H). HRMS m/z calcd for $C_{36}H_{28}N_4O_2S$+H$^+$ [M+H$^+$]: 581.2006, found: 581.2014. HPLC: 95% ($t_R$=17.3 min).

kk. Synthesis of N-(2,2-Diphenylethyl)-2-(2-(Pyrrolidin-1-yl)Pyrimidin-5-yl)Quinazolin-4-Amine (37)

This compound was prepared from 2-chloro-N-(2,2-diphenylethyl)quinazolin-4-amine and (2-(pyrrolidin-1-yl)pyrimidin-5-yl)boronic acid according to the procedure described for the preparation of compound 8. Yield 46%. Mp 208° C. TLC $R_f$ 0.30 (cyclohexane-EtOAc, 2:1). $^1$H NMR (400 MHz, DMSO-$d_6$) δ 9.30 (d, J=0.3 Hz, 2H), 8.36 (t, J=5.5 Hz, 1H), 8.12-8.05 (m, 1H), 7.74-7.62 (m, 2H), 7.43-7.33 (m, 5H), 7.32-7.23 (m, 4H), 7.22-7.13 (m, 2H), 4.69 (t, J=7.7 Hz, 1H), 4.30 (dd, J=7.8, 5.4 Hz, 2H), 3.63-3.55 (m, 4H), 2.02-1.93 (m, 4H). HRMS m/z calcd for $C_{30}H_{28}N_6$+H$^+$ [M+H$^+$]: 473.2449, found: 473.2454. HPLC: 100% ($t_R$=17.5 min).

ll. Synthesis of N-(2,2-Diphenylethyl)-2-(2-(Piperidin-1-yl)Pyrimidin-5-yl)Quinazolin-4-Amine (38)

This compound was prepared from 2-chloro-N-(2,2-diphenylethyl)quinazolin-4-amine and (2-(piperidin-1-yl)pyrimidin-5-yl)boronic acid according to the procedure described for the preparation of compound 8. Yield 57%. Mp 92° C. TLC $R_f$ 0.30 (cyclohexane-EtOAc, 2:1). $^1$H NMR (400 MHz, DMSO-$d_6$) δ 9.29 (s, 2H), 8.37 (t, J=5.5 Hz, 1H), 8.12-8.05 (m, 1H), 7.75-7.62 (m, 2H), 7.42-7.34 (m, 5H), 7.29 (dd, J=8.3, 6.9 Hz, 4H), 7.22-7.13 (m, 2H), 4.70 (t, J=7.7 Hz, 1H), 4.29 (dd, J=7.7, 5.4 Hz, 2H), 3.87 (t, J=5.4 Hz, 4H), 1.67 (q, J=6.1 Hz, 2H), 1.58 (dd, J=7.4, 4.0 Hz, 4H). HRMS m/z calcd for $C_{31}H_{30}N_6$+H$^+$ [M+H$^+$]: 487.2605, found: 487.2607. HPLC: 100% ($t_R$=20.2 min).

mm. Synthesis of N-(2,2-Diphenylethyl)-2-(Pyridin-4-yl)Quinazolin-4-Amine (39)

This compound was prepared from 2-chloro-N-(2,2-diphenylethyl)quinazolin-4-amine and pyridin-4-ylboronic acid according to the procedure described for the preparation of compound 8. Yield 71%. Mp 242° C. TLC $R_f$ 0.30 (cyclohexane-EtOAc, 2:1). $^1$H NMR (400 MHz, DMSO-$d_6$) δ 8.78-8.72 (m, 2H), 8.57 (t, J=5.4 Hz, 1H), 8.39-8.26 (m, 2H), 8.17 (dd, J=8.2, 1.1 Hz, 1H), 7.83-7.73 (m, 2H), 7.50 (ddd, J=8.3, 5.2, 2.9 Hz, 1H), 7.45-7.37 (m, 4H), 7.30 (dd, J=8.3, 6.9 Hz, 4H), 7.23-7.14 (m, 2H), 4.73 (t, J=7.6 Hz, 1H), 4.33 (dd, J=7.7, 5.4 Hz, 2H). HRMS m/z calcd for $C_{27}H_{22}N_4$+H$^+$ [M+H$^+$]: 403.1917, found: 403.1924. HPLC: 97% ($t_R$=16.1 min).

nn. Synthesis of N-(2,2-Diphenylethyl)-2-(1H-Indazol-5-yl)Quinazolin-4-Amine (40)

This compound was prepared from 2-chloro-N-(2,2-diphenylethyl)quinazolin-4-amine and indazole-5-boronic acid according to the procedure described for the preparation of compound 8. Yield 60%. Mp 191° C.; TLC $R_f$ 0.30 (cyclohexane-EtOAc, 2:1). $^1$H NMR (400 MHz, DMSO-$d_6$) δ 13.19 (s, 1H), 8.96 (dd, J=1.5, 0.8 Hz, 1H), 8.59 (dd, J=8.8, 1.5 Hz, 1H), 8.41 (t, J=5.4 Hz, 1H), 8.19 (s, 1H), 8.16-8.09 (m, 1H), 7.78-7.68 (m, 1H), 7.62 (dt, J=8.8, 0.9 Hz, 1H), 7.47-7.37 (m, 5H), 7.36-7.30 (m, 5H), 7.26-7.16 (m, 2H), 4.81 (t, J=7.5 Hz, 1H), 4.33 (dd, J=7.5, 5.3 Hz, 2H). HRMS m/z calcd for $C_{29}H_{23}N_5$+H$^+$ [M+H$^+$]: 442.2026, found: 442.2032. HPLC: 96% ($t_R$=14.7 min).

oo. Synthesis of N-(2,2-Diphenylethyl)-2-(2-(Methylamino)Pyrimidin-5-yl)Quinazolin-4-Amine (41)

This compound was prepared from 2-chloro-N-(2,2-diphenylethyl)quinazolin-4-amine and N-methyl-5-(4,4,5,5-tetramethyl-1,3,2-dioxaborolan-2-yl)pyrimidin-2-amine according to the procedure described for the preparation of compound 8. Yield 89%. Mp 78° C. TLC $R_f$ 0.35 (cyclohexane-EtOAc, 2:1). $^1$H NMR (400 MHz, DMSO-$d_6$) δ 9.25 (s, 2H), 8.39 (t, J=5.5 Hz, 1H), 8.12-8.05 (m, 1H), 7.75-7.62 (m, 2H), 7.56 (q, J=4.8 Hz, 1H), 7.43-7.34 (m, 5H), 7.29 (dd, J=8.3, 6.9 Hz, 4H), 7.22-7.13 (m, 2H), 4.71 (t, J=7.7 Hz, 1H), 4.28 (dd, J=7.7, 5.5 Hz, 2H), 2.90 (d, J=4.8 Hz, 3H). HRMS m/z calcd for $C_{27}H_{24}N_6$+H$^+$ [M+H$^+$]: 433.2135, found: 433.2139. HPLC: 99% ($t_R$=15.2 min).

pp. Synthesis of N-(2,2-Diphenylethyl)-2-(1H-Indol-2-yl)Quinazolin-4-Amine (42)

This compound was prepared from 2-chloro-N-(2,2-diphenylethyl)quinazolin-4-amine and 2-(4,4,5,5-tetramethyl-1,3,2-dioxaborolan-2-yl)-1H-indole according to the procedure described for the preparation of compound 42. Yield 71%. Mp 93° C. TLC $R_f$ 0.30 (cyclohexane-EtOAc, 2:1), $^1$H NMR (400 MHz, DMSO-$d_6$) δ 11.52 (d, J=2.1 Hz, 1H), 8.38-8.30 (m, 1H), 8.15-8.07 (m, 1H), 7.78-7.68 (m, 2H), 7.68-7.60 (m, 1H), 7.55 (dq, J=8.2, 0.9 Hz, 1H), 7.48-7.36 (m, 5H), 7.35-7.25 (m, 5H), 7.23-7.13 (m, 3H), 7.03 (ddd, J=8.0, 7.0, 1.0 Hz, 1H), 4.74 (t, J=7.7 Hz, 1H), 4.37 (dd, J=7.8, 5.4 Hz, 2H). HRMS m/z calcd for $C_{30}H_{24}N_4+H^+$ [M+H$^+$]: 441.2074, found: 441.2080. HPLC: 100% ($t_R$=9.6 min).

qq. Synthesis of Tert-Butyl (5-(4-((2,2-Diphenylethyl)Amino)Quinazolin-2-yl)Pyrimidin-2-yl)Carbamate (43)

This compound was prepared from 2-chloro-N-(2,2-diphenylethyl)quinazolin-4-amine and tert-butyl (5-(4,4,5,5-tetramethyl-1,3,2-dioxaborolan-2-yl)pyrimidin-2-yl)carbamate according to the procedure described for the preparation of compound 8. Yield 50%. Mp 189° C. TLC R$_f$ 0.35 (cyclohexane-EtOAc, 2:1). $^1$H NMR (400 MHz, DMSO-d$_6$) δ 10.35 (s, 1H), 9.48 (d, J=1.1 Hz, 2H), 8.54 (t, J=5.5 Hz, 1H), 8.14 (dd, J=8.3, 1.2 Hz, 1H), 7.80-7.71 (m, 2H), 7.49-7.43 (m, 1H), 7.43-7.37 (m, 4H), 7.33-7.24 (m, 4H), 7.22-7.13 (m, 2H), 4.72 (t, J=7.7 Hz, 1H), 4.32 (t, J=6.3 Hz, 2H), 1.50 (d, J=1.0 Hz, 9H). HRMS m/z calcd for $C_{31}H_{30}N_6O_2+H^+$ [M+H$^+$]: 519.2503, found: 519.2513. HPLC: 99% ($t_R$=10.6 min).

rr. Synthesis of 2-(2-Aminopyrimidin-5-yl)-N-(2,2-Diphenylethyl)Quinazolin-4-Amine (44)

This compound was prepared from 2-chloro-N-(2,2-diphenylethyl)quinazolin-4-amine and 5-(4,4,5,5-tetramethyl-1,3,2-dioxaborolan-2-yl)pyrimidin-2-amine according to the procedure described for the preparation of compound 8. Yield 50%. Mp 148° C. TLC R$_f$ 0.30 (cyclohexane-EtOAc, 2:1). $^1$H NMR (400 MHz, DMSO-d$_6$) δ 9.21 (d, J=0.7 Hz, 2H), 8.43 (t, J=5.6 Hz, 1H), 8.09 (d, J=8.2 Hz, 1H), 7.75-7.50 (m, 2H), 7.43-7.33 (m, 5H), 7.29 (dd, J=8.3, 6.9 Hz, 4H), 7.18 (t, J=7.3 Hz, 2H), 7.10 (s, 2H), 4.73 (t, J=7.6 Hz, 1H), 4.26 (t, J=6.5 Hz, 2H). HRMS m/z calcd for $C_{26}H_{22}N_6+H^+$ [M+H$^+$]: 419.1939, found: 419.1984. HPLC: 99% ($t_R$=10.8 min).

ss. Synthesis of N-(2,2-Diphenylethyl)-2-(2-((2,2,2-Trifluoroethyl)Amino)Pyrimidin-5-yl)Quinazolin-4-Amine (45)

This compound was prepared from 2-chloro-N-(2,2-diphenylethyl)quinazolin-4-amine and 5-(4,4,5,5-tetramethyl-1,3,2-dioxaborolan-2-yl)-N-(2,2,2-trifluoroethyl)pyrimidin-2-amine according to the procedure described for the preparation of compound 8. Yield 25%. Mp 224° C. TLC R$_f$ 0.30 (cyclohexane-EtOAc, 2:1). $^1$H NMR (400 MHz, DMSO-d$_6$) δ 9.31 (s, 2H), 8.44 (t, J=5.5 Hz, 1H), 8.24 (t, J=6.7 Hz, 1H), 8.11 (dd, J=8.2, 1.1 Hz, 1H), 7.77-7.64 (m, 2H), 7.45-7.36 (m, 5H), 7.33-7.23 (m, 4H), 7.22-7.13 (m, 2H), 4.70 (t, J=7.7 Hz, 1H), 4.34-4.18 (m, 4H). HRMS m/z calcd for $C_{28}H_{23}F_3N_6+H^+$ [M+H$^+$]: 501.2009, found: 501.2015. HPLC: 100% ($t_R$=11.6 min).

tt. Synthesis of 2-(2-(Benzylamino)Pyrimidin-5-yl)-N-(2,2-Diphenylethyl)Quinazolin-4-Amine (46)

This compound was prepared from 2-chloro-N-(2,2-diphenylethyl)quinazolin-4-amine and N-benzyl-5-(4,4,5,5-tetramethyl-1,3,2-dioxaborolan-2-yl)pyrimidin-2-amine according to the procedure described for the preparation of compound 8. Yield 71%. Mp 184° C. TLC R$_f$ 0.30 (cyclohexane-EtOAc, 2:1). $^1$H NMR (400 MHz, DMSO-d$_6$) δ 9.25 (s, 2H), 8.39 (t, J=5.5 Hz, 1H), 8.20 (t, J=6.4 Hz, 1H), 8.12-8.05 (m, 1H), 7.75-7.62 (m, 2H), 7.42-7.20 (m, 14H), 7.20-7.14 (m, 2H), 4.70 (t, J=7.7 Hz, 1H), 4.62 (d, J=6.3 Hz, 2H), 4.27 (t, J=6.5 Hz, 2H). HRMS m/z calcd for $C_{33}H_{28}N_6+H^+$ [M+H$^+$]: 509.2448, found: 509.2442. HPLC: 100% ($t_R$=13.9 min).

uu. Synthesis of N-(2,2-Diphenylethyl)-2-(2-((2-Methoxyethyl)Amino)Pyrimidin-5-yl)Quinazolin-4-Amine (47)

This compound was prepared from 2-chloro-N-(2,2-diphenylethyl)quinazolin-4-amine and N-(2-methoxyethyl)-5-(4,4,5,5-tetramethyl-1,3,2-dioxaborolan-2-yl)pyrimidin-2-amine according to the procedure described for the preparation of compound 8. Yield 81%. Mp 199° C. TLC R$_f$ 0.30 (cyclohexane-EtOAc, 2:1). $^1$H NMR (400 MHz, DMSO-d$_6$) δ 9.24 (s, 2H), 8.40 (t, J=5.5 Hz, 1H), 8.09 (dd, J=8.1, 1.2 Hz, 1H), 7.74-7.64 (m, 2H), 7.62 (t, J=5.5 Hz, 1H), 7.42-7.34 (m, 5H), 7.32-7.25 (m, 4H), 7.22-7.13 (m, 2H), 4.71 (t, J=7.7 Hz, 1H), 4.28 (dd, J=7.7, 5.4 Hz, 2H), 3.59-3.46 (m, 4H), 3.29 (s, 3H). HRMS m/z calcd for $C_{29}H_{28}N_6O+H^+$ [M+H$^+$]: 477.2397, found: 477.2406. HPLC: 99% ($t_R$=9.6 min).

vv. Synthesis of N-(2,2-Diphenylethyl)-2-(1H-Imidazol-1-yl)Quinazolin-4-Amine (48)

To a solution of 2-chloro-N-(2,2-diphenylethyl)quinazolin-4-amine (0.100 g, 0.28 mmol) in acetonitrile (5 mL) was added imidazole (0.038 g, 0.56 mmol) and K$_2$CO$_3$ (0.077 g, 0.56 mmol). The reaction mixture was heated under reflux for 18 hours, cooled and concentrated under reduced pressure. The residue obtained was purified by column chromatography using CHCl$_3$-MeOH (0-20%) as the eluent to obtain 0.023 g (21%) of the desired product. Mp 231° C. TLC R$_f$ 0.25 (cyclohexane-EtOAc, 2:1). $^1$H NMR (400 MHz, DMSO-d$_6$) δ 8.80 (t, J=5.5 Hz, 1H), 8.62 (t, J=1.1 Hz, 1H), 8.19-8.12 (m, 1H), 7.98 (t, J=1.3 Hz, 1H), 7.75 (ddd, J=8.3, 6.9, 1.3 Hz, 1H), 7.69-7.61 (m, 1H), 7.47-7.38 (m, 5H), 7.36-7.23 (m, 4H), 7.21-7.14 (m, 2H), 7.12 (dd, J=1.5, 1.0 Hz, 1H), 4.64 (t, J=7.7 Hz, 1H), 4.30 (dd, J=7.7, 5.5 Hz, 2H). HRMS m/z calcd for $C_{25}H_{21}N_5+H^+$ [M+H$^+$]: 392.1870, found: 392.1867. HPLC: 99% ($t_R$=12.1 min).

ww. Synthesis of N-(2,2-Diphenylethyl)-2-(Quinolin-5-yl)Quinazolin-4-Amine (49)

This compound was prepared from 2-chloro-N-(2,2-diphenylethyl)quinazolin-4-amine and quinolin-5-ylboronic acid according to the procedure described for the preparation of compound 8. Yield 95%. Mp 207° C. TLC R$_f$ 0.30 (cyclohexane-EtOAc, 2:1). $^1$H NMR (400 MHz, DMSO-d$_6$) δ 9.40 (ddd, J=8.7, 1.7, 0.8 Hz, 1H), 8.98-8.91 (m, 1H), 8.52 (t, J=5.5 Hz, 1H), 8.34 (dd, J=7.3, 1.3 Hz, 1H), 8.23-8.17 (m, 1H), 8.16 (dt, J=8.4, 1.1 Hz, 1H), 7.91 (td, J=8.5, 7.1 Hz, 1H), 7.84-7.74 (m, 2H), 7.58-7.48 (m, 2H), 7.37-7.31 (m, 4H), 7.31-7.23 (m, 4H), 7.22-7.13 (m, 2H), 4.74 (t, J=7.7 Hz, 1H), 4.24 (dd, J=7.7, 5.4 Hz, 2H). HRMS m/z calcd for $C_{31}H_{24}N_4+H^+$ [M+H$^+$]: 453.2074, found: 453.2075. HPLC: 96% ($t_R$=12.2 min).

xx. Synthesis of N-(2,2-Diphenylethyl)-2-(Quinolin-6-yl)Quinazolin-4-Amine (50)

This compound was prepared from 2-chloro-N-(2,2-diphenylethyl)quinazolin-4-amine and quinolin-6-ylboronic acid according to the procedure described for the preparation of compound 8. Yield 45%. Mp 92° C. TLC $R_f$ 0.30 (cyclohexane-EtOAc, 2:1). $^1$H NMR (400 MHz, DMSO-d$_6$) δ 9.10 (d, J=1.9 Hz, 1H), 8.97 (dd, J=4.2, 1.7 Hz, 1H), 8.89 (dd, J=8.9, 1.9 Hz, 1H), 8.55 (t, J=5.5 Hz, 1H), 8.47 (dt, J=8.2, 1.3 Hz, 1H), 8.20-8.16 (m, 1H), 8.14 (d, J=8.8 Hz, 1H), 7.86-7.73 (m, 2H), 7.62 (dd, J=8.3, 4.2 Hz, 1H), 7.52-7.43 (m, 5H), 7.33 (dd, J=8.3, 6.9 Hz, 4H), 7.26-7.17 (m, 2H), 4.82 (t, J=7.5 Hz, 1H), 4.38 (dd, J=7.6, 5.3 Hz, 2H). HRMS m/z calcd for C$_{31}$H$_{24}$N$_4$+H$^+$ [M+H$^+$]: 453.2074, found: 453.2071. HPLC: 99% ($t_R$=14.2 min).

yy. Synthesis of N-(2,2-Diphenylethyl)-2-(1H-Pyrazol-1-yl)Quinazolin-4-Amine (51)

This compound was prepared from 2-chloro-N-(2,2-diphenylethyl)quinazolin-4-amine and pyrazole according to the procedure described for the preparation of compound 48. Yield 37%. Mp 191° C. TLC $R_f$ 0.25 (cyclohexane-EtOAc, 1:1). $^1$H NMR (400 MHz, DMSO-d$_6$) δ 8.74-8.66 (m, 2H), 8.18-8.11 (m, 1H), 7.82 (dd, J=1.6, 0.7 Hz, 1H), 7.75 (ddd, J=8.3, 6.9, 1.3 Hz, 1H), 7.67 (dd, J=8.4, 1.2 Hz, 1H), 7.46-7.37 (m, 5H), 7.33-7.24 (m, 4H), 7.23-7.13 (m, 2H), 6.57 (dd, J=2.6, 1.6 Hz, 1H), 4.72 (t, J=7.7 Hz, 1H), 4.28 (dd, J=7.6, 5.3 Hz, 2H). HRMS m/z calcd for C$_{25}$H$_{21}$N$_5$+H$^+$ [M+H$^+$]: 392.1870, found: 392.1863. HPLC: 100% ($t_R$=11.5 min).

zz. Synthesis of N-(2,2-Diphenylethyl)-2-(1H-1,2,4-Triazol-1-yl)Quinazolin-4-Amine (52)

This compound was prepared from 2-chloro-N-(2,2-diphenylethyl)quinazolin-4-amine and 1,2,4-triazole according to the procedure described for the preparation of compound 48. Yield 55%. Mp 216° C. TLC $R_f$ 0.25 (cyclohexane-EtOAc, 1:1). $^1$H NMR (400 MHz, DMSO-d$_6$) δ 9.46 (d, J=0.5 Hz, 1H), 8.85 (t, J=5.5 Hz, 1H), 8.27 (d, J=0.5 Hz, 1H), 8.23-8.16 (m, 1H), 7.79 (ddd, J=8.3, 6.9, 1.2 Hz, 1H), 7.71 (dd, J=8.3, 1.2 Hz, 1H), 7.49 (ddd, J=8.2, 6.9, 1.3 Hz, 1H), 7.46-7.40 (m, 4H), 7.27 (dd, J=8.4, 6.9 Hz, 4H), 7.21-7.12 (m, 2H), 4.67 (t, J=7.7 Hz, 1H), 4.32 (dd, J=7.8, 5.4 Hz, 2H). HRMS m/z calcd for C$_{24}$H$_{20}$N$_6$+H$^+$ [M+H$^+$]: 393.1822, found: 393.1841. HPLC: 100% ($t_R$=10.1 min).

aaa. Synthesis of N-(2-(6-Chloropyridin-2-yl)-2-Phenylethyl)-2-(Pyridin-3-yl)Quinazolin-4-Amine (53)

To a stirred solution of 4-chloro-2-(pyridin-3-yl)quinazoline (0.100 g, 0.41 mmol) in THF (5 mL) was added dropwise N,N-diisopropylethylamine (0.10 mL, 0.62 mmol) and 2-(6-chloropyridin-2-yl)-2-phenylethanamine (0.106 mg, 0.46 mmol). After stirring for 4 hours at room temperature, the reaction mixture was diluted with water (5 mL) and extracted with EtOAc (3×5 mL). The combined organic layers were washed with water (3×5 mL), dried over Na$_2$SO$_4$, and filtered. The filtrate was concentrated under reduced pressure. The residue obtained was purified by column chromatography using hexanes:EtOAc (0-70%) as eluent to obtain 0.055 g (30%) of the desired product. Mp 83° C. TLC $R_f$ 0.25 (cyclohexane-EtOAc, 1:1), $^1$H NMR (400 MHz, DMSO-d$_6$) δ 9.62 (dd, J=2.2, 0.8 Hz, 1H), 8.76 (dt, J=8.0, 2.0 Hz, 1H), 8.69 (dd, J=4.8, 1.7 Hz, 1H), 8.55 (t, J=5.6 Hz, 1H), 8.18-8.11 (m, 1H), 7.82-7.70 (m, 3H), 7.54 (ddd, J=8.0, 4.8, 0.8 Hz, 1H), 7.50-7.43 (m, 2H), 7.41 (dd, J=7.7, 0.8 Hz, 2H), 7.37-7.29 (m, 2H), 7.27-7.18 (m, 2H), 4.84 (t, J=7.3 Hz, 1H), 4.45 (ddd, J=13.3, 8.0, 5.5 Hz, 1H), 4.29 (dt, J=12.8, 6.1 Hz, 1H). HRMS m/z calcd for C$_{26}$H$_{20}$ClN$_5$+H$^+$ [M+H$^+$]: 438.1480, found: 438.1488. HPLC: 99% ($t_R$=11.7 min).

bbb. Synthesis of 2-(2,4-Dimethylthiazol-5-yl)-N-(2,2-Diphenylethyl)Quinazolin-4-Amine (54)

This compound was prepared from 2-chloro-N-(2,2-diphenylethyl)quinazolin-4-amine and 2,4-dimethyl-5-(4,4,5,5-tetramethyl-1,3,2-dioxaborolan-2-yl)thiazole according to the procedure described for the preparation of compound 8. Yield 74%. Mp 78° C. TLC $R_f$ 0.30 (cyclohexane-EtOAc, 1:1). $^1$H NMR (400 MHz, DMSO-d$_6$) δ 8.42 (t, J=5.5 Hz, 1H), 8.07 (ddd, J=8.2, 1.4, 0.7 Hz, 1H), 7.71 (dddd, J=7.5, 6.9, 1.3, 0.6 Hz, 1H), 7.62 (ddd, J=8.4, 1.4, 0.7 Hz, 1H), 7.43-7.33 (m, 5H), 7.29 (dd, J=8.4, 6.8 Hz, 4H), 7.23-7.13 (m, 2H), 4.69 (t, J=7.8 Hz, 1H), 4.23 (dd, J=7.9, 5.5 Hz, 2H), 2.81 (s, 3H), 2.63 (s, 3H). HRMS m/z calcd for C$_{27}$H$_{24}$N$_4$S+H$^+$ [M+H$^+$]: 437.1794. found: 437.1795. HPLC: 100% ($t_R$=11.6 min).

ccc. Synthesis of N-(2,2-Diphenylethyl)-2-(Imidazo[1,2-a]Pyridin-6-yl)Quinazolin-4-Amine (55)

This compound was prepared from 2-chloro-N-(2,2-diphenylethyl)quinazolin-4-amine and imidazo[1,2-a]pyridin-6-ylboronic acid according to the procedure described for the preparation of compound 8. Yield 41%. Mp 204° C. TLC $R_f$ 0.25 (cyclohexane-EtOAc, 1:1). $^1$H NMR (400 MHz, DMSO-d$_6$) δ 9.53 (dd, J=1.7, 1.0 Hz, 1H), 8.50 (t, J=5.4 Hz, 1H), 8.29 (dd, J=9.5, 1.7 Hz, 1H), 8.19-8.12 (m, 1H), 8.09 (t, J=0.9 Hz, 1H), 7.79-7.71 (m, 2H), 7.68-7.64 (m, 2H), 7.49-7.40 (m, 5H), 7.31 (dd, J=8.3, 6.9 Hz, 4H), 7.24-7.15 (m, 2H), 4.73 (t, J=7.6 Hz, 1H), 4.36 (dd, J=7.6, 5.4 Hz, 2H). HRMS m/z calcd for C$_{29}$H$_{23}$N$_5$+H$^+$ [M+H$^+$]: 442.2026, found: 442.2035. HPLC: 100% ($t_R$=12.7 min).

ddd. Synthesis of N-(2,2-Diphenylethyl)-2-(Quinoxalin-6-yl)Quinazolin-4-Amine (56)

This compound was prepared from 2-chloro-N-(2,2-diphenylethyl)quinazolin-4-amine and 6-(4,4,5,5-tetramethyl-1,3,2-dioxaborolan-2-yl)quinoxaline according to the procedure described for the preparation of compound 8. Yield 90%. Mp 198° C. TLC $R_f$ 0.25 (cyclohexane-EtOAc, 1:1). $^1$H NMR (400 MHz, DMSO-d$_6$) δ 9.23 (d, J=1.8 Hz, 1H), 9.03 (dd, J=16.5, 1.8 Hz, 2H), 8.99 (dd, J=8.8, 1.9 Hz, 1H), 8.57 (t, J=5.5 Hz, 1H), 8.23 (d, J=8.8 Hz, 1H), 8.21-8.16 (m, 1H), 7.88-7.75 (m, 2H), 7.50 (ddd, J=8.2, 6.7, 1.5 Hz, 1H), 7.47-7.41 (m, 4H), 7.32 (dd, J=8.3, 6.9 Hz, 4H), 7.25-7.15 (m, 2H), 4.83 (t, J=7.7 Hz, 1H), 4.38 (dd, J=7.7, 5.4 Hz, 2H). HRMS m/z calcd for C$_{30}$H$_{23}$N$_5$+H$^+$ [M+H$^+$]: 454.2026, found: 454.2029. HPLC: 100% ($t_R$=13.4 min).

eee. Synthesis of 2-(2-(Dimethylamino)Pyrimidin-5-yl)-N-(2-(6-(2-(Dimethylamino)Pyrimidin-5-yl)Pyridin-2-yl)-2-Phenylethyl)Quinazolin-4-Amine (59)

This compound was prepared from 2-chloro-N-(2-(6-chloropyridin-2-yl)-2-phenylethyl)quinazolin-4-amine and (2-(dimethylamino)pyrimidin-5-yl)boronic acid according to the procedure described for the preparation of compound 8. Yield 56%. Mp 112° C. TLC $R_f$ 0.35 (cyclohexane-EtOAc, 1:1). $^1$H NMR (400 MHz, DMSO-d$_6$) δ 9.29 (d, J=0.5 Hz, 2H), 9.08 (d, J=0.5 Hz, 2H), 8.40 (t, J=5.6 Hz, 1H), 8.08 (dd, J=8.4, 1.2 Hz, 1H), 7.74-7.61 (m, 4H), 7.56-7.49 (m, 2H), 7.40-7.27 (m, 3H), 7.25-7.15 (m, 2H), 4.85 (t, J=7.4 Hz, 1H), 4.69 (dt, J=13.6, 6.7 Hz, 1H), 4.21 (dt, J=12.4, 5.9 Hz, 1H), 3.22 (s, 6H), 3.19 (s, 6H). HRMS m/z calcd for $C_{33}H_{32}N_{10}+H^+$ [M+H$^+$]: 569.2885, found: 569.2877. HPLC: 99% ($t_R$=14.7 min).

fff. Synthesis of N-(2-(6-(1H-Indol-5-yl)Pyridin-2-yl)-2-Phenylethyl)-2-(1H-Indol-5-yl)Quinazolin-4-Amine (58)

This compound was prepared from 2-chloro-N-(2-(6-chloropyridin-2-yl)-2-phenylethyl)quinazolin-4-amine and (1H-indol-5-yl)boronic acid according to the procedure described for the preparation of compound 8. Yield 55%. Mp 151° C. TLC $R_f$ 0.35 (cyclohexane-EtOAc, 1:1). $^1$H NMR (400 MHz, DMSO-$d_6$) δ 11.23 (s, 1H), 11.19 (s, 1H), 8.84 (d, J=1.2 Hz, 1H), 8.44-8.32 (m, 3H), 8.09 (d, J=8.2 Hz, 1H), 7.99 (dd, J=8.6, 1.7 Hz, 1H), 7.84-7.65 (m, 4H), 7.63-7.56 (m, 2H), 7.46 (dd, J=8.7, 2.7 Hz, 2H), 7.35 (dddd, J=16.5, 8.2, 4.1, 2.3 Hz, 5H), 7.22 (dq, J=7.4, 3.4 Hz, 2H), 6.53-6.46 (m, 2H), 4.99 (t, J=7.2 Hz, 1H), 4.68-4.58 (m, 1H), 4.49-4.39 (m, 1H). HRMS m/z calcd for $C_{37}H_{28}N_6+H^+$ [M+H$^+$]: 557.2448, found: 557.2449. HPLC: 98% ($t_R$=10.9 min).

ggg. Synthesis of N-(2,2-Diphenylethyl)-6-Methoxy-2-(Pyridin-3-yl)Quinazolin-4-Amine (59)

2,4-Dichloro-6-methoxyquinazoline was reacted with 2-chloro-N-(2,2-diphenylethyl)-6-methoxyquinazolin-4-amine as described in Step 1 for the preparation of compound 4 to obtain 2-chloro-N-(2,2-diphenylethyl)-6-methoxyquinazolin-4-amine. This compound was further coupled with pyridin-3-ylboronic acid according to the procedure described for the preparation of compound 8 to obtain the title compound. Yield 57%. Mp 77° C. TLC $R_f$ 0.50 (cyclohexane-EtOAc, 1:1). $^1$H NMR (400 MHz, DMSO-$d_6$) δ 9.61 (dd, J=2.2, 0.8 Hz, 1H), 8.72 (dt, J=7.9, 1.9 Hz, 1H), 8.66 (dd, J=4.8, 1.7 Hz, 1H), 8.38 (t, J=5.5 Hz, 1H), 7.72 (d, J=9.1 Hz, 1H), 7.60 (d, J=2.8 Hz, 1H), 7.53 (ddd, J=8.0, 4.7, 0.9 Hz, 1H), 7.46-7.37 (m, 5H), 7.30 (dd, J=8.4, 6.9 Hz, 4H), 7.24-7.14 (m, 2H), 4.75 (t, J=7.5 Hz, 1H), 4.33 (dd, J=7.6, 5.4 Hz, 2H), 3.85 (s, 3H). HRMS m/z calcd for $C_{28}H_{24}N_4O+H^+$ [M+H$^+$]: 433.2023, found: 433.2028. HPLC: 100% ($t_R$=12.8 min).

hhh. Synthesis of 2-(2-(Dimethylamino)Pyrimidin-5-yl)-N-(2,2-Diphenylethyl)-6-Methoxyquinazolin-4-Amine (60)

This compound was prepared from 2-chloro-N-(2,2-diphenylethyl)-6-methoxyquinazolin-4-amine and (2-(dimethylamino)pyrimidin-5-yl)boronic acid according to the procedure described for the preparation of compound 8. Yield 74%. Mp 198° C. TLC $R_f$ 0.35 (cyclohexane-EtOAc, 1:1), $^1$H NMR (400 MHz, DMSO-$d_6$) δ 9.27 (d, J=0.6 Hz, 2H), 8.24 (t, J=5.5 Hz, 1H), 7.62 (dd, J=9.1, 0.6 Hz, 1H), 7.55 (d, J=2.7 Hz, 1H), 7.44-7.38 (m, 4H), 7.36 (ddd, J=9.1, 2.8, 0.7 Hz, 1H), 7.32-7.25 (m, 4H), 7.23-7.13 (m, 2H), 4.70 (t, J=7.7 Hz, 1H), 4.31 (dd, J=7.7, 5.4 Hz, 2H), 3.83 (s, 3H), 3.22 (s, 6H). HRMS m/z calcd for $C_{29}H_{28}N_6O+H^+$ [M+H$^+$]: 477.2397, found: 477.2397. HPLC: 98% ($t_R$=14.5 min).

iii. Synthesis of N-(2,2-Diphenylethyl)-2-(1H-Indol-5-yl)-6-Methoxyquinazolin-4-Amine (61)

This compound was prepared from 2-chloro-N-(2,2-diphenylethyl)-6-methoxyquinazolin-4-amine and (1H-indol-5-yl)boronic acid according to the procedure described for the preparation of compound 8. Yield 83%. Mp 112° C. TLC $R_f$ 0.35 (cyclohexan-EtOAc, 1:1). $^1$H NMR (400 MHz, DMSO-$d_6$) δ 9.27 (d, J=0.5 Hz, 2H), 7.62 (d, J=9.0 Hz, 1H), 7.54 (d, J=2.9 Hz, 2H), 7.40 (d, J=7.5 Hz, 5H), 7.37 (m, 6H), 7.44-7.32 (m, 2H), 7.29 (t, J=7.6 Hz, 2H), 4.86 (t, J=7.7 Hz, 1H), 4.32 (dd, J=7.7, 5.4 Hz, 2H), 3.83 (s, 3H). HRMS m/z calcd for $C_{31}H_{26}N_4O+H^+$ [M+H$^+$]: 471.2179, found: 471.2178. HPLC: 95% ($t_R$=13.4 min).

jjj. Synthesis of Tert-Butyl 5-(4-((2,2-Diphenylethyl)Amino)Quinazolin-2-yl)-1H-Benzo [D]Imidazole-1-Carboxylate (62)

This compound was prepared from 2-chloro-N-(2,2-diphenylethyl)quinazolin-4-amine and tert-butyl 5-(4,4,5,5-tetramethyl-1,3,2-dioxaborolan-2-yl)-1H-benzo[d]imidazole-1-carboxylate according to the procedure described for the preparation of compound 8. Yield 25%. Mp 183° C. TLC $R_f$ 0.30 (cyclohexane-EtOAc, 1:1). $^1$H NMR (400 MHz, DMSO-$d_6$) δ 9.22 (dd, J=1.6, 0.7 Hz, 1H), 8.75 (s, 1H), 8.60 (dd, J=8.5, 1.6 Hz, 1H), 8.39 (d, J=5.6 Hz, 1H), 8.12 (d, J=8.2 Hz, 1H), 7.85 (dd, J=8.5, 0.6 Hz, 1H), 7.75 (d, J=3.8 Hz, 2H), 7.48-7.38 (m, 5H), 7.29 (t, J=7.6 Hz, 4H), 7.23-7.14 (m, 2H), 4.79 (t, J=7.9 Hz, 1H), 4.38-4.30 (m, 2H), 1.66 (s, 9H). HRMS m/z calcd for $C_{34}H_{31}N_5O_2+H^+$ [M+H$^+$]: 542.2551, found: 542.2541. HPLC: 96% ($t_R$=17.7 min).

kkk. Synthesis of 2-(1H-Benzo[D][1,2,3]Triazol-5-yl)-N-(2,2-Diphenylethyl)Quinazolin-4-Amine (63)

This compound was prepared from 2-chloro-N-(2,2-diphenylethyl)quinazolin-4-amine and (1H-benzo[d][1,2,3]triazol-5-yl)boronic acid according to the procedure described for the preparation of compound 8. Yield 25%. Mp 220° C.; TLC $R_f$ 0.25 (cyclohexane-EtOAc, 1:1). $^1$H NMR (400 MHz, DMSO-$d_6$) δ 9.02 (s, 1H), 8.66 (d, J=8.8 Hz, 1H), 8.47 (t, J=5.5 Hz, 1H), 8.15 (d, J=8.2 Hz, 1H), 7.98 (s, 2H), 7.82-7.71 (m, 2H), 7.49-7.39 (m, 5H), 7.32 (dd, J=8.4, 6.9 Hz, 4H), 7.25-7.15 (m, 2H), 4.80 (t, J=7.7 Hz, 1H), 4.36 (dd, J=7.7, 5.4 Hz, 2H). HRMS m/z calcd for $C_{28}H_{22}N_6+H^+$ [M+H$^+$]: 443.1979, found: 443.1975. HPLC: 96% ($t_R$=10.7 min).

lll. Synthesis of N-(2,2-Diphenylethyl)-2-(1-Methyl-1H-Benzo [D]Imidazol-6-yl)Quinazolin-4-Amine (64)

This compound was prepared from 2-chloro-N-(2,2-diphenylethyl)quinazolin-4-amine and (1-methyl-1H-benzo[d]imidazol-5-yl)boronic acid according to the procedure described for the preparation of compound 8. Yield 18%. mp 248° C. TLC $R_f$ 0.35 (cyclohexane-EtOAc, 1:1). $^1$H NMR (400 MHz, DMSO-$d_6$) δ 8.67 (dd, J=1.6, 0.6 Hz, 1H), 8.50 (dd, J=8.5, 1.6 Hz, 1H), 8.45 (t, J=5.5 Hz, 1H), 8.28 (s, 1H), 8.13 (dd, J=8.2, 1.2 Hz, 1H), 7.81-7.69 (m, 3H), 7.48-7.37 (m, 5H), 7.32 (dd, J=8.3, 7.0 Hz, 4H), 7.25-7.16 (m, 2H), 4.87 (t, J=7.6 Hz, 1H), 4.33 (dd, J=7.6, 5.4 Hz, 2H), 3.89 (s, 3H). HRMS m/z calcd for $C_{30}H_{25}N_5+H^+$ [M+H$^+$]: 456.2183, found: 456.2181. HPLC: 100% ($t_R$=11.6 min).

mmm. Synthesis of N-(2,2-Diphenylethyl)-2-(1-Methyl-1H-Indazol-4-yl)Quinazolin-4-Amine (65)

This compound was prepared from 2-chloro-N-(2,2-diphenylethyl)quinazolin-4-amine and (1-methyl-1H-indazol-4-yl)boronic acid according to the procedure described for the preparation of compound 8. Yield 63%. Mp 201° C. TLC $R_f$ 0.35 (cyclohexane-EtOAc, 1:1). $^1$H NMR (400 MHz, DMSO-$d_6$) δ 9.03 (d, J=0.9 Hz, 1H), 8.45-8.36 (m, 2H), 8.18-8.11 (m, 1H), 7.91-7.84 (m, 1H), 7.83-7.74 (m, 2H), 7.55 (dd, J=8.3, 7.3 Hz, 1H), 7.46 (ddd, J=8.2, 6.9, 1.3 Hz, 1H), 7.42-7.37 (m, 4H), 7.30 (dd, J=8.4, 6.9 Hz, 4H), 7.24-7.14 (m, 2H), 4.79 (t, J=7.8 Hz, 1H), 4.35 (dd, J=7.8, 5.3 Hz, 2H), 4.12 (s, 3H). HRMS m/z calcd for $C_{30}H_{25}N_5$+H$^+$ [M+H$^+$]: 456.2183, found: 456.2181. HPLC: 100% ($t_R$=12.6 min).

nnn. Synthesis of N-(2,2-Diphenylethyl)-2-(2-Methyl-2H-Indazol-5-yl)Quinazolin-4-Amine (66)

This compound was prepared from 2-chloro-N-(2,2-diphenylethyl)quinazolin-4-amine and (2-methyl-2H-indazol-5-yl)boronic acid according to the procedure described for the preparation of compound 8. Yield 47%. Mp 211° C. TLC $R_f$ 0.35 (cyclohexane-EtOAc, 1:1), $^1$H NMR (400 MHz, DMSO-$d_6$) δ 8.92 (dd, J=1.6, 0.9 Hz, 1H), 8.49 (t, J=0.7 Hz, 1H), 8.46 (dd, J=9.1, 1.6 Hz, 1H), 8.40 (t, J=5.5 Hz, 1H), 8.12 (dt, J=8.4, 1.0 Hz, 1H), 7.95 (dd, J=1.8, 0.9 Hz, 2H), 7.76-7.69 (m, 2H), 7.68-7.58 (m, 2H), 7.47-7.37 (m, 2H), 7.33 (dd, J=8.3, 7.0 Hz, 4H), 7.26-7.17 (m, 2H), 4.81 (t, J=7.5 Hz, 1H), 4.32 (dd, J=7.6, 5.4 Hz, 2H), 4.24-4.20 (m, 3H). HRMS m/z calcd for $C_{30}H_{25}N_5$+H$^+$ [M+H$^+$]: 456.2183, found: 456.2186. HPLC: 99% ($t_R$=13.1 min).

ooo. Synthesis of N-(2,2-Diphenylethyl)-2-(1-Methyl-1H-Indazol-5-yl)Quinazolin-4-Amine (67)

This compound was prepared from 2-chloro-N-(2,2-diphenylethyl)quinazolin-4-amine and (1-methyl-1H-indazol-5-yl)boronic acid according to the procedure described for the preparation of compound 8. Yield 87%. Mp 200° C. TLC $R_f$ 0.35 (cyclohexane-EtOAc, 1:1), $^1$H NMR (400 MHz, DMSO-$d_6$) δ 8.94 (dd, J=1.5, 0.8 Hz, 1H), 8.63 (dd, J=8.9, 1.5 Hz, 1H), 8.43 (t, J=5.5 Hz, 1H), 8.20-8.06 (m, 2H), 7.82-7.68 (m, 3H), 7.47-7.37 (m, 5H), 7.33 (dd, J=8.3, 6.9 Hz, 4H), 7.26-7.16 (m, 2H), 4.80 (t, J=7.5 Hz, 1H), 4.33 (dd, J=7.5, 5.4 Hz, 2H), 4.11 (s, 3H). HRMS m/z calcd for $C_{30}H_{25}N_5$+H$^+$ [M+H$^+$]: 456.2183, found: 456.2188. HPLC: 96% ($t_R$=12.7 min).

ppp. Synthesis of N-(2,2-Diphenylethyl)-2-(2-Methyl-2H-Indazol-4-yl)Quinazolin-4-Amine (68)

This compound was prepared from 2-chloro-N-(2,2-diphenylethyl)quinazolin-4-amine and (2-methyl-2H-indazol-4-yl)boronic acid according to the procedure described for the preparation of compound 8. Yield 66%. Mp 121° C. TLC $R_f$ 0.35 (cyclohexane-EtOAc, 1:1). $^1$H NMR (400 MHz, DMSO-$d_6$) δ 9.09 (s, 1H), 8.43-8.35 (m, 2H), 8.13 (d, J=8.1 Hz, 1H), 7.89 (dd, J=8.4, 1.2 Hz, 1H), 7.82-7.71 (m, 2H), 7.49-7.36 (m, 6H), 7.31 (dd, J=8.4, 6.9 Hz, 4H), 7.25-7.16 (m, 2H), 4.79 (t, J=7.6 Hz, 1H), 4.36 (dd, J=7.7, 5.4 Hz, 2H), 4.08 (s, 3H). HRMS m/z calcd for $C_{30}H_{25}N_5$+H$^+$ [M+H$^+$]: 456.2183, found: 456.2175. HPLC: 100% ($t_R$=12.5 min).

qqq. Synthesis of 2-(6-(Dimethylamino)Pyridin-3-yl)-N-(2,2-Diphenylethyl)Quinazolin-4-Amine (69)

This compound was prepared from 2-chloro-N-(2,2-diphenylethyl)quinazolin-4-amine and (6-(dimethylamino)pyridin-3-yl)boronic acid according to the procedure described for the preparation of compound 8. Yield 61%. Mp 199° C.; TLC $R_f$ 0.35 (cyclohexane-EtOAc, 1:1). $^1$H NMR (400 MHz, DMSO-$d_6$) δ 9.22 (dd, J=2.3, 0.7 Hz, 1H), 8.50 (dd, J=8.9, 2.3 Hz, 1H), 8.29 (t, J=5.5 Hz, 1H), 8.10-8.03 (m, 1H), 7.73-7.61 (m, 2H), 7.42-7.37 (m, 4H), 7.34 (ddd, J=8.2, 6.4, 1.7 Hz, 1H), 7.29 (dd, J=8.4, 6.9 Hz, 4H), 7.23-7.14 (m, 2H), 6.74 (dd, J=9.0, 0.7 Hz, 1H), 4.73 (t, J=7.7 Hz, 1H), 4.29 (dd, J=7.8, 5.4 Hz, 2H), 3.13 (s, 6H). HRMS m/z calcd for $C_{29}H_{27}N_5$+H$^+$ [M+H$^+$]: 446.2339, found: 446.2339. HPLC: 98% ($t_R$=12.5 min).

rrr. Synthesis of 2-(Benzo [D]Thiazol-6-yl)-N-(2,2-Diphenylethyl)Quinazolin-4-Amine (70)

This compound was prepared from 2-chloro-N-(2,2-diphenylethyl)quinazolin-4-amine and 6-(4,4,5,5-tetramethyl-1,3,2-dioxaborolan-2-yl)benzo[d]thiazole according to the procedure described for the preparation of compound 8. Yield 65%. Mp 198° C. TLC $R_f$ 0.30 (cyclohexane-EtOAc, 1:1). $^1$H NMR (400 MHz, DMSO-$d_6$) δ 9.50 (s, 1H), 9.24 (dd, J=1.6, 0.6 Hz, 1H), 8.72 (dd, J=8.6, 1.7 Hz, 1H), 8.53 (t, J=5.5 Hz, 1H), 8.24-8.13 (m, 2H), 7.83-7.72 (m, 2H), 7.50-7.41 (m, 5H), 7.37-7.28 (m, 4H), 7.26-7.16 (m, 2H), 4.79 (t, J=7.4 Hz, 1H), 4.35 (dd, J=7.5, 5.4 Hz, 2H). HRMS m/z calcd for $C_{29}H_{22}N_4S$+H$^+$ [M+H$^+$]: 459.1638, found: 459.1642. HPLC: 99% ($t_R$=13.4 min).

sss. Synthesis of Tert-Butyl 7-(4-((2,2-Diphenylethyl)Amino)Quinazolin-2-yl)-3,4-Dihydroquinoline-1(2H)-Carboxylate (71)

This compound was prepared from 2-chloro-N-(2,2-diphenylethyl)quinazolin-4-amine and (1-(tert-butoxycarbonyl)-1,2,3,4-tetrahydroquinolin-7-yl)boronic acid according to the procedure described for the preparation of compound 8. Yield 82%. Mp 89° C.; TLC $R_f$ 0.30 (cyclohexane-EtOAc, 1:1). $^1$H NMR (400 MHz, DMSO-$d_6$) δ 8.83 (d, J=1.6 Hz, 1H), 8.34 (t, J=5.4 Hz, 1H), 8.18-8.07 (m, 2H), 7.77-7.65 (m, 2H), 7.45-7.35 (m, 5H), 7.32-7.21 (m, 5H), 7.20-7.15 (m, 2H), 4.76 (t, J=7.7 Hz, 1H), 4.31 (dd, J=7.8, 5.3 Hz, 2H), 3.75-3.67 (m, 2H), 2.82 (t, J=6.6 Hz, 2H), 1.89 (p, J=6.5 Hz, 2H), 1.44 (s, 9H). HRMS m/z calcd for $C_{36}H_{36}N_4O_2$+H$^+$ [M+H$^+$]: 557.2911, found: 557.2909. HPLC: 100% ($t_R$=15.2 min).

ttt. Synthesis of Tert-Butyl 3-(4-((2,2-Diphenylethyl)Amino)Quinazolin-2-yl)-1H-Indole-1-Carboxylate (72)

This compound was prepared from 2-chloro-N-(2,2-diphenylethyl)quinazolin-4-amine and (1-(tert-butoxycarbonyl)-1H-indol-3-yl)boronic acid according to the procedure described for the preparation of compound 8. Yield 73%. Mp 90° C. TLC $R_f$ 0.30 (cyclohexane-EtOAc, 1:1), $^1$H NMR (400 MHz, DMSO-$d_6$) δ 8.87-8.80 (m, 1H), 8.50 (s, 1H), 8.39 (t, J=5.6 Hz, 1H), 8.19-8.14 (m, 1H), 8.10 (d, J=8.2 Hz, 1H), 7.81-7.69 (m, 2H), 7.45-7.35 (m, 6H), 7.30 (dd, J=8.4, 6.9 Hz, 4H), 7.25-7.16 (m, 3H), 4.76 (t, J=7.8 Hz, 1H), 4.37-4.29 (m, 2H), 1.67 (s, 9H). HRMS m/z calcd for $C_{35}H_{32}N_4O_2$+H$^+$ [M+H$^+$]: 541.2598, found: 541.2601. HPLC: 100% ($t_R$=15.5 min).

uuu. Synthesis of Tert-Butyl 3-(4-((2,2-Diphenylethyl)Amino)Quinazolin-2-yl)-1H-Pyrrolo[2,3-B]Pyridine-1-Carboxylate (73)

This compound was prepared from 2-chloro-N-(2,2-diphenylethyl)quinazolin-4-amine and tert-butyl 3-(4,4,5,5-tetramethyl-1,3,2-dioxaborolan-2-yl)-1H-pyrrolo[2,3-b]

pyridine-1-carboxylate according to the procedure described for the preparation of compound 8. Yield 22%. Mp 105° C. TLC $R_f$ 0.35 (cyclohexane-EtOAc, 1:1). $^1$H NMR (400 MHz, DMSO-$d_6$) δ 9.05 (dd, J=7.9, 1.8 Hz, 1H), 8.56 (s, 1H), 8.49-8.40 (m, 2H), 8.11 (d, J=8.1 Hz, 1H), 7.81-7.70 (m, 2H), 7.47-7.36 (m, 5H), 7.35-7.23 (m, 5H), 7.23-7.17 (m, 2H), 4.75 (t, J=7.7 Hz, 1H), 4.33 (dd, J=7.7, 5.5 Hz, 2H), 1.65 (s, 9H). HRMS m/z calcd for $C_{34}H_{31}N_5O_2+H^+$ [M+H$^+$]: 542.2551, found: 542.2551. HPLC: 98% ($t_R$=18.6 min).

vvv. Synthesis of Tert-Butyl 5-(4-((2,2-Diphenylethyl)Amino)Quinazolin-2-yl)Indoline-1-Carboxylate (74)

This compound was prepared from 2-chloro-N-(2,2-diphenylethyl)quinazolin-4-amine and tert-butyl 5-(4,4,5,5-tetramethyl-1,3,2-dioxaborolan-2-yl)indoline-1-carboxylate according to the procedure described for the preparation of compound 8. Yield 75%. Mp 127° C. TLC $R_f$ 0.30 (cyclohexane-EtOAc, 1:1), $^1$H NMR (400 MHz, DMSO-$d_6$) δ 8.41 (t, J=5.4 Hz, 1H), 8.38-8.33 (m, 2H), 8.10 (d, J=8.3 Hz, 1H), 7.76-7.66 (m, 2H), 7.45-7.35 (m, 5H), 7.31 (dd, J=8.4, 6.9 Hz, 5H), 7.25-7.15 (m, 2H), 4.78 (t, J=7.5 Hz, 1H), 4.31-4.23 (m, 2H), 4.00 (t, J=8.7 Hz, 2H), 3.16 (t, J=8.7 Hz, 2H), 1.55 (s, 9H). HRMS m/z calcd for $C_{35}H_{34}N_4O_2+H^+$ [M+H$^+$]: 543.2755, found: 543.2746. HPLC: 100% ($t_R$=16.8 min).

www. Synthesis of N-(2,2-Diphenylethyl)-2-(1H-Pyrazol-4-yl)Quinazolin-4-Amine (75)

This compound was prepared from 2-chloro-N-(2,2-diphenylethyl)quinazolin-4-amine and 4-(4,4,5,5-tetramethyl-1,3,2-dioxaborolan-2-yl)-1H-pyrazole according to the procedure described for the preparation of compound 8. Yield 31%. Mp 233° C. TLC $R_f$ 0.25 (cyclohexane-EtOAc, 1:1). $^1$H NMR (400 MHz, DMSO-$d_6$) δ 13.07 (s, 1H), 8.27 (q, J=8.4, 5.5 Hz, 2H), 8.17-8.09 (m, 1H), 8.08-8.01 (m, 1H), 7.71-7.57 (m, 2H), 7.44-7.37 (m, 4H), 7.37-7.26 (m, 5H), 7.23-7.13 (m, 2H), 4.73 (t, J=7.7 Hz, 1H), 4.25 (dd, J=7.7, 5.4 Hz, 2H). HRMS m/z calcd for $C_{25}H_{21}N_5+H^+$ [M+H$^+$]: 392.1869, found: 392.1869. HPLC: 99% ($t_R$=11.5 min).

xxx. Synthesis of N-(2,2-Diphenylethyl)-2-(1-Methyl-1H-Pyrazol-4-yl)Quinazolin-4-Amine (76)

This compound was prepared from 2-chloro-N-(2,2-diphenylethyl)quinazolin-4-amine and 1-methyl-4-(4,4,5,5-tetramethyl-1,3,2-dioxaborolan-2-yl)-1H-pyrazole according to the procedure described for the preparation of compound 8. Yield 95%. Mp 211° C. TLC $R_f$ 0.25 (cyclohexane-EtOAc, 1:1). $^1$H NMR (400 MHz, DMSO-$d_6$) δ 8.29 (t, J=0.6 Hz, 1H), 8.25 (t, J=5.5 Hz, 1H), 8.08-8.00 (m, 2H), 7.80 (d, J=0.8 Hz, 2H), 7.71-7.57 (m, 2H), 7.56 (d, J=0.8 Hz, 2H), 7.44-7.37 (m, 2H), 7.37-7.25 (m, 3H), 7.24-7.13 (m, 2H), 4.70 (t, J=7.6 Hz, 1H), 4.25 (dd, J=7.7, 5.4 Hz, 2H), 3.93 (s, 3H). HRMS m/z calcd for $C_{26}H_{23}N_5+H^+$ [M+H$^+$]: 406.2026, found: 406.2016. HPLC: 99% ($t_R$=11.8 min).

yyy. Synthesis of N-(2,2-Diphenylethyl)-2-(1-Methyl-1H-Indol-5-yl)Quinazolin-4-Amine (77)

This compound was prepared from 2-chloro-N-(2,2-diphenylethyl)quinazolin-4-amine and (1-methyl-1H-indol-5-yl)boronic acid according to the procedure described for the preparation of compound 8. Yield 19%. Mp 222° C. TLC $R_f$ 0.25 (cyclohexane-EtOAc, 1:1). $^1$H NMR (400 MHz, DMSO-$d_6$) δ 8.81 (dd, J=1.5, 0.7 Hz, 1H), 8.47-8.31 (m, 2H), 8.10 (d, J=8.2 Hz, 1H), 7.76-7.65 (m, 2H), 7.56-7.49 (m, 1H), 7.47-7.28 (m, 10H), 7.26-7.17 (m, 2H), 6.57-6.50 (m, 1H), 4.85 (t, J=7.5 Hz, 1H), 4.31 (dd, J=7.6, 5.3 Hz, 2H), 3.85 (s, 3H). HRMS m/z calcd for $C_{31}H_{26}N_4+H^+$ [M+H$^+$]: 455.2230, found: 455.2230. HPLC: 98% ($t_R$=11.8 min).

zzz. Synthesis of 5-(4-((2,2-Diphenylethyl)Amino) Quinazolin-2-yl)Indolin-2-One (78)

This compound was prepared from 2-chloro-N-(2,2-diphenylethyl)quinazolin-4-amine and 5-(4,4,5,5-tetramethyl-1,3,2-dioxaborolan-2-yl)indolin-2-one according to the procedure described for the preparation of compound 8. Yield 55%. Mp 244° C. TLC $R_f$ 0.25 (cyclohexane-EtOAc, 1:1). $^1$H NMR (400 MHz, DMSO-$d_6$) δ 10.59 (s, 1H), 8.45-8.34 (m, 3H), 8.13-8.06 (m, 1H), 7.75-7.64 (m, 2H), 7.44-7.35 (m, 5H), 7.35-7.28 (m, 4H), 7.25-7.15 (m, 2H), 6.93 (d, J=8.2 Hz, 1H), 4.77 (t, J=7.5 Hz, 1H), 4.27 (dd, J=7.5, 5.3 Hz, 2H), 3.59 (s, 2H). HRMS m/z calcd for $C_{30}H_{24}N_4O+H^+$ [M+H$^+$]: 457.2023, found: 457.2026. HPLC: 100% ($t_R$=11.8 min).

aaaa. Synthesis of 5-(4-((2,2-Diphenylethyl)Amino) Quinazolin-2-yl)-1H-Benzo[D]Imidazol-2-ol (79)

This compound was prepared from 2-chloro-N-(2,2-diphenylethyl)quinazolin-4-amine and 5-(4,4,5,5-tetramethyl-1,3,2-dioxaborolan-2-yl)-1H-benzo[d]imidazol-2(3H)-one according to the procedure described for the preparation of compound 8. Yield 52%. Mp 215° C. TLC $R_f$ 0.25 (cyclohexane-EtOAc, 1:1). $^1$H NMR (400 MHz, DMSO-$d_6$) δ 10.79 (d, J=10.8 Hz, 2H), 8.30 (t, J=5.3 Hz, 1H), 8.23 (dd, J=8.2, 1.6 Hz, 1H), 8.13 (d, J=1.5 Hz, 1H), 8.11-8.05 (m, 1H), 7.75-7.65 (m, 2H), 7.44-7.34 (m, 5H), 7.31 (dd, J=8.4, 6.9 Hz, 4H), 7.24-7.14 (m, 2H), 7.02 (d, J=8.2 Hz, 1H), 4.77 (t, J=7.8 Hz, 1H), 4.29 (dd, J=7.8, 5.3 Hz, 2H). HRMS m/z calcd for $C_{29}H_{23}N_5O+H^+$ [M+H$^+$]: 458.1975. found: 458.1975, HPLC: 99% ($t_R$=12.0 min).

bbbb. Synthesis of 2-((2-(2-(Dimethylamino)Pyrimidin-5-yl)Quinazolin-4-yl)Amino)-1,1-Diphenylethanol (80)

i. Step 1

To a stirred solution of 2,4-dichloroquinazoline (0.300 g, 1.51 mmol) in THF (5 mL) was added dropwise N,N-diisopropylethylamine (0.32 mL, 2.27 mmol) and 2-amino-1,1-diphenylethanol (0.353 g, 1.66 mmol). After stirring for 4 hours at room temperature, the reaction mixture was diluted with water (5 mL) and extracted with EtOAc (3×5 mL). The combined organic layers were washed with water (3×5 mL), dried over $Na_2SO_4$, and filtered. The filtrate was concentrated under reduced pressure. The organic layer was separated, dried over anhydrous $Na_2SO_4$, filtered and the filtrate was concentrated under reduced pressure. The residue obtained was purified by column chromatography using hexanes:EtOAc (0-70%) as eluent to obtain 0.465 g (82%) of 2-((2-chloroquinazolin-4-yl)amino)-1,1-diphenylethanol.

ii. Step 2

The above compound was reacted with (2-(dimethylamino)pyrimidin-5-yl)boronic acid according to the procedure described for the preparation of compound 8. Yield 50%. Mp 247° C. TLC $R_f$ 0.25 (cyclohexane-EtOAc, 1:1). $^1$H NMR (400 MHz, DMSO-$d_6$) δ 9.30 (s, 2H), 8.13-8.06 (m, 1H), 7.82 (t, J=5.5 Hz, 1H), 7.77-7.63 (m, 2H), 7.59-

7.51 (m, 4H), 7.42 (ddd, J=8.2, 6.7, 1.4 Hz, 1H), 7.32-7.22 (m, 4H), 7.21-7.12 (m, 2H), 6.64 (s, 1H), 4.50 (d, J=5.3 Hz, 2H), 3.23 (s, 6H). HRMS m/z calcd for $C_{28}H_{26}N_6O+H^+$ [M+H$^+$]: 463.2241, found: 463.2240. HPLC: 99% ($t_R$=13.3 min).

cccc. 2-((2-(1H-Indol-5-yl)Quinazolin-4-yl)Amino)-1,1-Diphenylethanol (81)

This compound was prepared from 2-((2-chloroquinazolin-4-yl)amino)-1,1-diphenylethanol and (1H-indol-5-yl)boronic acid according to the procedure described for the preparation of compound 8. Yield 66%. Mp 202° C. TLC R$_f$ 0.25 (cyclohexane-EtOAc, 1:1). $^1$H NMR (400 MHz, DMSO-d$_6$) δ 11.26 (s, 1H), 8.76 (d, J=1.5 Hz, 1H), 8.32 (dd, J=8.6, 1.6 Hz, 1H), 8.09 (d, J=8.2 Hz, 1H), 7.83 (t, J=5.4 Hz, 1H), 7.79-7.69 (m, 2H), 7.63-7.55 (m, 4H), 7.50 (dd, J=8.6, 1.0 Hz, 1H), 7.47-7.36 (m, 2H), 7.31 (dd, J=8.4, 7.0 Hz, 4H), 7.24-7.15 (m, 2H), 6.98 (s, 1H), 6.63-6.56 (m, 1H), 4.53 (d, J=5.2 Hz, 2H). HRMS m/z calcd for $C_{30}H_{24}N_4O+H^+$ [M+H$^+$]: 457.2023. found: 457.2025. HPLC: 99% ($t_R$=11.2 min).

dddd. N-(2,2-Diphenylethyl)-2-(1H-Indol-3-yl)Quinazolin-4-Amine (82)

A solution of tert-butyl 3-(4-((2,2-diphenylethyl)amino)quinazolin-2-yl)-1H-indole-1-carboxylate (100 mg, 0.185 mmol) in 50% TFA in CH$_2$Cl$_2$ (3 mL) was stirred overnight at room temperature. TLC indicated complete conversion of starting material to the product. The reaction mixture was concentrated under reduced pressure and purified to obtain the desired product. Yield 67%. Mp 234° C. TLC R$_f$ 0.25 (cyclohexane-EtOAc, 1:1). $^1$H NMR (400 MHz, DMSO-d$_6$) δ 9.06 (s, 1H), 8.30 (t, J=5.3 Hz, 1H), 8.23 (dd, J=8.2, 1.6 Hz, 2H), 8.13 (d, J=1.5 Hz, 2H), 8.11-8.05 (m, 2H), 7.75-7.65 (m, 2H), 7.44-7.34 (m, 2H), 7.31 (dd, J=8.4, 6.9 Hz, 4H), 7.24-7.14 (m, 4H), 6.81 (t, J=7.5 Hz, 1H), 4.77 (t, J=7.8 Hz, 1H), 4.55 (d, J=8.0 Hz, 2H). HRMS m/z calcd for $C_{30}H_{24}N_4+H^+$ [M+H$^+$]: 441.2074, found: 441.2081. HPLC: 100% ($t_R$=11.6 min).

eeee. N-(2,2-Diphenylethyl)-2-(1,2,3,4-Tetrahydroquinolin-7-yl)Quinazolin-4-Amine (83)

To a solution of tert-butyl 7-(4-((2,2-diphenylethyl)amino)quinazolin-2-yl)-3,4-dihydroquinoline-1(2H)-carboxylate (100 mg, 0.180 mmol) in 50% TFA in CH$_2$Cl$_2$ (3 mL) was stirred overnight at room temperature. TLC indicated complete conversion of starting material to the product. The reaction mixture was concentrated under reduced pressure and residue obtain was further purified to obtain the desired product. Yield 99%. Mp 220° C. TLC R$_f$ 0.25 (cyclohexane-EtOAc, 1:1). $^1$H NMR (400 MHz, DMSO-d$_6$) δ 8.19 (s, 1H), 7.80 (s, 2H), 7.53 (s, 2H), 7.44-7.36 (m, 5H), 7.34-7.25 (m, 5H), 7.24-7.14 (m, 3H), 7.04 (s, 1H), 4.72 (s, 1H), 4.36 (s, 2H), 2.77 (t, J=6.3 Hz, 2H), 1.85 (p, J=6.3 Hz, 2H), 1.09 (t, J=7.0 Hz, 2H). HRMS m/z calcd for $C_{31}H_{28}N_4+H^+$ [M+H$^+$]: 457.2387, found: 457.2392. HPLC: 97% ($t_R$=12.7 min).

ffff. N-(2,2-Diphenylethyl)-2-(Indolin-5-yl)Quinazolin-4-Amine (84)

A solution of tert-butyl 5-(4-((2,2-diphenylethyl)amino)quinazolin-2-yl)indoline-1-carboxylate (100 mg, 0.184 mmol) in 50% TFA in CH$_2$Cl$_2$ (3 mL) was stirred overnight at room temperature. Volatiles were removed under reduced pressure and the residue was purified to give the title compound. Yield 86%. Mp 213° C. TLC R$_f$ 0.25 (cyclohexane-EtOAc, 1:1). $^1$H NMR (400 MHz, DMSO-d$_6$) δ 13.13 (s, 1H), 9.70 (s, 2H), 8.21 (d, J=8.1 Hz, 1H), 8.16-8.06 (m, 1H), 7.82 (d, J=9.4 Hz, 1H), 7.54 (s, 1H), 7.45-7.37 (m, 4H), 7.31 (dd, J=8.4, 6.9 Hz, 4H), 7.26-7.16 (m, 2H), 6.87-6.77 (m, 1H), 6.61 (d, J=8.3 Hz, 1H), 4.70 (t, J=7.5 Hz, 1H), 4.37 (t, J=6.5 Hz, 2H), 3.64 (t, J=8.6 Hz, 2H), 3.07 (t, J=8.6 Hz, 2H). HRMS m/z calcd for $C_{30}H_{26}N_4+H^+$ [M+H$^+$]: 443.2230, found: 443.2235. HPLC: 99% ($t_R$=11.2 min).

gggg. 2-(1H-Benzo [D]Imidazol-5-yl)-N-(2,2-Diphenylethyl)Quinazolin-4-Amine (85)

A solution of tert-butyl 5-(4-((2,2-diphenylethyl)amino)quinazolin-2-yl)indoline-1-carboxylate (65 mg, 0.120 mmol) was dissolved in 50% TFA in CH$_2$Cl$_2$ (3 mL) and the solution was stirred overnight at room temperature. The reaction mixture was evaporated to dryness under reduced pressure and residue was purified to obtain the title compound. Yield 99%. Mp 142° C. TLC R$_f$ 0.25 (cyclohexane-EtOAc, 1:1). $^1$H NMR (400 MHz, DMSO-d$_6$) δ 8.80 (d, J=1.5 Hz, 1H), 8.62 (m, 2H), 7.63-7.55 (m, 2H), 7.50 (dd, J=8.6, 1.0 Hz, 1H), 7.47-7.36 (m, 4H), 7.31 (dd, J=8.4, 7.0 Hz, 4H), 7.24-7.15 (m, 4H), 6.98 (s, 1H), 6.63-6.56 (m, 1H), 4.78 (t, J=6.5 Hz, 1H), 4.47 (d, J=5.2 Hz, 2H). HRMS m/z calcd for $C_{29}H_{23}N_5+H^+$ [M+H$^+$]: 442.2026. found: 442.2026, HPLC: 99% ($t_R$=11.7 min).

hhhh. N-Benzhydryl-2-(Imidazo[1,2-A]Pyridin-6-yl)Quinazolin-4-Amine (86)

This compound was prepared from N-benzhydryl-2-chloroquinazolin-4-amine and imidazo[1,2-a]pyridin-6-ylboronic acid according to the procedure described for the preparation of compound 8. Yield 43%. Mp 258° C. TLC R$_f$ 0.25 (cyclohexane-EtOAc, 1:1). $^1$H NMR (400 MHz, DMSO-d$_6$) δ 9.53 (dd, J=1.7, 1.0 Hz, 1H), 9.05 (d, J=8.1 Hz, 1H), 8.64-8.56 (m, 1H), 8.23 (dd, J=9.5, 1.7 Hz, 1H), 8.14 (t, J=1.0 Hz, 1H), 7.86-7.74 (m, 2H), 7.65-7.58 (m, 2H), 7.58-7.46 (m, 5H), 7.44-7.35 (m, 4H), 7.33-7.24 (m, 2H), 7.11 (d, J=8.0 Hz, 1H). FIRMS m/z calcd for $C_{28}H_{21}N_5+H^+$ [M+H$^+$]: 428.1870, found: 428.1863. HPLC: 99% ($t_R$=14.1 min).

iiii N-(3,3-Diphenylpropyl)-2-(Imidazo[1,2-A]Pyridin-6-yl)Quinazolin-4-Amine (87)

This compound was prepared from 2-chloro-N-(3,3-diphenylpropyl)quinazolin-4-amine and imidazo[1,2-a]pyridin-6-ylboronic acid according to the procedure described for the preparation of compound 8. Yield 90%. Mp 237° C. TLC R$_f$ 0.25 (cyclohexane-EtOAc, 1:1). $^1$H NMR (400 MHz, DMSO-d$_6$) δ 9.34 (dd, J=1.7, 1.0 Hz, 1H), 8.42 (t, J=5.6 Hz, 1H), 8.24 (dt, J=8.3, 0.9 Hz, 1H), 8.10 (dd, J=9.5, 1.7 Hz, 1H), 8.08 (dd, J=1.3, 0.7 Hz, 1H), 7.83-7.68 (m, 2H), 7.67-7.56 (m, 2H), 7.49 (ddd, J=8.2, 6.5, 1.7 Hz, 1H), 7.42-7.34 (m, 4H), 7.29 (dd, J=8.4, 6.9 Hz, 4H), 7.23-7.13 (m, 2H), 4.18 (t, J=7.7 Hz, 1H), 3.68 (td, J=7.8, 7.3, 5.6 Hz, 4H). HRMS m/z calcd for $C_{30}H_{25}N_5+H^+$ [M+H$^+$]: 456.2183, found: 456.2185. HPLC: 97% ($t_R$=14.9 min).

jjjj. 2-(6-Aminopyridin-3-yl)-N-(2,2-Diphenylethyl)Quinazolin-4-Amine (88)

This compound was prepared from 2-chloro-N-(2,2-diphenylethyl)quinazolin-4-amine and (2-aminopyrimidin-5- yl)boronic acid according to the procedure described for the preparation of compound 8. Yield 55%. Mp 86° C. TLC $R_f$ 0.25 (cyclohexane-EtOAc, 1:1). $^1$H NMR (400 MHz, DMSO-$d_6$) δ 9.07 (dd, J=2.3, 0.7 Hz, 1H), 8.39 (dd, J=8.7, 2.3 Hz, 1H), 8.31 (t, J=5.5 Hz, 1H), 8.06 (d, J=8.2 Hz, 2H), 7.76-7.60 (m, 2H), 7.42-7.25 (m, 6H), 7.23-7.14 (m, 2H), 6.52 (dd, J=8.6, 0.8 Hz, 1H), 6.47-6.40 (m, 1H), 6.37 (s, 2H), 5.81 (s, 1H), 4.76 (t, J=7.6 Hz, 1H), 4.30-4.21 (m, 2H). HRMS m/z calcd for $C_{27}H_{23}N_5+H^+$ [M+H$^+$]: 418.2026, found: 418.2023. HPLC: 95% ($t_R$=11.6 min).

kkkk. N-(2,2-Diphenylethyl)-2-(Imidazo[1,2-A]Pyrimidin-6-yl)Quinazolin-4-Amine (89)

To a solution of 2-(2-aminopyrimidin-5-yl)-N-(2,2-diphenylethyl)quinazolin-4-amine (25 mg, 0.060 mmol) in ethanol (2.0 mL) was added 2-chloroacetaldehyde (0.001 mL). The mixture was refluxed for 16 hours. TLC indicated complete conversion of starting material. The reaction mixture was concentrated under reduced pressure and the crude product was further purified to obtain the desired product. Yield 57%. Mp 210° C. TLC $R_f$ 0.25 (cyclohexane-EtOAc, 1:1), $^1$H NMR (400 MHz, DMSO-$d_6$) δ 9.83 (d, J=2.6 Hz, 1H), 9.52 (d, J=2.4 Hz, 1H), 8.57 (t, J=5.6 Hz, 1H), 8.17 (d, J=8.2 Hz, 1H), 8.09 (d, J=1.4 Hz, 1H), 7.83-7.71 (m, 3H), 7.52-7.41 (m, 5H), 7.30 (t, J=7.7 Hz, 4H), 7.23-7.14 (m, 2H), 4.72 (t, J=7.6 Hz, 1H), 4.41-4.33 (m, 2H). HRMS m/z calcd for $C_{28}H_{22}N_6+H^+$ [M+H$^+$]: 443.1979, found: 443.1980. HPLC: 100% ($t_R$=12.9 min).

llll. N-(2,2-Diphenylethyl)-2-(9H-Purin-9-yl)Quinazolin-4-Amine (90)

To a solution of 2-chloro-N-(2,2-diphenylethyl)quinazolin-4-amine (50 mg, 0.14 mmol) in N,N-dimethylformamide (2 mL) was added purine (33.4 mg, 0.28 mmol) and N,N-diisopropylethylamine (0.05 mL, 0.28 mmol). The reaction mixture was heated under reflux for 24 hours, cooled to room temperature and then concentrated under reduced pressure. The residue was purified by column chromatography to afford the desired compound. Yield 19%. Mp 264° C. TLC $R_f$ 0.25 (cyclohexane-EtOAc, 2:1). $^1$H NMR (400 MHz, DMSO-$d_6$) δ 10.01 (d, J=0.7 Hz, 1H), 9.64 (d, J=0.7 Hz, 1H), 9.12 (d, J=0.7 Hz, 1H), 8.92 (t, J=5.5 Hz, 1H), 8.26-8.18 (m, 1H), 7.90-7.78 (m, 2H), 7.54-7.42 (m, 5H), 7.27 (dd, J=8.3, 6.9 Hz, 4H), 7.21-7.12 (m, 2H), 4.67 (t, J=7.7 Hz, 1H), 4.45-4.37 (m, 2H). HRMS m/z calcd for $C_{27}H_{21}N_7+H^+$ [M+H$^+$]: 444.1931, found: 444.1917. HPLC: 99% ($t_R$=13.5 min).

mmmm. 2-(2,3-Dimethylimidazo[1,2-A]Pyridin-6-yl)-N-(2,2-Diphenylethyl)Quinazolin-4-Amine (91)

To a solution of 2-(6-aminopyridin-3-yl)-N-(2,2-diphenylethyl)quinazolin-4-amine (30 mg, 0.072 mmol)) in ethanol (3.0 mL) 3-bromo-2-butanone (0.01 mL) was added. The reaction mixture was refluxed overnight, concentrated under reduced pressure and the crude product thus obtained was purified to obtain the desired product. Yield 44%. Mp 232° C. TLC $R_f$ 0.25 (cyclohexane-EtOAc, 1:1). $^1$H NMR (400 MHz, DMSO-$d_6$) δ 9.10-9.05 (m, 1H), 8.39 (dd, J=8.7, 2.3 Hz, 1H), 8.31 (t, J=5.5 Hz, 1H), 8.06 (d, J=8.1 Hz, 1H), 7.72-7.60 (m, 2H), 7.42-7.25 (m, 7H), 7.23-7.14 (m, 2H), 6.52 (dd, J=8.7, 0.7 Hz, 1H), 6.37 (s, 2H), 4.76 (t, J=7.7 Hz, 1H), 4.30-4.21 (m, 2H), 2.50 (s, 6H). HRMS m/z calcd for $C_{31}H_{27}N_5+H^+$ [M+H$^+$]: 470.2339, found: 470.2334. HPLC: 95% ($t_R$=16.7 min).

nnnn. N-Benzhydryl-2-(6-(Dimethylamino)Pyridin-3-yl)Quinazolin-4-Amine (92)

This compound was prepared from N-benzhydryl-2-chloroquinazolin-4-amine and (6-(dimethylamino)pyridin-3-yl) boronic acid according to the procedure described for the preparation of compound 8. Yield 40%. Mp 207° C. TLC $R_f$ 0.25 (cyclohexane-EtOAc, 1:1), $^1$H NMR (400 MHz, DMSO-$d_6$) δ 9.13 (dt, J=2.4, 0.6 Hz, 1H), 8.82 (d, J=8.1 Hz, 1H), 8.53 (dd, J=8.0, 1.2 Hz, 1H), 8.44 (ddd, J=9.0, 2.4, 0.5 Hz, 1H), 7.79-7.65 (m, 2H), 7.52-7.47 (m, 4H), 7.43 (ddd, J=8.2, 6.8, 1.5 Hz, 1H), 7.40-7.34 (m, 4H), 7.32-7.23 (m, 2H), 7.02 (d, J=8.0 Hz, 1H), 6.70 (dt, J=9.0, 0.6 Hz, 1H), 3.11 (d, J=0.5 Hz, 6H). HRMS m/z calcd for $C_{28}H_{25}N_5+H^+$[M+H$^+$]: 432.2183, found: 432.2174. HPLC: 99% ($t_R$=14.4 min).

oooo. 2-(6-(Dimethylamino)Pyridin-3-yl)-N-(3,3-Diphenylpropyl)Quinazolin-4-Amine (93)

This compound was prepared from 2-chloro-N-(3,3-diphenylpropyl)quinazolin-4-amine and (6-(dimethylamino)pyridin-3-yl)boronic acid according to the procedure described for the preparation of compound 8. Yield 24%. Mp 195° C. TLC $R_f$ 0.40 (cyclohexane-EtOAc, 1:1). $^1$H NMR (400 MHz, DMSO-$d_6$) δ 9.09 (d, J=7.7 Hz, 1H)), 7.41-7.27 (m, 3H), 7.24-7.15 (m, 2H), 6.79-6.70 (m, 12H), 4.15 (t, J=7.7 Hz, 1H), 3.65-3.55 (m, 4H), 3.13 (s, 6H). HRMS m/z calcd for $C_{30}H_{29}N_5+H^+$ [M+H$^+$]: 460.2496, found: 460.2497. HPLC: 99% ($t_R$=15.2 min).

pppp. Synthesis of 2-(Imidazo[1,2-A]Pyridin-6-yl)-N-(2-Phenyl-2-(Pyridin-2-yl)Ethyl)Quinazolin-4-Amine (94)

This compound was prepared from 2-chloro-N-(2-phenyl-2-(pyridin-2-yl)ethyl)quinazolin-5-amine and imidazo[1,2-a]pyrimidin-6-ylboronic acid according to the procedure described for the preparation of compound 8. Yield 81%. Mp 238° C. TLC $R_f$ 0.25 (cyclohexane-EtOAc, 1:1). $^1$H NMR (400 MHz, DMSO-$d_6$) δ 9.53 (dt, J=1.6, 0.8 Hz, 1H), 8.63 (ddd, J=4.9, 1.9, 0.9 Hz, 1H), 8.51 (t, J=5.4 Hz, 1H), 8.29 (dd, J=9.5, 1.6 Hz, 1H), 8.18-8.10 (m, 1H), 8.07 (dd, J=1.3, 0.7 Hz, 1H), 7.80-7.60 (m, 5H), 7.51-7.46 (m, 2H), 7.46-7.37 (m, 2H), 7.35-7.27 (m, 2H), 7.27-7.16 (m, 2H), 4.88 (t, J=7.2 Hz, 1H), 4.50 (ddd, J=12.9, 7.5, 5.3 Hz, 1H), 4.35 (dt, J=12.9, 6.3 Hz, 1H). HRMS m/z calcd for $C_{28}H_{22}N_6+H^+$ [M+H$^+$]: 443.1979, found: 443.1985. HPLC: 100% ($t_R$=5.81 min).

qqqq. Synthesis of 2-(2-Aminopyrimidin-5-yl)-N-(2-Phenyl-2-(Pyridin-2-yl)Ethyl)Quinazolin-4-Amine (95)

i. Step 1

To a stirred solution of 2,4-dichloroquinazoline (1.50 g, 7.54 mmol) in THF (50 mL) was added dropwise N,N-diisopropylethylamine (1.97 mL, 11.30 mmol) and 2-phenyl-2-(pyridin-2-yl)ethanamine (1.79 mg, 9.04 mmol). After stirring for 4 hours at room temperature, the reaction mixture was diluted with water (50 mL) and extracted with EtOAc (3×50 mL). The combined organic layers were washed with water (3×50 mL), dried over $Na_2SO_4$, and filtered. The filtrate was concentrated under reduced pressure. The residue obtained was purified by column chromatography using hexanes:EtOAc (10-80%) as eluent to obtain 1.80 g (66%) of 2-chloro-N-(2-phenyl-2-(pyridin-2-yl)ethyl)quinazolin- 5-amine. TLC $R_f$ 0.30 (cyclohexane-EtOAc, 1:1), $^1$H NMR (400 MHz, DMSO-$d_6$) δ 8.77 (t, J=5.5 Hz, 1H), 8.58 (ddd, J=4.8, 1.9, 0.9 Hz, 1H), 8.15-8.07 (m, 1H), 7.72 (dtd, J=26.2, 8.0, 1.6 Hz, 1H), 7.63-7.55 (m, 1H), 7.46 (ddd, J=8.2, 7.0, 1.2 Hz, 1H), 7.42-7.13 (m, 6H), 4.72 (t, J=7.6 Hz, 1H), 4.32-4.16 (m, 2H), 3.35-3.22 (m, 2H). HRMS m/z calcd for $C_{11}H_{17}ClN_4$+H$^+$ [M+H$^+$]: 361.1215, found: 361.1224.

ii. Step 2

The above compound was reacted with 5-(4,4,5,5-tetramethyl-1,3,2-dioxaborolan-2-yl)pyrimidin-2-amine according to the procedure described for the preparation of compound 8 to obtain the desired compound. Yield 69%. Mp 194° C. TLC $R_f$ 0.25 (cyclohexane-EtOAc, 1:1). $^1$H NMR (400 MHz, DMSO-$d_6$) δ 9.20 (s, 2H), 8.59 (ddd, J=4.9, 1.9, 0.9 Hz, 1H), 8.42 (t, J=5.6 Hz, 1H), 8.07 (dt, J=8.4, 0.9 Hz, 1H), 7.75-7.62 (m, 3H), 7.47-7.41 (m, 2H), 7.39-7.33 (m, 2H), 7.31-7.25 (m, 2H), 7.25-7.15 (m, 2H), 7.10 (s, 2H), 4.86 (t, J=7.3 Hz, 1H), 4.40 (ddd, J=12.9, 7.6, 5.3 Hz, 1H), 4.29 (dt, J=13.0, 6.1 Hz, 1H). HRMS m/z calcd for $C_{25}H_{21}N_7$+H$^+$ [M+H$^+$]: 420.1931, found: 420.1931. HPLC: 100% ($t_R$=5.77 min).

rrrr. Synthesis of 2-((2-(Imidazo[1,2-A]Pyridin-6-yl) Quinazolin-4-yl)Amino)-1,1-Diphenylethanol (96)

i. Step 1

To a stirred solution of 2,4-dichloroquinazoline (0.350 g, 1.76 mmol) in THF (15 mL) was added dropwise N,N-diisopropylethylamine (0.46 mL, 2.64 mmol) and 2-amino-1,1-diphenylethanol (0.450 mg, 2.11 mmol). After stirring for 4 hours at room temperature, the reaction mixture was diluted with water (15 mL) and extracted with EtOAc (3×15 mL). The combined organic layers were washed with water (3×15 mL), dried over $Na_2SO_4$, and filtered. The filtrate was concentrated under reduced pressure. The organic layer was separated, dried over anhydrous $Na_2SO_4$ and concentrated under reduced pressure. The residue obtained was purified by column chromatography using hexanes:EtOAc (10-80%) as eluent to obtain 0.470 g (71%) of 2-((2-chloroquinazolin-5-yl)amino)-1,1-diphenylethanol. TLC $R_f$ 0.40 (cyclohexane-EtOAc, 2:1), $^1$H NMR (400 MHz, DMSO-$d_6$) δ 8.20-8.12 (m, 1H), 7.78 (ddd, J=8.3, 7.0, 1.3 Hz, 1H), 7.60 (ddt, J=8.3, 1.3, 0.6 Hz, 1H), 7.55-7.44 (m, 5H), 7.33-7.24 (m, 5H), 7.23-7.14 (m, 1H), 6.36 (s, 1H), 4.34 (d, J=4.5 Hz, 2H), 2.53-2.47 (m, 1H). HRMS m/z calcd for $C_{22}H_{18}ClN_3O$+H$^+$ [M+H$^+$]: 376.1211, found: 376.1214.

ii. Step 2

The above compound was reacted with imidazo[1,2-a]pyridin-6-ylboronic acid according to the procedure described for the preparation of compound 8. Yield 58%. Mp 234° C. TLC $R_f$ 0.25 (cyclohexane-EtOAc, 1:1), $^1$H NMR (400 MHz, DMSO-$d_6$) δ 9.56 (dd, J=1.7, 1.0 Hz, 1H), 8.27 (dd, J=9.5, 1.7 Hz, 1H), 8.20 (t, J=0.9 Hz, 1H), 8.17-8.11 (m, 1H), 7.82-7.72 (m, 3H), 7.67 (dt, J=9.5, 0.8 Hz, 1H), 7.64 (d, J=1.2 Hz, 1H), 7.61-7.54 (m, 4H), 7.47 (ddd, J=8.3, 6.6, 1.7 Hz, 1H), 7.32-7.23 (m, 4H), 7.21-7.12 (m, 2H), 6.50 (s, 1H), 4.57 (d, J=5.2 Hz, 2H). HRMS m/z calcd for $C_{29}H_{23}N_5O$+H$^+$ [M+H$^+$]: 458.1975, found: 458.1997. HPLC: 100% ($t_R$=6.20 min).

ssss. Synthesis of 2-((2-(2-Aminopyrimidin-5-yl) Quinazolin-4-yl)Amino)-1,1-Diphenylethanol (97)

This compound was prepared from 2-((2-chloroquinazolin-5-yl)amino)-1,1-diphenylethanol and 5-(4,4,5,5-tetramethyl-1,3,2-dioxaborolan-2-yl)pyrimidin-2-amine according to the procedure described for the preparation of compound 8. Yield 78%. Mp 222° C. TLC $R_f$ 0.25 (cyclohexane-EtOAc, 1:1). $^1$H NMR (400 MHz, DMSO-$d_6$) δ 9.19 (s, 2H), 8.14-8.06 (m, 1H), 7.86 (t, J=5.5 Hz, 1H), 7.78-7.64 (m, 2H), 7.59-7.51 (m, 4H), 7.42 (ddd, J=8.2, 6.7, 1.4 Hz, 1H), 7.32-7.22 (m, 4H), 7.21-7.14 (m, 2H), 7.11 (s, 2H), 6.66 (s, 1H), 4.49 (d, J=5.3 Hz, 2H). HRMS m/z calcd for $C_{26}H_{22}N_6O$+H$^+$ [M+H$^+$]: 435.1928, found: 435.1926. HPLC: 100% ($t_R$=6.08 min).

tttt. Synthesis of 2-(Imidazo[1,2-A]Pyrimidin-6-yl)-N-(2-Phenyl-2-(Pyridin-2-yl)Ethyl)Quinazolin-4-Amine (98)

To a solution of 2-(2-aminopyrimidin-5-yl)-N-(2-phenyl-2-(pyridin-2-yl)ethyl)quinazolin-4-amine (50 mg, 0.119 mmol) in ethanol (5.0 mL) was added 2-chloroacetaldehyde (0.10 mL). After refluxing the reaction mixture overnight, volatiles were removed under reduced pressure and the residue was purified to obtain the desired product. Yield 30%. Mp 211° C. TLC $R_f$ 0.25 (cyclohexane-EtOAc, 1:1), $^1$H NMR (400 MHz, DMSO-$d_6$) δ 9.85-9.79 (m, 1H), 9.54-9.48 (m, 1H), 8.65-8.53 (m, 2H), 8.19-8.12 (m, 1H), 8.08 (d, J=1.4 Hz, 1H), 7.83-7.73 (m, 3H), 7.69 (td, J=7.7, 1.9 Hz, 1H), 7.51-7.43 (m, 3H), 7.39 (dt, J=7.9, 1.0 Hz, 1H), 7.29 (td, J=7.2, 6.6, 1.2 Hz, 2H), 7.26-7.15 (m, 2H), 4.87 (t, J=7.3 Hz, 1H), 4.51 (dt, J=13.0, 6.3 Hz, 1H), 4.37 (dt, J=13.0, 6.4 Hz, 1H). HRMS m/z calcd for $C_{27}H_{21}N_7$+H$^+$ [M+H$^+$]: 444.1931, found: 444.1914. HPLC: 100% ($t_R$=6.23 min).

uuuu. Synthesis of 2-((2-(Imidazo[1,2-A]Pyrimidin-6-yl)Quinazolin-4-yl)Amino)-1,1-Diphenylethanol (99)

A solution of 2-((2-(2-aminopyrimidin-5-yl)quinazolin-4-yl)amino)-1,1-diphenylethanol (50 mg, 0.115 mmol) in ethanol (5.0 mL) was treated with 2-chloroacetaldehyde (0.10 mL) and the mixture was refluxed overnight. The reaction mixture was then concentrated under reduced pressure and the residue obtained was purified to obtain the title compound. Yield 60%. Mp 219° C. TLC $R_f$ 0.25 (cyclohexane-EtOAc, 1:1). $^1$H NMR (400 MHz, DMSO-$d_6$) δ 10.04 (d, J=2.3 Hz, 1H), 9.75 (d, J=2.3 Hz, 1H), 8.35 (d, J=2.0 Hz, 1H), 8.29-8.21 (m, 1H), 8.17-8.11 (m, 1H), 8.05 (s, 1H), 7.88-7.75 (m, 2H), 7.61-7.48 (m, 5H), 7.30-7.19 (m, 4H), 7.20-7.11 (m, 2H), 6.39 (s, 1H), 4.61 (d, J=5.4 Hz, 2H). HRMS m/z calcd for $C_{28}H_{22}N_6O$+H$^+$[M+H$^+$]: 459.1928, found: 459.1914. HPLC: 100% ($t_R$=6.67 min).

vvvv. Synthesis of N-(2-Cyclohexyl-2-Phenylethyl)-2-(Imidazo[1,2-A]Pyridin-6-yl)Quinazolin-4-Amine (100)

i. step 1

To a stirred solution of 2,4-dichloroquinazoline (1.60 g, 8.04 mmol) in THF (50 mL) was added dropwise N,N-diisopropylethylamine (2.12 mL, 12.06 mmol) and 2-cyclohexyl-2-phenylethanamine (1.96 mg, 9.65 mmol). After stirring for 4 hours at room temperature, the reaction mixture was diluted with water (50 mL) and extracted with EtOAc (3×50 mL). The combined organic layers were washed with water (3×50 mL), dried over $Na_2SO_4$, and filtered. The filtrate was concentrated under reduced pressure. The residue obtained was purified by column chromatography using hexanes:EtOAc (10-80%) as eluent to obtain 2.0 g (68%) of 2-chloro-N-(2-cyclohexyl-2-phenylethyl)quinazolin-4-amine. TLC $R_f$ 0.40 (cyclohexane-EtOAc, 2:1). $^1$H NMR (400 MHz, DMSO-d$_6$) δ 8.53 (t, J=5.6 Hz, 1H), 8.09 (ddd, J=8.3, 1.4, 0.6 Hz, 1H), 7.74 (tdd, J=7.6, 1.4, 0.6 Hz, 1H), 7.56 (ddd, J=8.3, 1.3, 0.6 Hz, 1H), 7.45 (ddd, J=8.3, 7.0, 1.3 Hz, 1H), 7.28-7.09 (m, 5H), 4.08-3.92 (m, 1H), 3.77 (ddd, J=13.2, 8.9, 6.3 Hz, 1H), 3.46-3.20 (m, 1H), 3.31 (s, 3H), 2.98 (q, J=7.3 Hz, 1H), 1.91 (d, J=12.6 Hz, 1H), 1.75-1.60 (m, 1H), 1.56 (q, J=14.5, 13.3 Hz, 2H), 1.30-1.06 (m, 1H), 1.09-0.93 (m, 1H), 0.84-0.70 (m, 1H). HRMS m/z calcd for C$_{22}$H$_{24}$ClN$_3$+H$^+$ [M+H$^+$]: 366.1732, found: 366.1732.

ii. Step 2

The above intermediate was reacted with imidazo[1,2-a]pyridin-6-ylboronic acid according to the procedure described for the preparation of compound 8 to obtain the title compound. Yield 58%. Mp 210° C. TLC R$_f$ 0.25 (cyclohexane-EtOAc, 1:1). $^1$H NMR (400 MHz, DMSO-d$_6$) δ 9.49 (dd, J=1.7, 1.0 Hz, 1H), 8.30-8.20 (m, 2H), 8.16-8.09 (m, 1H), 8.09-8.04 (m, 1H), 7.78-7.67 (m, 2H), 7.67-7.60 (m, 2H), 7.43 (ddd, J=8.2, 6.3, 1.9 Hz, 1H), 7.29-7.18 (m, 4H), 7.13 (ddd, J=8.6, 5.5, 2.4 Hz, 1H), 4.19 (dt, J=13.2, 5.5 Hz, 1H), 3.96 (ddd, J=13.7, 8.4, 6.1 Hz, 1H), 3.11-3.01 (m, 1H), 2.07-1.99 (m, 1H), 1.79-1.66 (m, 2H), 1.58 (d, J=10.7 Hz, 3H), 1.34-1.19 (m, 1H), 1.09 (td, J=14.1, 13.6, 10.1 Hz, 3H), 0.89-0.74 (m, 1H). HRMS m/z calcd for C$_{29}$H$_{29}$N$_5$+H$^+$ [M+H$^+$]: 448.2496, found: 448.2494. HPLC: 100% (t$_R$=6.99 min).

wwww. Synthesis of 2-(2-Aminopyrimidin-5-yl)-N-(2-Cyclohexyl-2-Phenylethyl)Quinazolin-4-Amine (101)

This compound was prepared from 2-chloro-N-(2-cyclohexyl-2-phenylethyl)quinazolin-4-amine and 5-(4,4,5,5-tetramethyl-1,3,2-dioxaborolan-2-yl)pyrimidin-2-amine according to the procedure described for the preparation of compound 8. Yield 60%. Mp 105° C. TLC R$_f$ 0.25 (cyclohexane-EtOAc, 1:1). $^1$H NMR (400 MHz, DMSO-d$_6$) δ 9.19 (s, 2H), 8.15 (t, J=5.6 Hz, 1H), 8.08-8.01 (m, 1H), 7.73-7.50 (m, 4H), 7.35 (ddd, J=8.2, 6.6, 1.6 Hz, 1H), 7.27-7.11 (m, 3H), 7.08 (s, 2H), 4.18 (dt, J=12.0, 5.6 Hz, 1H), 3.79 (ddd, J=13.6, 8.6, 5.9 Hz, 1H), 3.23-3.04 (m, 2H), 2.02-1.94 (m, 2H), 1.70 (t, J=13.8 Hz, 2H), 1.56 (d, J=13.5 Hz, 2H), 1.32-1.01 (m, 3H), 0.79 (q, J=11.3 Hz, 1H). HRMS m/z calcd for C$_{26}$H$_{28}$N$_6$+H$^+$ [M H$^+$]: 425.2448, found: 425.2454. HPLC: 100% (t$_R$=5.63 min).

xxxx. Synthesis of N-(2-Cyclohexyl-2-Phenylethyl)-2-(Imidazo[1,2-A]Pyrimidin-6-yl)Quinazolin-4-Amine (102)

A solution of 2-(2-aminopyrimidin-5-yl)-N-(2-cyclohexyl-2-phenylethyl)quinazolin-4-amine (60 mg, 0.141 mmol) and 2-chloroacetaldehyde (0.10 mL) in ethanol (5.0 mL) was refluxed overnight. The reaction mixture was concentrated under reduced pressure and the residue was purified to give the desired product. Yield 20%. Mp 202° C. TLC R$_f$ 0.25 (cyclohexane-EtOAc, 1:1). $^1$H NMR (400 MHz, DMSO-d$_6$) δ 9.79 (dd, J=2.3, 0.8 Hz, 1H), 9.49 (dd, J=2.4, 0.8 Hz, 1H), 8.32 (t, J=5.5 Hz, 1H), 8.17-8.11 (m, 1H), 8.08 (d, J=1.4 Hz, 1H), 7.80 (d, J=1.4 Hz, 1H), 7.79-7.70 (m, 2H), 7.45 (ddd, J=8.2, 6.4, 1.7 Hz, 1H), 7.29-7.17 (m, 4H), 7.16-7.07 (m, 1H), 4.24-4.13 (m, 1H), 3.98 (dt, J=13.7, 7.0 Hz, 1H), 3.06 (q, J=7.3 Hz, 1H), 2.03 (d, J=12.8 Hz, 1H), 1.74 (t, J=9.2 Hz, 2H), 1.57 (d, J=11.9 Hz, 2H), 1.31-1.21 (m, 2H), 1.09 (q, J=12.5 Hz, 3H), 0.88-0.77 (m, 1H). HRMS m/z calcd for C$_{28}$H$_{28}$N$_6$+H$^+$ [M H$^+$]: 449.2448, found: 449.2436. HPLC: 100% (t$_R$=7.49 min).

yyyy. Synthesis of 2-(Imidazo[1,2-A]Pyridin-6-yl)-N-(2-Phenyl-2-(Pyrimidin-2-yl)Ethyl)Quinazolin-4-Amine (103)

i. Step 1

To a stirred solution of 2,4-dichloroquinazoline (0.600 g, 3.01 mmol) in THF (20 mL) was added dropwise N,N-diisopropylethylamine (0.79 mL, 4.52 mmol) and 2-phenyl-2-(pyrimidin-2-yl)ethanamine (0.721 mg, 3.62 mmol). After stirring for 4 hours at room temperature, the reaction mixture was diluted with water (20 mL) and extracted with EtOAc (3×20 mL). The combined organic layers were washed with water (3×20 mL), dried over Na$_2$SO$_4$, and filtered. The filtrate was concentrated under reduced pressure. The organic layer was separated, dried over anhydrous Na$_2$SO$_4$ and concentrated under reduced pressure. The residue obtained was purified by column chromatography using hexanes:EtOAc (10-80%) as eluent to obtain 0.60 g (55%) of 2-chloro-N-(2-phenyl-2-(pyrimidin-2-yl)ethyl)quinazolin-4-amine. TLC R$_f$ 0.30 (cyclohexane-EtOAc, 1:1). $^1$H NMR (400 MHz, DMSO-d$_6$) δ 8.77 (dd, J=5.0, 0.8 Hz, 1H), 7.77-7.64 (m, 1H), 7.53 (ddd, J=8.4, 1.3, 0.6 Hz, 2H), 7.40 (dddd, J=8.2, 6.7, 1.5, 0.8 Hz, 2H), 7.37-7.26 (m, 4H), 7.30-7.18 (m, 2H), 7.08 (t, J=5.7 Hz, 1H), 4.79 (dd, J=8.2, 5.4 Hz, 2H), 4.53-4.32 (m, 1H). HRMS m/z calcd for C$_{20}$H$_{16}$ClN$_5$+H$^+$ [M+H$^+$]: 362.1167, found: 362.1170.

ii. Step 2

The above intermediate was coupled with imidazo[1,2-a]pyridin-6-ylboronic acid according to the procedure described for the preparation of compound 8 to obtain the title compound. Yield 57%. Mp 207° C. TLC R$_f$ 0.40 (CHCl$_3$-MeOH, 9:1), $^1$H NMR (400 MHz, DMSO-d$_6$) δ 9.53 (s, 1H), 8.81 (d, J=4.9 Hz, 1H), 8.54 (t, J=5.4 Hz, 1H), 8.29 (dd, J=9.5, 1.6 Hz, 1H), 8.18-8.10 (m, 1H), 8.07 (dd, J=1.3, 0.7 Hz, 1H), 7.80-7.60 (m, 4H), 7.51-7.46 (m, 2H), 7.46-7.37 (m, 2H), 7.36-7.27 (m, 2H), 7.24-7.20 (m, 2H), 5.01 (t, J=7.2 Hz, 1H), 4.51 (ddd, J=12.9, 7.5, 5.3 Hz, 1H), 4.35 (dt, J=12.9, 6.3 Hz, 1H). HRMS m/z calcd for C$_{27}$H$_{21}$N$_7$+H$^+$ [M+H$^+$]: 444.1931, found: 444.1925. HPLC: 100% (t$_R$=5.79 min).

zzzz. Synthesis of 2-(2-Aminopyrimidin-5-yl)-N-(2Phenyl-2-(Pyrimidin-2-yl)Ethyl)Quinazolin-4-Amine (104)

This compound was prepared from 2-chloro-N-(2-phenyl-2-(pyrimidin-2-yl)ethyl)quinazolin-4-amine and 5-(4,4,5,5-tetramethyl-1,3,2-dioxaborolan-2-yl)pyrimidin-2-amine according to the procedure described for the preparation of compound 8. Yield 56%. Mp 211° C.; TLC R$_f$ 0.35 (CHCl$_3$-MeOH, 9:1), $^1$H NMR (400 MHz, DMSO-d$_6$) δ 9.19 (d, J=0.7 Hz, 2H), 8.78 (dt, J=4.9, 0.5 Hz, 2H), 8.44 (t, J=5.6 Hz, 1H), 8.11-8.04 (m, 1H), 7.75-7.63 (m, 2H), 7.46-7.40 (m, 2H), 7.39-7.34 (m, 2H), 7.29 (dd, J=8.4, 6.8 Hz, 2H), 7.24-7.18 (m, 1H), 7.11 (s, 2H), 4.99 (t, J=7.3 Hz, 1H), 4.41 (ddd, J=13.0, 7.9, 5.2 Hz, 1H), 4.31 (dt, J=12.9, 6.2 Hz, 1H). HRMS m/z calcd for C$_{24}$H$_{20}$N$_8$+H$^+$ [M+H$^+$]: 421.1884, found: 421.1884. HPLC: 100% (t$_R$=5.74 min).

aaaaa. Synthesis of 2-([1,2,4]Triazolo[1,5-A]Pyridin-6-yl)-N-(2,2-Diphenylethyl)Quinazolin-4-Amine (105)

This compound was prepared from 2-chloro-N-(2,2-diphenylethyl)quinazolin-4-amine and 6-(4,4,5,5-tetramethyl-1,3,2-dioxaborolan-2-yl)-[1,2,4]triazolo[1,5-a]pyridine according to the procedure described for the preparation of compound 8. Yield 73%. Mp 197° C. TLC $R_f$ 0.35 (CHCl$_3$-MeOH, 9:1). $^1$H NMR (400 MHz, DMSO-d$_6$) δ 9.74 (d, J=1.1 Hz, 1H), 8.70 (dd, J=9.3, 1.6 Hz, 1H), 8.64-8.53 (m, 2H), 8.21-8.14 (m, 1H), 7.97 (d, J=9.3 Hz, 1H), 7.78 (d, J=3.9 Hz, 2H), 7.53-7.41 (m, 5H), 7.31 (t, J=7.6 Hz, 4H), 7.23-7.14 (m, 2H), 4.75 (t, J=7.6 Hz, 1H), 4.35 (dd, J=7.5, 5.2 Hz, 2H). HRMS m/z calcd for C$_{28}$H$_{22}$N$_6$+H$^+$ [M+H$^+$]: 443.1979, found: 443.1972. HPLC: 100% (t$_R$=5.97 min).

bbbbb. Synthesis of 2-(Imidazo[1,2-A]Pyridin-6-yl)-N-(2-Phenyl-2-(Pyridin-4-yl)Ethyl)Quinazolin-4-Amine (106)

i. Step 1

To a stirred solution of 2,4-dichloroquinazoline (0.500 g, 2.51 mmol) in THF (20 mL) was added dropwise N,N-diisopropylethylamine (0.88 mL, 5.02 mmol) and 2-phenyl-2-(pyridin-4-yl)ethanamine (0.747 mg, 3.77 mmol). After stirring for 4 hours at room temperature, the reaction mixture was diluted with water (20 mL) and extracted with EtOAc (3×20 mL). The combined organic layers were washed with water (3×20 mL), dried over Na$_2$SO$_4$, and filtered. The filtrate was concentrated under reduced pressure. The residue obtained was purified by column chromatography using hexanes:EtOAc (10-80%) as eluent to obtain 0.50 g (55%) of 2-chloro-N-(2-phenyl-2-(pyridin-4-yl)ethyl)quinazolin-4-amine. TLC $R_f$ 0.25 (cyclohexane-EtOAc, 1:1). $^1$H NMR (400 MHz, DMSO-d$_6$) δ 8.83 (t, J=5.5 Hz, 1H), 8.50-8.43 (m, 2H), 8.16-8.06 (m, 1H), 7.77 (ddd, J=8.3, 6.9, 1.3 Hz, 1H), 7.69-7.42 (m, 2H), 7.43-7.26 (m, 6H), 7.31-7.18 (m, 1H), 4.59 (q, J=7.0, 6.4 Hz, 1H), 4.27-4.08 (m, 2H). HRMS m/z calcd for C$_{21}$H$_{17}$ClN$_4$+H$^+$ [M+H$^+$]: 361.1214, found: 361.1211.

ii. Step 2

The above compound was reacted with imidazo[1,2-a]pyridin-6-ylboronic acid according to the procedure described for the preparation of compound 8. Yield 57%. Mp 234° C. TLC $R_f$ 0.35 (CHCl$_3$-MeOH, 9:1). $^1$H NMR (400 MHz, DMSO-d$_6$) δ 9.52 (dt, J=1.6, 0.7 Hz, 1H), 8.56 (d, J=4.7 Hz, 1H), 8.50-8.44 (m, 2H), 8.28 (dd, J=9.5, 1.7 Hz, 1H), 8.19-8.12 (m, 1H), 8.08 (dt, J=1.3, 0.6 Hz, 1H), 7.76 (dd, J=6.3, 1.3 Hz, 2H), 7.70-7.60 (m, 2H), 7.51-7.41 (m, 5H), 7.35 (dd, J=8.4, 6.9 Hz, 2H), 7.29-7.19 (m, 1H), 4.78-4.69 (m, 1H), 4.47-4.31 (m, 2H). HRMS m/z calcd for C$_{28}$H$_{22}$N$_6$+H$^+$ [M+H$^+$]: 443.1979, found: 443.1973. HPLC: 100% (t$_R$=5.42 min).

ccccc. Synthesis of 2-(2-Aminopyrimidin-5-yl)-N-(2-Phenyl-2-(Pyridin-4-yl)Ethyl)Quinazolin-4-Amine (107)

This compound was prepared from 2-chloro-N-(2-phenyl-2-(pyridin-4-yl)ethyl)quinazolin-4-amine and 5-(4,4,5,5-tetramethyl-1,3,2-dioxaborolan-2-yl)pyrimidin-2-amine according to the procedure described for the preparation of compound 8. Yield 56%. Mp 219° C. TLC $R_f$ 0.30 (CHCl$_3$-MeOH, 9:1). $^1$H NMR (400 MHz, DMSO-d$_6$) δ 9.20 (s, 2H), 8.50-8.42 (m, 3H), 8.12-8.05 (m, 1H), 7.76-7.64 (m, 2H), 7.45-7.36 (m, 5H), 7.33 (dd, J=8.4, 6.8 Hz, 2H), 7.26-7.20 (m, 1H), 7.09 (s, 2H), 4.74 (t, J=7.5 Hz, 1H), 4.37-4.20 (m, 2H). HRMS m/z calcd for C$_{25}$H$_{21}$N$_7$+H$^+$ [M+H$^+$]: 420.1931, found: 420.1928. HPLC: 97% (t$_R$=5.19 min).

ddddd. Synthesis of N-(2,2-Diphenylethyl)-2-(Tetrazolo[1,5-A]Pyridin-6-yl)Quinazolin-4-Amine (108)

i. Step 1

To a stirred solution of N-benzhydryl-2-chloroquinazolin-4-amine (0.400 g, 1.12 mmol) in dioxane-water (20 mL: 2.0 mL) was added (6-fluoropyridin-3-yl)boronic acid (0.235 g, 1.50 mmol) and K$_2$CO$_3$ (0.307 g, 2.22 mmol). The reaction mixture was purged with argon and stirred for 15 minutes at room temperature. Tetrakis(triphenylphosphine)palladium (0.128 g, 0.112 mmol) was added and the reaction mixture was heated under reflux for 15 hours. The reaction mixture was then cooled to room temperature, diluted with water and extracted with EtOAc (2×20 mL). The organic layer was separated, dried over anhydrous Na$_2$SO$_4$ and concentrated under reduced pressure. The residue obtained was purified by column chromatography using hexanes:EtOAc (0-70%) as eluent to obtain 0.350 g (75%) of N-(2,2-diphenylethyl)-2-(6-fluoropyridin-3-yl)quinazolin-4-amine. Mp 141° C., TLC $R_f$ 0.40 (cyclohexane-EtOAc, 1:1). $^1$H NMR (400 MHz, DMSO-d$_6$) δ 9.26 (dt, J=2.4, 0.7 Hz, 1H), 8.92 (td, J=8.4, 2.5 Hz, 1H), 8.55 (t, J=5.5 Hz, 1H), 8.19-8.12 (m, 1H), 7.82-7.72 (m, 2H), 7.47 (ddd, J=8.3, 5.2, 3.0 Hz, 1H), 7.46-7.35 (m, 4H), 7.38-7.25 (m, 5H), 7.23-7.13 (m, 2H), 4.72 (t, J=7.7 Hz, 1H), 4.32 (dd, J=7.6, 5.4 Hz, 2H). HRMS m/z calcd for C$_{27}$H$_{21}$FN$_4$+H$^+$ [M+H$^+$]: 421.1823, found: 421.1823.

ii. Step 2

To a solution of the above intermediate (100 mg, 0.24 mmol) in DMSO (2.0 mL) was added sodium azide (0.71 mmol). The mixture was heated at 140° C. overnight. The reaction mixture was cooled and treated with water (1.0 mL). The precipitate obtained was collected by filtration, washed with water (2 mL) and Et$_2$O (5 mL) and dried to obtain the desired product. Yield 62%. Mp 227° C. TLC $R_f$ 0.30 (CHCl$_3$-MeOH, 9:1). $^1$H NMR (400 MHz, DMSO-d$_6$) δ 10.00 (d, J=1.1 Hz, 1H), 8.84 (dd, J=9.3, 1.6 Hz, 1H), 8.64-8.53 (m, 1H), 8.21-8.14 (m, 1H), 7.97 (d, J=9.3 Hz, 1H), 7.81 (d, J=3.9 Hz, 2H), 7.53-7.41 (m, 5H), 7.31 (t, J=7.6 Hz, 4H), 7.23-7.14 (m, 2H), 4.74 (t, J=7.6 Hz, 1H), 4.38 (dd, J=7.5, 5.2 Hz, 2H). HRMS m/z calcd for C$_{27}$H$_{21}$N$_7$+H$^+$ [M+H$^+$]: 444.1931, found: 444.1927. HPLC: 100% (t$_R$=6.63 min).

eeeee. Synthesis of 2-(Imidazo[1,2-A]Pyrimidin-6-yl)-N-(2-Phenyl-2-(Pyrimidin-2-yl)Ethyl)Quinazolin-4-Amine (109)

2-(2-Aminopyrimidin-5-yl)-N-(2-phenyl-2-(pyrimidin-2-yl)ethyl)quinazolin-4-amine (50 mg, 0.119 mmol) was dissolved in isopropanol (3.0 mL) and 2-chloroacetaldehyde (0.10 mL) was added. The reaction mixture was refluxed overnight and then concentrated under reduced pressure. The residue obtained was further purified to yield the desired product. Yield 38%. Mp 180° C. TLC $R_f$ 0.30 (CHCl$_3$-MeOH, 9:1). $^1$H NMR (400 MHz, DMSO-d$_6$) δ 9.81 (d, J=2.4 Hz, 1H), 9.50 (d, J=2.3 Hz, 1H), 8.80 (d, J=4.9 Hz, 2H), 8.61 (t, J=5.5 Hz, 1H), 8.16 (d, J=8.3 Hz, 1H), 8.09 (d, J=1.4 Hz, 1H), 7.83-7.72 (m, 3H), 7.51-7.42 (m, 3H), 7.41-7.26 (m, 3H), 7.25-7.16 (m, 1H), 4.99 (t, J=7.3 Hz, 1H), 4.57-4.46 (m, 1H), 4.38 (dt, J=13.0, 6.4 Hz, 1H). HRMS m/z calcd for C$_{26}$H$_{20}$N$_8$+H$^+$ [M+H$^+$]: 445.1884, found: 445.1884. HPLC: 100% (t$_R$=6.22 min).

fffff. Synthesis of 2-(Imidazo[1,2-A]Pyrimidin-6-yl)-N-(2-Phenyl-2-(Pyridin-4-yl)Ethyl)Quinazolin-4-Amine (110)

This compound was prepared by refluxing a solution of 2-(2-aminopyrimidin-5-yl)-N-(2-phenyl-2-(pyridin-4-yl)ethyl)quinazolin-4-amine (50 mg, 0.119 mmol) and 2-chloroacetaldehyde (0.10 mL) in isopropanol (3.0 mL) overnight. The reaction mixture was concentrated under reduced pressure and purified to give the product. Yield 57%. Mp 224° C. TLC $R_f$ 0.30 (CHCl$_3$-MeOH, 9:1). $^1$H NMR (400 MHz, DMSO-d$_6$) δ 9.83 (d, J=2.4 Hz, 1H), 9.51 (d, J=2.4 Hz, 1H), 8.61 (s, 1H), 8.49-8.42 (m, 2H), 8.16 (d, J=8.2 Hz, 1H), 8.08 (d, J=1.5 Hz, 1H), 7.83-7.73 (m, 3H), 7.53-7.43 (m, 5H), 7.33 (t, J=7.6 Hz, 2H), 7.28-7.19 (m, 1H), 4.73 (t, J=7.6 Hz, 1H), 4.39 (m, 2H). HRMS m/z calcd for $C_{27}H_{21}N_7$+H$^+$ [M+H$^+$]: 444.1931, found: 444.1924. HPLC: 100% (t$_R$=5.66 min).

ggggg. Synthesis of 2-(3-((Dimethylamino)methyl)-1H-Indol-5-yl)-N-(2,2-Diphenylethyl)Quinazolin-4-Amine (111)

To a solution of N-(2,2-diphenylethyl)-2-(1H-indol-5-yl)quinazolin-4-amine (500 mg, 0.11 mmol) in dry CHCl$_3$ (5.0 mL) was added N,N-dimethylmethyleneiminium iodide (27 mg, 0.15 mmol). The reaction mixture was refluxed for 2 hours, allowed to cool to room temperature and basified with 25% aqueous NH$_4$OH. The mixture was concentrated under reduced pressure and the residue was purified to give the product. Yield 87%. Mp 182° C. TLC $R_f$ 0.45 (CHCl$_3$-MeOH, 9:1). $^1$H NMR (400 MHz, DMSO-d$_6$+NaOD) δ 8.63 (dt, J=1.8, 0.8 Hz, 1H), 7.96-7.87 (m, 2H), 7.41 (ddd, J=10.0, 8.0, 2.9 Hz, 8H), 7.31-7.06 (m, 8H), 6.99 (dq, J=8.0, 3.9 Hz, 1H), 4.80 (td, J=9.0, 8.0, 3.0 Hz, 1H), 4.26 (d, J=7.7 Hz, 2H), 3.58 (s, 2H), 2.12 (s, 6H). HRMS m/z calcd for $C_{33}H_{31}N_5$+H$^+$ [M+H$^+$]: 498.2652, found: 498.2646. HPLC: 100% (t$_R$=5.97 min).

hhhhh. Synthesis of 2-(3-((Dimethylamino)methyl)Imidazo[1,2-A]pyridin-6-yl)-N-(2,2-Diphenylethyl)Quinazolin-4-Amine (112)

To a solution of N-(2,2-diphenylethyl)-2-(imidazo[1,2-a]pyridin-6-yl)quinazolin-4-amine (500 mg, 0.11 mmol) in dry CHCl$_3$ (5.0 mL) was added N,N-dimethylmethyleneiminium iodide (27 mg, 0.15 mmol). The reaction mixture was refluxed for 2 hours, allowed to cool to room temperature and basified with 25% aqueous NH$_4$OH. The mixture was concentrated under reduced pressure and the residue was purified to give the desired product. Yield 61%. Mp 240° C. TLC $R_f$ 0.45 (CHCl$_3$-MeOH, 9:1). $^1$H NMR (400 MHz, DMSO-d$_6$) δ 9.46 (dd, J=1.7, 1.0 Hz, 1H), 8.43 (t, J=5.5 Hz, 1H), 8.33 (dd, J=9.5, 1.7 Hz, 1H), 8.14 (dt, J=8.3, 1.0 Hz, 1H), 7.80-7.70 (m, 2H), 7.65 (dd, J=9.5, 0.9 Hz, 1H), 7.54 (s, 1H), 7.50-7.36 (m, 5H), 7.32-7.23 (m, 4H), 7.22-7.12 (m, 2H), 4.70 (t, J=7.8 Hz, 1H), 4.39 (dd, J=7.9, 5.4 Hz, 2H), 3.73 (s, 2H), 2.04 (s, 6H). FIRMS m/z calcd for $C_{32}H_{30}N_6$+H$^+$ [M+H$^+$]: 499.2605, found: 499.2598. HPLC: 100% (t$_R$=6.19 min).

iiiii. Synthesis of Ethyl 6-(4-((2,2-Diphenylethyl)Amino)Quinazolin-2-yl)Imidazo[1,2-A]Pyridine-2-Carboxylate (113)

2-(6-Aminopyridin-3-yl)-N-(2,2-diphenylethyl)quinazolin-4-amine (500 mg, 1.20 mmol) was dissolved in ethanol (10 mL) and ethyl bromopyruvate (0.15 mL, 1.20 mmol) was added and the reaction mixture was refluxed for 12 hours. The reaction mixture was concentrated under reduced pressure and residue obtained was purified to give the product. Yield 63%. Mp 204° C. TLC $R_f$ 0.45 (CHCl$_3$-MeOH, 9:1). $^1$H NMR (400 MHz, DMSO-d$_6$) δ 9.58 (dd, J=1.7, 1.0 Hz, 1H), 8.74 (d, J=0.7 Hz, 1H), 8.49 (t, J=5.4 Hz, 1H), 8.39 (dd, J=9.6, 1.7 Hz, 1H), 8.16 (dt, J=8.3, 1.0 Hz, 1H), 7.81-7.68 (m, 3H), 7.51-7.41 (m, 5H), 7.30 (dd, J=8.3, 7.0 Hz, 4H), 7.22-7.13 (m, 2H), 4.70 (t, J=7.6 Hz, 1H), 4.36 (p, J=7.1 Hz, 4H), 1.36 (t, J=7.1 Hz, 3H). HRMS m/z calcd for $C_{32}H_{27}N_5O_2$+H$^+$ [M+H$^+$]: 514.2238, found: 514.2244. HPLC: 100% (t$_R$=7.49 min).

jjjjj. Synthesis of 2-([1,2,4]Triazolo[4,3-A]Pyridin-6-yl)-N-(2,2-Diphenylethyl)Quinazolin-4-amine (114)

A mixture of N-(2,2-diphenylethyl)-2-(6-fluoropyridin-3-yl)quinazolin-4-amine (100 mg, 0.238 mmol) and hydrazine hydrate (1.0 mL) was stirred at room temperature overnight. The reaction mixture was treated with 1N aqueous NaOH (1.0 mL) and stirred for 10 min. Water (1.0 mL) was added to the reaction mixture and the white solid that precipitated out was collected by filtration and washed with water (2 mL). The intermediate thus obtained was refluxed with formic acid (1.0 mL) for 12 hours. The reaction mixture was concentrated under reduced pressure and the crude product was purified to obtain the give the desired product. Yield 48%. Mp 224° C. TLC $R_f$ 0.35 (CHCl$_3$-MeOH, 9:1). $^1$H NMR (400 MHz, DMSO-d$_6$) δ 9.54 (t, J=1.3 Hz, 1H), 9.40 (d, J=0.8 Hz, 1H), 8.51 (t, J=5.4 Hz, 1H), 8.40 (dd, J=9.7, 1.6 Hz, 1H), 8.20-8.13 (m, 1H), 7.87 (dt, J=9.7, 1.0 Hz, 1H), 7.82-7.70 (m, 2H), 7.52-7.35 (m, 5H), 7.30 (dd, J=8.3, 6.9 Hz, 4H), 7.23-7.13 (m, 2H), 4.70 (t, J=7.7 Hz, 1H), 4.37 (dd, J=7.9, 5.3 Hz, 2H). HRMS m/z calcd for $C_{28}H_{22}N_6$+H$^+$ [M+H$^+$]: 443.1979, found: 443.1967. HPLC: 99% (t$_R$=7.11 min).

kkkkk. Synthesis of N-(2-(1H-Imidazol-1-yl)-2-Phenylethyl)-2-(Imidazo[1,2-A]Pyridin-6-yl)Quinazolin-4-Amine (115)

i. Step 1

To a stirred solution of 2,4-dichloroquinazoline (0.500 g, 2.51 mmol) in THF (20 mL) was added dropwise N,N-diisopropylethylamine (0.88 mL, 5.02 mmol) and 2-phenyl-2-(pyridin-4-yl)ethanamine (0.706 mg, 3.77 mmol). After stirring for 4 hours at room temperature, the reaction mixture was diluted with water (20 mL) and extracted with EtOAc (3×20 mL). The combined organic layers were washed with water (3×20 mL), dried over anhydrous Na$_2$SO$_4$, and filtered. The filtrate was concentrated under reduced pressure. The residue obtained was purified by column chromatography using hexanes:EtOAc (10-80%) as eluent to obtain 0.700 g (80%) of N-(2-(1H-imidazol-1-yl)-2-phenylethyl)-2-chloroquinazolin-4-amine. TLC $R_f$ 0.25 (cyclohexane-EtOAc, 1:1), $^1$H NMR (400 MHz, DMSO-d$_6$) δ 8.97 (s, 1H), 8.16 (dd, J=8.3, 1.4 Hz, 1H), 7.88-7.76 (m, 2H), 7.64 (dd, J=8.5, 1.2 Hz, 2H), 7.53 (ddd, J=8.3, 7.0, 1.3 Hz, 2H), 7.45-7.29 (m, 5H), 5.81 (dd, J=9.2, 5.2 Hz, 1H), 4.31 (t, J=11.7 Hz, 2H). HRMS m/z calcd for $C_{19}H_{16}ClN_5$+H$^+$ [M+H$^+$]: 350.1167, found: 350.1158.

ii. Step 2

The above compound was reacted with imidazo[1,2-a]pyridin-6-ylboronic acid according to the procedure described for the preparation of compound 8. Yield 81%. Mp 193° C. TLC $R_f$ 0.35 (CHCl$_3$-MeOH, 9:1), $^1$H NMR (400 MHz, DMSO-d$_6$) δ 9.54 (q, J=1.1 Hz, 1H), 8.67 (s, 1H), 8.29 (dt, J=9.5, 1.3 Hz, 1H), 8.18 (d, J=8.2 Hz, 1H), 8.07 (d, J=1.1 Hz, 1H), 7.92 (d, J=1.2 Hz, 1H), 7.79 (dt, J=6.0, 1.2 Hz, 2H), 7.70-7.62 (m, 2H), 7.55-7.31 (m, 7H), 6.90 (d, J=1.2 Hz, 1H), 5.96 (dd, J=8.9, 5.4 Hz, 1H), 4.57-4.39 (m, 2H). HRMS m/z calcd for $C_{26}H_{21}N_7+H^+$ [M+H$^+$]: 432.1931, found: 432.1927. HPLC: 100% ($t_R$=5.06 min).

lllll. Synthesis of N-(2,2-Diphenylethyl)-2-(3-(Methoxymethyl)-1H-Indol-5-yl)Quinazolin-4-Amine (116)

To a solution of N-(2,2-diphenylethyl)-2-(1H-indol-5-yl)quinazolin-4-amine (100 mg, 0.23 mmol) in methanol (2.0 mL) was added sodium methoxide in methanol (0.23 mL of 1M solution, 0.23 mmol) and paraformaldehyde (10 mg, 0.35 mmol). The reaction mixture was stirred for 4 hours at 40° C. TLC indicated complete disappearance of the starting material. The reaction mixture was concentrated under reduced pressure and purified to give the product. Yield 40%. Mp 129° C. TLC $R_f$ 0.45 (CHCl$_3$-MeOH, 9:1). $^1$H NMR (400 MHz, DMSO-d$_6$) δ 11.17 (d, J=2.5 Hz, 1H), 8.85 (dd, J=1.5, 0.8 Hz, 1H), 8.39 (dd, J=8.6, 1.6 Hz, 1H), 8.34-8.27 (m, 1H), 8.08 (dd, J=8.0, 1.2 Hz, 1H), 7.77-7.65 (m, 2H), 7.48-7.39 (m, 6H), 7.36 (ddd, J=8.2, 6.3, 1.8 Hz, 1H), 7.31 (dd, J=8.3, 6.9 Hz, 4H), 7.24-7.15 (m, 2H), 4.86 (t, J=7.8 Hz, 1H), 4.63 (s, 2H), 4.33 (dd, J=7.9, 5.4 Hz, 2H), 3.23 (d, J=0.5 Hz, 3H). HRMS m/z calcd for $C_{32}H_{28}N_4O+H^+$ [M+H$^+$]: 485.2336, found: 485.2333. HPLC: 100% ($t_R$=6.84 min).

mmmmm. Synthesis of 2-(Imidazo[1,2-A]Pyridin-6-yl)-N-(2-Phenyl-2-(1H-Pyrrol-2-yl)Ethyl)Quinazolin-4-Amine (117)

To the stirred solution of 2-chloro-N-(2-phenyl-2-(1H-pyrrol-2-yl)ethyl)quinazolin-4-amine (0.094 g, 0.27 mmol) in dioxane:water (2 mL:2 mL) was added (imidazo[1,2-a]pyridin-6-yl)boronic acid (0.089 g, 0.55 mmol) and K$_2$CO$_3$ (76.02 mg, 0.55 mmol). The reaction mixture was purged with argon and stirred for 15 minutes at room temperature. Tetrakis(triphenylphosphine)palladium (0.335 mg, 0.029 mmol) was added to the reaction mixture and the mixture was refluxed under microwave heating at 120° C. for 3-5 hours. The reaction mixture was then cooled to room temperature, diluted with water and extracted with EtOAc (2×10 mL). The organic layer was separated, dried over anhydrous Na$_2$SO$_4$ and concentrated under reduced pressure. The residue obtained was purified by column chromatography using hexanes:EtOAc (0-100%) as the eluent to obtain the desired product. Yield 65%. Mp 222-224° C. TLC $R_f$ 0.30 (EtOAc). $^1$H NMR (400 MHz, DMSO-d$_6$) δ 9.36 (s, 1H), 8.39 (dd, J=1.5 and 9.5 Hz, 1H), 8.05 (br s, 1H), 7.89 (d, J=7.5 Hz, 1H), 7.67-7.75 (m, 3H), 7.29-7.45 (m, 8H), 6.73 (m, 1H), 6.25-6.30 (m, 2H), 5.82 (t, J=5.9 Hz, 1H), 4.54 (t, J=7.4 Hz, 1H), 4.30-4.44 (m, 2H). HRMS m/z calcd for $C_{27}H_{22}N_6$ [M+H$^+$]: 431.1978, found: 431.1981. HPLC: 100% ($t_R$=6.08 min).

nnnnn. Synthesis of N-(2,2-Diphenylethyl)-2-(7-Methylimidazo[1,2-A]Pyridin-6-yl)Quinazolin-4-Amine (118)

This compound was prepared from 2-chloro-N-(2,2-diphenylethyl)quinazolin-4-amine and (7-methylimidazo[1,2-a]pyridin-6-yl)boronic acid according to the procedure described for the preparation of compound 117. Yield 40%. Mp 192-194° C. TLC $R_f$ 0.35 (EtOAc). $^1$H NMR (400 MHz, DMSO-d$_6$) δ 9.07 (s, 1H), 8.43 (d, J=5.3 Hz, 1H), 8.15 (d, J=7.8 Hz, 1H), 7.97 (br s, 1H), 7.71-7.78 (m, 2H), 7.56 (d, J=1.2 Hz, 1H), 7.46-7.49 (m, 1H), 7.45 (br s, 1H), 7.36 (d, J=7.4 Hz, 4H), 7.28 (t, J=7.5 Hz, 4H), 7.18 (t, J=7 Hz, 2H), 4.58 (t, J=7.6 Hz, 1H), 4.52 (t, J=6.4 Hz, 2H), 2.67 (s, 3H). HRMS m/z calcd for $C_{30}H_{25}N_5$ [M+H$^+$]: 456.2182, found: 456.2182. HPLC: 100% ($t_R$=6.2 min).

ooooo. 2-(Imidazo[1,2-A]Pyridin-6-yl)-N-(2-Phenyl-2-(Piperidin-1-yl)Ethyl)Quinazolin-4-Amine (119)

This compound was prepared from 2-chloro-N-(2-phenyl-2-(piperidin-1-yl)ethyl)quinazolin-4-amine and (imidazo[1,2-a]pyridin-6-yl)boronic acid according to the procedure described for the preparation of compound 117. Yield 66%. Mp 193-195° C. TLC $R_f$ 0.25 (EtOAc). $^1$H NMR (400 MHz, DMSO-d$_6$) δ 9.51 (dd, J=1.6, 0.9 Hz, 1H), 8.31-8.07 (m, 4H), 7.82-7.70 (m, 2H), 7.64 (m, 2H), 7.50-7.46 (m, 1H), 7.41-7.18 (m, 5H), 4.28 (m, 1H), 2.54-2.32 (m, 4H), 1.44 (m, 4H), 1.29-1.26 (m, 2H). HRMS m/z calcd for $C_{28}H_{28}N_6+H^+$ [M H$^+$]: 449.2448, found: 449.2446. HPLC: 100% ($t_R$=5.11 min).

ppppp. Synthesis of 2-(Imidazo[1,2-A]Pyrimidin-6-yl)-N-(2-Phenyl-2-(Piperidin-1-yl)Ethyl)Quinazolin-4-Amine (120)

i. Step 1

2-Chloro-N-(2-phenyl-2-(piperidin-1-yl)ethyl)quinazolin-4-amine was reacted with 5-(4,4,5,5-tetramethyl-1,3,2-dioxaborolan-2-yl)pyrimidin-2-amine according to the procedure described for the preparation of compound 117 to afford 2-(2-aminopyrimidin-5-yl)-N-(2-phenyl-2-(piperidin-1-yl)ethyl)quinazolin-4-amine. Yield 61%. $^1$H NMR (400 MHz, DMSO-d$_6$) δ 9.18 (s, 1H), 8.13 (t, J=5.1 Hz, 1H), 8.09 (m, 1H), 7.71-7.27 (m, 8H), 7.07 (br s, 2H), 4.24 (m, 1H), 4.10 (m, 1H), 3.86-3.92 (m, 1H), 2.49-2.32 (m, 4H), 1.44 (m, 4H), 1.27 (m, 2H). HRMS m/z calcd for $C_{25}H_{27}N_7+H^+$ [M+H$^+$]: 426.2400, found: 426.2388. HPLC: 100% ($t_R$=4.95 min).

ii. Step 2

A solution of the above intermediate (60 mg, 0.141 mmol) and 2-chloroacetaldehyde (0.36 mL of 50% aqueous solution, 2.82 mmol) in ethanol (5.0 mL) was refluxed for 16 hours. After removal of the solvent the crude product was pre-adsorbed on silica gel and chromatographed to obtain the title compound. Yield 54%. Mp 158-160° C. TLC $R_f$ 0.2 (CH$_2$Cl$_2$-MeOH, 9.5:0.5). $^1$H NMR (400 MHz, DMSO-d$_6$) δ 9.82 (s, 1H), 9.50 (d, J=2.3 Hz, 1H), 8.30 (s, 1H), 8.17 (d, J=8.1 Hz, 1H), 8.08 (d, J=1.4 Hz, 1H), 7.84-7.73 (m, 3H), 7.51 (ddd, J=8.2, 6.4, 1.7 Hz, 1H), 7.32 (s, 5H), 4.31 (s, 1H), 4.03 (m, 2H), 3.54-2.32 (m, 4H), 1.45 (br s, 4H), 1.28 (br s, 2H). HRMS m/z calcd for $C_{27}H_{27}N_7+H^+$ [M+H$^+$]: 450.2400, found: 450.2397. HPLC: 100% ($t_R$=5.37 min).

qqqqq. Synthesis of 2-(Imidazo[1,2-A]Pyridin-6-yl)-N-(2-Phenyl-2-(Pyrrolidin-1-yl)Ethyl)Quinazolin-4-Amine (121)

This compound was prepared from 2-chloro-N-(2-phenyl-2-(pyrrolidin-1-yl)ethyl)quinazolin-4-amine and (imidazo[1,2-a]pyridin-6-yl)boronic acid according to the procedure described for the preparation of compound 117. Yield 65%. Mp 205-207° C. TLC $R_f$ 0.4 (CH$_2$Cl$_2$-MeOH, 9.6:0.4). $^1$H NMR (400 MHz, DMSO-d$_6$) δ 9.46 (m, 1H), 8.24 (dd, J=9.6, 1.7 Hz, 1H), 8.17-8.09 (m, 3H), 7.80-7.60 (m, 4H), 7.49-7.35 (m, 3H), 7.26-7.14 (m, 3H), 4.21 (s, 1H), 3.99 (m, 1H), 3.72 (s, 1H), 2.66 (m, 2H), 2.48-2.42 (m, 2H), 1.70 (br s, 4H). HRMS m/z calcd for $C_{27}H_{26}N_6$+H$^+$ [M+H$^+$]: 435.2291, found: 435.2280. HPLC: 100% ($t_R$=5.07 min).

rrrrr. Synthesis of 2-(Imidazo[1,2-A]Pyridin-6-yl)-N-(2-Morpholino-2-Phenylethyl)Quinazolin-4-Amine (122)

This compound was prepared from 2-chloro-N-(2-morpholino-2-phenylethylethyl)quinazolin-4-amine and (imidazo[1,2-a]pyridin-6-yl)boronic acid according to the procedure described for the preparation of compound 117. Yield 60%. Mp>250° C. TLC $R_f$ 0.4 (CH$_2$Cl$_2$-MeOH, 9.6:0.4). $^1$H NMR (400 MHz, DMSO-d$_6$) δ 9.48 (m, 1H), 8.29-8.13 (m, 3H), 8.09 (m, 1H), 7.82-7.70 (m, 2H), 7.68-7.60 (m, 2H), 7.59-7.43 (m, 1H), 7.41-7.16 (m, 5H), 4.30 (m, 1H), 4.08-3.90 (m, 2H), 3.55 (t, J=4.5 Hz, 4H), 3.38-3.23 (m, 4H), 2.47 (m, 4H). HRMS m/z calcd for $C_{27}H_{26}N_6$O+H$^+$ [M+H$^+$]: 451.2240, found: 451.2227. HPLC: 100% ($t_R$=5.1 min).

sssss. Synthesis of N-(2,2-Diphenylethyl)-2-(1H-Pyrrolo[2,3-B]Pyridin-5-yl)Quinazolin-4-Amine (123)

This compound was prepared from 2-chloro-N-(2,2-diphenylethyl)quinazolin-4-amine and 5-(4,4,5,5-tetramethyl-1,3,2-dioxaborolan-2-yl)-1H-pyrrolo[2,3-b]pyridine according to the procedure described for the preparation of compound 8. Yield 20%. Mp 193° C. TLC $R_f$ 0.25 (CHCl$_3$-MeOH, 9:1), $^1$H NMR (400 MHz, DMSO-d$_6$) δ 11.80 (s, 1H), 9.41 (d, J=2.6 Hz, 1H), 9.01 (d, J=2.4 Hz, 1H), 8.44 (t, J=5.6 Hz, 1H), 7.74-7.71 (m, 3H), 7.52-7.41 (m, 5H), 7.30 (t, J=7.7 Hz, 5H), 7.23-7.14 (m, 2H), 6.57 (dd, J=9.0, 2.5 Hz, 1H), 4.72 (t, J=7.6 Hz, 1H), 4.41-4.33 (m, 2H). HRMS m/z calcd for $C_{29}H_{23}N_5$+H$^+$ [M+H$^+$]: 442.2026, found: 442.2027. HPLC: 100% ($t_R$=6.73 min).

ttttt. N-(2,2-Diphenylethyl)-7-Fluoro-2-(Imidazo[1,2-A]Pyridin-6-yl)Quinazolin-4-Amine Hydrochloride (124)

This compound was prepared in two steps starting from 2-chloro-N-(2,2-diphenylethyl)-7-fluoroquinazolin-4-amine and imidazo(1,2-a)pyridine-6-boronic acid according to the procedure described for the preparation of compound 120. Yield 48%. mp 191° C.; TLC $R_f$ 0.35 (CHCl$_3$-MeOH, 9:1), $^1$H NMR (400 MHz, DMSO-d$_6$) δ 9.53 (q, J=1.3 Hz, 1H), 8.61 (d, J=4.9 Hz, 1H), 8.26 (ddd, J=9.2, 3.8, 2.2 Hz, 2H), 8.12-8.06 (m, 1H), 7.70-7.63 (m, 2H), 7.49-7.26 (m, 10H), 7.24-7.14 (m, 2H), 4.70 (t, J=7.5 Hz, 1H), 4.35 (t, J=6.0 Hz, 2H). HRMS m/z calcd for $C_{29}H_{22}FN_5$+H$^+$ [M+H$^+$]: 460.1932, found: 460.1930. HPLC: 100% ($t_R$=6.80 min). The free base was converted to the hydrochloride salt.

uuuuu. Synthesis of N-(2,2-Diphenylethyl)-2-(Imidazo[1,2-A]Pyridin-6-yl)-7-(3-Morpholinopropoxy)Quinazolin-4-Amine Hydrochloride (125)

N-(2,2-Diphenylethyl)-7-fluoro-2-(imidazo[1,2-a]pyridin-6-yl)quinazolin-4-amine free base described above (50 mg, 0.11 mmol), 3-morpholinopropanol (0.50 mL, 0.85 mmol), and potassium tert-butoxide (123 mg, 1.10 mmol) were heated at 120° C. overnight under argon. The reaction mixture was concentrated under reduced pressure and purified to give the product. Yield 63%. Mp 232° C. TLC $R_f$ 0.30 (CHCl$_3$-MeOH, 9:1), $^1$H NMR (400 MHz, DMSO-d$_6$) δ 9.51 (dd, J=1.7, 1.0 Hz, 1H), 8.34-8.23 (m, 2H), 8.10-8.01 (m, 2H), 7.69-7.61 (m, 2H), 7.47-7.39 (m, 4H), 7.31 (dd, J=8.3, 7.0 Hz, 4H), 7.22-7.15 (m, 2H), 7.12 (d, J=2.5 Hz, 1H), 7.04 (dd, J=9.0, 2.5 Hz, 1H), 4.70 (t, J=7.5 Hz, 1H), 4.36-4.27 (m, 2H), 4.16 (t, J=6.4 Hz, 2H), 3.62-3.55 (m, 4H), 3.32-3.23 (m, 1H), 2.45 (t, J=7.1 Hz, 1H), 2.38 (t, J=4.6 Hz, 4H), 1.93 (p, J=6.7 Hz, 2H). HRMS m/z calcd for $C_{36}H_{36}N_6O_2$+H$^+$ [M+H$^+$]: 585.2973, found: 585.2962. HPLC: 100% ($t_R$=5.90 min). The free base was converted to the hydrochloride salt. Mp 193° C. TLC $R_f$ 0.25 (CHCl$_3$-MeOH, 9:1). $^1$H NMR (400 MHz, DMSO-d$_6$) δ 10.56 (s, 1H), 9.81 (s, 1H), 8.84 (d, J=9.5 Hz, 1H), 8.51 (d, J=2.1 Hz, 1H), 8.25 (s, 1H), 8.13 (dd, J=30.1, 9.3 Hz, 2H), 7.47-7.40 (m, 5H), 7.29 (dd, J=8.3, 6.9 Hz, 4H), 7.22-7.10 (m, 3H), 4.68 (t, J=7.7 Hz, 1H), 4.38 (t, J=6.6 Hz, 2H), 4.24 (t, J=6.0 Hz, 2H), 3.99 (d, J=11.1 Hz, 2H), 3.82-3.71 (m, 2H), 3.49 (d, J=12.4 Hz, 2H), 3.27 (s, 2H), 3.12 (t, J=11.1 Hz, 2H), 2.24 (p, J=6.1 Hz, 2H). HRMS m/z $C_{36}H_{36}N_6O_2$+H$^+$ [M+H$^+$]: 585.2973, found: 585.2971. HPLC: 100% ($t_R$=5.98 min).

vvvvv. Synthesis of 2-(Imidazo[1,2-A]Pyridin-6-yl)-N-(2-(4-Methylpiperazin-1-yl)-2-Phenylethyl)Quinazolin-4-Amine (126)

This compound was prepared from 2-chloro-N-(2-(4-methylpiperazin-1-yl)-2-phenylethyl)quinazolin-4-amine and (imidazo[1,2-a]pyridin-6-yl)boronic acid according to the procedure described for the preparation of compound 117. Yield 59%. Mp 225-227° C. TLC $R_f$ 0.3 (EtOAc). $^1$H NMR (400 MHz, DMSO-d$_6$) δ 9.49 (m, 1H), 8.29-8.07 (m, 4H), 7.82-7.70 (m, 2H), 7.64 (m, 2H), 7.47 (ddd, J=8.2, 6.4, 1.8 Hz, 1H), 7.40-7.20 (m, 5H), 4.28 (m, 1H), 3.98 (m, 2H), 2.58-2.29 (m, 8H), 2.09 (s, 3H). HRMS m/z calcd for $C_{28}H_{29}N_7$+H$^+$ [M+H$^+$]: 464.2557, found: 464.2562. HPLC: 100% ($t_R$=5.08 min).

wwwww. Synthesis of 2-(Imidazo[1,2-A]Pyrimidin-6-yl)-N-(2-Phenyl-2-(Pyrrolidin-1-yl)Ethyl)Quinazolin-4-Amine (127)

i. Step 1

2-Chloro-N-(2-phenyl-2-(pyrrolidin-1-yl)ethyl)quinazolin-4-amine was reacted with 5-(4,4,5,5-tetramethyl-1,3,2-dioxaborolan-2-yl)pyrimidin-2-amine according to the procedure described for the preparation of compound 117 to afford 2-(2-aminopyrimidin-5-yl)-N-(2-phenyl-2-(pyrrolidin-1-yl)ethyl)quinazolin-4-amine. Yield 68%. $^1$H NMR (400 MHz, DMSO-d$_6$) δ 9.17 (s, 2H), 8.14 (br s, 1H), 8.04 (m, 1H), 7.72-7.64 (m, 2H), 7.39-7.10 (m, 8H), 4.24 (m, 1H), 3.73 (m, 2H), 3.76-3.32 (m, 4H), 1.68 (m, 4H). HRMS m/z calcd for $C_{24}H_{27}N_7$+H$^+$ [M+H$^+$]: 412.2244, found: 412.2247.

ii. Step 2

The above intermediate was reacted with 2-chloroacetaldehyde as described in Step 2 for the preparation of compound 120. Yield 59%. Mp 195-197° C. TLC $R_f$ 0.33 (CH$_2$Cl$_2$-MeOH, 9:1). $^1$H NMR (400 MHz, DMSO-d$_6$) δ 9.76 (d, J=2.4 Hz, 1H), 9.46 (d, J=2.3 Hz, 1H), 8.35 (s, 1H), 8.19-8.08 (m, 2H), 7.83-7.70 (m, 3H), 7.48 (t, J=7.6 Hz, 1H), 7.38 (s, 2H), 7.22-7.15 (m, 3H), 4.23 (s, 1H), 4.06-3.98 (m, 1H), 2.55-2.45 (m, 4H), 1.71 (br s, 4H). HRMS m/z calcd for $C_{26}H_{25}N_7$+H$^+$ [M+H$^+$]: 436.2244, found: 436.2248. HPLC: 100% ($t_R$=5.41 min).

xxxxx. Synthesis of 2-(Imidazo[1,2-A]Pyrimidin-6-yl)-N-(2-Morpholino-2-Phenylethyl)Quinazolin-4-Amine (128)

i. Step 1

2-Chloro-N-(2-morpholino-2-phenylethyl)quinazolin-4-amine was reacted with 5-(4,4,5,5-tetramethyl-1,3,2-dioxaborolan-2-yl)pyrimidin-2-amine according to the procedure described for the preparation of compound 117 to give 2-(2-aminopyrimidin-5-yl)-N-(2-morpholino-2-phenylethyl)quinazolin-4-amine. Yield 65%. $^1$H NMR (400 MHz, DMSO-$d_6$) δ 9.17 (s, 2H), 8.21-8.08 (m, 2H), 7.73-7.62 (m, 2H), 7.41-7.0 (m, 8H), 4.25 (m, 1H), 3.97-3.84 (m, 2H), 3.53 (m, 4H), 2.45 (m, 4H). HRMS m/z calcd for $C_{24}H_{25}N_7O+H^+$ [M+H$^+$]: 428.2193, found: 428.2198.

ii. Step 2

The above intermediate was reacted with 2-chloroacetaldehyde as described in Step 2 for the preparation of compound 120. Yield 59%. Mp 183-185° C. TLC $R_f$ 0.36 (CH$_2$Cl$_2$-MeOH, 9.5:0.5). $^1$H NMR (400 MHz, DMSO-$d_6$) δ 9.78 (d, J=2.4 Hz, 1H), 9.48 (d, J=2.3 Hz, 1H), 8.38-8.29 (m, 1H), 8.23-8.15 (m, 1H), 8.09 (d, J=1.5 Hz, 1H), 7.85-7.72 (m, 3H), 7.50 (ddd, J=8.2, 6.5, 1.7 Hz, 1H), 7.41-7.19 (m, 5H), 4.37-4.26 (m, 1H), 4.08-3.90 (m, 2H), 3.54 (m, 4H), 2.51-2.48 (m, 4H). HRMS m/z calcd for $C_{25}H_{26}N_7O+H^+$ [M+H$^+$]: 452.2193, found: 452.2196. HPLC: 100% ($t_R$=5.67 min).

yyyyy. Synthesis of 2-(Imidazo[1,2-A]Pyrimidin-6-yl)-N-(2-(4Methylpiperazin-1-yl)-2-Phenylethyl)Quinazolin-4-Amine (129)

i. Step 1

2-Chloro-N-(2-(4-methylpiperazin-1-yl)-2-phenylethyl)quinazolin-4-amine was coupled with 5-(4,4,5,5-tetramethyl-1,3,2-dioxaborolan-2-yl)pyrimidin-2-amine according to the procedure described for the preparation of compound 117 to afford 2-(2-aminopyrimidin-5-yl)-N-(2-(4-methylpiperazin-1-yl)-2-phenylethyl)quinazolin-4-amine. Yield 60%. $^1$H NMR (400 MHz, DMSO-$d_6$) δ 9.17 (s, 2H), 8.15 (t, J=4.5 Hz, 1H), 8.08 (m, 2H), 7.73-7.63 (m, 2H), 7.41-7.21 (m, 6H), 7.09 (br s, 2H), 4.25 (m, 1H), 3.97 (t, J=7.1 Hz, 1H), 3.85 (m, 1H), 2.52-2.52 (m, 8H), 2.11 (s, 3H). HRMS m/z calcd for $C_{25}H_{28}N_8+H^+$ [M+H$^+$]: 441.2509, found: 441.2501.

ii. Step 2

The above intermediate was reacted with 2-chloroacetaldehyde as described in Step 2 for the preparation of compound 120. Yield 73%. Mp 180-182° C. TLC $R_f$ 0.4 (CH$_2$Cl$_2$-MeOH, 4:1). $^1$H NMR (400 MHz, DMSO-$d_6$) δ 9.80 (d, J=2.4 Hz, 1H), 9.49 (d, J=2.3 Hz, 1H), 8.38 (d, J=6.0 Hz, 1H), 8.20 (dd, J=8.3, 1.1 Hz, 1H), 8.10 (d, J=1.4 Hz, 1H), 7.84-7.72 (m, 3H), 7.50 (ddd, J=8.2, 6.5, 1.7 Hz, 1H), 7.42-7.21 (m, 5H), 4.32 (m, 3H), 2.55-2.52 (m, 8H), 2.27 (s, 3H). HRMS m/z calcd for $C_{27}H_{28}N_8+H^+$ [M+H$^+$]: 465.2509, found: 465.2505. HPLC: 100% ($t_R$=5.51 min).

zzzzz. Synthesis of 2-(1H-Indol-5-yl)-N-(2-Phenyl-2-(Pyridin-3-yl)Ethyl)Quinazolin-4-Amine (130)

This compound was prepared from 2-chloro-N-(2 phenyl-2-(pyridin-3-yl)ethyl)quinazolin-4-amine and (1H-indol-5-yl)lboronic acid according to the procedure described for the preparation of compound 117. Yield 60%. Mp 109-111° C. TLC $R_f$ 0.15 (CH$_2$Cl$_2$-MeOH, 9.5:0.5). $^1$H NMR (400 MHz, DMSO-$d_6$) δ 11.24 (s, 1H), 8.79 (m, 1H), 8.68-8.63 (m, 1H), 8.45-8.32 (m, 3H), 8.13-8.06 (m, 1H), 7.86 (dt, J=8.0, 2.0 Hz, 1H), 7.76-7.70 (m, 2H), 7.49-7.43 (m, 3H), 7.41-7.23 (m, 6H), 6.53 (m, 1H), 4.87 (t, J=7.5 Hz, 1H), 4.35 (m, 2H). HRMS m/z calcd for $C_{29}H_{23}N_5+H^+$ [M+H$^+$]: 442.2026, found: 442.2030. HPLC: 99% ($t_R$=6.16 min).

aaaaaa. Synthesis of 2-(Imidazo[1,2-A]Pyridin-6-yl)-N-(2-Phenyl-2-(Pyridin-3-yl)Ethyl)Quinazolin-4-Amine (131)

This compound was prepared from 2-chloro-N-(2 phenyl-2-(pyridin-3-yl)ethyl)quinazolin-4-amine and (imidazo[1,2-a]pyridin-6-yl)boronic acid according to the procedure described for the preparation of compound 117. Yield 57%. Mp>250° C. TLC $R_f$ 0.40 (CH$_2$Cl$_2$-MeOH, 9.5:0.5). $^1$H NMR (400 MHz, DMSO-$d_6$) δ 9.53 (s, 1H), 8.66 (d, J=1.9 Hz, 1H), 53 (t, J=5.5 Hz, 1H), 8.38 (m, 1H), 8.28 (m, 1H), 8.08-8.15 (m, 2H), 7.88 (m, 1H), 7.78-7.72 (m, 2H), 7.66-7.63 (m, 2H), 7.05-7.21 (m, 6H), 4.75 (t, J=7.4 Hz, 1H), 4.45-3.32 (m, 2H). HRMS m/z calcd for $C_{28}H_{22}N_6+H^+$ [M+H$^+$]: 443.1978 found: 443.1974. HPLC: 97% ($t_R$=5.55 min).

bbbbbb. Synthesis of 2-([1,2,4]Triazolo[1,5-a]pyridin-6-yl)-N-(2-phenyl-2-(pyridin-3-yl)ethyl)quinazolin-4-amine (132)

This compound was prepared from 2-chloro-N-(2 phenyl-2-(pyridin-3-yl)ethyl)quinazolin-4-amine and ([1,2,4]triazolo[1,5-a]pyridin-6-yl)boronic acid according to the procedure described for the preparation of compound 117. Yield 65%. Mp>250° C. TLC $R_f$ 0.25 (CH$_2$Cl$_2$-MeOH, 9.5:0.5). $^1$H NMR (400 MHz, DMSO-$d_6$) δ 9.74 (s, 1H), 8.38 (m, 2H), 8.18-8.15 (m, 1H), 7.96 (m, 1H), 7.86-7.89 (m, 1H), 7.78 (m, 2H), 7.54-7.44 (m, 3H), 7.36-7.21 (m, 4H), 4.78 (t, J=7.6 Hz, 1H), 3.45-3.26 (m, 2H). HRMS m/z calcd for $C_{27}H_{21}N_7+H^+$ [M+H$^+$]: 444.1931 found: 444.1937. HPLC: 95% ($t_R$=6.35 min).

cccccc. Synthesis of N-(2,2-Diphenylethyl)-2-(Isoquinolin-6-yl)Quinazolin-4-Amine (133)

This compound was prepared from 2-chloro-N-(2,2-diphenylethyl)quinazolin-4-amine and (isoquinolin-6-yl)boronic acid according to the procedure described for the preparation of compound 117. Yield 66%. Mp 242-244° C. TLC $R_f$ 0.33 (CH$_2$Cl$_2$-EtOAc, 4:1). $^1$H NMR (400 MHz, DMSO-$d_6$) δ 9.40 (m, 1H), 9.10-9.05 (m, 1H), 8.81 (dd, J=8.6, 1.5 Hz, 1H), 8.63-8.54 (m, 2H), 8.29-8.15 (m, 2H), 7.92 (d, J=5.7 Hz, 1H), 7.87-7.75 (m, 2H), 7.67-7.42 (m, 5H), 7.33 (dd, J=8.3, 7.0 Hz, 4H), 7.26-7.17 (m, 2H), 4.82 (t, J=7.5 Hz, 1H), 4.37 (dd, J=7.5, 5.3 Hz, 2H). HRMS m/z calcd for $C_{31}H_{24}N_4+H^+$ [M+H$^+$]: 453.2073 found: 453.2081. HPLC: 97% ($t_R$=7.09 min).

dddddd. Synthesis of 2-(Imidazo[1,2-A]Pyrimidin-6-yl)-N-(2-Phenyl-2-(Pyridin-3-yl)Ethyl)Quinazolin-4-Amine (134)

i. Step 1

2-Chloro-N-(2 phenyl-2-(pyridin-3-yl)ethyl)quinazolin-4-amine was reacted with 5-(4,4,5,5-tetramethyl-1,3,2-dioxaborolan-2-yl)pyrimidin-2-amine according to the procedure described for the preparation of compound 117 to give 2-(2-aminopyrimidin-5-yl)-N-(2-phenyl-2-(pyridin-3-yl)ethyl)quinazolin-4-amine. Yield 62%. $^1$H NMR (400 MHz, DMSO-$d_6$) δ 9.20 (s, 2H), 8.61 (m, 1H), 8.46 (t, J=4.1 Hz, 1H), 8.38 (m, 1H), 8.0 (m, 1H), 7.83-7.63 (m, 3H), 7.47-7.20

(m, 7H), 7.09 (br s, 2H), 4.67 (t, J=7.4 Hz, 1H), 4.36-4.20 (m, 2H). HRMS m/z calcd for $C_{25}H_{21}N_7+H^+$ [M+H$^+$]: 420.1931, found: 420.1938.

ii. Step 2

The above intermediate was reacted with 2-chloroacetaldehyde as described in Step 2 for the preparation of compound 120. Yield 59%. Mp 221-223° C. TLC $R_f$ 0.2 (CH$_2$Cl$_2$-MeOH, 9.5:0.5). $^1$H NMR (400 MHz, DMSO-d$_6$) δ 9.85 (d, J=2.4 Hz, 1H), 9.51 (d, J=2.3 Hz, 1H), 8.69-8.58 (m, 2H), 8.37 (dd, J=4.8, 1.6 Hz, 1H), 8.20-8.13 (m, 1H), 8.09 (d, J=1.4 Hz, 1H), 7.91-7.72 (m, 4H), 7.48 (ddd, J=8.1, 6.6, 1.8 Hz, 3H), 7.38-7.13 (m, 5H), 4.75 (t, J=7.6 Hz, 1H), 4.52-4.31 (m, 2H), 3.33-3.24 (m, 2H). HRMS m/z calcd for $C_{27}H_{21}N_7+H^+$ [M+H$^+$]: 444.1931 found: 444.1932. HPLC: 95% ($t_R$=6.35 min).

eeeeee. Synthesis of 2-(Imidazo[1,2-A]Pyridin-6-yl)-4-(4-Phenyl-3,4-Dihydroisoquinolin-2(1H)-yl) Quinazoline (135)

This compound was prepared from 2-chloro-4-(4-phenyl-3,4-dihydroisoquinolin-2(1H)-yl)quinazoline and (imidazo[1,2-a]pyridin-6-yl)boronic acid according to the procedure described for the preparation of compound 117. Yield 52%. Mp 107-109° C. TLC $R_f$ 0.23 (CH$_2$Cl$_2$-EtOAc, 3:7). $^1$H NMR (400 MHz, DMSO-d$_6$) δ 9.57 (dd, J=1.7, 1.0 Hz, 1H), 8.27 (dd, J=9.5, 1.7 Hz, 1H), 8.17 (br s, 1H), 7.88-7.74 (m, 2H), 7.73-7.50 (m, 3H), 7.50-7.43 (m, 1H), 7.40-7.16 (m, 8H), 6.99-6.83 (m, 1H), 5.27 (d, J=16.8 Hz, 1H), 5.14 (d, J=16.7 Hz, 1H), 4.66 (t, J=5.6 Hz, 1H), 4.34-4.20 (m, 2H). HRMS m/z calcd for $C_{28}H_{31}N_5+H^+$ [M+H$^+$]: 454.2026 found: 454.2025. HPLC: 100% ($t_R$=6.91 min).

ffffff. Synthesis of N-(2,3-Diphenylpropyl)-2-(imidazo[1,2-a]pyridin-6-yl)quinazolin-4-amine (136)

This compound was prepared from 2-chloro-2,3-diphenylpropyl)quinazolin-4-amine and (imidazo[1,2-a]pyridin-6-yl)boronic acid according to the procedure described for the preparation of compound 117. Yield 71%. Mp 208-210° C. TLC $R_f$ 0.19 (CH$_2$Cl$_2$-EtOAc, 1:3). $^1$H NMR (400 MHz, DMSO-d$_6$) δ 9.50 (dd, J=1.7, 1.0 Hz, 1H), 8.38 (t, J=5.6 Hz, 1H), 8.22-8.11 (m, 3H), 7.80-7.50 (m, 4H), 7.44 (ddd, J=8.2, 6.4, 1.8 Hz, 1H), 7.33-7.26 (m, 2H), 7.26-7.06 (m, 8H), 4.08-3.89 (m, 2H), 3.58 (p, J=7.4 Hz, 1H), 3.32-3.16 (m, 1H), 3.02 (dd, J=13.7, 8.7 Hz, 1H). HRMS m/z calcd for $C_{28}H_{31}N_5+H^+$ [M+H$^+$]: 456.2182 found: 456.2197. HPLC: 100% ($t_R$=7.91 min).

gggggg. Synthesis of 2-(1-Methyl-1H-Indol-5-yl)-N-(2-Phenyl-2-(Pyridin-3-yl)Ethyl)Quinazolin-4-Amine (137)

This compound was prepared from 2-chloro-N-(2-phenyl-2-(pyridin-3-yl)ethyl)quinazolin-4-amine and (1-methyl-1H-indol-5-yl)boronic acid according to the procedure described for the preparation of compound 117. Yield 52%. Mp 91-93° C. TLC $R_f$ 0.28 (CH$_2$Cl$_2$-MeOH, 9.5:0.5). $^1$H NMR (400 MHz, DMSO-d$_6$) δ 8.82-8.77 (m, 1H), 8.65 (d, J=2.3 Hz, 1H), 8.45-8.36 (m, 3H), 8.13-8.02 (m, 1H), 7.85 (dt, J=8.0, 2.0 Hz, 1H), 7.79-7.66 (m, 2H), 7.55-7.23 (m, 9H), 6.53 (m, 1H), 4.87 (t, J=7.5 Hz, 1H), 4.35 (m, 2H), 3.85 (s, 3H). HRMS m/z calcd for $C_{28}H_{31}N_5+H^+$ [M+H$^+$]: 456.2182 found: 456.2186. HPLC: 92% ($t_R$=6.31 min).

hhhhhh. Synthesis of N-(5-(4-((2,2-Diphenylethyl) Amino)Quinazolin-2-yl)Pyridin-2-yl)Methanesulfonamide (138)

A solution of 2-(6-aminopyridin-3-yl)-N-(2,2-diphenylethyl)quinazolin-4-amine (40 mg, 0.096 mmol) in pyridine (3 mL) was cooled to 0° C. and methanesulfonyl chloride (14 mg, 0.12 mmol) was added. The reaction mixture was stirred at room temperature overnight, concentrated under reduced pressure and the residue obtained was purified to give the desired product. Yield 46%. Mp 210° C. TLC $R_f$ 0.40 (CHCl$_3$-MeOH, 9:1), $^1$H NMR (400 MHz, DMSO-d$_6$) δ 9.20 (s, 1H), 8.65 (dd, J=8.7, 2.3 Hz, 1H), 8.42 (t, J=5.5 Hz, 1H), 8.15-8.08 (m, 1H), 7.77-7.66 (m, 2H), 7.46-7.37 (m, 5H), 7.33-7.24 (m, 4H), 7.23-7.13 (m, 2H), 7.08 (d, J=8.7 Hz, 1H), 4.72 (t, J=7.7 Hz, 1H), 4.35-4.26 (m, 2H), 3.54-3.39 (m, 1H), 3.26 (s, 3H). HRMS m/z calcd for $C_{28}H_{25}N_5O_2S+H^+$ [M+H$^+$]: 496.1802, found: 496.1806, HPLC: 100% ($t_R$=6.53 min).

iiiiii. Synthesis of N-(5-(4-((2,2-Diphenylethyl) Amino)Quinazolin-2-yl)Pyrimidin-2-yl)Methanesulfonamide (139)

2-(2-Aminopyrimidin-5-yl)-N-(2,2-diphenylethyl)quinazolin-4-amine (40 mg, 0.096 mmol) was dissolved in pyridine (3 mL) and methanesulfonyl chloride (13 mg, 0.12 mmol) was added at 0° C. The reaction mixture was stirred at room temperature overnight. The reaction mixture was concentrated under reduced pressure and the residue obtained was purified to give the desired product. Yield 17%. Mp 214° C.; TLC $R_f$ 0.40 (CHCl$_3$-MeOH, 9:1), $^1$H NMR (400 MHz, DMSO-d$_6$) δ 9.45 (s, 2H), 8.50 (s, 1H), 8.13 (d, J=7.9 Hz, 1H), 7.77-7.70 (m, 4H), 7.45-7.37 (m, 4H), 7.28 (t, J=7.6 Hz, 4H), 7.22-7.13 (m, 2H), 4.70 (t, J=7.6 Hz, 1H), 4.36-4.28 (m, 2H), 3.26 (s, 3H). HRMS m/z calcd for $C_{27}H_{24}N_6O_2S+H^+$ [M+H$^+$]: 497.1754, found: 497.1751. HPLC: 100% ($t_R$=6.72 min).

jjjjjj. Synthesis of 2-(7-Methylimidazo[1,2-A]Pyridin-6-yl)-N-(2-Phenyl-2-(1H-Pyrrol-2-yl)Ethyl)Quinazolin-4-Amine (140)

This compound was prepared from 2-chloro-N-(2-phenyl-2-(1H-pyrrol-2-yl)ethyl)quinazolin-4-amine and (7-methylimidazo[1,2-a]pyridin-6-yl)boronic acid according to the procedure described for the preparation of compound 117. Yield 29%. Mp 242-244° C. TLC $R_f$ 0.13 ((CH$_2$Cl$_2$-MeOH, 9:1). $^1$H NMR (400 MHz, DMSO-d$_6$) δ 10.60 (s, 1H), 9.06 (s, 1H), 8.40 (q, J=5.6 Hz, 1H), 8.21-8.14 (m, 1H), 7.97 (dd, J=1.3, 0.7 Hz, 2H), 7.85-7.69 (m, 2H), 7.56 (d, J=1.2 Hz, 2H), 7.52-7.43 (m, 3H), 7.34-7.10 (m, 5H), 6.60 (td, J=2.6, 1.5 Hz, 1H), 6.06 (br s, 1H), 5.95 (q, J=2.8 Hz, 1H), 4.66 (t, J=7.6 Hz, 2H), 4.13 (m, 2H), 2.66 (s, 3H). HRMS m/z calcd for $C_{28}H_{24}N_6+H^+$ [M+H$^+$]: 445.2135 found: 445.2142. HPLC: 100% ($t_R$=5.83 min).

kkkkkk. Synthesis of N-(2,2-Diphenylethyl)-2-(Quinolin-8-yl)Quinazolin-4-Amine (141)

This compound was prepared from 2-chloro-N-(2,2-diphenylethyl)quinazolin-4-amine and (quinolin-8-yl)boronic acid according to the procedure described for the preparation of compound 117. Yield 68%. Mp 102-104° C. TLC $R_f$ 0.14 (EtOAc). $^1$H NMR (400 MHz, DMSO-d$_6$) δ 8.94 (dd, J=4.1, 1.8 Hz, 1H), 8.47 (dd, J=8.4, 1.8 Hz, 1H), 8.37 (t, J=5.4 Hz, 1H), 8.12 (m, 2H), 7.93 (dd, J=7.0, 1.5 Hz, 1H), 7.80-7.43

(m, 7H), 7.31-7.08 (m, 10H), 4.92 (t, J=7.7 Hz, 1H), 4.05 (dd, J=7.8, 5.3 Hz, 2H). HRMS m/z calcd for $C_{31}H_{24}N_4$+H$^+$ [M+H$^+$]: 453.2073 found: 453.2075. HPLC: 92% ($t_R$=6.84 min).

llllll. Synthesis of N-(2,3-Diphenylpropyl)-2-(Imidazo[1,2-A]Pyrimidin-6-yl)Quinazolin-4-Amine (142)

This compound was prepared in two steps starting from 2-chloro-N-(2,3-diphenylpropyl)quinazolin-4-amine and 5-(4,4,5,5-tetramethyl-1,3,2-dioxaborolan-2-yl)pyrimidin-2-amine following the same procedure as described for compound 120. Yield 47%. Mp 189-191° C. TLC $R_f$ 0.27 (EtOAc). $^1$H NMR (400 MHz, DMSO-d$_6$) δ 9.79 (d, J=2.3 Hz, 1H), 9.46 (d, J=2.3 Hz, 1H), 8.47 (t, J=5.6 Hz, 1H), 8.22-8.15 (m, 1H), 8.12 (d, J=1.4 Hz, 1H), 7.84-7.70 (m, 3H), 7.47 (ddd, J=8.2, 6.5, 1.7 Hz, 1H), 7.34-7.26 (m, 2H), 7.24-7.05 (m, 9H), 4.10-3.87 (m, 2H), 3.58 (p, J=7.6 Hz, 1H), 3.29-3.16 (m, 1H), 3.03 (dd, J=13.7, 8.9 Hz, 1H). HRMS m/z calcd for $C_{29}H_{24}N_6$+H$^+$ [M+H$^+$]: 457.2135 found: 457.2135. HPLC: 99% ($t_R$=7.14 min).

mmmmmm. Synthesis of 2-(Imidazo[1,2-A]Pyrimidin-6-yl)-4-(4-Phenyl-3,4-Dihydroisoquinolin-2(1H)-yl)Quinazoline (143)

This compound was prepared in two steps starting from 2-chloro-4-(phenyl-3,4-dihydroisoquinolin-2(1H)-yl)quinazoline and 5-(4,4,5,5-tetramethyl-1,3,2-dioxaborolan-2-yl)pyrimidin-2-amine following the same procedure as described for compound 120. Yield 56%. Mp 104-106° C. TLC $R_f$ 0.26 (EtOAc). $^1$H NMR (400 MHz, DMSO-d$_6$) δ 9.85 (d, J=2.4 Hz, 2H), 9.50 (d, J=2.5 Hz, 2H), 8.12 (d, J=1.5 Hz, 2H), 7.89-7.70 (m, 4H), 7.50-7.16 (m, 10H), 6.95 (d, J=7.6 Hz, 1H), 5.30 (d, J=16.8 Hz, 1H), 5.22-5.13 (m, 1H), 4.66 (t, J=5.6 Hz, 1H), 4.31 (d, J=5.6 Hz, 2H). HRMS m/z calcd for $C_{29}H_{22}N_6$+H$^+$ [M+H$^+$]: 455.1978 found: 455.1981. HPLC: 93% ($t_R$=7.46 min).

nnnnnn. Synthesis of N-(2-(Imidazo[1,2-A]Pyridin-6-yl)Quinazolin-4-yl)-2,2-Diphenylacetamide (144)

This compound was prepared from 2-chloro-N-(quinazolin-4-yl)-2,2-diphenylacetamide and (imidazo[1,2-a]pyridin-6-yl)boronic acid according to the procedure described for the preparation of compound 117. Yield 29%. Mp 218-220° C. TLC $R_f$ 0.2 (EtOAc). $^1$H NMR (400 MHz, DMSO-d$_6$) δ 11.31 (s, 1H), 9.46 (s, 1H), 8.28-8.13 (m, 3H), 7.98 (d, J=5.5 Hz, 2H), 7.72-7.50 (m, 3H), 7.49-7.25 (m, 10H), 5.78 (s, 1H). HRMS m/z calcd for $C_{29}H_{21}N_5O$+H$^+$ [M+H$^+$]: 456.1818 found: 456.1827. HPLC: 97% ($t_R$=6.76 min).

oooooo. Synthesis of 2-(Benzo[D]Thiazol-5-yl)-N-(2,2-Diphenylethyl)Quinazolin-4-amine (145)

This compound was prepared from 2-chloro-N-(2,2-diphenylethyl)quinazolin-4-amine and 5-(4,4,5,5-tetramethyl-1,3,2-dioxaborolan-2-yl)benzo[d]thiazole according to the procedure described for the preparation of compound 117. Yield 51%. Mp 224-226° C. TLC $R_f$ 0.29 (EtOAc). $^1$H NMR (400 MHz, DMSO-d$_6$) δ 9.48 (s, 1H), 9.24-9.18 (m, 1H), 8.68 (dd, J=8.5, 1.6 Hz, 1H), 8.49 (t, J=5.5 Hz, 1H), 8.33-8.25 (m, 1H), 8.19-8.12 (m, 1H), 7.83-7.72 (m, 2H), 7.45-7.15 (m, 11H), 4.82 (t, J=7.7 Hz, 1H), 4.35 (dd, J=7.7, 5.4 Hz, 2H). HRMS m/z calcd for $C_{29}H_{22}N_4S$+H$^+$ [M+H$^+$]: 459.1637 found: 459.1640. HPLC: 93% ($t_R$=6.71 min).

pppppp. Synthesis of (S)-Tert-Butyl (2-((2-(Imidazo[1,2-A]Pyridin-6-yl)Quinazolin-4-yl)Amino)-1-Phenylethyl)Carbamate (146)

This compound was prepared from (S)-tert-butyl (2-chloroquinazolin-4-yl)amino)-1-phenylethyl)carbamate and (imidazo[1,2-a]pyridin-6-yl)boronic acid according to the procedure described for the preparation of compound 117. Yield 60%. Mp 252-254° C. TLC $R_f$ 0.2 (CH$_2$Cl$_2$-EtOAc, 7:3). $^1$H NMR (400 MHz, DMSO-d$_6$) δ 9.72 (s, 1H), 8.41 (s, 1H), 8.31 (d, J=9.5 Hz, 1H), 8.17-8.08 (m, 2H), 7.82-7.72 (m, 2H), 7.69-7.61 (m, 2H), 7.57 (d, J=8.8 Hz, 1H), 7.47 (s, 1H), 7.39 (d, J=7.5 Hz, 2H), 7.33-7.17 (m, 3H), 5.35 (d, J=8.3 Hz, 1H), 3.95 (s, 1H), 3.85 (s, 1H), 1.36 (s, 9H). HRMS m/z calcd for $C_{28}H_{28}N_6O_2$+H$^+$ [M+H$^+$]: 481.2346 found: 481.2342. HPLC: 100% ($t_R$=6.26 min).

qqqqqq. Synthesis of N-(2,2-Diphenylethyl)-2-(Imidazo[1,2-A]pyridin-8-yl)Quinazolin-4-Amine (147)

This compound was prepared in two step starting from 2-chloro-N-(2,2-diphenylethyl)quinazolin-4-amine and (2-aminopyridin-3-yl)boronic acid using the same procedure described for compound 120. Yield 65%. Mp 182-184° C. TLC $R_f$ 0.4 (CH$_2$Cl$_2$-EtOAc, 7-3). $^1$H NMR (400 MHz, DMSO-d$_6$) δ 9.1 (d, J=6.6 Hz, 1H), 9.02 (d, J=7 Hz, 1H), 8.96 (m, 1H), 8.55 (d, J=2.1 Hz, 1H), 8.33-8.20 (m, 3H), 7.89 (ddd, J=8.4, 7.0, 1.2 Hz, 1H), 7.75 (t, J=7.1 Hz, 1H), 7.58 (ddd, J=8.3, 7.0, 1.3 Hz, 1H), 7.47-7.39 (m, 4H), 7.29 (t, J=7.6 Hz, 4H), 7.22-7.13 (m, 2H), 4.72 (t, J=7.7 Hz, 1H), 4.40 (dd, J=7.7, 5.5 Hz, 2H). HRMS m/z calcd for $C_{30}H_{26}N_4O$+H$^+$ [M+H$^+$]: 459.2179 found: 459.2178. HPLC: 100% ($t_R$=6.63 min).

rrrrrr. Synthesis of N-(1-Benzhydrylazetidin-3-yl)-2-(Imidazo[1,2-A]Pyridin-6-yl)Quinazolin-4-Amine (148)

This compound was prepared from N-(1-benzhydrylazetidin-3-yl)-2-chloroquinazolin-4-amine and (imidazo[1,2-a]pyridin-6-yl)boronic acid according to the procedure described for the preparation of compound 117. Yield 63%. Mp 67-69° C. TLC $R_f$ 0.4 (EtOAc). $^1$H NMR (400 MHz, DMSO-d$_6$) δ 9.56 (dd, J=1.7, 1.0 Hz, 1H), 8.56 (d, J=6.0 Hz, 1H), 8.40-8.32 (m, 1H), 8.28-8.16 (m, 2H), 7.85-7.72 (m, 2H), 7.73-7.57 (m, 2H), 7.59-7.14 (m, 11H), 5.03 (h, J=6.7 Hz, 1H), 4.56 (s, 1H), 3.71 (dd, J=8.0, 6.6 Hz, 2H), 3.17 (dd, J=8.0, 6.6 Hz, 2H). HRMS m/z calcd for $C_{31}H_{26}N_6$+H$^+$ [M+H$^+$]: 483.2291 found: 483.2294.

ssssss. Synthesis of (S)—N-(2-((2-(Imidazo[1,2-A]Pyridin-6-yl)Quinazolin-4-yl)Amino)-1-Phenylethyl)Acetamide (149)

This compound was prepared from (S)—N-(2-((2-chloroquinazolin-4-yl)amino)-1-phenylethyl)acetamide and (imidazo[1,2-a]pyridin-6-yl)boronic acid according to the procedure described for the preparation of compound 117. Yield 63%. Mp 99-101° C. TLC $R_f$ 0.26 (CH$_2$Cl$_2$-MeOH, 9:1). $^1$H NMR (400 MHz, Methanol-d$_4$) δ 9.80 (m, 1H), 8.46-8.42 (m, 2H), 8.30-8.27 (m, 2H), 8.14-8.12 (m, 2H), 7.77-7.76 (m, 2H), 7.59 (m, 2H), 7.46 (m, 1H), 7.40 (m, 2H), 7.30 (m, 2H), 7.23-7.20 (m, 1H), 7.68 (m, 1H), 4.02-3.84

(m, 2H), 1.93 (s, 3H). HRMS m/z calcd for $C_{25}H_{22}N_6O+H^+$ [M+H$^+$]: 423.19279 found: 423.1931. HPLC: 100% ($t_R$=5.55 min).

tttttt. Synthesis of (S)—N-(2-((2-(Imidazo[1,2-A]Pyridin-6-yl)Quinazolin-4-yl)Amino)-1-Phenylethyl)Benzamide (150)

This compound was prepared from (S)—N-(1-phenyl-2-(quinazolin-4-ylamino)ethyl)benzamide and (imidazo[1,2-a]pyridin-6-yl)boronic acid according to the procedure described for the preparation of compound 117. Yield 63%. Mp 97-99° C.; TLC $R_f$ 0.4 (CH$_2$Cl$_2$-MeOH, 9:1), $^1$H NMR (400 MHz, DMSO-d$_6$) δ 9.78 (s 1H), 8.95 (d, J=8.6 Hz, 1H), 8.57 (t, J=5.5 Hz, 1H), 8.31 (dd, J=9.5, 1.7 Hz, 1H), 8.21-8.10 (m, 2H), 7.93-7.85 (m, 2H), 7.83-7.73 (m, 2H), 7.70-7.62 (m, 2H), 7.57-7.29 (m, 9H), 7.29-7.20 (m, 1H), 5.88 (q, J=7.5 Hz, 1H), 4.14-3.98 (m, 2H). HRMS m/z calcd for $C_{30}H_{24}N_6O+H^+$ [M+H$^+$]: 485.2086 found: 485.2084. HPLC: 100% ($t_R$=5.55 min).

uuuuuu. Synthesis of 2-(7-Methylimidazo[1,2-A]Pyridin-6-yl)-N-(2-Phenyl-2-(Pyridin-4-yl)Ethyl)Quinazolin-4-Amine (151)

This compound was prepared from 2-chloro-N-(2-phenyl-2-(pyridin-4-yl)ethyl)quinazolin-4-amine and (7-methylimidazo[1,2-a]pyridin-6-yl)boronic acid according to the procedure described for the preparation of compound 8. Yield 33%. Mp 102-104° C. TLC $R_f$ 0.38 (CHCl$_3$-MeOH, 92.5:7.5). $^1$H NMR (400 MHz, DMSO-d$_6$) δ 9.09 (d, J=0.7 Hz, 1H), 8.52-8.42 (m, 3H), 8.15 (d, J=8.1 Hz, 1H), 7.97 (t, J=1.0 Hz, 1H), 7.84-7.68 (m, 2H), 7.56 (d, J=1.2 Hz, 1H), 7.52-7.43 (m, 2H), 7.39 (dt, J=6.1, 1.7 Hz, 4H), 7.32 (dd, J=8.4, 6.8 Hz, 3H), 7.28-7.17 (m, 1H), 4.68 (d, J=7.6 Hz, 1H), 4.27 (dd, J=14.9, 7.9 Hz, 2H), 1.42-0.93 (m, 2H). HRMS m/z calcd for $C_{29}H_{24}N_6+H^+$ [M+H$^+$]: 457.2135, found: 457.2138. HPLC: 100% ($t_R$=5.0 min).

vvvvvv. Synthesis of 2-((2-(7-Methylimidazo[1,2-A]Pyridin-6-yl)Quinazolin-4-yl)Amino)-1,1-Diphenylethanol (152)

This compound was prepared from 2-((2-chloroquinazolin-4-yl)amino)-1,1-diphenylethanol and (7-methylimidazo[1,2-a]pyridin-6-yl)boronic acid according to the procedure described for the preparation of compound 8. Yield 43%. Mp 164-180° C.; TLC $R_f$ 0.33 (CHCl$_3$-MeOH, 92.5:7.5), $^1$H NMR (400 MHz, DMSO-d$_6$) δ 8.92 (s, 1H), 8.12 (d, J=8.3 Hz, 1H), 8.01 (s, 1H), 7.87-7.74 (m, 2H), 7.62-7.53 (m, 6H), 7.29 (td, J=7.6, 1.8 Hz, 4H), 7.19 (td, J=7.2, 1.5 Hz, 2H), 4.46 (s, 2H), 3.84 (dd, J=4.7, 2.3 Hz, 3H), 2.61 (s, 3H). HRMS m/z calcd for $C_{30}H_{25}N_5O+H^+$ [M+H$^+$]: 472.2132, found: 472.2131. HPLC: 97% ($t_R$=5.9 min).

wwwwww. Synthesis of 1-(2-((2-(Imidazo[1,2-A]Pyridin-6-yl)Quinazolin-4-yl)Amino)-1-(4-Methoxyphenyl)ethyl)Cyclohexanol (153)

This compound was prepared from 1-(2-((2-chloroquinazolin-4-yl)amino)-1-(4-methoxyphenyl)ethyl)cyclohexanol and (imidazo[1,2-a]pyridin-6-yl)boronic acid according to the procedure described for the preparation of compound 117. Yield 52%. Mp 247-249° C. TLC $R_f$ 0.45 (CH$_2$Cl$_2$-MeOH, 9:1). $^1$H NMR (400 MHz, DMSO-d$_6$) δ 9.49 (s, 1H), 8.26 (dd, J=9.4, 1.4 Hz, 1H), 8.12 (t, J=5.5 Hz, 1H), 8.04 (m, 2H), 7.74-7.62 (m, 4H), 7.40 (m, 1H), 7.66 (d, J=8.4 Hz, 2H), 6.76 (d, J=8.6 Hz, 2H), 1.79-1.12 (m, 10H). HRMS m/z calcd for $C_{30}H_{31}N_5O_2+H^+$ [M+H$^+$]: 494.2550 found: 494.25519. HPLC: 100% ($t_R$=6.48 min).

xxxxxx. Synthesis of N-(2,2-Diphenylethyl)-2-(1-(Methylsulfonyl)-1H-Indol-5-yl)Quinazolin-4-Amine (154)

A mixture of N-(2,2-diphenylethyl)-2-(1H-indol-5-yl)quinazolin-4-amine and methanesulfonyl chloride (1.2 eq.) in DMSO was heated under microwave at 40° C. for 8 hours. Purification of the crude product yielded the title compound. Yield 28%. Mp 144-146° C. TLC $R_f$ 0.4 (CH$_2$Cl$_2$-EtOAc, 8:2). $^1$H NMR (400 MHz, DMSO-d$_6$) δ 8.84 (d, J=1.5 Hz, 1H), 8.59 (dd, J=8.8, 1.6 Hz, 1H), 8.45 (t, J=5.7 Hz, 1H), 8.14 (d, J=8.1 Hz, 1H), 7.99-7.90 (m, 1H), 7.75 (dd, J=5.9, 1.5 Hz, 2H), 7.66 (d, J=3.6 Hz, 1H), 7.47-7.38 (m, 5H), 7.37-7.16 (m, 6H), 6.94 (dd, J=3.7, 0.8 Hz, 1H), 4.81 (t, J=7.6 Hz, 1H), 4.33 (dd, J=7.5, 5.4 Hz, 2H), 3.49 (s, 3H), 3.39-3.23 (m, 3H), 1.24 (s, 1H). FIRMS m/z calcd for $C_{31}H_{26}N_4O_2S+H^+$ [M+H$^+$]: 519.1849 found: 519.1850. HPLC: 91% ($t_R$=6.9 min).

yyyyyy. Synthesis of 2-(Imidazo[1,2-A]Pyridin-6-yl)-N-(2-(pyridin-3-yl)-2-(1H-Pyrrol-2-yl)Ethyl)Quinazolin-4-Amine (155)

This compound was prepared from 2-chloro-N-(2-(pyridin-3-yl)-2-(1H-pyrrol-2-yl)ethyl)quinazolin-4-amine and imidazo[1,2-a]pyridin-6-ylboronic acid according to the procedure described for the preparation of compound 8. Yield 18%. Mp 121-124° C. TLC $R_f$ 0.22 (CHCl$_3$-MeOH, 92.5:7.5). $^1$H NMR (400 MHz, DMSO-d$_6$) δ 10.77 (s, 1H), 9.52 (dt, J=1.6, 0.8 Hz, 1H), 8.55-8.45 (m, 2H), 8.33 (ddd, J=4.7, 1.7, 0.6 Hz, 1H), 8.27 (ddd, J=9.4, 1.7, 0.6 Hz, 1H), 8.19-8.11 (m, 1H), 8.09 (dt, J=1.3, 0.7 Hz, 2H), 7.81-7.67 (m, 3H), 7.65 (ddt, J=5.5, 4.2, 0.8 Hz, 2H), 7.50-7.41 (m, 1H), 7.30-7.21 (m, 1H), 6.68 (tdd, J=2.5, 1.6, 0.6 Hz, 1H), 6.37-6.06 (m, 1H), 4.73 (t, J=7.6 Hz, 1H), 4.54-3.96 (m, 2H). HRMS m/z calcd for $C_{26}H_{21}N_7+H^+$ [M+H$^+$]: 432.1931, found: 432.1922. HPLC: 100% ($t_R$=5.1 min).

zzzzzz. Synthesis of 2-(7-Methylimidazo[1,2-A]Pyridin-6-yl)-N-(2-(Pyridin-3-yl)-2-(1H-Pyrrol-2-yl)Ethyl)Quinazolin-4-Amine (156)

This compound was prepared from 2-chloro-N-(2-(pyridin-3-yl)-2-(1H-pyrrol-2-yl)ethyl)quinazolin-4-amine and (7-methylimidazo[1,2-a]pyridin-6-yl)boronic acid according to the procedure described for the preparation of compound 8. Yield 31%. Mp 121-125° C. TLC $R_f$ 0.20 (CHCl$_3$-MeOH, 92.5:7.5). $^1$H NMR (400 MHz, DMSO-d$_6$) δ$^1$H NMR (400 MHz, DMSO-d$_6$) δ 10.71 (s, 1H), 9.06 (d, J=0.8 Hz, 1H), 8.46 (d, J=2.6 Hz, 2H), 8.35 (dd, J=4.7, 1.6 Hz, 1H), 8.16 (dd, J=8.0, 1.3 Hz, 1H), 7.98 (dd, J=1.3, 0.7 Hz, 1H), 7.83-7.69 (m, 2H), 7.65-7.40 (m, 6H), 7.25 (dd, J=7.9, 4.7 Hz, 1H), 6.10 (s, 1H), 6.04-5.92 (m, 1H), 4.69 (dd, J=8.4, 6.9 Hz, 1H), 4.17 (s, 1H), 2.66 (d, J=0.9 Hz, 3H). HRMS m/z calcd for $C_{27}H_{23}N_7+H^+$ [M+H$^+$]: 446.2087, found: 446.2083. HPLC: 97% ($t_R$=4.7 min).

aaaaaaa. Synthesis of N-(2,2-Di(Pyridin-4-yl)Ethyl)-2-(7-Methylimidazo[1,2-A]Pyridin-6-yl)Quinazolin-4-Amine (157)

This compound was prepared from 2-chloro-N-(2,2-di(pyridin-4-yl)ethyl)quinazolin-4-amine and (7-methylimidazo[1,2-a]pyridin-6-yl)boronic acid according to the procedure described for the preparation of compound 8. Yield 18%. Mp 170-175° C. TLC $R_f$ 0.16 (CHCl$_3$-MeOH, 92.5: 7.5). $^1$H NMR (400 MHz, DMSO-d$_6$) δ 9.10 (s, 1H), 8.55-8.46 (m, 6H), 8.31 (d, J=0.9 Hz, 1H), 8.17-8.12 (m, 1H), 8.00-7.94 (m, 1H), 7.84-7.69 (m, 2H), 7.57 (d, J=1.2 Hz, 1H), 7.49 (ddd, J=8.3, 6.5, 1.7 Hz, 1H), 7.45 (s, 1H), 4.70 (t, J=7.5 Hz, 1H), 4.33-4.23 (m, 2H), 3.33 (s, 1H), 2.65 (d, J=1.1 Hz, 3H), 1.23 (s, 1H). HRMS m/z calcd for C$_{28}$H$_{23}$N$_7$+H$^+$ [M+H$^+$]: 458.2087, found: 458.2092. HPLC: 100% ($t_R$=2.2 min).

bbbbbbb. Synthesis of N-(2,2-Di(Pyridin-4-yl) Ethyl)-2-(Imidazo[1,2-A]Pyridin-6-yl)Quinazolin-4-Amine (158)

This compound was prepared from 2-chloro-N-(2,2-di (pyridin-4-yl)ethyl)quinazolin-4-amine and imidazo[1,2-a] pyridin-6-ylboronic acid according to the procedure described for the preparation of compound 8. Yield 54%. Mp 192-196° C. TLC $R_f$ 0.33 (CHCl$_3$-MeOH, 92.5:7.5). $^1$H NMR (400 MHz, DMSO-d$_6$) δ 10.80-10.64 (m, 1H), 9.07 (d, J=0.8 Hz, 1H), 8.46 (t, J=4.1 Hz, 2H), 8.36 (dd, J=4.8, 1.6 Hz, 1H), 8.32 (s, 1H), 8.20-8.11 (m, 1H), 8.01-7.94 (m, 1H), 7.81-7.71 (m, 2H), 7.63 (dt, J=7.9, 2.0 Hz, 1H), 7.57 (d, J=1.2 Hz, 1H), 7.52-7.44 (m, 2H), 7.26 (dd, J=7.8, 4.7 Hz, 1H), 6.65 (td, J=2.7, 1.5 Hz, 1H), 6.10 (dq, J=2.9, 1.6 Hz, 1H), 5.99 (q, J=2.7 Hz, 1H), 4.70 (t, J=7.6 Hz, 1H), 4.19 (tp, J=11.8, 6.1 Hz, 2H). HRMS m/z calcd for C$_{27}$H$_{21}$N$_7$+H$^+$ [M+H$^+$]: 444.1937, found: 444.1927. HPLC: 100% ($t_R$=4.5 min).

ccccccc. Synthesis of 2-(Imidazo[1,2-A]pyridin-6-yl)-N-(2-(Pyridin-2-yl)-2-(1H-Pyrrol-2-yl)Ethyl) Quinazolin-4-Amine (159)

This compound was prepared from 2-chloro-N-(2-(pyridin-2-yl)-2-(1H-pyrrol-2-yl)ethyl)quinazolin-4-amine and imidazo[1,2-a]pyridin-6-ylboronic acid according to the procedure described for the preparation of compound 8. Yield 56%. Mp 235-237° C. TLC $R_f$ 0.33 (CHCl$_3$-MeOH, 92.5:7.5), $^1$H NMR (400 MHz, DMSO-d$_6$) δ 10.71 (s, 1H), 9.06 (d, J=0.8 Hz, 1H), 8.46 (d, J=2.6 Hz, 2H), 8.35 (dd, J=4.7, 1.6 Hz, 1H), 8.16 (dd, J=8.0, 1.3 Hz, 1H), 7.98 (dd, J=1.3, 0.7 Hz, 1H), 7.83-7.69 (m, 2H), 7.65-7.40 (m, 4H), 7.25 (dd, J=7.9, 4.7 Hz, 1H), 6.10 (s, 1H), 6.04-5.92 (m, 1H), 4.69 (dd, J=8.4, 6.9 Hz, 1H), 4.17 (s, 1H), 2.66 (d, J=0.9 Hz, 3H). HRMS m/z calcd for C$_{26}$H$_{21}$N$_7$+H$^+$ [M+H$^+$]: 432.1931, found: 432.1938. HPLC: 100% ($t_R$=5.4 min).

ddddddd. Synthesis of 2-(7-Methylimidazo[1,2-A] Pyridin-6-yl)-N-Phenethylquinazolin-4-Amine (160)

This compound was prepared from 2-chloro-N-phenethylquinazolin-4-amine and (7-methylimidazo[1,2-a]pyridin-6-yl)boronic acid according to the procedure described for the preparation of compound 8. Yield 32%. Mp 192-196° C. TLC $R_f$ 0.36 (CHCl$_3$-MeOH, 92.5:7.5). $^1$H NMR (400 MHz, DMSO-d$_6$) δ 9.06 (d, J=0.8 Hz, 1H), 8.49 (s, 1H), 8.26 (ddd, J=8.3, 1.4, 0.7 Hz, 1H), 8.00 (dd, J=1.4, 0.7 Hz, 1H), 7.85-7.70 (m, 2H), 7.56-7.48 (m, 2H), 7.45 (q, J=1.0 Hz, 1H), 7.29 (d, J=4.4 Hz, 4H), 7.25-7.15 (m, 1H), 3.85 (ddd, J=8.8, 7.5, 5.8 Hz, 2H), 3.07-2.97 (m, 2H), 2.67 (d, J=1.0 Hz, 3H). HRMS m/z calcd for C$_{24}$H$_{21}$N$_5$+H$^+$ [M+H$^+$]: 380.1869, found: 380.1888. HPLC: 100% ($t_R$=5.4 min).

eeeeeee. Synthesis of 2-(Imidazo[1,2-A]Pyridin-6-yl)-N-Phenethylquinazolin-4-Amine (161)

This compound was prepared from 2-chloro-N-phenethylquinazolin-4-amine and (imidazo[1,2-a]pyridin-6-yl)boronic acid according to the procedure described for the preparation of compound 8. Yield 34%. Mp 246-247° C. TLC $R_f$ 0.46 (CHCl$_3$-MeOH, 92.5:7.5). $^1$H NMR (400 MHz, DMSO-d$_6$) δ 9.54 (dd, J=1.8, 1.0 Hz, 1H), 8.48 (t, J=5.6 Hz, 1H), 8.31-8.22 (m, 2H), 8.16 (t, J=0.9 Hz, 1H), 7.83-7.71 (m, 2H), 7.68-7.63 (m, 2H), 7.49 (ddd, J=8.2, 6.2, 2.0 Hz, 1H), 7.39-7.26 (m, 4H), 7.25-7.16 (m, 1H), 4.16-3.70 (m, 2H), 3.09 (t, J=7.4 Hz, 2H). HRMS m/z calcd for C$_{23}$H$_{19}$N$_5$+H$^+$ [M+H$^+$]: 366.1713, found: 366.1710. HPLC: 100% ($t_R$=5.8 min).

fffffff. Synthesis of (S)-2-(7-Methylimidazo[1,2-A] Pyridin-6-yl)-N-(2-Phenyl-2-(1H-Pyrrol-1-yl)Ethyl) Quinazolin-4-Amine (162)

This compound was prepared from (S)-2-chloro-N-(2-phenyl-2-(1H-pyrrol-1-yl)ethyl)quinazolin-4-amine and (7-methylimidazo[1,2-a]pyridin-6-yl)boronic acid according to the procedure described for the preparation of compound 8. Yield 22%. Mp 196-198° C. TLC $R_f$ 0.58 (CHCl$_3$-MeOH, 90:10), $^1$H NMR (400 MHz, DMSO-d$_6$) δ 9.13 (s, 1H), 8.60-8.50 (m, 1H), 8.24-8.11 (m, 1H), 7.99-7.92 (m, 1H), 7.84-7.72 (m, 2H), 7.57 (d, J=1.2 Hz, 1H), 7.51 (ddd, J=8.2, 6.5, 1.8 Hz, 1H), 7.47-7.43 (m, 1H), 7.39-7.24 (m, 5H), 6.98 (t, J=2.1 Hz, 2H), 6.02 (t, J=2.1 Hz, 2H), 5.79 (t, J=7.2 Hz, 1H), 4.34 (t, J=6.5 Hz, 2H), 2.68 (d, J=1.1 Hz, 3H). HRMS m/z calcd for C$_{28}$H$_{24}$N$_6$+H$^+$ [M+H$^+$]: 445.2135, found: 445.2144. HPLC: 97% ($t_R$=6.1 min).

ggggggg. Synthesis of 2-(6,7-Dihydro-1H-Pyrrolo [3,2-C]Pyridin-5(4H)-yl)-N-(2,2-Diphenylethyl) Quinazolin-4-Amine (163)

A solutions of 2-chloro-N-(2,2-diphenylethyl)quinazolin-4-amine (0.125 g, 0.347 mmol) and 4,5,6,7-tetrahydro-1H-pyrrolo[3,2-c]pyridine (0.042 g, 0.347 mmol) in ethanol (5 mL) was refluxed overnight. The solvent was removed under reduced pressure and the residue was purified by chromatography over a column of silica gel using CHCl$_3$-MeOH (95:5). Yield 22%. Mp 166-168° C. TLC $R_f$ 0.58 (CHCl$_3$-MeOH, 90:10). $^1$H NMR (400 MHz, DMSO-d$_6$) δ 10.43 (d, J=2.7 Hz, 1H). 8.16-7.66 (m, 2H), 7.61-6.82 (m, 13H), 6.59 (t, J=2.6 Hz, 1H), 5.86 (t, J=2.5 Hz, 1H), 4.95-4.46 (m, 3H), 4.31-3.91 (m, 4H), 2.70 (t, J=5.8 Hz, 2H). HRMS m/z calcd for C$_{29}$H$_{27}$N$_5$+H$^+$ [M+H$^+$]: 446.2339, found: 446.2339. HPLC: 98% ($t_R$=6.2 min).

hhhhhhh. Synthesis of N-(2,2-Diphenylpropyl)-2-(Imidazo[1,2-A]Pyridin-6-yl)Quinazolin-4-Amine (164)

This compound was prepared from 2-chloro-N-(2,2-diphenylpropyl)quinazolin-4-amine and imidazo[1,2-a]pyridin-6-ylboronic acid according to the procedure described for the preparation of compound 8. Yield 24%. Mp 107-109° C. TLC $R_f$ 0.58 (CHCl$_3$-MeOH, 90:10). $^1$H NMR (400 MHz, DMSO-d$_6$) δ 9.49 (dd, J=1.8, 0.9 Hz, 1H), 8.33-8.18 (m, 2H), 8.17-8.02 (m, 2H), 7.81-7.67 (m, 2H), 7.67-7.51 (m, 2H), 7.43 (ddd, J=8.2, 6.3, 2.0 Hz, 1H), 7.30-7.19 (m, 4H), 7.18-7.10 (m, 1H), 4.16 (dt, J=13.3, 5.6 Hz, 1H), 3.97 (ddd, J=13.2, 8.4, 6.0 Hz, 1H), 3.17-2.90 (m, 1H), 2.08 (d, J=6.8 Hz, 1H), 1.07 (d, J=6.6 Hz, 3H), 0.79 (d, J=6.7 Hz, 3H).

HRMS m/z calcd for $C_{30}H_{25}N_5+H^+$ [M+H]$^+$ 456.2183, found: 456.2182. HPLC: 99% ($t_R$=6.7 min).

iiiiiii. Synthesis of N-(1,2-Diphenylethyl)-2-(Imidazo[1,2-A]pyridin-6-yl)Quinazolin-4-Amine (165)

This compound was prepared from 2-chloro-N-(1,2-diphenylethyl)quinazolin-4-amine and imidazo[1,2-a]pyridin-6-ylboronic acid according to the procedure described for the preparation of compound 8. Yield 42%. Mp 203-204° C. TLC R$_f$ 0.56 (CHCl$_3$-MeOH, 90:10), $^1$H NMR (400 MHz, DMSO-d$_6$) δ 9.44 (dd, J=1.7, 1.0 Hz, 1H), 8.67 (d, J=8.0 Hz, 1H), 8.50-8.37 (m, 1H), 8.25-8.11 (m, 2H), 7.85-7.46 (m, 8H), 7.45-7.03 (m, 7H), 5.89 (ddd, J=9.8, 7.8, 5.4 Hz, 1H), 3.45 (dd, J=13.9, 9.9 Hz, 1H), 3.24 (dd, J=13.9, 5.5 Hz, 1H). HRMS m/z calcd for $C_{29}H_{23}N_5+H^+$ [M+H]$^+$ 442.2026, found: 442.2028. HPLC: 99% ($t_R$=6.4 min).

jjjjjjj. Synthesis of N-(1,3-Diphenylpropyl)-2-(Imidazo[1,2-A]Pyridin-6-yl)Quinazolin-4-Amine (166)

This compound was prepared from 2-chloro-N-(1,3-diphenylpropyl)quinazolin-4-amine and imidazo[1,2-a]pyridin-6-ylboronic acid according to the procedure described for the preparation of compound 8. Yield 55%. Mp 190-192° C. TLC R$_f$ 0.60 (CHCl$_3$-MeOH, 90:10), $^1$H NMR (400 MHz, DMSO-d$_6$) δ 9.40 (dd, J=1.8, 0.9 Hz, 1H), 8.66 (d, J=7.9 Hz, 1H), 8.58-8.48 (m, 1H), 8.21-8.08 (m, 2H), 7.85-7.72 (m, 2H), 7.67-7.50 (m, 5H), 7.44-7.12 (m, 8H), 5.67 (ddd, J=9.6, 8.2, 5.7 Hz, 1H), 2.86 (ddd, J=14.5, 9.8, 5.2 Hz, 1H), 2.68 (ddd, J=13.8, 9.5, 6.3 Hz, 1H), 2.44 (dp, J=14.6, 5.3, 4.7 Hz, 1H), 2.30-2.16 (m, 1H). HRMS m/z calcd for $C_{30}H_{25}N_5+H^+$ [M+H]$^+$ 456.2182, found: 456.2179. HPLC: 100% ($t_R$=6.6 min).

kkkkkkk. Synthesis of N-(1,3-Diphenylpropyl)-2-(7-Methylimidazo[1,2-A]Pyridin-6-yl)Quinazolin-4-Amine (167)

This compound was prepared from 2-chloro-N-(1,3-diphenylpropyl)quinazolin-4-amine and (7-methylimidazo[1,2-a]pyridin-6-yl)boronic acid according to the procedure described for the preparation of compound 8. Yield 38%. Mp 119-120° C. TLC R$_f$ 0.49 (CHCl$_3$-MeOH, 90:10). $^1$H NMR (400 MHz, DMSO-d$_6$) δ 8.83 (s, 1H), 8.69-8.48 (m, 2H), 8.38-8.24 (m, 1H), 7.92 (dd, J=1.3, 0.7 Hz, 1H), 7.87-7.68 (m, 2H), 7.64-7.52 (m, 2H), 7.50-7.07 (m, 12H), 5.48 (ddd, J=9.1, 6.9, 5.0 Hz, 1H), 2.82 (ddd, J=14.4, 9.4, 5.1 Hz, 1H), 2.76-2.59 (m, 1H), 2.47-2.42 (m, 3H). HRMS m/z calcd for $C_{31}H_{27}N_5+H^+$ [M+H]$^+$ 470.2339, found: 470.2339. HPLC: 95% ($t_R$=6.6 min).

lllllll. Synthesis of 2-(Imidazo[1,2-A]Pyridin-6-yl)-N-(3-Methyl-2-Phenylbutyl)Quinazolin-4-Amine (168)

This compound was prepared from 2-chloro-N-(3-methyl-2-phenylbutyl)quinazolin-4-amine and imidazo[1,2-a]pyridin-6-ylboronic acid according to the procedure described for the preparation of compound 8. Yield 67%. Mp 195-196° C.; TLC R$_f$ 0.59 (CHCl$_3$-MeOH, 90:10), $^1$H NMR (400 MHz, DMSO-d$_6$) δ 9.49 (dd, J=1.8, 1.0 Hz, 1H), 8.36-8.20 (m, 2H), 8.16-8.07 (m, 2H), 7.79-7.50 (m, 4H), 7.43 (ddd, J=8.3, 6.2, 2.0 Hz, 1H), 7.31-7.20 (m, 4H), 7.21-7.10 (m, 1H), 4.16 (dt, J=13.3, 5.6 Hz, 1H), 3.97 (ddd, J=13.2, 8.4, 6.0 Hz, 1H), 3.09-2.99 (m, 1H), 2.07 (hept, J=7.0 Hz, 1H), 1.07 (d, J=6.7 Hz, 3H), 0.79 (d, J=6.7 Hz, 3H). HRMS m/z calcd for $C_{26}H_{25}N_5+H^+$ [M+H]$^+$ 408.2182, found: 408.2178. HPLC: 98% ($t_R$=6.4 min).

mmmmmmm. Synthesis of N-(3-Methyl-2-Phenylbutyl)-2-(7-Methylimidazo[1,2-A]Pyridin-6-yl)Quinazolin-4-Amine (169)

This compound was prepared from 2-chloro-N-(3-methyl-2-phenylbutyl)quinazolin-4-amine and (7-methylimidazo[1,2-a]pyridin-6-yl)boronic acid according to the procedure described for the preparation of compound 8. Yield 25%. Mp 115-118° C. TLC R$_f$ 0.62 (CHCl$_3$-MeOH, 90:10), $^1$H NMR (400 MHz, DMSO-d$_6$) δ 9.02 (s, 1H), 8.31 (d, J=0.5 Hz, 1H), 8.21-8.07 (m, 2H), 7.97 (d, J=1.2 Hz, 1H), 7.79-7.65 (m, 2H), 7.55 (d, J=1.2 Hz, 1H), 7.49-7.39 (m, 2H), 7.33-7.10 (m, 4H), 4.06 (dt, J=11.7, 5.7 Hz, 1H), 3.86 (ddd, J=13.8, 8.7, 6.2 Hz, 1H), 3.03 (q, J=7.0 Hz, 1H), 2.71-2.62 (m, 3H), 2.03 (dt, J=13.7, 6.8 Hz, 1H), 0.99 (d, J=6.7 Hz, 3H), 0.75 (d, J=6.7 Hz, 3H). HRMS m/z calcd for $C_{27}H_{27}N_5+H^+$ [M+H]$^+$ 422.2339, found: 422.2334. HPLC: 98% ($t_R$=6.2 min).

nnnnnnn. Synthesis of (1R,2S)—N,N-Diethyl-2-(((2-(Imidazo[1,2-A]Pyridin-6-yl)Quinazolin-4-yl)Amino)Methyl)-1-Phenylcyclopropanecarboxamide (170)

This compound was prepared from (1R)-2-(((2-chloroquinazolin-4-yl)amino)methyl)-N,N-diethyl-1-phenylcyclopropanecarboxamide and imidazo[1,2-a]pyridin-6-ylboronic acid according to the procedure described for the preparation of compound 8. Yield 28%. Mp 221-223° C. TLC R$_f$ 0.52 (CHCl$_3$-MeOH, 90:10). $^1$H NMR (400 MHz, DMSO-d$_6$) δ 9.64 (dd, J=1.7, 0.9 Hz, 1H), 8.61 (t, J=5.4 Hz, 1H), 8.34-8.18 (m, 2H), 8.13 (dd, J=1.3, 0.7 Hz, 1H), 7.85-7.72 (m, 2H), 7.72-7.59 (m, 1H), 7.53 (ddd, J=8.2, 6.2, 1.9 Hz, 1H), 7.39-7.18 (m, 5H), 3.89-3.45 (m, 4H), 3.36-3.06 (m, 3H), 2.37 (td, J=8.7, 4.3 Hz, 1H), 1.71 (dd, J=6.3, 4.6 Hz, 1H), 1.09-0.92 (m, 4H), 0.56 (q, J=6.7 Hz, 3H). HRMS m/z calcd for $C_{30}H_{30}N_6O+H^+$ [M+H]$^+$ 491.2553, found: 491.2554. HPLC: 96% ($t_R$=6.3 min).

ooooooo. Synthesis of (1R,2S)—N,N-Diethyl-2-(((2-(7-Methylimidazo[1,2-A]pyridin-6-yl)Quinazolin-4-yl)Amino)Methyl)-1-Phenylcyclopropanecarboxamide (171)

This compound was prepared from (1R)-2-(((2-chloroquinazolin-4-yl)amino)methyl)-N,N-diethyl-1-phenylcyclopropanecarboxamide and (7-methylimidazo[1,2-a]pyridin-6-yl)boronic acid according to the procedure described for the preparation of compound 8. Yield 14%. Mp 225-228° C. TLC R$_f$ 0.52 (CHCl$_3$-MeOH, 90:10), $^1$H NMR (400 MHz, DMSO-d$_6$) δ 9.14 (s, 1H), 8.55 (t, J=5.4 Hz, 1H), 8.31 (d, J=0.6 Hz, 1H), 8.29-8.22 (m, 1H), 7.99 (t, J=1.0 Hz, 1H), 7.85-7.72 (m, 2H), 7.60-7.49 (m, 2H), 7.44 (q, J=1.0 Hz, 1H), 7.33 (dd, J=8.4, 6.9 Hz, 2H), 7.23 (dt, J=7.6, 1.9 Hz, 3H), 3.88 (dt, J=13.8, 5.5 Hz, 1H), 3.59 (dd, J=14.3, 7.1 Hz, 1H), 3.45 (tt, J=13.3, 6.3 Hz, 2H), 3.10 (dq, J=14.6, 7.1 Hz, 2H), 2.69 (d, J=1.1 Hz, 3H), 1.58 (d, J=1.6 Hz, 1H), 1.11-0.87 (m, 4H), 0.53 (t, J=7.0 Hz, 3H). HRMS m/z calcd for $C_{31}H_{32}N_6O+H^+$ [M+H]$^+$ 505.2710, found: 505.2711. HPLC: 99% ($t_R$=6.2 min).

ppppppp. Synthesis of N-(1,2-Diphenylethyl)-2-(7-Methylimidazo[1,2-A]Pyridin-6-yl)Quinazolin-4-Amine (172)

This compound was prepared from 2-chloro-N-(1,2-diphenylethyl)quinazolin-4-amine and (7-methylimidazo[1,2- a]pyridin-6-yl)boronic acid according to the procedure described for the preparation of compound 8. Yield 21%. Mp 87-89° C. TLC $R_f$ 0.60 (CHCl$_3$-MeOH, 90:10), $^1$H NMR (400 MHz, DMSO-d$_6$) δ 8.82 (s, 1H), 8.61 (d, J=8.2 Hz, 1H), 8.53-8.41 (m, 1H), 8.31 (s, 1H), 7.93 (s, 1H), 7.78 (dd, J=6.9, 1.3 Hz, 1H), 7.70 (dd, J=8.4, 1.2 Hz, 1H), 7.61-7.48 (m, 5H), 7.44-7.28 (m, 5H), 7.21 (dd, J=8.2, 6.8 Hz, 3H), 7.14-7.05 (m, 1H), 5.93-5.49 (m, 1H), 2.42 (d, J=1.0 Hz, 3H). HRMS m/z calcd for C$_{30}$H$_{25}$N$_5$+H$^+$ [M+H$^+$]: 456.2182, found: 456.2180. HPLC: 99% (t$_R$=6.3 min).

qqqqqqq. Synthesis of N-(2,2-Di(pyridin-4-yl) Ethyl)-2-(1H-Indol-5-yl)Quinazolin-4-Amine (173)

This compound was prepared from 2-chloro-N-(2,2-di (pyridin-4-yl)ethyl)quinazolin-4-amine and (1H-indol-5-yl) boronic acid according to the procedure described for the preparation of compound 8. Yield 37%. Mp 201-202° C. TLC $R_f$ 0.32 (CHCl$_3$-MeOH, 90:10). $^1$H NMR (400 MHz, CDCl$_3$) δ 8.92 (q, J=1.0 Hz, 1H), 8.63 (dt, J=4.4, 1.3 Hz, 4H), 8.49 (dt, J=8.6, 1.3 Hz, 1H), 8.25 (s, 1H), 7.99-7.89 (m, 1H), 7.72 (ddt, J=8.3, 7.0, 1.3 Hz, 1H), 7.55-7.47 (m, 1H), 7.44 (d, J=8.2 Hz, 1H), 7.39-7.30 (m, 1H), 7.31-7.23 (m, 4H), 6.66 (ddt, J=3.1, 2.1, 1.0 Hz, 1H), 5.64 (t, J=5.9 Hz, 1H), 5.45-5.15 (m, 1H), 4.77 (t, J=7.4 Hz, 1H), 4.60-4.27 (m, 2H). HRMS m/z calcd for C$_{28}$H$_{22}$N$_6$+H$^+$ [M+H]$^+$ 443.1978, found: 443.1968. HPLC: 100% (t$_R$=5.1 min).

rrrrrrr. Synthesis of N-(2,2-Di(pyridin-4-yl)Ethyl)-2-(6,7-Dihydro-1H-Pyrrolo[3,2-C]Pyridin-5(4H)-yl) Quinazolin-4-Amine (174)

A mixture of 2-chloro-N-(2,2-di(pyridin-4-yl)ethyl)quinazolin-4-amine (0.178 g, 0.499 mmol) and 4,5,6,7-tetrahydro-1H-pyrrolo[3,2-c]pyridine (0.061 g, 0.499 mmol) in ethanol (5 mL) was refluxed overnight. The reaction mixture was cooled and the solid material obtained was filtered, washed with water. The crude product was recrystallized from ethanol to obtain the pure product. Yield 44%. Mp 224-226° C. TLC $R_f$ 0.16 (CHCl$_3$-MeOH, 90:10), $^1$H NMR (400 MHz, DMSO-d$_6$) δ 10.42 (s, 1H), 8.54-8.46 (m, 4H), 8.14 (s, 1H), 7.86-7.79 (m, 1H), 7.51-7.34 (m, 5H), 7.27 (d, J=8.3 Hz, 1H), 7.03-6.94 (m, 1H), 6.58 (t, J=2.6 Hz, 1H), 5.84 (t, J=2.5 Hz, 1H), 4.73 (d, J=12.2 Hz, 3H), 4.20-4.07 (m, 4H), 2.68 (dd, J=6.4, 4.7 Hz, 2H). HRMS m/z calcd for C$_{27}$H$_{25}$N$_7$+H$^+$ [M+H]$^+$ 448.22442, found: 448.2238. HPLC: 97% (t$_R$=4.6 min).

sssssss. Synthesis of 2-(Imidazo[1,2-A]Pyridin-6-yl)-N-(2-Phenoxy-2-Phenylethyl)Quinazolin-4-Amine (175)

This compound was prepared from 2-chloro-N-(2-phenoxy-2-phenylethyl)quinazolin-4-amine and imidazo[1,2-a] pyridin-6-ylboronic acid according to the procedure described for the preparation of compound 8. Yield 60%. Mp 286-288° C. TLC $R_f$ 0.59 (CHCl$_3$-MeOH, 90:10). $^1$H NMR (400 MHz, DMSO-d$_6$) δ 9.51 (dd, J=1.7, 1.0 Hz, 1H), 8.74 (t, J=5.6 Hz, 1H), 8.28 (ddd, J=11.2, 8.8, 1.3 Hz, 2H), 8.07 (dd, J=1.3, 0.7 Hz, 1H), 7.84-7.72 (m, 2H), 7.70-7.61 (m, 2H), 7.60-7.53 (m, 2H), 7.50 (ddd, J=8.2, 6.1, 2.1 Hz, 1H), 7.44-7.34 (m, 2H), 7.32-7.23 (m, 1H), 7.20-7.09 (m, 2H), 6.96-6.88 (m, 2H), 6.83 (tt, J=7.3, 1.1 Hz, 1H), 5.77 (dd, J=7.7, 4.5 Hz, 1H), 4.25-4.15 (m, 1H), 4.06 (ddd, J=13.4, 7.8, 5.4 Hz, 1H). HRMS m/z calcd for C$_{29}$H$_{23}$N$_5$ $_{O+H}{}^+$ [M°H]$^+$ 458.1975, found: 458.1968. HPLC: 99% (t$_R$=6.5 min).

tttttttt. Synthesis of N-(2,2-Di(Pyridin-4-yl)Ethyl)-2-(Imidazo[1,2-A]Pyrimidin-6-yl)Quinazolin-4-Amine (176)

i. Step 1

2-Chloro-N-(2,2-di(pyridin-4-yl)ethyl)quinazolin-4-amine was reacted with 5-(4,4,5,5-tetramethyl-1,3,2-dioxaborolan-2-yl)pyrimidin-2-amine according to the procedure described for the preparation of compound 8 to obtain 2-(2-aminopyrimidin-5-yl)-N-(2,2-di(pyridin-4-yl)ethyl) quinazolin-4-amine. Yield 46%. TLC $R_f$ 0.45 (CHCl$_3$-MeOH, 90:10). $^1$H NMR (400 MHz, DMSO-d$_6$) δ 8.78 (t, J=5.5 Hz, 1H), 8.13 (ddd, J=8.6, 1.3, 0.6 Hz, 1H), 7.76 (ddd, J=8.3, 7.0, 1.2 Hz, 1H), 7.60 (ddd, J=8.3, 1.3, 0.6 Hz, 1H), 7.47 (ddd, J=8.2, 7.0, 1.2 Hz, 1H), 7.36-7.24 (m, 8H), 7.22-7.15 (m, 3H), 4.60 (t, J=7.8 Hz, 1H), 4.15 (dd, J=7.8, 5.4 Hz, 2H). HRMS m/z calcd for C$_{24}$H$_{20}$N$_8$+H$^+$ [M+H]$^+$ 421.1883, found: 421.1873. HPLC: 100% (t$_R$=4.0 min).

ii. Step 2

A solution of the above intermediate (0.05 g, 0.119 mmol) and 2-chloroacetaldehyde (0.056 g, 0.357 mmol) in ethanol (3 mL) was refluxed overnight. The reaction mixture was cooled and concentrated under reduced pressure. The residue obtained was purified over a column of silica gel using CHCl$_3$-MeOH, 90:10. Yield 47%. Mp 256-258° C. TLC $R_f$ 0.16 (CHCl$_3$MeOH, 90:10). $^1$H NMR (400 MHz, DMSO-d$_6$) δ 9.83 (dd, J=2.4, 0.5 Hz, 1H), 9.50 (dd, J=2.4, 0.4 Hz, 1H), 8.64 (s, 1H), 8.54-8.41 (m, 5H), 8.23-8.03 (m, 2H), 7.84-7.71 (m, 2H), 7.54-7.39 (m, 5H), 4.74 (d, J=7.5 Hz, 1H), 4.41 (dd, =7.6, 5.5 Hz, 2H). HRMS m/z calcd for C$_{26}$H$_{20}$N$_8$+H$^+$ [M+H]$^+$ 445.1883, found: 445.1885. HPLC: 100% (t$_R$=6.5 min).

uuuuuuu. Synthesis of 2-(7-Methylimidazo[1,2-A] Pyridin-6-yl)-N-(2-Phenoxy-2-Phenylethyl)Quinazolin-4-Amine (177)

This compound was prepared from 2-chloro-N-(2-phenoxy-2-phenylethyl)quinazolin-4-amine and (7-methylimidazo[1,2-a]pyridin-6-yl)boronic acid according to the procedure described for the preparation of compound 8. Yield 15%. Mp 243-246° C. TLC $R_f$ 0.38 (CHCl$_3$-MeOH, 90:10). $^1$H NMR (400 MHz, DMSO-d$_6$) δ 9.08 (d, J=0.7 Hz, 1H), 8.71 (t, J=5.7 Hz, 1H), 8.34-8.26 (m, 1H), 7.95 (t, J=1.0 Hz, 1H), 7.85-7.72 (m, 2H), 7.59-7.43 (m, 5H), 7.40-7.23 (m, 3H), 7.17-7.07 (m, 2H), 6.95-6.86 (m, 2H), 6.81 (tt, J=7.3, 1.0 Hz, 1H), 5.71 (dd, J=7.1, 5.3 Hz, 1H), 4.12-3.96 (m, 2H), 2.67 (d, J=1.1 Hz, 3H). HRMS m/z calcd for C$_{30}$H$_{25}$N$_5$O+H$^+$ [M+H]$^+$ 472.2131, found: 472.2126. HPLC: 100% (t$_R$=4.6 min).

vvvvvvv. Synthesis of N-(2,2-Diphenylpropyl)-2-(7-Methylimidazo[1,2-A]Pyridin-6-yl)Quinazolin-4-Amine (178)

This compound was prepared from 2-chloro-N-(2,2-diphenylpropyl)quinazolin-4-amine and (7-methylimidazo[1, 2-a]pyridin-6-yl)boronic acid according to the procedure described for the preparation of compound 8. Yield 33%. Mp 275-277° C. TLC $R_f$ 0.42 (CHCl$_3$-MeOH, 90:10). $^1$H NMR (400 MHz, DMSO-d$_6$) δ 8.90 (s, 1H), 8.43-8.38 (m, 1H), 8.21-8.11 (m, 1H), 8.04-7.97 (m, 1H), 7.80-7.67 (m, 3H), 7.64 (t, J=6.0 Hz, 1H), 7.54 (d, J=1.2 Hz, 1H), 7.50-7.39 (m, 3H), 7.35-7.19 (m, 6H), 7.18-7.10 (m, 2H), 4.45 (d, J=5.9 Hz, 2H), 2.61 (d, J=1.1 Hz, 3H), 1.82 (s, 3H). HRMS m/z calcd for $C_{31}H_{27}N_5+H^+$ [M+H]$^+$ 470.2339, found: 470.2336. HPLC: 100% ($t_R$=6.5 min).

wwwwwww. Synthesis of N-(2-Cyclopropyl-2-Phenylethyl)-2-(7-Methylimidazo[1,2-A]Pyridin-6-yl)Quinazolin-4-Amine (179)

This compound was prepared from 2-chloro-N-(2-cyclopropyl-2-phenylethyl)quinazolin-4-amine and (7-methylimidazo[1,2-a]pyridin-6-yl)boronic acid according to the procedure described for the preparation of compound 8. Yield 31%. Mp 236-238° C.; TLC $R_f$ 0.57 (CHCl$_3$-MeOH, 85:15), $^1$H NMR (400 MHz, DMSO-d$_6$) δ 9.02 (s, 1H), 8.36 (t, J=5.7 Hz, 1H), 8.20 (dd, J=8.3, 1.1 Hz, 1H), 8.01-7.96 (m, 1H), 7.83-7.68 (m, 2H), 7.59-7.42 (m, 4H), 7.38-7.23 (m, 5H), 7.22-7.13 (m, 1H), 4.06-3.87 (m, 2H), 2.66 (d, J=1.0 Hz, 3H), 1.20-1.07 (m, 1H), 0.56 (td, J=8.3, 4.1 Hz, 1H), 0.29 (dtd, J=23.1, 9.8, 9.1, 4.5 Hz, 2H). HRMS m/z calcd for $C_{27}H_{25}N_6 5+H^+$ [M+H$^+$]: 420.21827, found: 420.21922. HPLC: 97.33% ($t_R$=5.9 min).

xxxxxxx. Synthesis of 2-(7-Methylimidazo[1,2-A]Pyridin-6-yl)-N-(2-(Pyridin-3-yl)Ethyl)Quinazolin-4-Amine (180)

This compound was prepared from (7-methylimidazo[1,2-a]pyridin-6-yl)boronic acid and 2-chloro-N-(2-(pyridin-4-yl)ethyl)quinazolin-4-amine according to the procedure described for the preparation of compound 8. Yield 48%. Mp 241-244° C. TLC $R_f$ 0.25 (CHCl$_3$-MeOH, 90:10), $^1$H NMR (400 MHz, DMSO-d$_6$) δ 9.06-9.01 (m, 1H), 8.53-8.45 (m, 2H), 8.43-8.37 (m, 1H), 8.27-8.22 (m, 1H), 8.00 (t, J=0.9 Hz, 1H), 7.83-7.72 (m, 2H), 7.71-7.65 (m, 1H), 7.57-7.49 (m, 2H), 7.44 (q, J=0.9 Hz, 1H), 7.29 (ddd, J=7.8, 4.8, 0.9 Hz, 1H), 3.93-3.85 (m, 2H), 3.05 (t, J=7.1 Hz, 2H), 2.65 (d, J=1.1 Hz, 3H). HRMS m/z calcd for $C_{23}H_{20}N_6+H^+$ [M+H$^+$]: 381.18222, found: 381.18190. HPLC: 100% ($t_R$=1.99 min).

yyyyyyy. Synthesis of 2-(7-Methylimidazo[1,2-A]Pyridin-6-yl)-N-(2-(Pyridin-4-yl)Ethyl)Quinazolin-4-Amine (181)

This compound was prepared from 2-chloro-N-(2-(pyridin-4-yl)ethyl)quinazolin-4-amine and (7-methylimidazo[1,2-a]pyridin-6-yl)boronic acid according to the procedure described for the preparation of compound 8. Yield 43%. Mp 234-236° C. TLC $R_f$ 0.25 (CHCl$_3$-MeOH, 85:15). $^1$H NMR (400 MHz, DMSO-d$_6$) δ 9.08-9.02 (m, 1H), 8.47-8.43 (m, 2H), 8.27-8.21 (m, 1H), 8.01 (p, J=1.0 Hz, 1H), 7.83-7.72 (m, 3H), 7.55 (q, J=1.0 Hz, 1H), 7.46-7.43 (m, 2H), 7.31 (ddd, J=4.5, 1.8, 0.8 Hz, 2H), 3.90 (q, J=6.8 Hz, 2H), 3.06 (t, J=7.1 Hz, 2H), 2.66 (q, J=1.0 Hz, 3H). HRMS m/z calcd for $C_{23}H_{20}N_6+H^+$ [M+H]$^+$, 381.18222, found: 381.18247. HPLC: 100% ($t_R$=2.754 min).

zzzzzzz. Synthesis of N-(2-Benzyl-3-Phenylpropyl)-2-(7-Methylimidazo[1,2-A]Pyridin-6-yl)Quinazolin-4-Amine (182)

This compound was prepared from N-(2-benzyl-3-phenylpropyl)-2-chloroquinazolin-4-amine and (7-methylimidazo[1,2-a]pyridin-6-yl)boronic acid according to the procedure described for the preparation of compound 8. Yield 37%. Mp 181-184° C. TLC $R_f$ 0.64 (CHCl$_3$-MeOH, 85:15), $^1$H NMR (400 MHz, DMSO-d$_6$) δ 8.91 (s, 1H), 8.30-8.20 (m, 2H), 7.97 (dd, J=1.3, 0.7 Hz, 1H), 7.82-7.67 (m, 2H), 7.55 (dd, J=1.2, 0.6 Hz, 1H), 7.51 (ddd, J=8.3, 6.7, 1.4 Hz, 1H), 7.44-7.38 (m, 1H), 7.22-7.13 (m, 8H), 7.10 (ddd, J=8.7, 5.6, 2.4 Hz, 2H), 3.57 (t, J=5.6 Hz, 2H), 3.40 (s, 1H), 3.26-3.24 (m, 2H), 2.75-2.64 (m, 2H), 2.64-2.55 (m, 2H), 2.45 (s, 1H). HRMS m/z calcd for $C_{32}H_{29}N_5+H^+$ [M+H$^+$]: 484.24957, found: 484.24958. HPLC: 97.3% ($t_R$=6.406 min).

aaaaaaaa. Synthesis of (7-Methylimidazo[1,2-A]Pyridin-6-yl)-N-(2-(Pyridin-2-yl)Ethyl)Quinazolin-4-Amine (183)

This compound was prepared from 2-chloro-N-(2-(pyridin-2-yl)ethyl)quinazolin-4-amine and (7-methylimidazo[1,2-a]pyridin-6-yl)boronic acid according to the procedure described for the preparation of compound 8. Yield 47%. Mp 224-228° C. TLC $R_f$ 0.43 (CHCl$_3$-MeOH, 85:15). $^1$H NMR (400 MHz, DMSO-d$_6$) δ 9.08 (s, 1H), 8.55-8.45 (m, 2H), 8.28-8.20 (m, 1H), 8.00 (t, J=0.9 Hz, 1H), 7.85-7.64 (m, 3H), 7.57-7.47 (m, 2H), 7.44 (q, J=0.9 Hz, 1H), 7.31 (dt, J=7.8, 1.1 Hz, 1H), 7.21 (ddd, J=7.6, 4.8, 1.2 Hz, 1H), 4.05-3.93 (m, 2H), 3.18 (dd, J=8.1, 6.6 Hz, 2H), 2.67 (d, J=1.1 Hz, 3H). HRMS m/z calcd for $C_{23}H_{20}N_6+H^+$ [M+H$^+$]: 381.18222, found: 381.18292. HPLC: 100% ($t_R$=2.754 min).

bbbbbbbb. Synthesis of 2-(7-Methylimidazo[1,2-A]Pyridin-6-yl)-N-(2-Phenylpropyl)Quinazolin-4-Amine (184)

This compound was prepared from 2-chloro-N-(2-phenylpropyl)quinazolin-4-amine and (7-methylimidazo[1,2-a]pyridin-6-yl)boronic acid according to the procedure described for the preparation of compound 8. Yield 51%. Mp 208-212° C. TLC $R_f$ 0.57 (CHCl$_3$-MeOH, 85:15), $^1$H NMR (400 MHz, DMSO-d$_6$) δ 9.07-8.99 (m, 1H), 8.42 (t, J=5.7 Hz, 1H), 8.25 (ddd, J=8.5, 1.3, 0.6 Hz, 1H), 8.00 (dd, J=1.3, 0.7 Hz, 1H), 7.82-7.69 (m, 2H), 7.55 (d, J=1.2 Hz, 1H), 7.51 (ddd, J=8.2, 6.7, 1.5 Hz, 1H), 7.45 (dd, J=1.7, 0.9 Hz, 1H), 7.35-7.25 (m, 5H), 7.22-7.13 (m, 1H), 3.91-3.81 (m, 1H), 3.69 (ddd, J=13.2, 7.9, 5.5 Hz, 1H), 2.67 (d, J=1.1 Hz, 3H), 1.31 (d, J=6.9 Hz, 3H). HRMS m/z calcd for $C_{25}H_{23}N_5+H^+$ [M+H$^+$]: 394.2062, found: 394.2038. HPLC: 100% ($t_R$=5.684 min).

cccccccc. Synthesis of 2-(7-Methylimidazo[1,2-A]Pyridin-6-yl)-N-(2-(Pyridin-4-yl)-2-(1H-Pyrrol-2-yl)Ethyl)Quinazolin-4-Amine (185)

This compound was prepared from 2-chloro-N-(2-(pyridin-4-yl)-2-(1H-pyrrol-2-yl)ethyl)quinazolin-4-amine and (7-methylimidazo[1,2-a]pyridin-6-yl)boronic acid id according to the procedure described for the preparation of compound 8. Yield 21%. Mp 214-216° C. TLC $R_f$ 0.23 (CHCl$_3$-MeOH, 85:15). $^1$H NMR (400 MHz, DMSO-d$_6$) δ 10.72 (s, 1H), 9.06 (s, 1H), 8.53-8.35 (m, 2H), 8.31 (s, 1H), 8.20-8.07 (m, 1H), 7.97 (t, J=1.0 Hz, 1H), 7.83-7.69 (m, 2H), 7.59-7.38 (m, 3H), 7.28-7.19 (m, 2H), 6.65 (td, J=2.6, 1.5 Hz, 1H), 6.10 (t, J=2.6 Hz, 1H), 5.98 (p, J=2.8 Hz, 1H), 4.71-4.57 (m, 1H), 4.15 (qq, J=13.7, 6.3 Hz, 2H), 2.69-2.60 (m, 3H). HRMS m/z calcd for $C_{27}H_{23}N_7+H^+$ [M+H$^+$]: 446.20877, found: 446.20824. HPLC: 100% ($t_R$=4.639 min).

dddddddd. Synthesis of (2-((2-(7-Methylimidazo[1,2-A]Pyridin-6-yl)Quinazolin-4-yl)Amino)-1-Phenylethanol (186)

This compound was prepared from 2-((2-chloroquinazolin-4-yl)amino)-1-phenylethanol and (7-methylimidazo[1,2- a]pyridin-6-yl)boronic acid according to the procedure described for the preparation of compound 8. Yield 23%. Mp 221-224° C. TLC $R_f$ 0.46 (CHCl$_3$-MeOH, 85:15). $^1$H NMR (400 MHz, DMSO-d$_6$) δ 9.04 (s, 1H), 8.51 (t, J=5.7 Hz, 1H), 8.32 (dd, J=8.1, 1.0 Hz, 1H), 7.99 (t, J=0.9 Hz, 1H), 7.84-7.71 (m, 2H), 7.58-7.38 (m, 5H), 7.37-7.19 (m, 3H), 5.62 (d, J=4.3 Hz, 1H), 5.01 (dt, J=8.4, 4.3 Hz, 1H), 3.96-3.85 (m, 1H), 3.61 (ddd, J=13.3, 8.2, 5.2 Hz, 1H), 2.66 (d, J=1.1 Hz, 3H). HRMS m/z calcd for $C_{24}H_{21}N_5O$+H$^+$ [M+H$^+$]: 396.18189, found: 396.18235. HPLC: 100% (t$_R$=5.08 min).

eeeeeeee. Synthesis of N-(2-Methoxy-2-phenylethyl)-2-(7-methylimidazo[1,2-a]pyridin-6-yl)quinazolin-4-amine (187)

This compound was prepared from 2-chloro-N-(2-methoxy-2-phenylethyl)quinazolin-4-amine and (7-methylimidazo[1,2-a]pyridin-6-yl)boronic acid according to the procedure described for the preparation of compound 8. Yield 25%. Mp 215-218° C. TLC $R_f$ 0.61 (CHCl$_3$-MeOH, 85:15. $^1$H NMR (400 MHz, DMSO-d$_6$) δ 9.05 (s, 1H), 8.57 (t, J=5.5 Hz, 1H), 8.36-8.27 (m, 1H), 8.02-7.94 (m, 1H), 7.83-7.70 (m, 2H), 7.58-7.49 (m, 2H), 7.47-7.42 (m, 1H), 7.37 (d, J=4.3 Hz, 4H), 7.35-7.25 (m, 1H), 4.64 (dd, J=8.0, 4.4 Hz, 1H), 3.87 (dt, J=13.5, 5.1 Hz, 1H), 3.76 (ddd, J=13.6, 8.1, 5.4 Hz, 1H), 3.18 (s, 3H), 2.66 (d, J=1.0 Hz, 3H). HRMS m/z calcd for $C_{25}H_{23}N_5O$+H$^+$ [M+H$^+$]: 410.19754, found: 410.19757. HPLC: 99.08% (t$_R$=5.6 min).

ffffffff. Synthesis of 2-(7-Methylimidazo[1,2-A]Pyridin-6-yl)-N-(2-Phenylbutyl)Quinazolin-4-Amine (188)

This compound was prepared from 2-chloro-N-(2-phenylbutyl)quinazolin-4-amine and (7-methylimidazo[1,2-a]pyridin-6-yl)boronic acid according to the procedure described for the preparation of compound 8. Yield 32%. Mp 232-234° C. TLC $R_f$ 0.61 (CHCl$_3$-MeOH, 85:15). $^1$H NMR (400 MHz, DMSO-d$_6$) δ 9.03 (s, 1H), 8.36 (t, J=5.6 Hz, 1H), 8.26-8.19 (m, 1H), 8.01-7.96 (m, 1H), 7.82-7.69 (m, 2H), 7.61-7.42 (m, 3H), 7.33-7.14 (m, 4H), 3.81 (t, J=6.4 Hz, 2H), 3.38-3.28 (m, 2H), 3.13-3.00 (m, 1H), 2.67 (d, J=1.0 Hz, 3H), 1.86 (dtd, J=14.6, 7.4, 4.8 Hz, 1H), 1.64 (ddt, J=17.1, 14.5, 7.4 Hz, 1H), 0.76 (t, J=7.3 Hz, 3H). HRMS m/z calcd for $C_{26}H_{25}N_5$+H$^+$[M+H$^+$]: 408.21827, found: 408.21925. HPLC: 100% (t$_R$=5.4 min).

gggggggg. Synthesis of N-(2,2-Diphenylethyl)-2-(Isoindolin-2-yl)Quinazolin-4-Amine (189)

A mixture of 2-chloro-N-(2,2-diphenylethyl)quinazolin-4-amine (0.36 g, 1.0 mmol) and isoindoline (0.119 g, 1.0 mmol) in ethanol (7 mL) was heated under reflux overnight. The reaction mixture was cooled and the solvent was removed under reduced pressure. The residue obtained was purified over a column of silica gel using CHCl$_3$-MeOH, 95:5 as the eluent. Yield 27%. Mp 293-295° C. TLC $R_f$ 0.83 (CHCl$_3$-MeOH, 90:10), $^1$H NMR (400 MHz, DMSO-d$_6$) δ 12.30 (s, 1H), 9.80 (t, J=5.6 Hz, 1H), 8.28 (dd, J=8.4, 1.3 Hz, 1H), 7.93 (dd, J=8.4, 1.1 Hz, 1H), 7.80 (ddd, J=8.3, 7.1, 1.2 Hz, 1H), 7.51-7.25 (m, 12H), 5.10 (s, 4H), 4.78 (t, J=7.7 Hz, 1H), 4.31 (dd, J=7.7, 5.4 Hz, 2H). HRMS m/z calcd for $C_{30}H_{26}N_4$+H$^+$ [M+H$^+$]: 443.22302, found: 443.22271. HPLC: 98% (t$_R$=7.1 min).

hhhhhhhh. Synthesis of 2-(3,4-Dihydro-1H-Pyrido[3,4-B]Indol-2(9H)-yl)-N-(2,2-Diphenylethyl)Quinazolin-4-Amine (190)

A mixture of 2-chloro-N-(2,2-diphenylethyl)quinazolin-4-amine (0.18 g, 0.5 mmol) and 2,3,4,9-tetrahydro-1H-pyrido[3,4-b]indole (0.086 g, 0.5 mmol) in ethanol (7 mL) was heated under reflux overnight. The reaction mixture was cooled and the solid material that separates was collected by filtration and washed with ethanol to give the pure product. Yield 44%. Mp 185-87° C. TLC $R_f$ 0.81 (CHCl$_3$-MeOH, 90:10), $^1$H NMR (400 MHz, DMSO-d$_6$) δ 12.24 (s, 1H), 11.10 (s, 1H), 8.18 (d, J=8.2 Hz, 1H), 7.80 (dd, J=16.2, 9.0 Hz, 2H), 7.52-7.44 (m, 1H), 7.44-7.35 (m, 6H), 7.28 (t, J=7.5 Hz, 4H), 7.22-7.14 (m, 2H), 7.09 (ddd, J=8.2, 7.1, 1.2 Hz, 1H), 7.01 (ddd, J=8.0, 7.1, 1.1 Hz, 1H), 5.16 (s, 2H), 4.66 (t, J=7.9 Hz, 1H), 4.29 (dt, J=14.8, 6.4 Hz, 4H), 2.93 (t, J=5.4 Hz, 2H). HRMS m/z calcd for $C_{33}H_{29}N_5$+H$^+$ [M+H$^+$]: 496.24957, found: 496.24913. HPLC: 100% (t$_R$=7.16 min).

iiiiiiii. Synthesis of 2-(3,4-Dihydro-1H-Pyrido[4,3-B]Indol-2(5H)-yl)-N-(2,2-Diphenylethyl)Quinazolin-4-Amine (191)

A mixture of 2-chloro-N-(2,2-diphenylethyl)quinazolin-4-amine (0.180 g, 0.5 mmol), 2,3,4,5-tetrahydro-1H-pyrido[4,3-b]indole (0.086 g, 0.5 mmol) in ethanol (7 mL) was heated under reflux overnight. The reaction mixture was cooled and the solvent was removed under reduced pressure. The residue obtained was purified over a column of silica gel using CHCl$_3$-MeOH, 95:5 as the eluent. Yield 0.088 g (36%). Mp 258-260° C. TLC $R_f$ 0.52 (CHCl$_3$-MeOH, 90:10). $^1$H NMR (400 MHz, DMSO-d$_6$) δ 12.35 (s, 1H), 11.08 (s, 1H), 8.29-8.07 (m, 1H), 7.92 (d, J=8.2 Hz, 1H), 7.79 (dd, J=8.5, 7.0 Hz, 1H), 7.43-7.38 (m, 5H), 7.37-7.25 (m, 5H), 7.25-7.19 (m, 3H), 7.07 (dd, J=8.0, 1.2 Hz, 1H), 7.03 (d, J=7.5 Hz, 1H), 5.13 (s, 2H), 4.69 (t, J=7.6 Hz, 1H), 4.31 (dt, J=24.1, 5.8 Hz, 4H), 3.04 (t, J=5.6 Hz, 2H). HRMS m/z calcd for $C_{33}H_{29}N_5$+H$^+$ [M+H$^+$]: 496.24957, found: 496.24924. HPLC: 100% (t$_R$=7.093 min).

jjjjjjjj. Synthesis of N1,N1-Dimethyl-N3-(2-(7-Methylimidazo[1,2-A]Pyridin-6-yl)Quinazolin-4-yl)-2-Phenylpropane-1,3-Diamine (192)

This compound was prepared from N1-(2-chloroquinazolin-4-yl)-N3,N3-dimethyl-2-phenylpropane-1,3-diamine and (7-methylimidazo[1,2-a]pyridin-6-yl)boronic acid according to the procedure described for the preparation of compound 8. Yield 28%. Mp 250-252° C. TLC $R_f$ 0.65 (CHCl$_3$-MeOH, 90:10). $^1$H NMR (400 MHz, DMSO-d$_6$) δ 8.99 (s, 1H), 8.54 (dd, J=6.2, 4.6 Hz, 1H), 7.98 (t, J=0.9 Hz, 1H), 7.83-7.69 (m, 2H), 7.58-7.41 (m, 3H), 7.32-7.12 (m, 6H), 3.93 (ddd, J=13.3, 6.6, 4.4 Hz, 1H), 3.80 (ddd, J=13.6, 8.1, 6.3 Hz, 1H), 3.54-3.22 (m, 1H), 2.78-2.67 (m, 1H), 2.64 (d, J=1.0 Hz, 3H), 2.47 (dd, J=12.1, 6.6 Hz, 1H), 2.17 (s, 6H). HRMS m/z calcd for $C_{27}H_{28}N_6$+H$^+$ [M+H$^+$]: 437.24482, found: 437.24427. HPLC: 95.8% (t$_R$=4.703 min).

kkkkkkkk. Synthesis of 2-(3,4-Dihydroisoquinolin-2(1H)-yl)-N-(2,2-Diphenylethyl)Quinazolin-4-Amine (193)

A mixture of 2-chloro-N-(2,2-diphenylethyl)quinazolin-4-amine (0.234 g, 0.65 mmol) and 1,2,3,4-tetrahydroisoquinoline (0.087 g, 0.65 mmol) in ethanol (7 mL) was heated under reflux overnight. The reaction mixture was cooled and the solid that separates was collected by filtration and washed with a few drops of ethanol to obtain the pure product. Yield 51%. Mp 250-253° C. TLC $R_f$ 0.52 (CHCl$_3$-MeOH, 90:10). $^1$H NMR (400 MHz, DMSO-d$_6$) δ 12.45 (s, 1H), 9.79 (d, J=7.3 Hz, 1H), 8.25 (dd, J=8.4, 1.3 Hz, 1H), 8.01 (d, J=8.4 Hz, 1H), 7.77 (ddd, J=8.4, 7.1, 1.2 Hz, 1H), 7.43-7.15 (m, 14H), 5.09 (s, 2H), 4.70 (t, J=7.6 Hz, 2H), 4.28 (dd, J=7.6, 5.4 Hz, 2H), 4.14 (t, J=5.9 Hz, 2H), 3.03 (t, J=6.0 Hz, 2H). HRMS m/z calcd for C$_{31}$H$_{28}$N$_4$+H$^+$ [M+H$^+$]: 457.23867, found: 457.23863. HPLC: 98.43% (t$_R$=7.117 min).

lllllll. Synthesis of N-(2-Cyclopentyl-2-Phenyl-ethyl)-2-(7-Methylimidazo[1,2-A]pyridin-6-yl)Qui-nazolin-4-Amine (194)

i. Step 1

2-Chloro-N-(2-cyclopentyl-2-phenylethyl)quinazolin-4-amine was coupled with 4-methyl-5-(4,4,5,5-tetramethyl-1,3,2-dioxaborolan-2-yl)pyridin-2-amine according to the procedure described for the preparation of compound 8 to obtain 2-(6-amino-4-methylpyridin-3-yl)-N-(2-cyclopentyl-2-phenylethyl)quinazolin-4-amine. Yield 37%. MS m/z 424 (M+H)$^+$.

ii. Step 2

To a solution of the above intermediate (90 mg, 0.212 mmol) in ethanol (5 mL) was added 2-chloroacetaldehyde (2 mL of 50% aqueous solution) and the mixture was heated under reflux overnight. The crude product obtained after removal of the solvent was purified by column chromatography over silica gel using CHCl$_3$-MeOH, 96:4 as the eluent. Yield 51%. Mp 106-108° C. TLC $R_f$ 0.52 (CHCl$_3$-MeOH, 90:10), $^1$H NMR (400 MHz, DMSO-d$_6$) δ 9.00 (d, J=0.8 Hz, 1H), 8.17 (t, J=5.6 Hz, 1H), 8.11 (ddd, J=8.4, 1.3, 0.6 Hz, 1H), 7.97 (t, J=1.0 Hz, 1H), 7.77-7.66 (m, 2H), 7.56 (d, J=1.2 Hz, 1H), 7.49-7.39 (m, 4H), 7.26-7.17 (m, 6H), 7.12 (ddt, J=6.3, 5.3, 2.7 Hz, 1H), 4.06-3.93 (m, 1H), 3.81 (ddd, J=13.1, 9.1, 6.2 Hz, 1H), 3.01 (d, J=5.3 Hz, 1H), 2.66 (d, J=1.0 Hz, 3H), 2.09-1.85 (m, 1H), 1.36 (dd, J=9.2, 3.7 Hz, 2H). HRMS m/z calcd for C$_{29}$H$_{29}$N$_5$+H$^+$ [M+H$^+$]: 448.24824, found: 448.24814. HPLC: 99.95% (t$_R$=6.684 min).

mmmmmmmm. Synthesis of N N-(2,2-Diphenyl-ethyl)-2-(5-Methylimidazo[1,2-A]Pyridin-6-yl)Qui-nazolin-4-Amine (195)

i. Step 1

2-Chloro-N-(2,2-diphenylethyl)quinazolin-4-amine was reacted with 6-methyl-5-(4,4,5,5-tetramethyl-1,3,2-dioxaborolan-2-yl)pyridin-2-amine according to the procedure described for the preparation of compound 8 to obtain 2-(6-amino-2-methylpyridin-3-yl)-N-(2,2-diphenylethyl)quinazolin-4-amine. MS m/z 432 (M+H)$^+$.

ii. Step 2

A solution of the above intermediate (0.12 g, 0.278 mmol) in ethanol (5 mL) was treated with 2-chloroacetaldehyde (3 mL of 50% aqueous solution). The mixture was heated under reflux overnight, cooled and volatiles were removed under reduced pressure. The residue was treated with saturated aqueous NaHCO$_3$ and extracted with CHCl$_3$. The organic layer was dried over anhydrous Na$_2$SO$_4$, filtered and the filtrate was evaporated under reduced pressure. The crude product thus obtained was purified by column chromatography over silica gel using CHCl$_3$-MeOH, 96:4 as the eluent. Yield 24%. Mp 111-112° C.; TLC $R_f$ 0.61 (CHCl$_3$-MeOH, 90:10), $^1$H NMR (400 MHz, DMSO-d$_6$) δ 8.46 (t, J=5.5 Hz, 1H), 8.02-7.91 (m, 2H), 7.82-7.68 (m, 3H), 7.59 (dq, J=9.4, 0.6 Hz, 1H), 7.53-7.44 (m, 1H), 7.43-7.24 (m, 9H), 7.18 (ddt, J=8.3, 6.6, 1.4 Hz, 2H), 4.71 (t, J=7.7 Hz, 1H), 4.25 (dd, J=8.0, 5.2 Hz, 2H), 3.47-3.23 (m, 3H). HRMS m/z calcd for C$_{30}$H$_{25}$N$_5$+H$^+$ [M+H$^+$]: 456.21827, found: 456.21790. HPLC: 99.62% (t$_R$=6.423 min).

nnnnnnnn. Synthesis of N1,N1-Dimethyl-N2-(2-(7-Methylimidazo[1,2-A]Pyridin-6-yl)Quinazolin-4-yl)-1-Phenylethane-1,2-Diamine (196)

i. Step 1

N2-(2-Chloroquinazolin-4-yl)-N1,N1-dimethyl-1-phenylethane-1,2-diamine was reacted with 6-methyl-5-(4,4,5,5-tetramethyl-1,3,2-dioxaborolan-2-yl)pyridin-2-amine according to the procedure described for the preparation of compound 8 to obtain N2-(2-(6-amino-4-methylpyridin-3-yl)quinazolin-4-yl)-N1,N1-dimethyl-1-phenylethane-1,2-diamine. MS [M+H]$^+$ 399.

ii. Step 2

To a solution of the above intermediate (0.099 g, 0.248 mmol) in ethanol (5 mL) was added a 2-chloroacetaldehyde (3 mL of 50% aqueous solution). The mixture was heated under reflux for overnight, cooled and the solvents were removed under reduced pressure. The residue was treated with saturated aqueous NaHCO$_3$ and then extracted with CHCl$_3$. The extracts were dried over anhydrous Na$_2$SO$_4$, filtered and the filtrate was evaporated to dryness under reduced pressure. The residue obtained was purified by column chromatography over a column of silica gel using CHCl$_3$-MeOH, 90:10 to yield the title compound. Yield 30%. Mp 239-241° C. TLC $R_f$ 0.59 (CHCl$_3$-MeOH, 90:10). $^1$H NMR (400 MHz, DMSO-d$_6$) δ 9.02 (d, J=0.8 Hz, 1H), 8.23-8.11 (m, 2H), 7.98-7.90 (m, 1H), 7.82-7.68 (m, 1H), 7.55 (d, J=1.2 Hz, 1H), 7.52-7.45 (m, 1H), 7.44 (q, J=0.9 Hz, 1H), 7.31 (d, J=4.3 Hz, 5H), 7.28-7.21 (m, 1H), 4.14 (d, J=1.8 Hz, 1H), 3.90 (q, J=3.2, 2.4 Hz, 2H), 2.65 (d, J=1.0 Hz, 3H), 2.16 (s, 6H). HRMS m/z calcd for C$_{26}$H$_{26}$N$_6$+H$^+$ [M+H]$^+$ 423.2291, found: 427.22800 HPLC: 97% (t$_R$=4.755 min).

oooooooo. Synthesis of N-(2,2-Diphenylethyl)-2-(5-Methylimidazo[1,2-A]pyridin-8-yl)Quinazolin-4-Amine (197)

i. Step 1

A dry flask was charged with 3-bromo-6-methylpyridin-2-amine (1.0 g, 5.35 mmol), potassium acetate (2.52 g, 16.04 mmol), 4,4,4',4',5,5,5',5'-octamethyl-2,2'-bi(1,3,2-dioxaborolane) (1.629 g, 6.42 mmol) and dioxane (50 mL). Argon was bubbled through the solution for 15 minutes and [1,1'-Bis(diphenylphosphino)ferrocene]dichloropalladium(II) dichloromethane adduct (0.437 g, 0.535 mmol) was added. The reaction mixture was heated under reflux in a bath at 115° C. for 18 hours. The reaction mixture was allowed to cool to room temperature, EtOAc (50 mL) was added and the solid that separates was filtered off, washed with additional EtOAc. The combined EtOAc solutions were washed with H$_2$O (2×40 mL), brine (25 mL), dried over anhydrous Na$_2$SO$_4$ and filtered. The filtrate was concentrated under reduced pressure and the residue was purified by chromatography over a column of silica using EtOAc as the eluent to obtain 0.25 g (20%) of 6-methyl-3-(4,4,5,5-tetramethyl-1,3,2-dioxaborolan-2-yl)pyridin-2-amine as an off-white solid. [M+H]$^+$ 235.

ii. Step 2

The boronic ester obtained above was reacted with 2-chloro-N-(2,2-diphenylethyl)quinazolin-4-amine according to the procedure described for the preparation of compound 8 to obtain 2-(2-amino-6-methylpyridin-3-yl)-N-(2,2-diphenylethyl)quinazolin-4-amine. Yield 50%. [M+H]$^+$ 432.

iii. Step 3

A solution of the above intermediate (0.05 g. 0.637 mmol) and 2-chloroacetaldehyde (3 mL of 50% aqueous solution) in ethanol (5 mL) was heated under reflux for overnight, cooled and concentrated under reduced pressure. The residue obtained was treated with saturated aqueous NaHCO$_3$ solution and extracted with CHCl$_3$. The organic layer was dried over anhydrous Na$_2$SO$_4$, filtered, and the filtrate was evaporated to dryness. The crude product was purified by column chromatography using silica gel eluting with CHCl$_3$-MeOH, 90:10 to obtain (0.039 g, 30%) of the pure product. Mp 232-234° C. TLC R$_f$ 0.31 (CHCl$_3$-MeOH, 90:10), $^1$H NMR (400 MHz, DMSO-d$_6$) δ 9.05-8.92 (m, 2H), 8.50 (d, J=2.2 Hz, 1H), 8.35-8.23 (m, 3H), 7.89 (ddd, J=8.3, 7.0, 1.3 Hz, 1H), 7.66-7.53 (m, 2H), 7.47-7.39 (m, 4H), 7.33-7.24 (m, 4H), 7.25-7.13 (m, 2H), 4.72 (t, J=7.7 Hz, 1H), 4.40 (dd, J=7.6, 5.4 Hz, 2H), 2.91 (d, J=0.9 Hz, 3H). HRMS m/z calcd for C$_{30}$H$_{25}$N$_5$+H$^+$ [M+H]$^+$ 456.1827. found: 456.2176. HPLC: 100% (t$_R$=6.902 min).

ppppppppp. Synthesis of 6-(4-((2,2-Diphenylethyl)Amino)Quinazolin-2-yl)-5,7-Dimethyl-2,3-Dihydroimidazo[1,2-A]Pyridin-3-ol (198)

i. Step 1

To a dry flask was added 5-bromo-4,6-dimethylpyridin-2-amine (2.0 g, 5.35 mmol), potassium acetate (4.76 g, 30.30 mmol), 4,4,4',4',5,5,5',5'-octamethyl-2,2'-bi(1,3,2-dioxaborolane) (3.08 g, 12.12 mmol) and dioxane (100 mL). Argon was bubbled through the solution for 15 minutes and [1,1'-Bis(diphenylphosphino)ferrocene]dichloropalladium (II) dichloromethane adduct (0.412 g, 0.505 mmol) was added. The reaction mixture was heated under reflux in a bath at 115° C. for 18 hr. After cooling to room temperature, EtOAc (50 mL) was added and the precipitated solid was filtered off, washed with additional EtOAc and the combined organic extracts were washed with H$_2$O (2×40 mL), brine (25 mL), dried over anhydrous Na$_2$SO$_4$, filtered, and the filtrate was evaporated under reduced pressure. The residue was purified by silica gel column chromatography using EtOAc as the eluent to obtain 0.415 g (17%) of 4,6-dimethyl-5-(4,4,5,5-tetramethyl-1,3,2-dioxaborolan-2-yl)pyridin-2-amine as an off-white solid. [M+H]$^+$ 249.

ii. Step 2

The boronic ester obtained above was coupled with (4,6-dimethyl-5-(4,4,5,5-tetramethyl-1,3,2-dioxaborolan-2-yl)pyridin-2-amine according to the procedure described for the preparation of compound 8 to obtain 2-(6-amino-2,4-dimethylpyridin-3-yl)-N-(2,2-diphenylethyl)quinazolin-4-amine. Yield 45%. $^1$H NMR (400 MHz, DMSO-d$_6$) δ 8.72 (s, 1H) 7.97-7.89 (m, 1H), 7.58 (ddd, J=8.3, 6.9, 1.3 Hz, 1H), 7.44 (dd, J=8.5, 1.2 Hz, 1H), 7.41-7.34 (m, 4H), 7.30-7.22 (m, 3H), 7.18-7.11 (m, 5H), 6.64 (q, J=0.8 Hz, 1H), 6.18 (dd, J=1.4, 0.7 Hz, 1H), 5.61 (s, 1H), 4.68 (s, 1H), 4.22 (dd, J=8.1, 5.4 Hz, 2H), 2.36 (s, 3H), 2.16 (d, J=7.3 Hz, 5H), 2.08 (t, J=0.7 Hz, 2H). MS [M+H]$^+$ 446.

iii. Step 3

A solution of the above intermediate (80 mg, 0.17 mmol), 2-chloroacetaldehyde (3 mL of 50% aqueous solution) in ethanol (5 mL) was hearted under reflux overnight. An additional 3 mL of 2-chloroacetadehyde solution was added and the mixture was heated under reflux for additional 6 hours. The reaction mixture was cooled, concentrated under reduced pressure and the residue was partitioned between CHCl$_3$ and saturated aqueous NaHCO$_3$. The organic layer was separated, dried over anhydrous Na$_2$SO$_4$, filtered and concentrated. The residue was purified over a column of silica gel using CHCl$_3$-MeOH, 90:10). The product thus obtained was heated under reflux with p-toluenesulfonic acid monohydrate (0.047 g, 0.246 mmol) in toluene (3 mL) overnight. The solvent was removed under reduced pressure and the crude product was purified over a column of silica gel using CHCl$_3$-MeOH as the eluent and the product obtained was washed with saturated aqueous NaHCO$_3$ and CHCl$_3$ to yield 0.026 g (45%) of the desired product. Mp 178-180° C. TLC R$_f$ 0.77 (CHCl$_3$-MeOH, 90:10). $^1$H NMR (400 MHz, DMSO-d$_6$) δ 9.77 (s, 1H), 8.70 (d, J=2.9 Hz, 1H), 8.52-8.41 (m, 3H), 8.15-8.05 (m, 2H), 7.78 (ddd, J=8.2, 7.2, 1.1 Hz, 1H), 7.51-7.45 (m, 2H), 7.23-7.16 (m, 3H), 7.13-7.05 (m, 1H), 4.67 (t, J=7.7 Hz, 1H), 4.34 (d, J=7.8 Hz, 2H), 2.53 (d, J=0.6 Hz, 2H), 2.29 (s, 3H), 1.97 (d, J=0.7 Hz, 3H). HRMS m/z calcd for C$_{31}$H$_{27}$N$_5$+H$^+$ [M+H$^+$]: 470.23392. found: 470.23412. HPLC: 95.96% (t$_R$=6.996 min).

qqqqqqqqq. Synthesis of N-(2,2-Diphenylethyl)-2-(Pyrazolo[1,5-a]Pyrimidin-6-yl)Quinazolin-4-Amine (199)

i. Step 1

To a dry flask was added 6-bromopyrazolo[1,5-a]pyrimidine (2.0 g, 10.1 mmol), potassium acetate (4.47 g, 30.3 mmol), 4,4,4',4',5,5,5',5'-octamethyl-2,2'-bi(1,3,2-dioxaborolane) (0.414 g, 12.12 mmol) and dioxane (50 mL). Argon was bubbled through the solution for 15 minutes and [1,1'-Bis(diphenylphosphino)ferrocene]dichloropalladium (II) dichloromethane adduct (0.412 g, 0.505 mmol) was added. The mixture was refluxed in a bath at 115° C. for 18 hours. After cooling to room temperature, EtOAc (50 mL) was added and the solid obtained was filtered-off. The solid was washed with additional EtOAc. The organic extracts were combined, washed with H$_2$O (2×40 mL), brine (25 mL), dried over Na$_2$SO$_4$ and filtered and concentrated under reduced pressure. The crude product was purified by silica gel column chromatography using EtOAc as the eluent to obtain 0.56 g (23%) of 6-(4,4,5,5-tetramethyl-1,3,2-dioxaborolan-2-yl)pyrazolo[1,5-a]pyrimidine as an off-white solid. MS [M+H]$^+$ 246.

ii. Step 2

The boronic ester obtained above was reacted with 2-chloro-N-(2,2-diphenylethyl)quinazolin-4-amine according to the procedure described for the preparation of compound 8 to obtain the desired product. Yield 37%. Mp 122-124° C. TLC R$_f$ 0.88 (CHCl$_3$-MeOH, 90:10), $^1$H NMR (400 MHz, DMSO-d$_6$) δ 9.76 (dd, J=2.1, 0.9 Hz, 1H), 9.53 (d, J=2.0 Hz, 1H), 8.59 (t, J=5.5 Hz, 1H), 8.36 (d, J=2.3 Hz, 1H), 8.21-8.13 (m, 1H), 7.81-7.73 (m, 2H), 7.53-7.41 (m, 5H), 7.30 (dd, J=8.3, 6.9 Hz, 4H), 7.23-7.14 (m, 2H), 6.84 (dd, J=2.3, 0.9 Hz, 1H), 4.75 (t, J=7.6 Hz, 1H), 4.36 (dd, J=7.5, 5.6 Hz, 2H). HRMS m/z calcd for C$_{28}$H$_{22}$N$_6$+H$^+$ [M+H$^+$]: 443.19787. found: 443.19822. HPLC: 100% (t$_R$=7.72 min).

rrrrrrrr. Synthesis of N-(2,2-Diphenylethyl)-2-(7-(Trifluoromethyl)Imidazo[1,2-a]Pyridin-6-yl)Quinazolin-4-Amine (200)

i. Step 1

To a dry flask was added 6-bromopyrazolo[1,5-a]pyrimidine (1.0 g, 4.15 mmol), potassium acetate (1.957 g, 12.45 mmol), 4,4,4',4',5,5,5',5'-octamethyl-2,2'-bi(1,3,2-dioxaborolane) (1.580 g, 6.22 mmol) and dioxane (25 mL). Argon was bubbled through the solution for 15 minutes and [1,1'-Bis(diphenylphosphino)ferrocene]-dichloropalladium(II) dichloromethane adduct (0.412 g, 0.505 mmol) was added. The reaction mixture was refluxed in a bath at 115° C. for 18 hours. The solid that separates on cooling was filtered off, washed with EtOAc and the combined organic extracts were washed with $H_2O$ (2×40 mL), brine (25 mL), dried over anhydrous $Na_2SO_4$, filtered and the filtrate was concentrated under reduced pressure. The residue was purified by silica gel column chromatography using EtOAc as the eluent to obtain 0.35 g (29%) of 5-(4,4,5,5-tetramethyl-1,3,2-dioxaborolan-2-yl)-4-(trifluoromethyl)pyridin-2-amine as an off-white solid. MS $[M+H]^+$ 289.

ii. Step 2

The boronic ester obtained above was coupled with 2-chloro-N-(2,2-diphenylethyl)quinazolin-4-amine according to the procedure described for the preparation of compound 8 to obtain 2-(6-amino-4-(trifluoromethyl)pyridin-3-yl)-N-(2,2-diphenylethyl)quinazolin-4-amine. Yield 50%. MS $[M+H]^+$ 486.

iii. Step 3

The above intermediate (0.01 g, 0.206 mmol) was dissolved in ethanol (5 mL) and 2-chloroacetaldehyde (3 mL of 50% aqueous solution) was added. The reaction mixture was heated under reflux for overnight, cooled to room temperature and the volatiles were removed under reduced pressure. The crude product was purified by column chromatography over silica gel using $CHCl_3$-MeOH, 90:10 as the eluent to obtain the pure product. Mp 215-216° C. TLC $R_f$ 0.90 ($CHCl_3$-MeOH, 90:10). $^1$H NMR (400 MHz, DMSO-$d_6$) δ 9.12 (s, 1H), 8.43 (t, J=5.4 Hz, 1H), 8.36-8.23 (m, 1H), 8.20-8.12 (m, 2H), 7.88 (d, J=1.2 Hz, 1H), 7.83-7.68 (m, 2H), 7.50 (ddd, J=8.2, 6.8, 1.4 Hz, 1H), 7.35-7.21 (m, 8H), 7.20-7.11 (m, 2H), 4.65 (t, J=7.9 Hz, 1H), 4.22 (dd, J=8.0, 5.4 Hz, 2H). HRMS m/z calcd for $C_{30}H_{22}F_3N_5+H^+$ $[M+H]^+$ 510.19001 found: 510.19039. HPLC: 99.54% ($t_R$=7.20 min).

sssssss. Synthesis of 2-(6,7-Dihydro-1H-Pyrrolo[3,2-c]Pyridin-5(4H)-yl)-N-(3-Methyl-2-Phenylbutyl)Quinazolin-4-Amine (201)

A mixture of 2-chloro-N-(3-methyl-2-phenylbutyl)quinazolin-4-amine (0.150 g, 0.46 mmol), and 4,5,6,7-tetrahydro-1H-pyrrolo[3,2-c]pyridine (0.056 g, 0.46 mmol) in ethanol (7 mL) was heated under reflux overnight. The crude product obtained after removal of the solvent was chromatographed over a column of silica gel using $CHCl_3$-MeOH, 96:4 as the eluent. The product obtained was recrystallized from ethanol to give 90 mg (48%) of the title compound. Mp 221-223° C. TLC $R_f$ 0.52 ($CHCl_3$-MeOH, 90:10). $^1$H NMR (400 MHz, DMSO-$d_6$) δ 12.01 (s, 1H), 10.67 (s, 1H), 9.39 (s, 1H), 8.15-8.07 (m, 1H), 7.86-7.71 (m, 2H), 7.36 (ddd, J=8.2, 7.0, 1.3 Hz, 1H), 7.27-7.11 (m, 4H), 6.67 (t, J=2.6 Hz, 1H), 5.90 (t, J=2.5 Hz, 1H), 4.91-4.76 (m, 2H), 4.29-4.01 (m, 3H), 3.83 (ddd, J=13.0, 9.0, 6.2 Hz, 1H), 3.03-2.92 (m, 1H), 2.86-2.77 (m, 2H), 2.03 (dq, J=12.6, 6.2, 5.7 Hz, 1H), 1.05 (d, J=6.6 Hz, 3H), 0.75 (d, J=6.6 Hz, 3H). HRMS m/z calcd for $C_{26}H_{29}N_5+H^+[M+H^+]$: 412.24957. found: 412.24961. HPLC: 100% ($t_R$=6.79 min).

ttttttt. Synthesis of 2-(6,7-Dihydro-1H-Pyrrolo[3,2-c]Pyridin-5(4H)-yl)-N-Phenethylquinazolin-4-Amine (202)

A mixture 2-chloro-N-phenethylquinazolin-4-amine (0.232 g, 0.819 mmol), and 4,5,6,7-tetrahydro-1H-pyrrolo[3,2-c]pyridine (0.15 g, 1.228 mmol) in ethanol (7 mL) was heated under reflux overnight. The crude product obtained after removal of the solvent was chromatographed over a column of silica gel using $CHCl_3$-MeOH, 96:4, and then recrystallized from ethanol to obtain 0.11 g (37%) of the desired product. Mp 161-163° C. TLC $R_f$ 0.48 ($CHCl_3$-MeOH, 90:10). $^1$H NMR (400 MHz, DMSO-$d_6$) δ 12.20 (s, 1H), 10.67 (d, J=3.1 Hz, 1H), 9.75 (s, 1H), 8.29 (d, J=8.2 Hz, 1H), 7.96-7.89 (m, 1H), 7.80 (ddd, J=8.4, 7.1, 1.2 Hz, 1H), 7.42 (ddd, J=8.3, 7.1, 1.1 Hz, 1H), 7.36-7.17 (m, 4H), 6.66 (t, J=2.6 Hz, 1H), 5.92 (t, J=2.5 Hz, 1H), 4.86 (s, 2H), 4.22 (t, J=5.8 Hz, 2H), 3.83 (dt, J=8.4, 6.2 Hz, 2H), 3.05-2.97 (m, 2H), 2.86-2.78 (m, 2H). HRMS m/z calcd for $C_{23}H_{23}N_5+H^+$ $[M+H^+]$: 370.20262. found: 370.20283. HPLC: 100% ($t_R$=6.468 min).

uuuuuuuu. Synthesis of N-(2,2-Bis(4-Fluorophenyl)Ethyl)-2-(7-Methylimidazo[1,2-a]Pyridin-6-yl)Quinazolin-4-Amine (203)

i. Step 1

A solution of 2,2-Bis(4-fluorophenyl)ethanamine (1.5 g, 6.43 mmol) and 2,4-dichloroquinazoline (1.280 g, 6.43 mmol) and triethylamine (1.30 g, 12.86 mmol) in THF (25 mL) was stirred at room temperature overnight. The reaction mixture was filtered and the filtrate was concentrated under reduced pressure. The residue thus obtained was recrystallized from ethanol to give 1.8 g (77%) of N-(2,2-bis(4-fluorophenyl)ethyl)-2-chloroquinazolin-4-amine. $^1$H NMR (400 MHz, DMSO-$d_6$) δ 8.86-8.75 (m, 1H), 8.17-8.09 (m, 1H), 7.78 (ddd, J=8.2, 7.0, 1.2 Hz, 1H), 7.61 (dd, J=8.5, 1.1 Hz, 1H), 7.59-7.45 (m, 1H), 7.43-7.23 (m, 4H), 7.25-7.07 (m, 4H), 4.61 (t, J=7.8 Hz, 1H), 4.22-4.08 (m, 2H). MS $[M+H]^+$ 396.

ii. Step 2

The above intermediate was reacted with 4-methyl-5-(4,4,5,5-tetramethyl-1,3,2-dioxaborolan-2-yl)pyridin-2-amine according to the procedure described for the preparation of compound 8 to obtain 2-(6-amino-4-methylpyridin-3-yl)-N-(2,2-bis(4-fluorophenyl)ethyl)quinazolin-4-amine. Yield 34%. MS $[M+H]^+$ 468.

iii. Step 3

A solution of the above intermediate (0.08 g, 0.171 mmol) in ethanol (5 mL) was treated with 2-chloroacetaldehyde (3 mL of 50% aqueous solution). The mixture was refluxed overnight. The reaction mixture was cooled and volatiles were removed under reduced pressure. The residue was partitioned between saturated aqueous $NaHCO_3$ and $CHCl_3$. The organic layer was separated, dried over anhydrous $Na_2SO_4$, filtered and the solvent was removed under reduced pressure. The crude product thus obtained was purified by column chromatography over silica gel using $CHCl_3$-MeOH, 90:10 to obtain the pure product. Mp 210-212° C. TLC $R_f$ 0.68 ($CHCl_3$-MeOH, 85:15). $^1$H NMR (400 MHz, DMSO-$d_6$) δ 9.07 (d, J=6.8 Hz, 1H), 8.42 (t, J=5.4 Hz, 1H), 8.19-8.11 (m, 1H), 7.97 (s, 1H), 7.82-7.69 (m, 2H), 7.62-7.32 (m, 7H), 7.17-7.05 (m, 4H), 4.69 (t, J=7.6 Hz, 1H), 4.30-4.17 (m, 2H), 2.66 (d, J=1.1 Hz, 3H). HRMS m/z calcd for $C_{30}H_{23}F_3N_5+H^+$ [M+H]$^+$ 492.19943. found: 492.19912. HPLC: 100% ($t_R$=6.79 min).

vvvvvvvv. Synthesis of N-(2,2-Diphenylethyl)-N-Methyl-2-(7-Methylimidazo[1,2-a]Pyridin-6-yl)Quinazolin-4-Amine (204)

i. Step 1

To a solution of 2,4-dichloroquinazoline (0.942 g, 4.73 mmol) in THF (25 mL) was added N-methyl-2,2-diphenylethanamine (1.0 g, 4.73 mmol) and triethylamine (0.958 g, 9.47 mmol). The mixture was stirred at room temperature overnight and filtered. The filtrate was concentrated under reduced pressure and the residue obtained was purified by a silica gel column chromatography using CHCl$_3$-MeOH, 98:2 as the eluent to yield 1.22 g (69%) of 2-chloro-N-(2,2-diphenylethyl)-N-methylquinazolin-4-amine. $^1$H NMR (400 MHz, DMSO-d6) δ 7.87 (dd, J=8.6, 1.3 Hz, 1H), 7.71 (ddd, J=8.3, 6.9, 1.3 Hz, 1H), 7.59 (dd, J=8.3, 1.3 Hz, 1H), 7.40-7.10 (m, 11H), 4.58 (t, J=7.9 Hz, 1H), 4.45 (d, J=7.9 Hz, 2H, 3.22 (s, 3H). MS [M+H]$^+$ 374.

ii. Step 2

A mixture of the above intermediate (0.15 g, 0.401 mmol), (7-methylimidazo[1,2-a]pyridin-6-yl)boronic acid (0.071 g, 0.401 mmol), K$_2$CO$_3$ (0.111 g, 0.802 mmol) and palladium tetrakis(triphenylphosphine)palladium (0.005 g, 0.004 mmol) in dioxane-water (3:2 mL) was heated at 110-115° C. under an atmosphere of argon overnight. The reaction mixture was cooled and the volatiles were removed under reduced pressure. The residue was partitioned between CHCl$_3$ and H$_2$O, the organic extracts were separated, dried over anhydrous Na$_2$SO$_4$, filtered, and the solvent was removed under reduced pressure. The residue obtained was purified over a column of silica gel using CHCl$_3$-MeOH, 92.5:7.5 to yield 0.068 g (31%) of the desired product. Mp 58-60° C. TLC R$_f$ 0.46 (CHCl$_3$-MeOH, 90:10). $^1$H NMR (400 MHz, DMSO-d$_6$) δ 8.99 (s, 1H), 7.96-7.85 (m, 2H), 7.82-7.73 (m, 2H), 7.55 (d, J=1.2 Hz, 1H), 7.45-7.39 (m, 2H), 7.36-7.30 (m, 4H), 7.29-7.21 (m, 4H), 7.18 (d, J=7.2 Hz, 1H), 4.65 (d, J=7.5 Hz, 1H), 4.56 (d, J=7.7 Hz, 2H), 3.27 (s, 3H), 2.58 (d, J=1.0 Hz, 3H). FIRMS m/z calcd for $C_{31}H_{27}N_{65}+H^+$ [M H$^+$]: 470.23392. found: 470.23356. HPLC: 100% ($t_R$=6.868 min).

3. Assay for Dopamine Reuptake Inhibition

Uptake inhibition assay for the dopamine transporter was conducted in rat brain synaptosomes as described elsewhere with minor modifications (Rothman et al., *Synapse* 39, 32-41 (2001)). Freshly removed caudate was homogenized in 10% ice-cold sucrose with 12 strokes of a hand-held Potter-Elvehj em homogenizer followed by centrifugation at 1000×g for 10 min. The supernatants were saved on ice and used immediately. Transporter activity was assessed using 5 nM [$^3$H]dopamine. The assay buffer was Krebs-phosphate buffer containing 154.4 mM NaCl, 2.9 mM KCl, 1.1 mM CaCl$_2$, 0.83 mM MgCl$_2$, 5 mM glucose, 1 mg/mL ascorbic acid, and 50 μM pargyline. The selectivity of the uptake assay for dopamine active transporter (DAT) was optimized by including 100 nM citalopram and 100 nM desipramine as blockers of serotonin transporter (SERT) and norepinephrine transporter (NET) in the sucrose solution and assay buffer. Uptake inhibition assays were conducted at 25° C. and were initiated by adding 100 μl of tissue to 900 μL assay buffer containing test drug and [$^3$H]dopamine. Test drugs were diluted in assay buffer containing 1 mg/mL bovine serum albumin. Nonspecific uptake was measured by incubating in the presence of 10 μM indatraline. The reactions were stopped after 15 minutes by rapid vacuum filtration with a cell harvester (BRANDEL) over GF/B filters (Whatman) presoaked in wash buffer maintained at 25° C. (10 mM Tris-HCl, pH 7.4/150 mM NaCl). Filters were rinsed with 6 mL wash buffer and retained tritium was quantified by a MicroBeta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and $EC_{50}$ value. The dopamine uptake inhibition potency and efficacy of the compounds are shown in Table 2. The compound numbers in Table 2 correspond to the respective compound numbers given in Table 1 and in the Examples.

TABLE 2

| No. | DA Uptake EC$_{50}$ (nM ± SD) | DA Uptake Emax (% I ± SD) |
|---|---|---|
| 1 | 443 ± 88 | 82 ± 3 |
| 2 | 480 | 100 |
| 3 | 150 | 100 |
| 4 | 60 | 100 |
| 5 | 416 ± 22 | 83 ± 1 |
| 6 | 575 ± 51 | 78 ± 1 |
| 7 | 910 | 100 |
| 9 | 140 | 100 |
| 10 | 250 | <100 |
| 11 | 770 | 100 |
| 12 | 174 ± 58 | 66 ± 4 |
| 13 | 212 ± 49 | 71 ± 3 |
| 14 | 234 ± 36 | 74 ± 2 |
| 16 | 20 ± 1 | 73 ± 1 |
| 17 | 10 ± 1 | 74 ± 1 |
| 18 | 160 | <100 |
| 20 | 672 ± 204 | 67 ± 4 |
| 21 | 16 ± 4 | 81 ± 3 |
| 22 | 750 | 100 |
| 23 | 720 | 100 |
| 24 | 46 | 100 |
| 25 | 1090 | <100 |
| 26 | 560 | 100 |
| 27 | 580 | 100 |
| 28 | 620 | <100 |
| 29 | 36 ± 2 | 71 ± 1 |
| 30 | 9.0 ± 1.5 | 71 ± 2 |
| 31 | 89 ± 23 | 81 ± 4 |
| 32 | 189 ± 37 | 68 ± 3 |
| 34 | 123 ± 20 | 68 ± 2 |
| 35 | 475 ± 85 | 72 ± 3 |
| 37 | 121 ± 27 | 66 ± 3 |
| 38 | 1420 | 100 |
| 39 | 47 ± 6 | 78 ± 2 |
| 40 | 124 ± 37 | 74 ± 4 |
| 41 | 11 ± 1 | 71 ± 1 |
| 42 | 200 | <100 |
| 43 | 1890 | <100 |
| 44 | 79 ± 19 | 81 ± 3 |
| 45 | 175 ± 68 | 58 ± 4 |
| 46 | 544 ± 248 | 60 ± 6 |
| 47 | 148 ± 40 | 73 ± 4 |
| 48 | 38 ± 5 | 73 ± 2 |
| 49 | 130 ± 16 | 73 ± 2 |
| 50 | 26 ± 7 | 68 ± 3 |
| 51 | 510 | <100 |
| 52 | 680 | 100 |
| 54 | 72 ± 12 | 80 ± 2 |
| 55 | 2.3 ± 0.4 | 68 ± 2 |
| 56 | 89 ± 13 | 70 ± 2 |
| 57 | 55 ± 18 | 61 ± 3 |
| 58 | 478 ± 154 | 65 ± 5 |
| 59 | 529 ± 146 | 56 ± 3 |
| 60 | 947 ± 402 | 55 ± 6 |
| 61 | 115 ± 20 | 80 ± 3 |
| 62 | 4210 | <100 |
| 63 | 192 ± 37 | 72 ± 3 |
| 64 | 19 ± 3 | 75 ± 2 |

TABLE 2-continued

| No. | DA Uptake EC$_{50}$ (nM ± SD) | DA Uptake Emax (% I ± SD) |
|---|---|---|
| 65 | 155 ± 92 | 50 ± 6 |
| 66 | 19 ± 4 | 69 ± 2 |
| 67 | 43 ± 9 | 66 ± 2 |
| 68 | 195 ± 70 | 55 ± 4 |
| 69 | 7.3 ± 2.2 | 63 ± 3 |
| 70 | 45 ± 15 | 67 ± 4 |
| 71 | 890 | <100 |
| 73 | 1310 | <100 |
| 75 | 62 | 100 |
| 76 | 170 | <100 |
| 77 | 28 ± 5 | 69 ± 2 |
| 78 | 30 ± 5 | 77 ± 2 |
| 79 | 51 ± 14 | 94 ± 4 |
| 80 | 13 ± 2 | 73 ± 2 |
| 81 | 11 ± 2 | 70 ± 2 |
| 82 | 239 ± 84 | 93 ± 7 |
| 83 | 132 ± 43 | 69 ± 4 |
| 84 | 18 ± 4 | 75 ± 3 |
| 85 | >5000 | ND |
| 86 | 55 ± 6 | 70 ± 1 |
| 87 | 78 ± 9 | 75 ± 1 |
| 88 | 41 ± 13 | 86 ± 5 |
| 89 | 2.1 ± 0.3 | 68 ± 1 |
| 90 | 94 ± 10 | 75 ± 2 |
| 91 | 25 ± 3 | 72 ± 2 |
| 92 | 34 ± 5 | 68 ± 2 |
| 93 | 29 ± 4 | 76 ± 2 |
| 94 | 36 ± 4 | 69 ± 1 |
| 95 | 385 ± 89 | 72 ± 4 |
| 96 | 9.2 ± 1.2 | 70 ± 1 |
| 97 | 665 ± 150 | 90 ± 5 |
| 98 | 18 ± 3 | 71 ± 2 |
| 99 | 9.3 ± 1.1 | 65 ± 1 |
| 100 | 12 ± 2 | 72 ± 2 |
| 101 | 79 ± 19 | 75 ± 3 |
| 102 | 6.0 ± 0.7 | 70 ± 1 |
| 103 | 553 ± 82 | 73 ± 2 |
| 105 | 8.8 ± 1.1 | 63 ± 1 |
| 106 | 11 ± 2 | 77 ± 2 |
| 107 | 197 ± 40 | 81 ± 3 |
| 108 | 229 ± 54 | 47 ± 2 |
| 109 | 377 ± 78 | 57 ± 2 |
| 110 | 5.6 ± 0.8 | 64 ± 1 |
| 111 | 381 ± 42 | 101 ± 2 |
| 113 | 74 ± 9 | 64 ± 1 |
| 114 | 67 ± 7 | 68 ± 1 |
| 115 | 83 ± 27 | 58 ± 3 |
| 116 | 165 ± 15 | 69 ± 1 |
| 117 | 6.1 ± 1 | 64 ± 2 |
| 118 | 0.5 ± 0.1 | 63 ± 2 |
| 119 | 117 ± 35 | 83 ± 5 |
| 120 | 89 ± 27 | 81 ± 4 |
| 121 | 170 ± 50 | 83 ± 5 |
| 123 | 31 ± 5 | 69 ± 2 |
| 124 | 7.4 ± 1.1 | 69 ± 1 |
| 125 | 75 ± 25 | 52 ± 3 |
| 128 | 55 ± 10 | 69 ± 2 |
| 129 | 49 ± 9 | 71 ± 2 |
| 130 | 40 ± 5 | 74 ± 2 |
| 131 | 21 ± 3 | 70 ± 2 |
| 132 | 103 ± 26 | 55 ± 3 |
| 133 | 194 ± 30 | 70 ± 2 |
| 134 | 31 ± 7 | 72 ± 3 |
| 135 | 1495 ± 342 | 70 ± 4 |
| 136 | 34 ± 4 | 78 ± 2 |
| 137 | 44 ± 8 | 76 ± 2 |
| 138 | 26 ± 3 | 63 ± 1 |
| 139 | 205 ± 32 | 67 ± 2 |
| 140 | 1.2 ± 0.1 | 69 ± 1 |
| 141 | 45 ± 7 | 98 ± 3 |
| 142 | 15 ± 3 | 73 ± 2 |
| 143 | 502 ± 84 | 73 ± 2 |
| 144 | 160 ± 28 | 61 ± 2 |
| 145 | 533 ± 89 | 67 ± 2 |
| 146 | 414 ± 44 | 65 ± 1 |
| 147 | 92 ± 21 | 92 ± 4 |
| 148 | 91 ± 21 | 81 ± 3 |
| 149 | 3718 ± 608 | 80 ± 4 |
| 151 | 1.9 ± 0.3 | 72 ± 2 |
| 152 | 1.7 ± 0.1 | 69 ± 1 |
| 153 | 41 ± 8 | 70 ± 2 |
| 154 | 56 ± 13 | 73 ± 3 |
| 155 | 175 ± 65 | 77 ± 6 |
| 156 | 14 ± 3 | 68 ± 2 |
| 157 | 15 ± 3 | 74 ± 2 |
| 158 | 66 ± 10 | 68 ± 2 |
| 159 | 425 ± 65 | 71 ± 2 |
| 160 | 11 ± 1 | 69 ± 1 |
| 161 | 168 ± 22 | 51 ± 1 |
| 162 | 2.2 ± 0.4 | 62 ± 2 |
| 163 | 3.7 ± 1.5 | 87 ± 6 |
| 164 | 6.4 ± 1.6 | 76 ± 3 |
| 165 | 14 ± 2 | 78 ± 2 |
| 166 | 42 ± 7 | 68 ± 2 |
| 167 | 9.4 ± 2.3 | 76 ± 3 |
| 168 | 24 ± 5 | 75 ± 2 |
| 169 | 1.8 ± 0.4 | 64 ± 2 |
| 170 | 78 ± 14 | 72 ± 2 |
| 171 | 16 ± 7 | 73 ± 5 |
| 172 | 5.0 ± 1.1 | 76 ± 2 |
| 173 | 140 ± 30 | 80 ± 3 |
| 174 | 31 ± 10 | 88 ± 4 |
| 175 | 106 ± 19 | 68 ± 2 |
| 176 | 299 ± 45 | 70 ± 2 |
| 177 | 2.3 ± 0.5 | 75 ± 3 |
| 178 | 5.0 ± 1.1 | 76 ± 3 |
| 179 | 3.0 ± 1.0 | 80 ± 4 |
| 180 | 252 ± 22 | 73 ± 1 |
| 181 | 85 ± 5 | 72 ± 1 |
| 182 | 8.3 ± 0.9 | 75 ± 1 |
| 183 | 912 ± 195 | 77 ± 4 |
| 184 | 5.3 ± 2 | 81 ± 4 |
| 185 | 11 ± 2 | 71 ± 2 |
| 186 | 14 ± 3 | 74 ± 2 |
| 187 | 5.7 ± 1.6 | 74 ± 3 |
| 188 | 1.4 ± 0.2 | 75 ± 2 |
| 189 | 24 ± 7 | 83 ± 4 |
| 190 | 6.9 ± 2.0 | 80 ± 3 |
| 191 | 16 ± 3 | 78 ± 2 |
| 192 | 10 ± 3 | 77 ± 4 |
| 193 | 1.7 ± 0.4 | 77 ± 3 |
| 194 | 1.6 ± 0.3 | 74 ± 2 |
| 195 | 34 ± 6 | 74 ± 2 |
| 196 | 14 ± 5 | 77 ± 4 |
| 197 | 208 ± 34 | 92 ± 3 |
| 198 | 543 ± 90 | 106 ± 4 |
| 199 | 9.1 ± 2.1 | 73 ± 3 |
| 200 | 2.3 ± 0.3 | 74 ± 2 |
| 201 | 7.2 ± 2.6 | 88 ± 5 |
| 202 | 94 ± 18 | 100 ± 3 |
| 203 | 1.7 ± 0.2 | 72 ± 1 |

4. Assay for Serotonin Reuptake Inhibition

Uptake inhibition assay for the serotonin transporter was conducted in rat brain synaptosomes as described elsewhere with minor modifications (Rothman et al., *Synapse* 39, 32-41 (2001)). Freshly removed whole brain minus cerebellum and caudate was homogenized in 10% ice-cold sucrose with 12 strokes of a hand-held Potter-Elvehjem homogenizer followed by centrifugation at 1000×g for 10 min. The supernatants were saved on ice and used immediately. Transporter activity at SERT was assessed using 5 nM [$^3$H]serotonin. The assay buffer was Krebs-phosphate buffer containing 154.4 mM NaCl, 2.9 mM KCl, 1.1 mM CaCl$_2$, 0.83 mM MgCl$_2$, 5 mM glucose, 1 mg/mL ascorbic acid, and 50 μM pargyline. The sucrose solution and assay buffer contained 50 nM GBR12935 and 100 nM nomifensine to prevent uptake of [$^3$H]serotonin by DAT and NET, respectively. Uptake inhibition assays were conducted at 25° C. and were initiated by adding 100 μL of tissue to 900 μL assay buffer containing test drug and [$^3$H]serotonin. Test drugs were diluted in assay buffer containing 1 mg/mL bovine serum albumin. Nonspecific uptake was measured by incubating in the presence of 10 μM indatraline. The reactions were stopped after 30 min by rapid vacuum filtration with a cell harvester (BRANDEL) over GF/B filters (Whatman) presoaked in wash buffer maintained at 25° C. (10 mM Tris-HCl, pH 7.4/150 mM NaCl). Filters were rinsed with 6 mL wash buffer and retained tritium was quantified by a MicroBeta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and $EC_{50}$ value. The serotonin uptake inhibition potency and efficacy of the compounds are shown in Table 3. The compound numbers in Table 3 correspond to the respective compound numbers given in Table 1 and in the Examples.

TABLE 3

| No. | 5HT Uptake $EC_{50}$ (nM ± SD) | 5HT Uptake Emax (% I ± SD) |
|---|---|---|
| 12 | 699 ± 164 | 48 ± 3 |
| 13 | 6382 ± 2636 | 56 ± 9 |
| 16 | 37 ± 18 | 55 ± 5 |
| 17 | 68 ± 13 | 54 ± 2 |
| 20 | 3805 ± 1645 | 50 ± 7 |
| 21 | 89 ± 51 | 43 ± 4 |
| 30 | 56 ± 21 | 52 ± 3 |
| 41 | 57 ± 18 | 60 ± 3 |
| 55 | 23 ± 5 | 52 ± 2 |
| 66 | 106 ± 19 | 61 ± 2 |
| 69 | 42 ± 12 | 51 ± 2 |
| 80 | 54 ± 7 | 51 ± 1 |
| 81 | 35 ± 9 | 57 ± 2 |
| 89 | 4.7 ± 0.6 | 51 ± 1 |
| 96 | 16 ± 5 | 55 ± 2 |
| 98 | 28 ± 6 | 54 ± 2 |
| 99 | 3.9 ± 0.4 | 56 ± 1 |
| 100 | 83 ± 28 | 59 ± 4 |
| 102 | 23 ± 3 | 54 ± 1 |
| 105 | 13 ± 6 | 35 ± 3 |
| 110 | 11 ± 3 | 51 ± 2 |
| 117 | 18 ± 4 | 56 ± 2 |
| 118 | 3.2 ± 0.9 | 58 ± 3 |
| 124 | 25 ± 7 | 49 ± 2 |
| 131 | 35 ± 11 | 59 ± 3 |
| 140 | 3.1 ± 0.7 | 54 ± 2 |

5. Assay for Norepinephrine Reuptake Inhibition

Uptake inhibition assay for the norepinephrine transporter was conducted in rat brain synaptosomes as described elsewhere with minor modifications (Rothman et al., Synapse 39, 32-41 (2001)). Freshly removed whole brain minus cerebellum and caudate was homogenized in 10% ice-cold sucrose with 12 strokes of a hand-held Potter-Elvehjem homogenizer followed by centrifugation at 1000×g for 10 minutes. The supernatants were saved on ice and used immediately. Transporter activity at NET was assessed using 10 nM [$^3$H]norepinephrine. The assay buffer was Krebs-phosphate buffer containing 154.4 mM NaCl, 2.9 mM KCl, 1.1 mM CaCl$_2$, 0.83 mM MgCl$_2$, 5 mM glucose, 1 mg/mL ascorbic acid, and 50 μM pargyline. Alternatively, the assay buffer was Krebs phosphate buffer (pH 7.4) containing 126 mM NaCl, 2.4 mM KCl, 0.5 mM KH$_2$PO$_4$, 1.1 mM CaCl$_2$, 0.83 mM MgCl$_2$, 0.5 mM Na$_2$SO$_4$, 11.1 mM glucose, 13.7 mM Na$_2$HPO$_4$, 1 mg/mL ascorbic acid, and 50 μM pargyline. The sucrose solution and assay buffer contained 50 nM GBR12935 to prevent uptake of [$^3$H]norepinephrine by DAT. Uptake inhibition assays were conducted at 37° C. and were initiated by adding 100 μL of tissue to 900 μL assay buffer containing test drug and [$^3$H]norepinephrine. Test drugs were diluted in assay buffer containing 1 mg/mL bovine serum albumin. Nonspecific uptake was measured by incubating in the presence of 10 μM indatraline. The reactions were stopped after 10 minutes by rapid vacuum filtration with a cell harvester (BRANDEL) over GF/B filters (Whatman) presoaked in wash buffer maintained at 25° C. (10 mM Tris-HCl, pH 7.4/150 mM NaCl). Filters were rinsed with 6 mL wash buffer and retained tritium was quantified by a MicroBeta liquid scintillation counter (PerkinElmer) after overnight extraction in 0.6 mL of liquid scintillation cocktail (Cytoscint, ICN). The data from three experiments were pooled and fit to a dose-response curve equation (using Kaleidagraph), to yield an $E_{max}$ and $EC_{50}$ value. The norepinephrine uptake inhibition potency and efficacy of the compounds are shown in Table 4. The compound numbers in Table 4 correspond to the respective compound numbers given in Table 1 and in the Examples.

TABLE 4

| No. | NE Uptake $EC_{50}$ (nM ± SD) | NE Uptake Emax (% I ± SD) |
|---|---|---|
| 12 | 1740 ± 1150 | 64 ± 10 |
| 13 | 5850 ± 1746 | 62 ± 5 |
| 16 | 181 ± 46 | 73 ± 4 |
| 17 | 290 ± 52 | 70 ± 3 |
| 20 | 8126 ± 2273 | 64 ± 5 |
| 21 | 346 ± 59 | 77 ± 3 |
| 30 | 204 ± 47 | 62 ± 3 |
| 41 | 179 ± 27 | 78 ± 2 |
| 55 | 52 ± 15 | 72 ± 4 |
| 66 | 229 ± 43 | 71 ± 3 |
| 69 | 147 ± 63 | 71 ± 6 |
| 80 | 259 ± 41 | 71 ± 2 |
| 81 | 203 ± 79 | 73 ± 6 |
| 89 | 63 ± 9 | 69 ± 2 |
| 96 | 98 ± 23 | 65 ± 3 |
| 98 | 132 ± 16 | 77 ± 2 |
| 99 | 69 ± 18 | 76 ± 3 |
| 100 | 153 ± 55 | 65 ± 4 |
| 102 | 95 ± 12 | 70 ± 2 |
| 105 | 86 ± 55 | 40 ± 5 |
| 110 | 60 ± 10 | 69 ± 2 |
| 117 | 88 ± 15 | 81 ± 2 |
| 118 | 21 ± 7 | 67 ± 3 |
| 131 | 78 ± 17 | 75 ± 3 |
| 124 | 94 ± 22 | 63 ± 3 |
| 140 | 11 ± 4 | 70 ± 4 |

6. Assay for Dopamine Transporter-Mediated Release

Dopamine transporter-mediated release assays were carried out as previously described with minor modifications (Rothman et al., J. Pharmacol. Exp. Ther. 307, 138-145 (2003)). Synaptosomes were prepared from rat caudate tissue as described for uptake inhibition assays, except that the sucrose solution contained 1 μM reserpine to block vesicular uptake of substrates. Synaptosomal preparations were incubated to steady state with 9 nM [$^3$H]1-methyl-4-phenylpyridinium ([$^3$H]MPP$^+$) (60 min, 25° C.) in Krebs-phosphate uptake assay buffer containing 1 μM reserpine to block vesicular uptake of substrates and 100 nM citalopram and 100 nM desipramine to block uptake of [$^3$H]MPP$^+$ by SERT and NET. Subsequently, 850 μL of synaptosomes preloaded with [$^3$H]MPP$^+$ were added to polystyrene test tubes that contained 150 μL of test compound in assay buffer containing 1 mg/mL BSA. After 30 minutes at 25° C., the release reaction was terminated by rapid vacuum filtration as described for uptake inhibition assays. Nonspecific values were measured by incubations in the presence of 10 μM tyramine. The retained tritium was quantified as described for uptake inhibition assays. The effect of compounds on DAT-mediated [$^3$H]MPP$^+$ release was determined in the absence and presence of 100 nM D-amphetamine. The ability of the compounds to shift D-amphetamine-induced DAT-mediated [$^3$H]MPP$^+$ release, using blocking concentrations about 25-times greater than the corresponding EC$_{50}$ for DAT uptake inhibition, were then determined. Dose-response curves were generated using eight concentrations of test drug. Following are the definitions of the parameters used in calculating the release dose-response curves: Total Binding (TB)=cpm in the absence of any drug; Nonspecific Binding (NS)=cpm in the presence of 10 µM tyramine; Maximal Release (MR)=TB-NS; Specific Release (SR)= (cpm in the presence of drug)−NS; % MAX Release=100−SR/MR*100.

The data from three experiments, expressed as % MAX Release, were then fit to a dose-response curve equation: $Y=E_{max} \times ([D]/([D]EC_{50})$ for the best fit estimates of the $E_{max}$ and $EC_{50}$ using either KaleidaGraph version 3.6.4 or MLAB-PC (Nightingale et al., *J. Pharmacol. Exp. Ther.* 314, 906-915 (2005)). In some cases, dose response curves were fit to a two-component equation: $Y=E_{max1} \times ([D]/([D]EC_{50}-1)+E_{max2} \times ([D]/([D]+EC_{50}-2)$. Statistical significance of the one-site versus two-site fits was based on F-test results. In "shift" experiments, a substrate dose-response curve was generated in the absence and presence of a test drug. Apparent $K_e$ values were calculated according to the equation: [Test Drug]/(EC$_{50-2}$/EC$_{50-1}$−1 1), where EC$_{50-2}$ is the EC$_{50}$ value in the presence of the test drug and EC$_{50-1}$ is the value in the absence of the uptake inhibitor. The effect of selected compounds on D-amphetamine-induced dopamine transporter-mediated [$^3$H]MPP$^+$ release is given in Table 5. The compound numbers in Table 5 correspond to the respective compound numbers given in Table 1 and in the Examples.

TABLE 5

| No. | Compd Concentration (nM) | D-Amphetamine EC$_{50}$ (nM ± SD) | D-Amphetamine Emax (% ± SD) | Ke App (nM) |
|---|---|---|---|---|
| NA | none | 6.4 ± 1.2 | 104 ± 4 | — |
| 12 | 5000 | 10.6 ± 0.7 | 98 ± 1 | 7050 |
| 13 | 5000 | 7.4 ± 1.0 | 96 ± 3 | 25830 |
| 16 | 500 | 7.9 ± 0.9 | 101 ± 3 | 1820 |
| 17 | 250 | 9.6 ± 1.0 | 94 ± 2 | 456 |
| 20 | 12500 | 7.4 ± 0.8 | 103 ± 2 | 64580 |
| 21 | 500 | 9.7 ± 1.0 | 78 ± 2 | 886 |
| 55 | 50 | 5.4 ± 0.6 | 103 ± 3 | −388 |
| 69 | 250 | 7.9 ± 0.6 | 99 ± 2 | 912 |
| 89 | 50 | 6.1 ± 0.7 | 102 ± 2 | −1070 |
| 102 | 150 | 7.0 ± 1.3 | 104 ± 4 | 1600 |
| 105 | 250 | 6.4 ± 1.1 | 105 ± 4 | NA |
| 110 | 150 | 7.2 ± 1.5 | 104 ± 5 | 1200 |
| 117 | 150 | 7.0 ± 1.3 | 105 ± 4 | 1600 |
| 118 | 12.5 | 6.7 ± 0.9 | 104 ± 3 | 267 |
| 124 | 200 | 6.8 ± 1.5 | 104 ± 5 | 3200 |
| 140 | 25 | 9.3 ± 1.3 | 105 ± 3 | 55 |
| 151 | 50 | 7.2 ± 1.0 | 103 ± 3 | 400 |
| 152 | 50 | 6.9 ± 1.3 | 104 ± 4 | 46 |

7. Assay for Dopamine Transporter Binding

The ability of test drugs to inhibit [$^3$H]WIN35428 binding to DAT in rat caudate membranes was assessed as follows. For each experiment, caudates from four rat brains were suspended in 15 mL ice cold assay buffer (50 mM sodium phosphate pH 7.4) and homogenized using a polytron (setting 6, 20 sec). The homogenate was centrifuged at 30,000×g for 10 minutes at 4° C. The pellet was resuspended with vigorous vortexing in 15 mL fresh ice cold assay buffer, and the centrifugation was repeated. The pellet was resuspended in 15 mL fresh ice cold assay buffer with vigorous vortexing followed by six strokes with a glass-on-glass hand-held homogenizer and was diluted to a final volume of 235 mL in ice cold assay buffer. [$^3$H]WIN35428 was diluted to 10 nM in assay buffer that contained 25 µg/mL chymostatin, 25 µg/mL leupeptin, 0.1 mM EDTA, and 0.1 mM EGTA. Each assay tube contained 0.75 mL membrane preparation, 0.15 mL test drug diluted in assay buffer containing 1 mg/mL bovine serum albumin, and 0.1 mL [$^3$H]WIN35428 preparation (final concentration of 1 nM). Assays were initiated by the addition of membranes and were terminated after 2 hours at 25° C. by rapid vacuum filtration. Retained tritium was measured as described. The data from three experiments were pooled and fit to a dose-response curve equation (using Kaleidagraph), to yield an $E_{max}$ and $EC_{50}$ value. The compound numbers in Table 6 correspond to the respective compound numbers given in Table 1 and in the Examples.

TABLE 6

| No. | WIN Binding EC$_{50}$ (µM ± SD) | WIN Binding Emax (% I ± SD) |
|---|---|---|
| 12 | 1.8 ± 0.4 | 71 ± 4 |
| 13 | 2.7 ± 0.3 | 77 ± 2 |
| 16 | 1.7 ± 0.2 | 76 ± 2 |
| 17 | 0.9 ± 0.2 | 87 ± 4 |
| 20 | 2.2 ± 0.5 | 72 ± 4 |
| 21 | 0.2 ± 0.0 | 94 ± 2 |
| 69 | 1.2 ± 0.2 | 83 ± 3 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

8. Screening Methods

All of the test compounds were synthesized as described herein. Next, 8-point dose-response curves were generated for each compound (1-20,000 nM) in the [$^3$H]DA uptake assay. The data from three experiments were pooled and fit to a dose-response curve equation (using KaleidaGraph; Synergy Software, Reading, Pa.) to yield an $E_{max}$ and IC$_{50}$ value. Compounds were then selected for further evaluation only if they had an IC$_{50}$≤20 nM (high potency) and an $E_{max}$≤70% (partial efficacy). Compounds that displayed properties of full-efficacy inhibitors of [$^3$H]DA uptake were not tested further. A subset of potent partial inhibitors was then tested for dose-response effects in the [$^3$H]NE and [$^3$H]5-HT uptake inhibition assays. In addition, these same compounds were tested for their ability to alter DAT-mediated release of [$^3$H]MPP$^+$ in the absence and presence of 100 nM d-amphetamine. Selected compounds were also tested for their ability to inhibit [$^3$H]WIN35428 binding to rat caudate DAT.

9. Testing of Compounds in Animal Models

The antidepressant efficacy of compounds of the present invention can be evaluated using the forced swimming test (FST) (Porsolt et al., *Nature* 266, 730-732 (1997)) and by the mouse tail suspension model (TST) (Stem et al., *Psychopharmacology* 85, 367-370 (1985)).

10. Initial Screen of Compounds

Figure 1B:
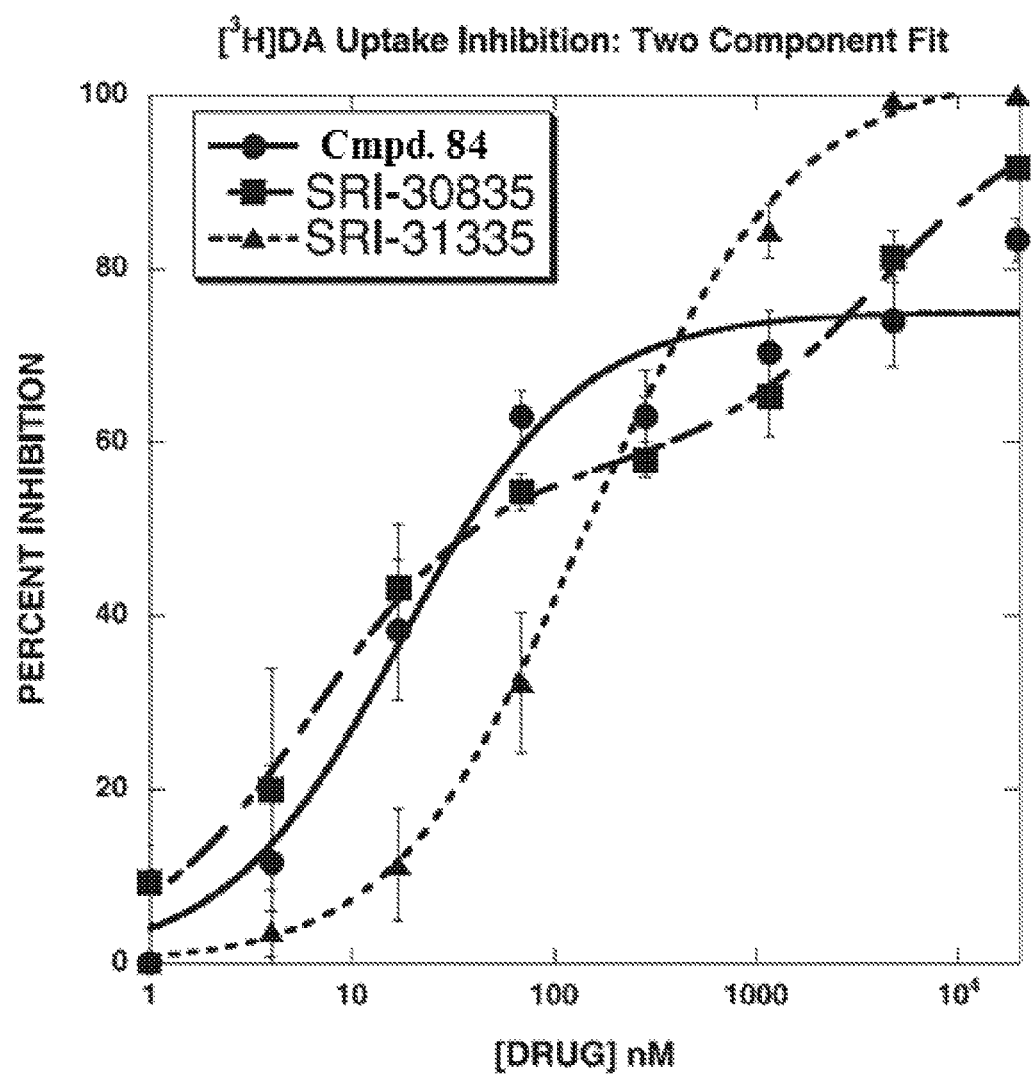

Compounds were first evaluated in the [$^3$H]DA uptake inhibition assay. Some agents acted as full-efficacy [$^3$H]DA uptake inhibitors (for example, see SRI-31335, Table 7 and FIG. 1A). A large set of agents also acted as partial inhibitors when the dose-response curves were fit to the one-component equation (for example, see compound 84). However, upon visual inspection, it is clear that whereas compound 84 dose-response curve is well described by a one-component equation, the SRI-30835 dose-response curve is not. Fitting the same three dose-response curves to a two-component equation led to a highly significant improvement in the goodness-of-fit for SRI-30835, but not the other two agents (FIG. 1B, Table 8). Without wishing to be bound by theory, these data illustrate that the initial set of compounds binned into three groups of [$^3$H]DA uptake inhibitors: (1) apparent full-efficacy one-component agents; (2) apparent full-efficacy agents; and (3) partial-efficacy agents. Further studies were thus focused on partial-efficacy agents. Interestingly, preliminary experiments suggest that some of the apparent full-efficacy one-component agents may also act as allosteric modulators (data not shown).

TABLE 7

| No. | SRI No. | Structure |
|---|---|---|
| 12 | SRI-29070 | 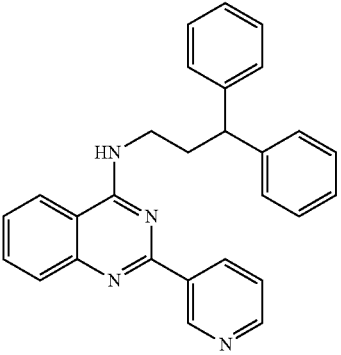 [SMILES: c1ccc(C(CCNc2nc(-c3cccnc3)nc3ccccc23)c2ccccc2)cc1] |
| 13 | SRI-29072 | 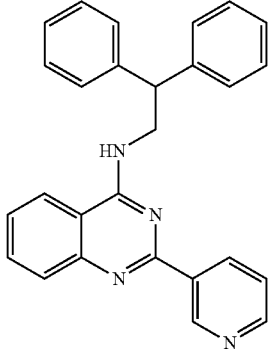 [SMILES: c1ccc(C(CNc2nc(-c3cccnc3)nc3ccccc23)c2ccccc2)cc1] |

TABLE 7-continued

| No. | SRI No. | Structure |
|---|---|---|
| 16 | SRI-29153 | 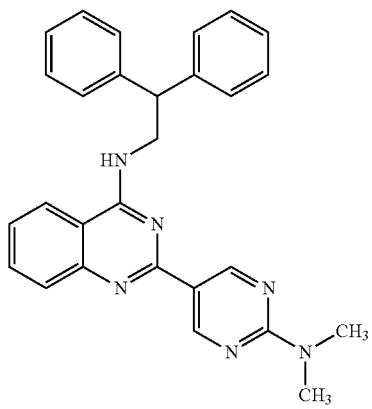 [SMILES: CN(C)c1ncc(-c2nc(NCC(c3ccccc3)c3ccccc3)c3ccccc3n2)cn1] |
| 17 | SRI-29155 | 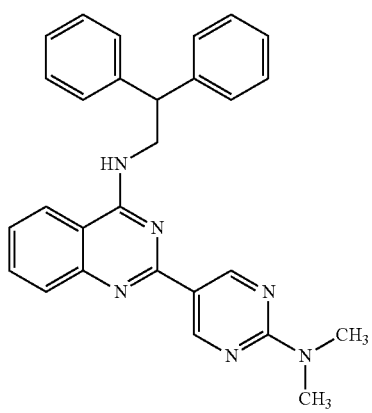 [SMILES: CN(C)c1ncc(-c2nc(NCC(c3ccccc3)c3ccccc3)c3ccccc3n2)cn1] |
| 20 | SRI-29212 | 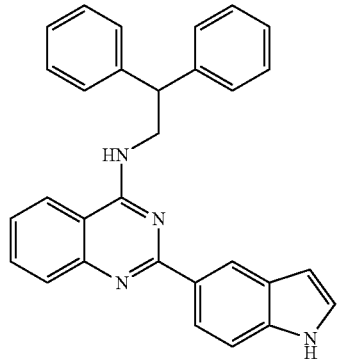 [SMILES: c1ccc(C(CNc2nc(-c3ccc4[nH]ccc4c3)nc3ccccc23)c2ccccc2)cc1] |
| 21 | SRI-29213 | 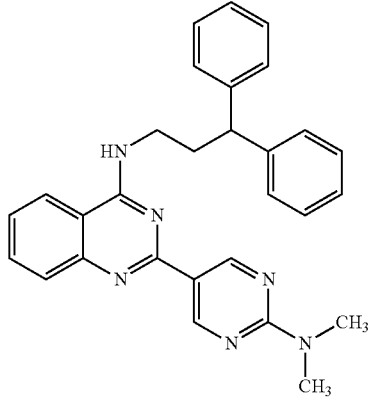 [SMILES: CN(C)c1ncc(-c2nc(NCCC(c3ccccc3)c3ccccc3)c3ccccc3n2)cn1] |

TABLE 7-continued

| No. | SRI No. | Structure |
|---|---|---|
| 30 | SRI-29338 | (structure) |
| 41 | SRI-29554 | (structure) |
| 55 | SRI-29574 | (structure) |
| — | SRI-29577 | (structure) |
| 66 | SRI-29776 | (structure) |
| 69 | SRI-29779 | (structure) |
| — | SRI-29786 | (structure) |
| 80 | SRI-29982 | (structure) |

TABLE 7-continued

| No. | SRI No. | Structure |
|---|---|---|
| 81 | SRI-29983 | (structure) |
| 84 | SRI-29986 | (structure) |
| 89 | SRI-29991 | (structure) |
| — | SRI-30504 | (structure) |－

| No. | SRI No. | Structure |
|---|---|---|
| 98 | SRI-30507 | (structure) |
| 99 | SRI-30508 | (structure) |
| 100 | SRI-30513 | (structure) |
| 102 | SRI-20517 | (structure) |

TABLE 7-continued

| No. | SRI No. | Structure |
|---|---|---|
| 105 | SRI-30522 | 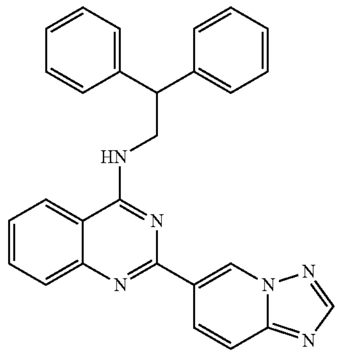 [SMILES: c1ccc(C(CNc2nc(-c3ccc4ncnn4c3)nc3ccccc23)c2ccccc2)cc1] |
| — | SRI-30524 | |
| 110 | SRI-30810 | 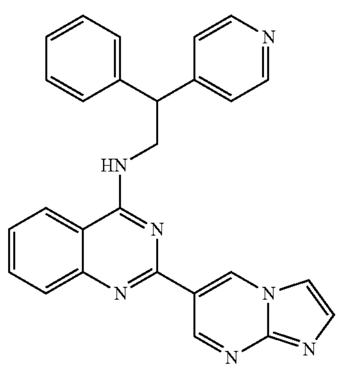 [SMILES: c1ccc(C(CNc2nc(-c3cnc4nccn4c3)nc3ccccc23)c2ccncc2)cc1] |
| 117 | SRI-30826 | 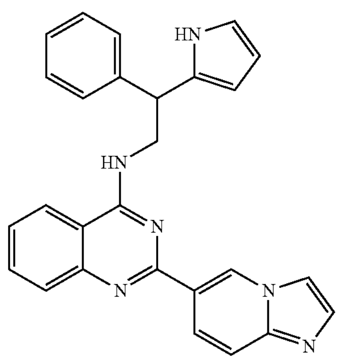 [SMILES: c1ccc(C(CNc2nc(-c3ccc4nccn4c3)nc3ccccc23)c2ccc[nH]2)cc1] |
| 118 | SRI-30827 | |
| — | SRI-30828 | |
| — | SRI-30835 | |
| 131 | SRI-30946 | |

TABLE 7-continued

| No. | SRI No. | Structure |
|---|---|---|
| 124 | SRI-31034 | 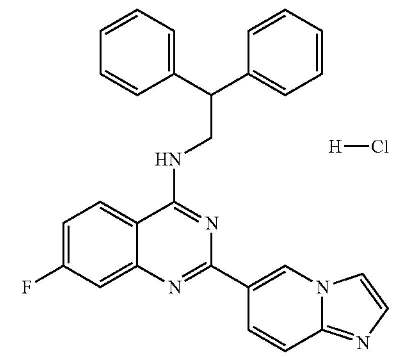 [SMILES: Fc1ccc2c(NCC(c3ccccc3)c3ccccc3)nc(-c3ccc4nccn4c3)nc2c1 ; Cl] |
| — | SRI-31039 | |
| 140 | SRI-31040 | 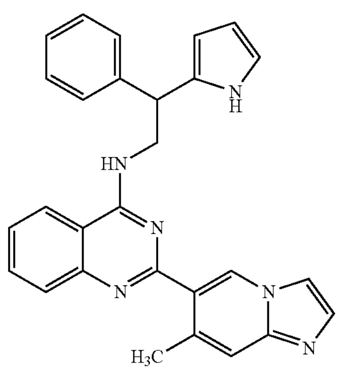 [SMILES: Cc1cc2nccn2cc1-c1nc(NCC(c2ccccc2)c2ccc[nH]2)c2ccccc2n1] |
| — | SRI-31043 | |

TABLE 7-continued

| No. | SRI No. | Structure |
|---|---|---|
| 151 | SRI-31142 | 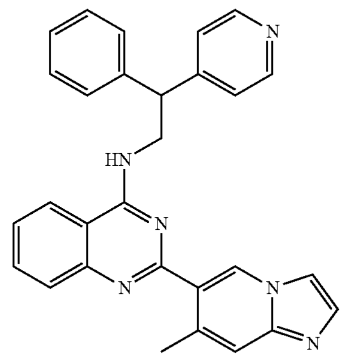 [SMILES: Cc1cc2nccn2cc1-c1nc(NCC(c2ccccc2)c2ccncc2)c2ccccc2n1] |
| 152 | SRI-31143 | 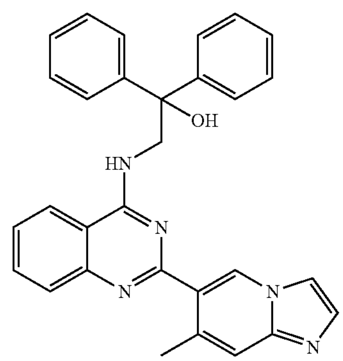 [SMILES: Cc1cc2nccn2cc1-c1nc(NCC(O)(c2ccccc2)c2ccccc2)c2ccccc2n1] |
| — | SRI-31335 | 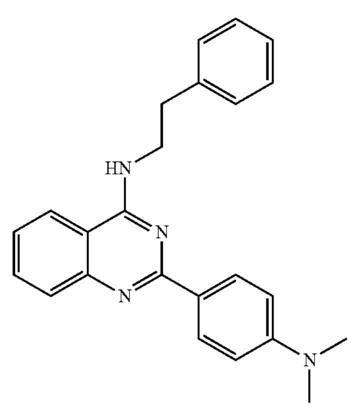 [SMILES: CN(C)c1ccc(-c2nc(NCCc3ccccc3)c3ccccc3n2)cc1] |

TABLE 8

| No. | One-Site IC$_{50}$ (nM) | One-Site E$_{max}$ (% I) | Sum-of-Squares One-Site Fit | F Test |
|---|---|---|---|---|
| 84 | 18 ± 4 | 75 ± 3 | 175 | 0 |
| SRI-31335 | 156 ± 12 | 100 ± 1.5 | 28.9 | 1.56 |
| SRI-30835 | 15 ± 7 | 75 ± 5 | 677 | 140* |

| No. | Two-Site IC$_{50-1}$ (nM) | Two-Site E$_{max-1}$ (% I) | Two-Site IC$_{50-2}$ (nM) | Two-Site E$_{max-2}$ (% I) | Sum-of-Squares Two-Site Fit |
|---|---|---|---|---|---|
| 84 | 18 × 10$^5$ ± 1.7 × 10$^5$ | 37 × 10$^8$ ± 2.7 × 10$^8$ | 18 × 10$^5$ ± 1 × 10$^5$ | 37 × 10$^8$ ± 0.7 × 10$^8$ | 175 |
| SRI-31335 | 99 ± 63 | 76 ± 54 | 564 ± 1177 | 27 ± 53 | 19.0 |
| SRI-30835 | 6 ± 0.9 | 57 ± 2 | 4000 ± 1330 | 42 ± 4 | 14.2 |

*P < 0.001 vs. one-component fit (F test).

Figure 2:
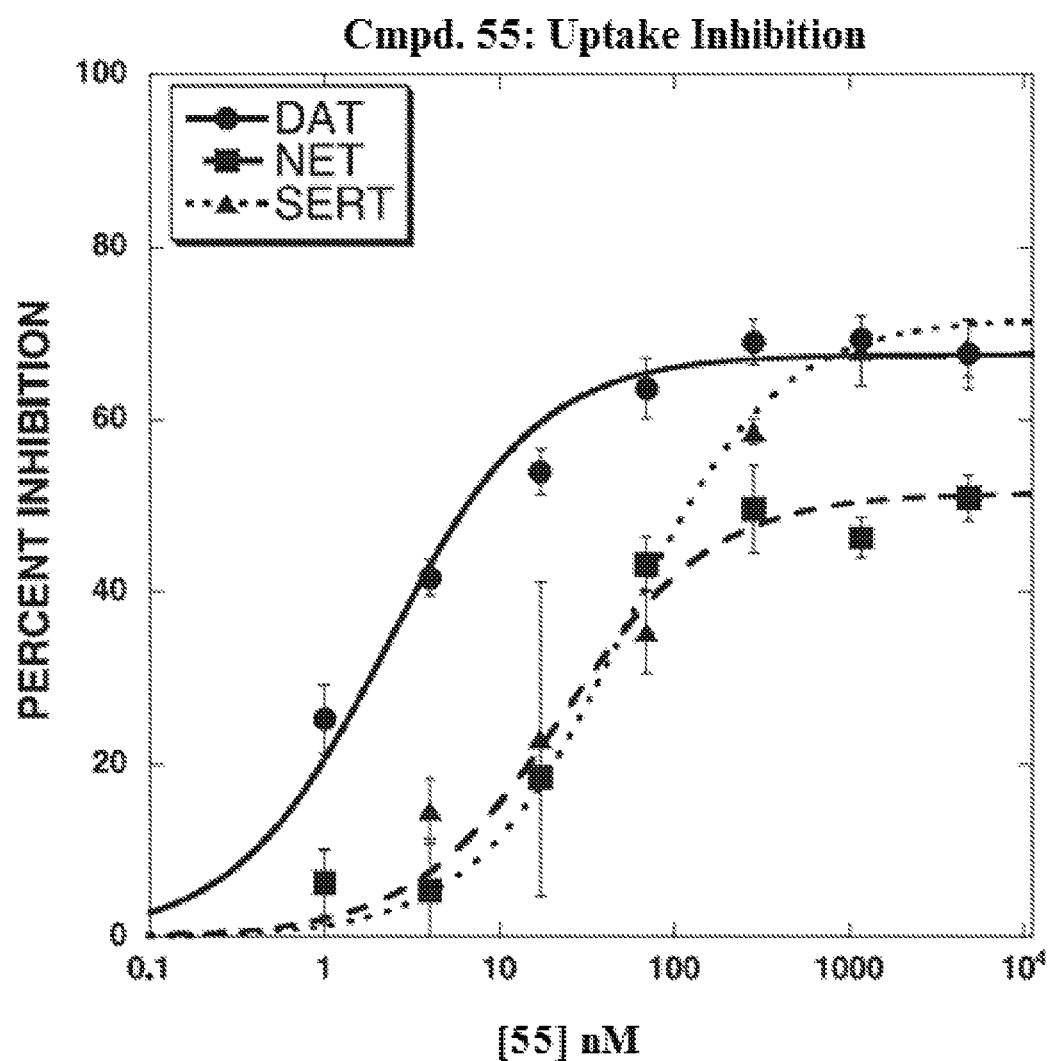
FIG. 2 shows representative data illustrating inhibition of [$^3$H]DA, [$^3$H]5-HT, and [$^3$H]NE by compound 55 in rat brain synaptosomes.
Figure 3A:
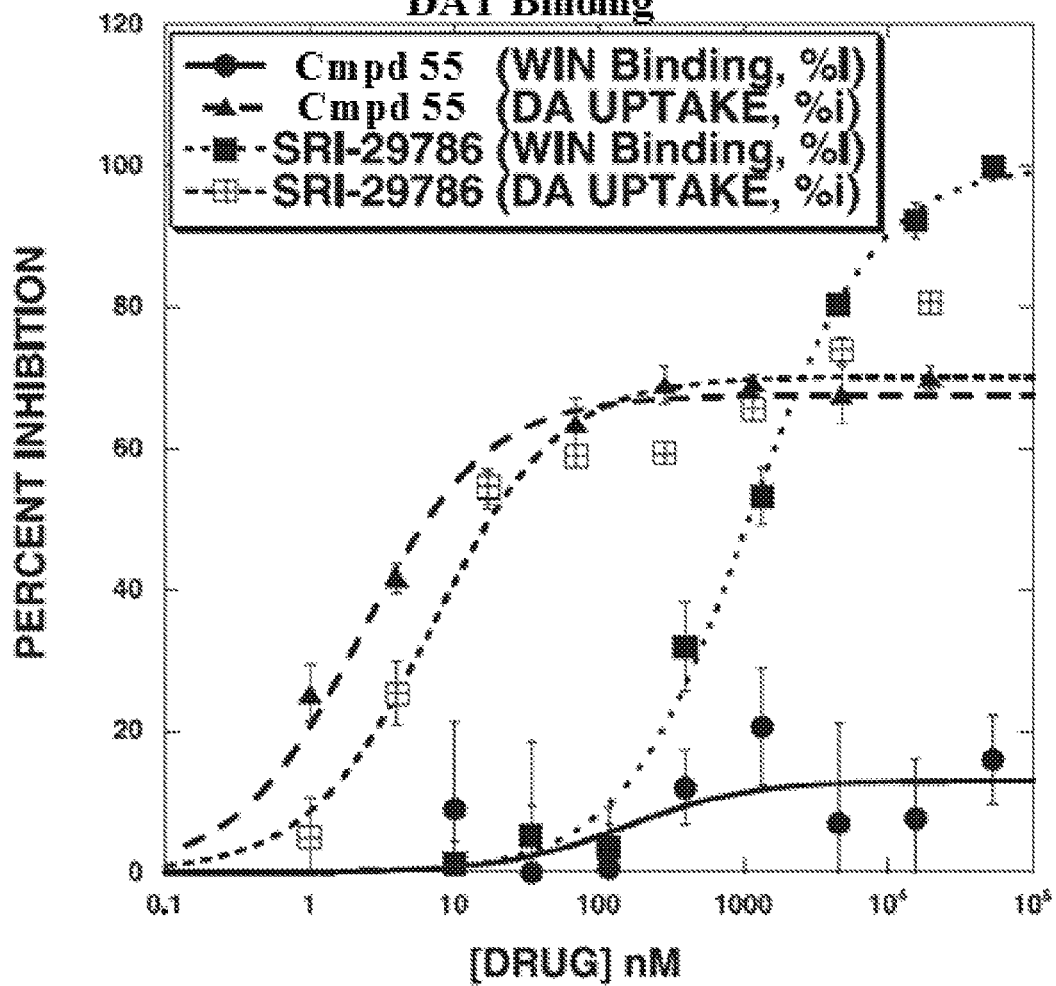
FIG. 3A shows representative data comparing the inhibition of [$^3$H]WIN35428 binding versus [$^3$H]DA uptake by compound 55 and SRI-29786.
Figure 3B:
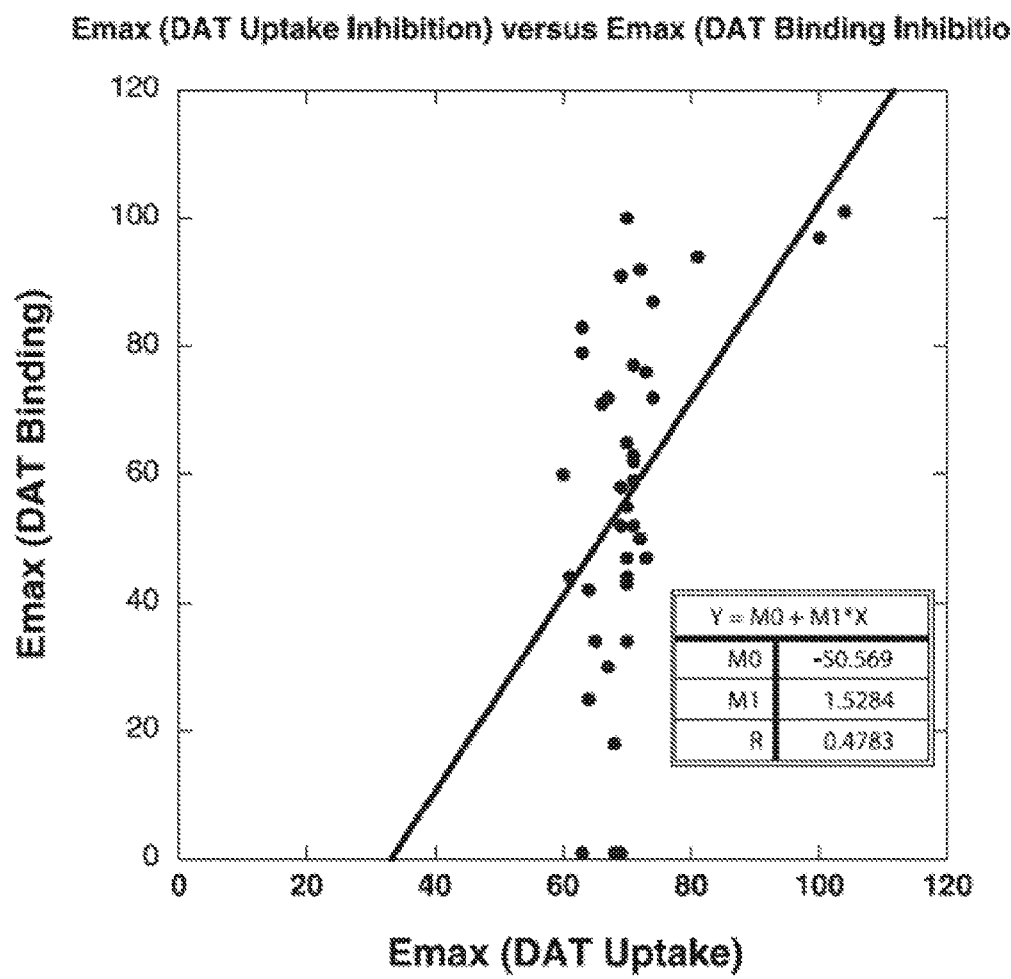
FIG. 3B shows a representative correlation plot of DAT uptake $E_{max}$ versus DAT binding $E_{max}$ for compounds shown in Table 7 herein below.

11. Evaluation of Test Agents for Inhibition of DAT<SERT, and NET Uptake and DAT Binding As shown in FIG. 2, compound 55 is a partial inhibitor not only of DAT uptake but also of SERT and NET uptake. All agents tested (see Table 9) were partial inhibitors of DAT, SERT, and NET uptake, though in general the efficacy was lower at SERT than at NET and DAT. Although many of the test agents had similar IC$_{50}$ values for BAT uptake inhibition, in general the order of potency was DAT>SERT>NET. Another striking aspect of the data set was that most compounds were ~3 orders of magnitude less potent in inhibiting [$^3$H]WIN35428 binding to DAT than in blocking uptake of [$^3$H]DA. This is illustrated in FIG. 3A for two compounds. Compound 55 partially inhibited DAT uptake (IC$_{50}$=2.3±0.4 nM) while being inactive in inhibiting DAT binding. In contrast, SRI-9786 partially inhibited DAT uptake (IC$_{50}$=7.1±2.2 nM) but also inhibited DAT binding, with full efficacy and an IC$_{50}$ value (1100±10 nM) 155-fold weaker than the IC$_{50}$ for inhibition of DAT uptake. Overall, only 5 of the 26 compounds were full efficacy inhibitors of DAT binding, and in most cases the agents were much less potent at DAT binding inhibition than at DAT uptake inhibition. In contrast, the prototypical DAT blockers GBR12935 and cocaine displayed similar potency and efficacy in both assays. There was no significant correlation between the E$_{max}$ values observed in the DAT uptake and binding assays (FIG. 3B).

TABLE 9

Summary of results obtained for the 36 partial-efficacy DAT uptake blockers
Dose-response curves for each indicated agent were generated as described in *Materials and Methods* for
DAT, NET, and SERT uptake inhibition and DAT binding. Each value is the mean ± S.D.; n = 3.

| Drug | DAT Uptake IC$_{50}$ nM | DAT Uptake E$_{max}$ % | NET Uptake IC$_{50}$ nM | NET Uptake E$_{max}$ % | SERT Uptake IC$_{50}$ nM | SERT Uptake E$_{max}$ % | DAT Binding IC$_{50}$ nM | DAT Binding ε$_{max}$ % | 5-HT/DA IC$_{50}$ (Uptake) | NE/DA IC$_{50}$ (Uptake) |
|---|---|---|---|---|---|---|---|---|---|---|
| SRI-29070 | 174 ± 58 | 66 ± 4 | 1740 ± 1150 | 64 ± 10 | 699 ± 164 | 48 ± 3 | 1.8 ± 0.4 | 71 ± 4 | 4 | 10 |
| SRI-29072 | 212 ± 49 | 71 ± 3 | 5850 ± 1746 | 62 ± 5 | 6382 ± 2636 | 56 ± 9 | 2.7 ± 0.3 | 77 ± 2 | 30 | 28 |
| SRI-29153 | 20 ± 1 | 73 ± 1 | 181 ± 46 | 73 ± 4 | 37 ± 18 | 55 ± 5 | 1.7 ± 0.2 | 76 ± 2 | 1.9 | 9 |
| SRI-29155 | 10 ± 1.0 | 74 ± 1 | 290 ± 52 | 70 ± 3 | 68 ± 13 | 54 ± 2 | 0.9 ± 0.2 | 87 ± 4 | 6.8 | 29 |
| SRI-29212 | 672 ± 204 | 67 ± 4 | 8126 ± 2273 | 64 ± 5 | 3805 ± 1645 | 50 ± 7 | 2.2 ± 0.5 | 72 ± 4 | 5.7 | 12 |
| SRI-29213 | 16 ± 4 | 81 ± 3 | 346 ± 59 | 77 ± 3 | 89 ± 51 | 43 ± 4 | 0.2 ± 0.0 | 94 ± 2 | 5.6 | 22 |
| SRI-29338 | 9.0 ± 1.5 | 71 ± 2 | 204 ± 47 | 62 ± 3 | 56 ± 21 | 52 ± 3 | 1.18 ± 0.93 | 63 ± 4 | 6 | 23 |
| SRI-29554 | 11 ± 1 | 71 ± 1 | 179 ± 27 | 78 ± 2 | 57 ± 18 | 60 ± 3 | 0.98 ± 0.46 | 59 ± 6 | 5 | 16 |
| SRI-29574 | 2.3 ± 0.4 | 68 ± 2 | 52 ± 15 | 72 ± 4 | 23 ± 5 | 52 ± 2 | Inactive | Inactive | 10 | 23 |
| SRI-29577 | 4.4 ± 0.8 | 70 ± 2 | 90 ± 15 | 71 ± 2 | 20 ± 5 | 56 ± 2 | 3.4 ± 1.2 | 65 ± 6 | 4.6 | 20 |
| SRI-29776 | 19 ± 4 | 69 ± 2 | 229 ± 43 | 71 ± 3 | 106 ± 19 | 61 ± 2 | 6.09 ± 0.97 | 58 ± 3 | 6 | 12 |
| SRI-29779 | 7.3 ± 2.2 | 63 ± 3 | 147 ± 63 | 71 ± 6 | 42 ± 12 | 51 ± 2 | 1.2 ± 0.2 | 83 ± 3 | 5.8 | 20 |
| SRI-29786 | 7.1 ± 2.2 | 70 ± 3 | 143 ± 61 | 68 ± 7 | 49 ± 27 | 44 ± 4 | 1.1 ± 0.1 | 100 ± 3 | 6.9 | 20 |
| SRI-29982 | 13 ± 2 | 73 ± 2 | 259 ± 41 | 71 ± 2 | 54 ± 7 | 51 ± 1 | 2.46 ± 1.21 | 47 ± 6 | 4 | 20 |
| SRI-29983 | 11 ± 2 | 70 ± 2 | 203 ± 79 | 73 ± 6 | 35 ± 9 | 57 ± 2 | 1.29 ± 0.34 | 55 ± 3 | 3 | 19 |
| SRI-29991 | 2.1 ± 0.3 | 68 ± 1 | 63 ± 9 | 69 ± 2 | 4.7 ± 0.6 | 51 ± 1 | 1.22 ± 1.12 | 18 ± 4 | 2 | 30 |
| SRI-30503 | 9.2 ± 1.2 | 70 ± 1 | 98 ± 23 | 65 ± 3 | 16 ± 5 | 55 ± 2 | 0.67 ± 0.37 | 34 ± 4 | 2 | 11 |
| SRI-30504 | 11 ± 2 | 70 ± 2 | 426 ± 49 | 70 ± 2 | 50 ± 14 | 55 ± 3 | 0.97 ± 0.65 | 47 ± 7 | 5 | 39 |
| SRI-30507 | 18 ± 3 | 71 ± 2 | 132 ± 16 | 77 ± 2 | 28 ± 6 | 54 ± 2 | 4.80 ± 1.81 | 62 ± 7 | 2 | 7 |
| SRI-30508 | 9.3 ± 1.1 | 65 ± 1 | 69 ± 18 | 76 ± 9 | 3.9 ± 0.4 | 56 ± 1 | 0.15 ± 0.09 | 34 ± 3 | 0.4 | 8 |
| SRI-30513 | 12 ± 2 | 72 ± 2 | 153 ± 55 | 65 ± 4 | 83 ± 28 | 59 ± 4 | 2.97 ± 1.03 | 50 ± 4 | 7 | 13 |
| SRI-30517 | 6.0 ± 0.7 | 70 ± 1 | 95 ± 12 | 70 ± 2 | 23 ± 3 | 54 ± 1 | 0.16 ± 0.08 | 43 ± 4 | 4 | 16 |
| SRI-30522 | 8.8 ± 1.1 | 63 ± 1 | 86 ± 55 | 40 ± 5 | 13 ± 6 | 35 ± 3 | Inactive | Inactive | 1 | 10 |
| SRI-30524 | 4.8 ± 0.6 | 71 ± 1 | 44 ± 6 | 76 ± 2 | 8.7 ± 0.9 | 56 ± 1 | 2.36 ± 1.17 | 52 ± 6 | 2 | 9 |
| SRI-30810 | 5.6 ± 0.8 | 64 ± 1 | 60 ± 10 | 69 ± 2 | 11 ± 3 | 51 ± 2 | 0.82 ± 0.36 | 25 ± 2 | 2 | 11 |
| SRI-30826 | 6.1 ± 1 | 64 ± 2 | 88 ± 15 | 81 ± 2 | 18 ± 4 | 56 ± 2 | 1.28 ± 0.40 | 42 ± 3 | 3 | 14 |
| SRI-30827 | 0.5 ± 0.1 | 63 ± 2 | 21 ± 7 | 67 ± 3 | 3.2 ± 0.9 | 58 ± 3 | 1.99 ± 0.33 | 79 ± 3 | 6 | 42 |
| SRI-30828 | 8.9 ± 1.6 | 60 ± 2 | 144 ± 30 | 65 ± 3 | 20 ± 5 | 50 ± 2 | 2.61 ± 1.14 | 60 ± 7 | 2 | 16 |
| SRI-30837 | 11 ± 1 | 61 ± 1 | 300 ± 56 | 75 ± 3 | 67 ± 8 | 55 ± 1 | 1.70 ± 0.62 | 44 ± 4 | 6 | 27 |
| SRI-30946 | 21 ± 3 | 70 ± 2 | 78 ± 17 | 75 ± 3 | 35 ± 11 | 59 ± 3 | 1.17 ± 0.32 | 44 ± 3 | 2 | 4 |

TABLE 9-continued

Summary of results obtained for the 36 partial-efficacy DAT uptake blockers
Dose-response curves for each indicated agent were generated as described in *Materials and Methods* for
DAT, NET, and SERT uptake inhibition and DAT binding. Each value is the mean ± S.D.; n = 3.

| Drug | DAT Uptake IC$_{50}$ nM | DAT Uptake E$_{max}$ % | NET Uptake IC$_{50}$ nM | NET Uptake E$_{max}$ % | SERT Uptake IC$_{50}$ nM | SERT Uptake E$_{max}$ % | DAT Binding IC$_{50}$ nM | DAT Binding ε$_{max}$ % | 5-HT/DA IC$_{50}$ (Uptake) | NE/DA IC$_{50}$ (Uptake) |
|---|---|---|---|---|---|---|---|---|---|---|
| SRI-31034 | 7.4 ± 1.1 | 69 ± 1 | 94 ± 22 | 63 ± 3 | 25 ± 7 | 49 ± 2 | Inactive | Inactive | 3 | 13 |
| SRI-31039 | 7.4 ± 2 | 74 ± 4 | 31 ± 7 | 71 ± 3 | 8.0 ± 2.8 | 58 ± 3 | 3.15 ± 1.11 | 72 ± 7 | 1 | 4 |
| SRI-31040 | 1.2 ± 0.1 | 69 ± 1 | 11 ± 4 | 70 ± 4 | 3.1 ± 0.7 | 54 ± 2 | 3.74 ± 1.10 | 91 ± 7 | 3 | 9 |
| SRI-31043 | 11 ± 1 | 67 ± 1 | 47 ± 10 | 67 ± 2 | 22 ± 5 | 51 ± 2 | 2.16 ± 0.97 | 30 ± 3 | 2 | 4 |
| SRI-31142 | 1.9 ± 0.3 | 72 ± 2 | 17 ± 4 | 61 ± 2 | 2.4 ± 0.4 | 48 ± 1 | 2.34 ± 0.45 | 92 ± 4 | 1.3 | 9 |
| SRI-31143 | 1.7 ± 0.1 | 69 ± 1 | 16 ± 5 | 69 ± 4 | 3.0 ± 0.6 | 51 ± 2 | 3.39 ± 1.99 | 52 ± 8 | 1.8 | 9 |
| Cocaine | 200 ± 19 | 100 ± 2 | 329 ± 22 | 102 ± 2 | 273 ± 24 | 98 ± 2 | 0.28 ± 0.03 | 97 ± 3 | 1.4 | 1.7 |
| GBR12935 | 1.1 ± 0.1 | 104 ± 3 | N.D. | N.D. | N.D. | N.D. | 2.0 × 10$^{-3}$ ± 0.08 × 10$^{-3}$ | 101 ± 0.9 | | |

N.D., not determined.

12. Effect of Test Agents on DAT-Mediated [$^3$H]MPP$^+$ Release

Figure 4A:
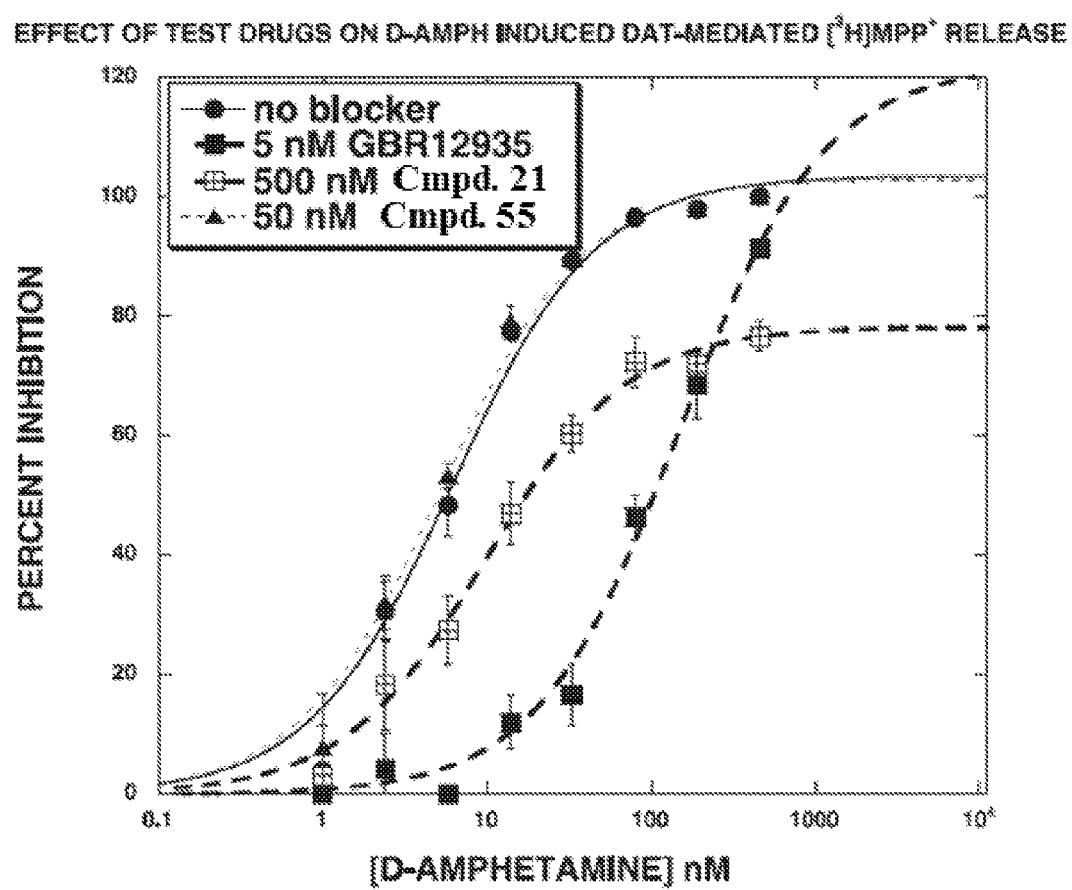
FIG. 4A and FIG. 4B show representative data illustrating the effect of 500 nM compound 21 and 50 nM compound 55 on DAT-mediated [$^3$H]MPP$^+$ release (4A) and D-AMPH induced [$^3$H]dopamine release (4B).
Figure 4B:
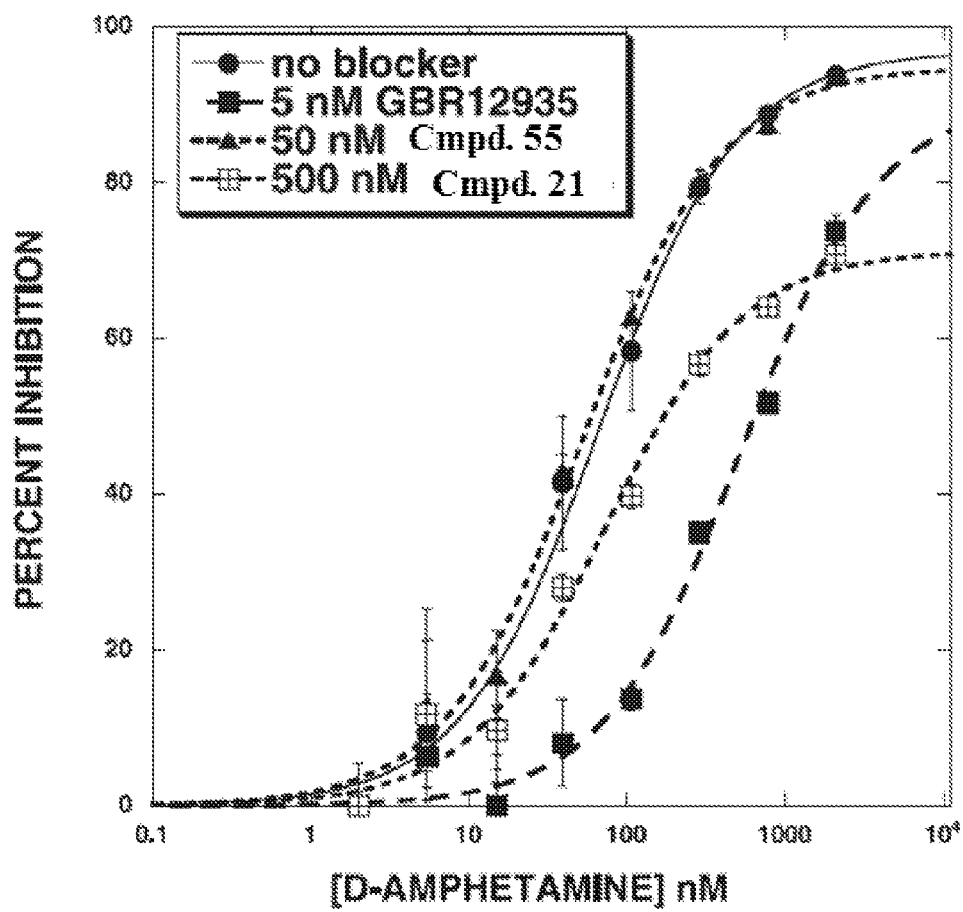

The first set of release experiments determined the effect of test agents on DAT-mediated [$^3$H]MPP$^+$ release in the absence and presence of 100 nM d-amphetamine. Overall, at concentrations of <1 μM, none of the agents altered DAT-mediated [$^3$H]MPP$^+$ release in the absence or presence of 100 nM d-amphetamine (data not shown). The ability of these agents to shift d-amphetamine-induced DAT-mediated [$^3$H]MPP$^+$ release, using blocking concentrations ~25 times greater than the corresponding IC$_{50}$ for DAT uptake inhibition, were then determined. FIG. 4A reports representative results. Compound 21 had no significant effect on the d-amphetamine EC$_{50}$ or E$_{max}$ value. Compound 55, in contrast, significantly increased the EC$_{50}$ value and also decreased the E$_{max}$ value. Of the 23 agents tested in this manner (see Table 10), only compound 55 increased EC$_{50}$ and decreased E$_{max}$. GBR12935, a competitive DAT uptake inhibitor, shifted the d-amphetamine release curve to the right in a parallel fashion without changing the E$_{max}$ value. Similar results were obtained when [$^3$H]DA was used instead of [$^3$H]MPP$^+$ (FIG. 4B).

TABLE 10

Figure 5A:
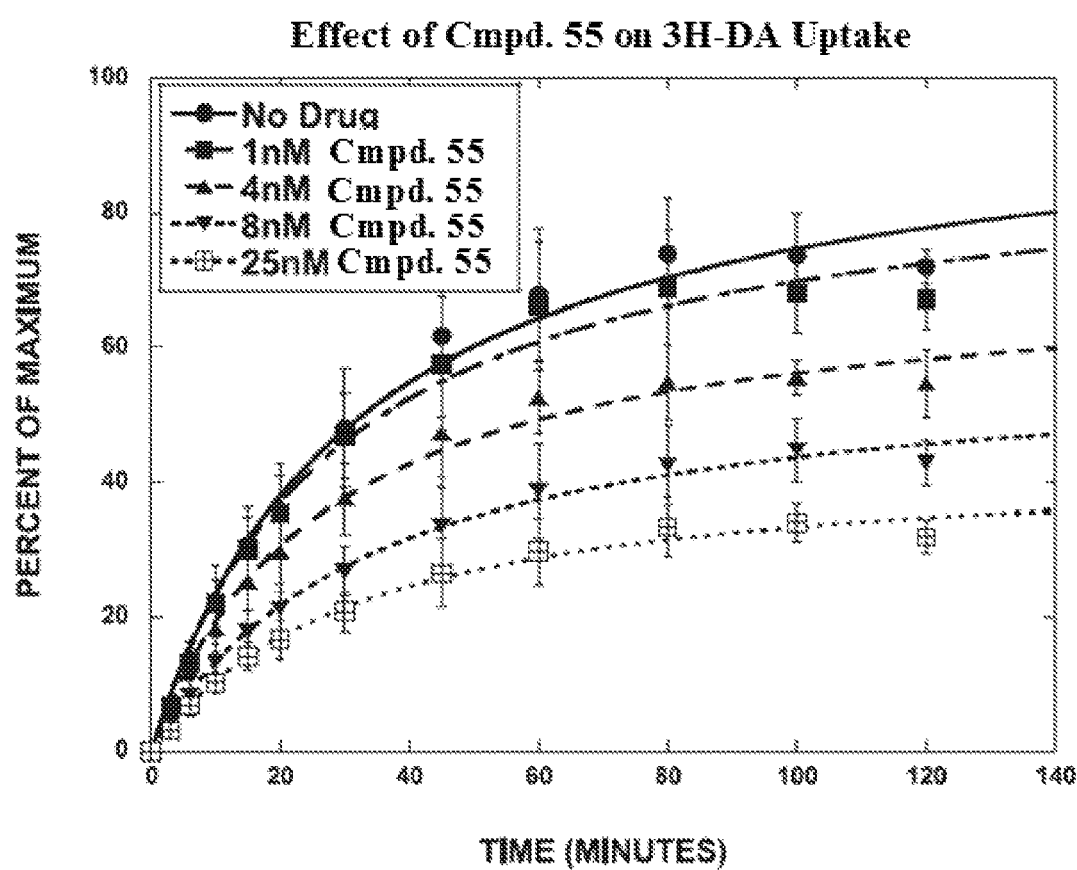
FIG. 5A and FIG. 5B show representative data illustrating the effect of compound 55 on [$^3$H]DA uptake (5A) and accumulation (5B).

Effect of test agents on d-amphetamine-induced, DAT-mediated [$^3$H]MPP$^+$ or [$^3$H]DA release
d-Amphetamine dose-response curves were generated in the absence and presence of each test agent as described in *Materials
and Methods* and illustrated in FIG. 5A. Each value is the mean ± S.D.; n = 3. The apparent K$_c$ was calculated
according to the following equation: Apparent K$_c$ = [Blocker]/((EC$_{50-2}$/EC$_{50-1}$) − 1), where
EC$_{50-1}$ is the EC$_{50}$ in the absence of blocker and EC$_{50-2}$ is the EC$_{50}$ in the presence of blocker.
A negative apparent K$_c$ occurs when a shifted EC$_{50}$ is less than the control EC$_{50}$ value.

| Blocker | IC$_{50}$ for DAT Uptake Inhibition nM | E$_{max}$ for DAT Uptake Inhibition % | Blocker Concentration nM | d-Amphetamine EC$_{50}$ nM | d-Amphetamine E$_{max}$ % | Apparent K$_c$ nM |
|---|---|---|---|---|---|---|
| [$^3$H]MPP$^+$ Release | | | | | | |
| None | — | — | — | 6.4 ± 1.2 | 104 ± 4 | — |
| SRI-29574 | 2 | 68 | 50 | 5.4 ± 0.6 | 103 ± 3 | −368 |
| SRI-29577 | 4 | 70 | 125 | 4.8 ± 0.4 | 102 ± 2 | −553 |
| SRI-29786 | 7 | 70 | 250 | 7.0 ± 0.5 | 101 ± 2 | 1940 |
| SRI-29779 | 7 | 63 | 250 | 7.9 ± 0.6 | 99 ± 2 | 912 |
| SRI-29155 | 10 | 74 | 250 | 9.6 ± 1.0* | 94 ± 2* | 456 |
| SRI-29213 | 16 | 81 | 500 | 9.7 ± 1.0* | 78 ± 2*** | 886 |
| SRI-29153 | 20 | 73 | 500 | 7.9 ± 0.9 | 101 ± 3 | 1820 |
| SRI-29070 | 174 | 66 | 5000 | 10.6 ± 0.7** | 98 ± 1 | 7050 |
| SRI-29072 | 212 | 71 | 5000 | 7.4 ± 1.0 | 96 ± 3 | 25830 |
| SRI-29212 | 672 | 67 | 12,500 | 7.4 ± 0.8 | 103 ± 2 | 64580 |
| SRI-29991 | 2 | 68 | 50 | 6.1 ± 0.7 | 102 ± 2 | −1070 |
| SRI-30517 | 6 | 70 | 150 | 7.0 ± 1.3 | 104 ± 4 | 1600 |
| SRI-30522 | 9 | 63 | 250 | 6.4 ± 1.1 | 105 ± 4 | N.A. |
| SRI-30524 | 5 | 71 | 125 | 7.1 ± 0.9 | 103 ± 3 | 1140 |
| SRI-30810 | 6 | 64 | 150 | 7.2 ± 1.5 | 104 ± 5 | 1200 |
| SRI-30826 | 6 | 64 | 150 | 7.0 ± 1.3 | 105 ± 4 | 1600 |
| SRI-30827 | 0.5 | 63 | 12.5 | 6.7 ± 0.9 | 104 ± 3 | 267 |
| SRI-31034 | 7 | 69 | 200 | 6.8 ± 1.5 | 104 ± 5 | 3200 |
| SRI-31040 | 1 | 69 | 25 | 9.3 ± 1.3* | 105 ± 3 | 55 |
| SRI-31142 | 2 | 72 | 50 | 7.2 ± 1.0 | 103 ± 3 | 400 |
| SRI-31143 | 2 | 67 | 50 | 6.9 ± 1.3 | 104 ± 4 | 46 |
| GBR12935 | 2 | 100 | 5 | 150 ± 25*** | 122 ± 8* | 0.22 |
| [$^3$H]DA Release | | | | | | |
| None | — | — | — | 67 ± 10 | 97 ± 3 | — |
| GBR12935 | 2 | 100 | 5 | 519 ± 95** | 91 ± 6 | 0.74 |

TABLE 10-continued

Effect of test agents on d-amphetamine-induced, DAT-mediated [$^3$H]MPP$^+$ or [$^3$H]DA release
d-Amphetamine dose-response curves were generated in the absence and presence of each test agent as described in *Materials and Methods* and illustrated in FIG. 5A. Each value is the mean ± S.D.; n = 3. The apparent $K_c$ was calculated according to the following equation: Apparent $K_c$ = [Blocker]/(($EC_{50-2}/EC_{50-1}$) − 1), where $EC_{50-1}$ is the $EC_{50}$ in the absence of blocker and $EC_{50-2}$ is the $EC_{50}$ in the presence of blocker. A negative apparent $K_c$ occurs when a shifted $EC_{50}$ is less than the control $EC_{50}$ value.

| Blocker | $IC_{50}$ for DAT Uptake Inhibition nM | $E_{max}$ for DAT Uptake Inhibition % | Blocker Concentration nM | d-Amphetamine $EC_{50}$ nM | d-Amphetamine $E_{max}$ % | Apparent $K_c$ nM |
|---|---|---|---|---|---|---|
| SRI-29574 | 2 | 68 | 50 | 53 ± 6 | 95 ± 2 | −239 |
| SRI-29213 | 16 | 81 | 500 | 72 ± 12 | 71 ± 3*** | 6700 |

N.A., not applicable.
*P < 0.05 vs. control (Student's t test);
**P < 0.01 vs. control (Student's t test);
***P < 0.001 vs. control (Student's t test).

13. Effect of Compound 55 and Cocaine on [$^3$H]Da Uptake/Accumulation

Figure 5B:
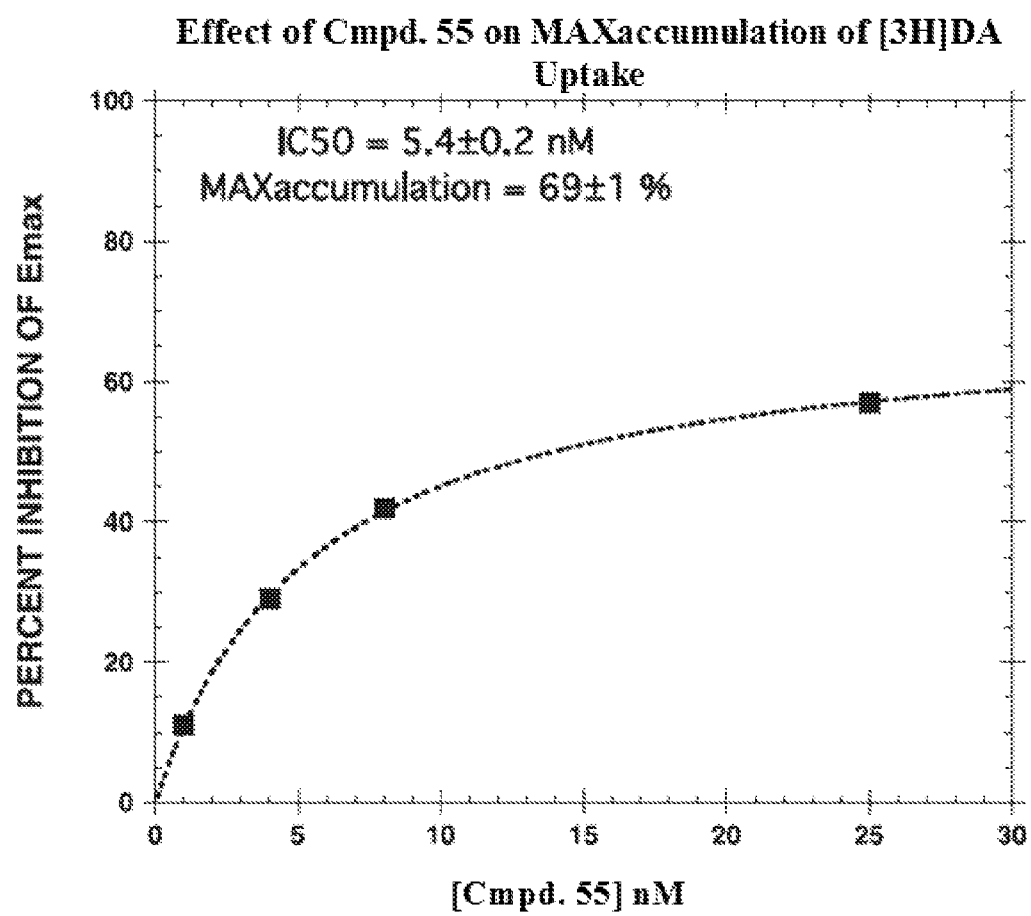
Figure 6A:
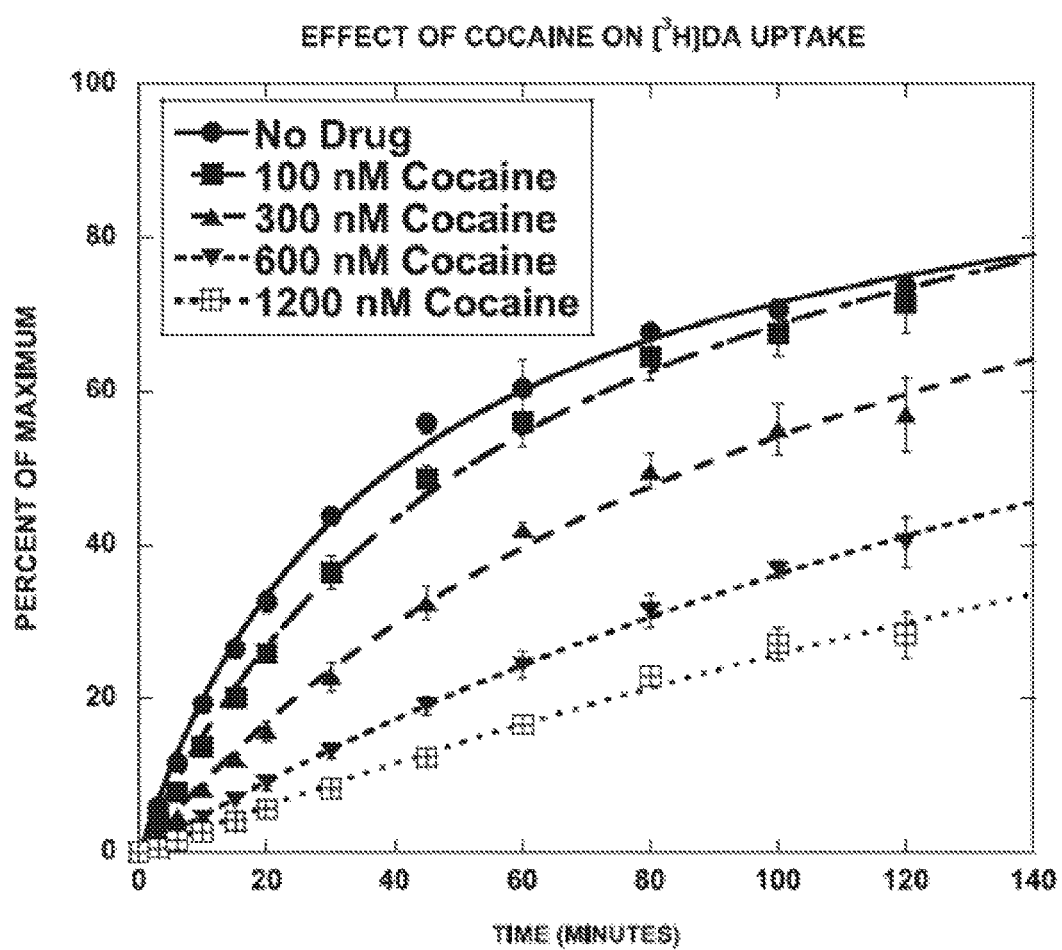
FIG. 6A and FIG. 6B show representative data illustrating the effect of cocaine on [$^3$H]DA uptake (6A) and accumulation (6B).
Figure 6B:
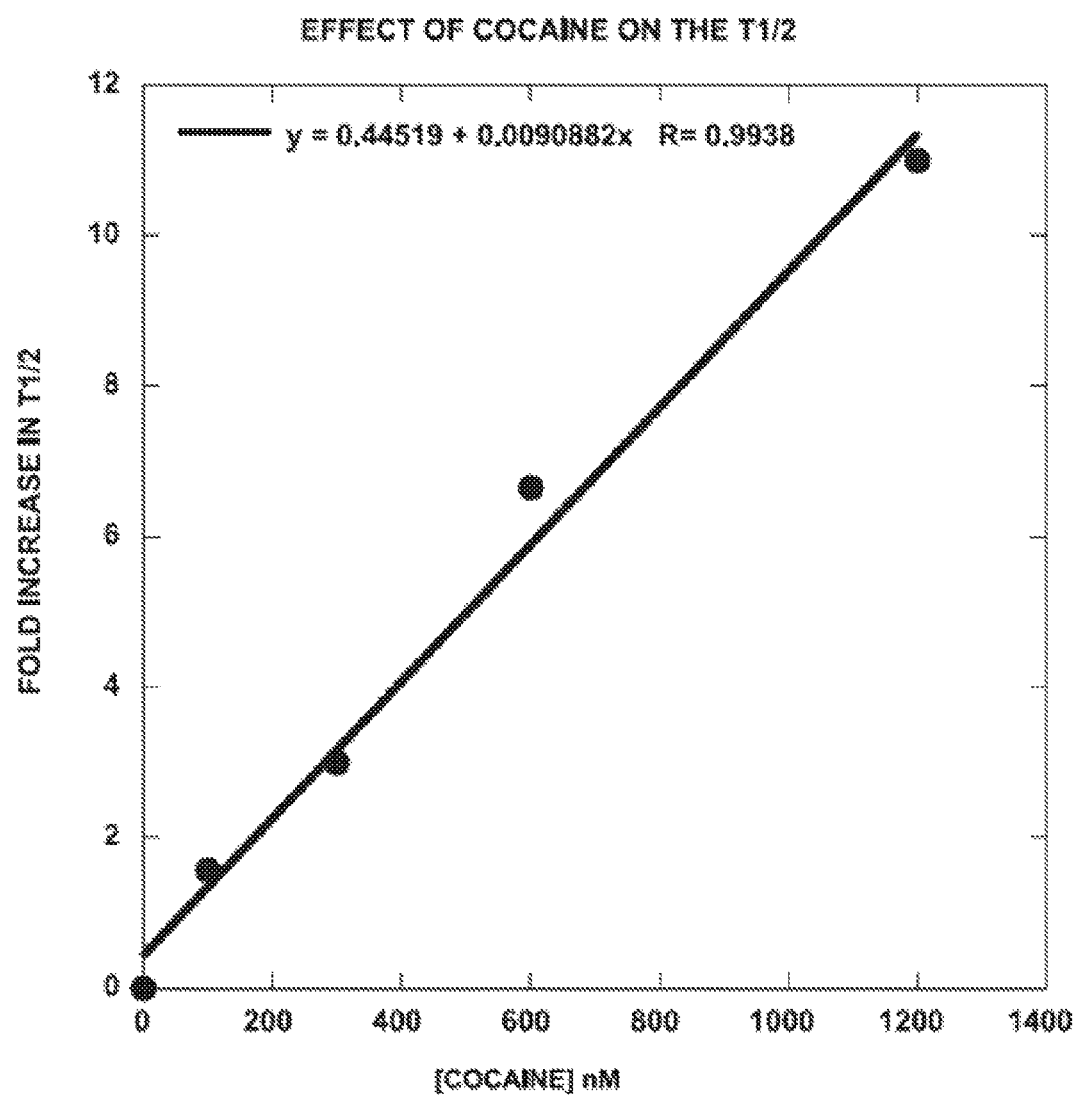

Next, the effect of compound 55, a potent partial [$^3$H]DA uptake inhibitor, on the time course of [$^3$H]DA uptake, in comparison with cocaine. It was hypothesized that compound 55 would reduce the maximum level of [$^3$H]DA accumulation, consistent with noncompetitive inhibition. As reported in FIG. 5A and Table 11, compound 55 had no significant effect on the time to half-maximal accumulation ($t_{1/2}$) but decreased the $E_{max}$ in a dose-dependent manner (FIG. 5B) ($EC_{50}$=5.4±0.2 nM; $E_{max}$=69±1%). In contrast, the most striking effect of cocaine (FIG. 6A and FIG. 6B) was to increase the $t_{1/2}$ in a dose-dependent linear manner. The effect of cocaine on the $E_{max}$ was more complex. Post hoc Student's t test showed that two of the four $E_{max}$ values were not significantly different from control, indicating that cocaine did not have a consistent effect on the $E_{max}$. Viewed collectively, these data suggest that compound 55 may be a noncompetitive inhibitor of [$^3$H]DA uptake.

TABLE 11

| [55] (nM) | $t_{1/2}$ (min) | $E_{max}$ | Inhibition of the $E_{max}$ value (%) |
|---|---|---|---|
| 0 | 32 ± 4 | 98 ± 4 | 0 |
| 1 | 28 ± 3 | 89 ± 4 | 11 |
| 4 | 27 ± 3 | 71 ± 2* | 29 |
| 8 | 34 ± 3 | 58 ± 2* | 42 |
| 25 | 31 ± 3 | 43 ± 3* | 57 |

*P < 0.05 vs. control (unpaired Student's t test).

What is claimed is:
1. A compound having the formula (II)

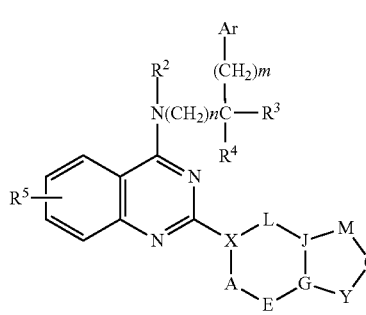

wherein
n is 0, 1 or 2;
m is 0, 1 or 2;
$R^2$ is H or lower alkyl group;
Ar is a phenyl or heterocyclic group;
$R^3$ is H, alkyl, cycloalkyl, heterocycloalkyl, aryl, aralkyl, heteroaryl, or heteroarylalkyl;
$R^4$ is H, alkyl, hydroxy, alkoxy, aryloxy, heteroaryloxy, amino, alkylamino or dialkylamino, provided that $R^3$ and $R^4$ are not simultaneously H; or
$R^3$ and $R^4$ together form a carbocycle or heterocycle;
$R^5$ is H, halogen, alkyl, aryl, hydroxy, alkoxy, aryloxy, amino, alkylamino or dialkylamino; and

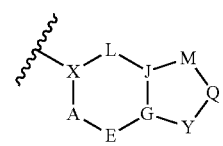

represents a bicyclic heterocycle wherein X is a nitrogen or a carbon atom; wherein each of L and E are independently selected from CR'R'', N, O, and S; wherein each of J and G are independently selected from CR' and N;
wherein each occurrence of R' and R'' are independently selected from hydrogen and C1-C4 alkyl;
wherein Y is selected from S, O, CR', CR'R'', and NR$^{14}$;
wherein Q is selected from S, O, NR', C=O, CR'R''', and CR$^{15}$; wherein M is selected from S, O, NR', CR'R''', and CR$^{16}$;
wherein A is selected from NR', CR'R'', and CR$^{17}$;
wherein R$^{14}$ is H, lower alkyl, acyl, sulfonyl, aryl, or heteroaryl; wherein each of R$^{15}$, R$^{16}$ and R$^{17}$ are independently H, halogen, lower alkyl, hydroxy, alkoxy, aryloxy, acyl, sulfonyl, aryl, heteroaryl, amino, alkylamino or dialkylamino;
wherein each occurrence of R''' is independently selected from hydrogen and C1-C4 alkyl, or wherein each occurrence of R''', together with the intermediate carbon atoms, comprise a 6-membered ring, with unsaturation allowed for appropriate valence, pharmaceutically acceptable salts thereof, deuterated forms thereof, and mixtures thereof.
2. A compound selected from the group consisting of:
2-(2-(Dimethylamino)pyrimidin-5-yl)-N-(2,2-diphenylethyl)quinazolin-4-amine;

N-(2,2-Diphenylethyl)-2-(1H-indol-5-yl)quinazolin-4-amine;
N-(3,3-Diphenylpropyl)-2-(1H-indol-5-yl)quinazolin-4-amine;
N-(2,2-Diphenylethyl)-2-(1H-indol-5-yl)-6,7-dimethoxyquinazolin-4-amine;
N-(2,2-Diphenylethyl)-2-(2-methoxypyrimidin-5-yl)quinazolin-4-amine;
N-(2,2-Diphenylethyl)-2-(2-(methylthio)pyrimidin-5-yl)quinazolin-4-amine;
N-(2,2-Diphenylethyl)-2-(pyridin-4-yl)quinazolin-4-amine;
N-(2,2-Diphenylethyl)-2-(2-(methylamino)pyrimidin-5-yl)quinazolin-4-amine;
N-(2,2-Diphenylethyl)-2-(1H-imidazol-1-yl)quinazolin-4-amine;
N-(2,2-Diphenylethyl)-2-(quinolin-6-yl)quinazolin-4-amine;
N-(2,2-Diphenylethyl)-2-(imidazo[1,2-a]pyridin-6-yl)quinazolin-4-amine;
N-(2,2-Diphenylethyl)-2-(1-methyl-1H-benzo[d]imidazol-6-yl)quinazolin-4-amine;
N-(2,2-Diphenylethyl)-2-(2-methyl-2H-indazol-5-yl)quinazolin-4-amine;
N-(2,2-Diphenylethyl)-2-(1-methyl-1H-indazol-5-yl)quinazolin-4-amine;
2-(6-(Dimethylamino)pyridin-3-yl)-N-(2,2-diphenylethyl)quinazolin-4-amine;
2-(Benzo[d]thiazol-6-yl)-N-(2,2-diphenylethyl)quinazolin-4-amine;
N-(2,2-Diphenylethyl)-2-(1-methyl-1H-indol-5-yl)quinazolin-4-amine;
5-(4-((2,2-Diphenylethyl)amino)quinazolin-2-yl)indolin-2-one;
2-((2-(2-(Dimethylamino)pyrimidin-5-yl)quinazolin-4-yl)amino)-1,1-diphenylethanol;
2-((2-(1H-Indol-5-yl)quinazolin-4-yl)amino)-1,1-diphenylethanol;
N-(2,2-Diphenylethyl)-2-(indolin-5-yl)quinazolin-4-amine;
2-(6-Aminopyridin-3-yl)-N-(2,2-diphenylethyl)quinazolin-4-amine;
N-(2,2-Diphenylethyl)-2-(imidazo[1,2-a]pyrimidin-6-yl)quinazolin-4-amine;
2-(2,3-Dimethylimidazo[1,2-a]pyridin-6-yl)-N-(2,2-diphenylethyl)quinazolin-4-amine;
N-Benzhydryl-2-(6-(dimethylamino)pyridin-3-yl)quinazolin-4-amine;
2-(6-(Dimethylamino)pyridin-3-yl)-N-(3,3-diphenylpropyl)quinazolin-4-amine;
2-(Imidazo[1,2-a]pyridin-6-yl)-N-(2-phenyl-2-(pyridin-2-yl)ethyl)quinazolin-4-amine;
2-((2-(Imidazo[1,2-a]pyridin-6-yl)quinazolin-4-yl)amino)-1,1-diphenylethanol;
2-(Imidazo[1,2-a]pyrimidin-6-yl)-N-(2-phenyl-2-(pyridin-2-yl)ethyl)quinazolin-4-amine;
2-((2-(Imidazo[1,2-a]pyrimidin-6-yl)quinazolin-4-yl)amino)-1,1-diphenylethanol;
N-(2-Cyclohexyl-2-phenylethyl)-2-(imidazo[1,2-a]pyridin-6-yl)quinazolin-4-amine;
N-(2-Cyclohexyl-2-phenylethyl)-2-(imidazo[1,2-a]pyrimidin-6-yl)quinazolin-4-amine;
2-([1,2,4]Triazolo[1,5-a]pyridin-6-yl)-N-(2,2-diphenylethyl)quinazolin-4-amine;
2-(Imidazo[1,2-a]pyridin-6-yl)-N-(2-phenyl-2-(pyridin-4-yl)ethyl)quinazolin-4-amine;
2-(Imidazo[1,2-a]pyrimidin-6-yl)-N-(2-phenyl-2-(pyridin-4-yl)ethyl)quinazolin-4-amine;
2-(Imidazo[1,2-a]pyridin-6-yl)-N-(2-phenyl-2-(1H-pyrrol-2-yl)ethyl)quinazolin-4-amine;
N-(2,2-Diphenylethyl)-2-(7-methylimidazo[1,2-a]pyridin-6-yl)quinazolin-4-amine;
N-(2,2-Diphenylethyl)-2-(1H-pyrrolo[2,3-b]pyridin-5-yl)quinazolin-4-amine;
N-(2,2-Diphenylethyl)-7-fluoro-2-(imidazo[1,2-a]pyridin-6-yl)quinazolin-4-amine hydrochloride;
2-(Imidazo[1,2-a]pyrimidin-6-yl)-N-(2-(4-methylpiperazin-1-yl)-2-phenylethyl)quinazolin-4-amine;
2-(1H-Indol-5-yl)-N-(2-phenyl-2-(pyridin-3-yl)ethyl)quinazolin-4-amine;
2-(Imidazo[1,2-a]pyridin-6-yl)-N-(2-phenyl-2-(pyridin-3-yl)ethyl)quinazolin-4-amine;
2-(Imidazo[1,2-a]pyrimidin-6-yl)-N-(2-phenyl-2-(pyridin-3-yl)ethyl)quinazolin-4-amine;
N-(2,3-Diphenylpropyl)-2-(imidazo[1,2-a]pyridin-6-yl)quinazolin-4-amine;
2-(1-Methyl-1H-indol-5-yl)-N-(2-phenyl-2-(pyridin-3-yl)ethyl)quinazolin-4-amine;
N-(5-(4-((2,2-Diphenylethyl)amino)quinazolin-2-yl)pyridin-2-yl)methanesulfonamide;
2-(7-Methylimidazo[1,2-a]pyridin-6-yl)-N-(2-phenyl-2-(1H-pyrrol-2-yl)ethyl)quinazolin-4-amine;
N-(2,2-Diphenylethyl)-2-(quinolin-8-yl)quinazolin-4-amine;
N-(2,3-Diphenylpropyl)-2-(imidazo[1,2-a]pyrimidin-6-yl)quinazolin-4-amine;
2-(7-Methylimidazo[1,2-a]pyridin-6-yl)-N-(2-phenyl-2-(pyridin-4-yl)ethyl)quinazolin-4-amine;
2-((2-(7-Methylimidazo[1,2-a]pyridin-6-yl)quinazolin-4-yl)amino)-1,1-diphenylethanol;
1-(2-((2-(Imidazo[1,2-a]pyridin-6-yl)quinazolin-4-yl)amino)-1-(4-methoxyphenyl)ethyl)cyclohexanol;
2-(7-Methylimidazo[1,2-a]pyridin-6-yl)-N-(2-(pyridin-3-yl)-2-(1H-pyrrol-2-yl)ethyl)quinazolin-4-amine;
N-(2,2-Di(pyridin-4-yl)ethyl)-2-(7-methylimidazo[1,2-a]pyridin-6-yl)quinazolin-4-amine;
(S)-2-(7-Methylimidazo[1,2-a]pyridin-6-yl)-N-(2-phenyl-2-(1H-pyrrol-1-yl)ethyl)quinazolin-4-amine;
2-(6,7-Dihydro-1H-pyrrolo[3,2-c]pyridin-5(4H)-yl)-N-(2,2-diphenylethyl)quinazolin-4-amine;
N-(2,2-Diphenylpropyl)-2-(imidazo[1,2-a]pyridin-6-yl)quinazolin-4-amine;
N-(1,2-Diphenylethyl)-2-(imidazo[1,2-a]pyridin-6-yl)quinazolin-4-amine;
N-(1,3-Diphenylpropyl)-2-(imidazo[1,2-a]pyridin-6-yl)quinazolin-4-amine;
N-(1,3-Diphenylpropyl)-2-(7-methylimidazo[1,2-a]pyridin-6-yl)quinazolin-4-amine;
2-(Imidazo[1,2-a]pyridin-6-yl)-N-(3-methyl-2-phenylbutyl)quinazolin-4-amine;
N-(3-Methyl-2-phenylbutyl)-2-(7-methylimidazo[1,2-a]pyridin-6-yl)quinazolin-4-amine;
N-(1,2-Diphenylethyl)-2-(7-methylimidazo[1,2-a]pyridin-6-yl)quinazolin-4-amine;
N-(2,2-Di(pyridin-4-yl)ethyl)-2-(6,7-dihydro-1H-pyrrolo[3,2-c]pyridin-5(4H)-yl)quinazolin-4-amine;
2-(7-Methylimidazo[1,2-a]pyridin-6-yl)-N-(2-phenoxy-2-phenylethyl)quinazolin-4-amine;
N-(2,2-Diphenylpropyl)-2-(7-methylimidazo[1,2-a]pyridin-6-yl)quinazolin-4-amine;
N-(2-Cyclopropyl-2-phenylethyl)-2-(7-methylimidazo[1,2-a]pyridin-6-yl)quinazolin-4-amine;

N-(2-Benzyl-3-phenylpropyl)-2-(7-methylimidazo[1,2-a]pyridin-6-yl)quinazolin-4-amine;

2-(7-Methylimidazo[1,2-a]pyridin-6-yl)-N-(2-phenylpropyl)quinazolin-4-amine;

2-(7-Methylimidazo[1,2-a]pyridin-6-yl)-N-(2-(pyridin-4-yl)-2-(1H-pyrrol-2-yl)ethyl)quinazolin-4-amine;

2-((2-(7-Methylimidazo[1,2-a]pyridin-6-yl)quinazolin-4-yl)amino)-1-phenylethanol;

N-(2-Methoxy-2-phenylethyl)-2-(7-methylimidazo[1,2-a]pyridin-6-yl)quinazolin-4-amine;

2-(7-Methylimidazo[1,2-a]pyridin-6-yl)-N-(2-phenylbutyl)quinazolin-4-amine;

N-(2,2-Diphenylethyl)-2-(isoindolin-2-yl)quinazolin-4-amine;

2-(3,4-Dihydro-1H-pyrido[3,4-b]indol-2(9H)-yl)-N-(2,2-diphenylethyl)quinazolin-4-amine;

2-(3,4-Dihydro-1H-pyrido[4,3-b]indol-2(5H)-yl)-N-(2,2-diphenylethyl)quinazolin-4-amine;

N1,N1-Dimethyl-N3-(2-(7-methylimidazo[1,2-a]pyridin-6-yl)quinazolin-4-yl)-2-phenylpropane-1,3-diamine;

2-(3,4-Dihydroisoquinolin-2(1H)-yl)-N-(2,2-diphenylethyl)quinazolin-4-amine;

N-(2-Cyclopentyl-2-phenylethyl)-2-(7-methylimidazo[1,2-a]pyridin-6-yl)quinazolin-4-amine;

N-(2,2-Diphenylethyl)-2-(5-methylimidazo[1,2-a]pyridin-6-yl)quinazolin-4-amine;

N1,N1-Dimethyl-N2-(2-(7-methylimidazo[1,2-a]pyridin-6-yl)quinazolin-4-yl)-1-phenylethane-1,2-diamine;

N-(2,2-Diphenylethyl)-2-(pyrazolo[1,5-a]pyrimidin-6-yl)quinazolin-4-amine;

N-(2,2-Diphenylethyl)-2-(7-(trifluoromethyl)imidazo[1,2-a]pyridin-6-yl)quinazolin-4-amine;

2-(6,7-Dihydro-1H-pyrrolo[3,2-c]pyridin-5(4H)-yl)-N-(3-methyl-2-phenylbutyl)quinazolin-4-amine; and N-(2,2-Bis(4-fluorophenyl)ethyl)-2-(7-methylimidazo[1,2-a]pyridin-6-yl)quinazolin-4-amine; or pharmaceutically acceptable salts thereof, deuterated forms thereof, and mixtures thereof.

3. A compound having a structure selected from:

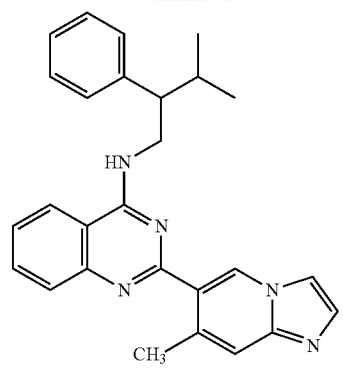

,

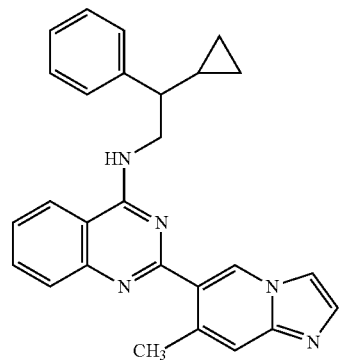

,

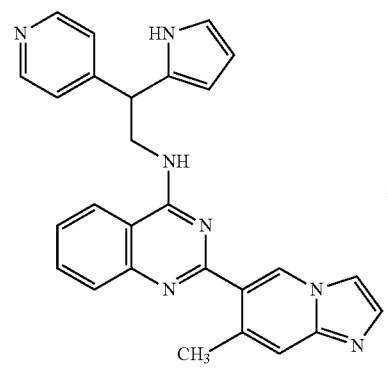

,

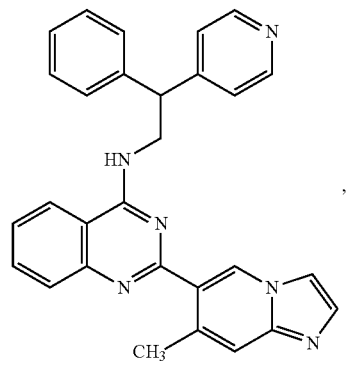 [SMILES: Cc1cc2nccn2cc1-c1nc(NCC(c2ccccc2)c2ccncc2)c2ccccc2n1]

,

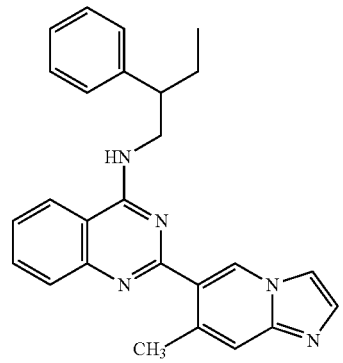

,

-continued
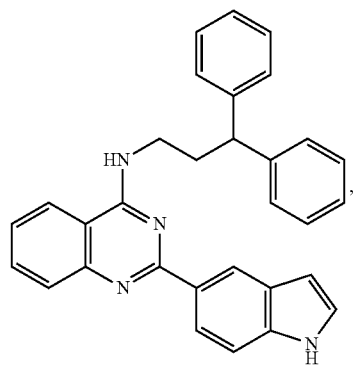
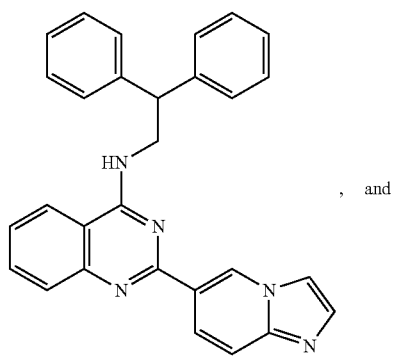, and
-continued
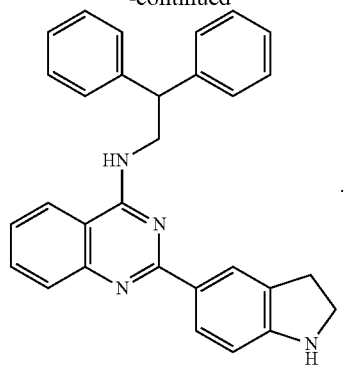
4. The compound according to claim 3 having a structure:
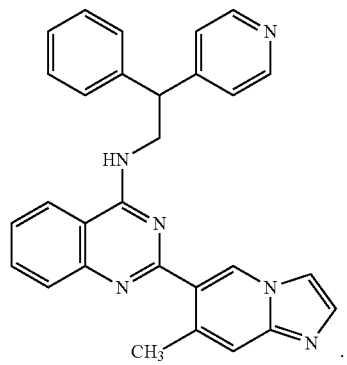
* * * * *